(12) United States Patent
Sasikumar et al.

(10) Patent No.: US 8,618,123 B2
(45) Date of Patent: Dec. 31, 2013

(54) BENZENESULFONYL-CHROMANE, THIOCHROMANE, TETRAHYDRONAPHTHALENE AND RELATED GAMMA SECRETASE INHIBITORS

(75) Inventors: Thavalakulamgara K. Sasikumar, Edison, NJ (US); Duane A. Burnett, Bernardsville, NJ (US); Theodros Asberom, West Orange, NJ (US); Wen-Lian Wu, Edison, NJ (US); Hongmei Li, Warren, NJ (US); Ruo Xu, Watchung, NJ (US); Hubert B. Josien, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 569 days.

(21) Appl. No.: 12/668,550

(22) PCT Filed: Jul. 15, 2008

(86) PCT No.: PCT/US2008/008646
§ 371 (c)(1),
(2), (4) Date: Jan. 20, 2011

(87) PCT Pub. No.: WO2009/011851
PCT Pub. Date: Jan. 22, 2009

(65) Prior Publication Data
US 2011/0110948 A1  May 12, 2011

Related U.S. Application Data

(60) Provisional application No. 60/950,160, filed on Jul. 17, 2007.

(51) Int. Cl.

| | | |
|---|---|---|
| A01N 43/42 | (2006.01) |
| A01N 43/18 | (2006.01) |
| A01N 43/16 | (2006.01) |
| A01N 41/10 | (2006.01) |
| A61K 31/44 | (2006.01) |
| A61K 31/38 | (2006.01) |
| A61K 31/35 | (2006.01) |
| A61K 31/10 | (2006.01) |
| C07D 221/18 | (2006.01) |
| C07D 221/22 | (2006.01) |
| C07D 409/00 | (2006.01) |
| C07D 335/04 | (2006.01) |
| C07D 495/00 | (2006.01) |
| C07D 311/78 | (2006.01) |
| C07D 311/94 | (2006.01) |
| C07C 315/00 | (2006.01) |
| C07C 317/00 | (2006.01) |

(52) U.S. Cl.
USPC ........... 514/280; 514/284; 514/432; 514/453; 514/709; 546/42; 546/61; 549/24; 549/382; 549/383; 568/34

(58) Field of Classification Search
USPC ........... 514/709, 280, 284, 432, 453; 568/34; 546/42, 61; 549/24, 382, 383
See application file for complete search history.

(56) References Cited

FOREIGN PATENT DOCUMENTS

| WO | 0050391 | 8/2000 |
|---|---|---|
| WO | 03014075 A2 | 2/2003 |
| WO | 2004031137 A2 | 4/2004 |
| WO | 2004101539 A1 | 11/2004 |
| WO | 2007084595 A2 | 7/2007 |
| WO | WO 2007084595 A2 * | 7/2007 |
| WO | 2007143523 A2 | 12/2007 |
| WO | 2009008980 A2 | 1/2009 |

OTHER PUBLICATIONS

WO09008980 Search Report, Nov. 6, 2008.
PCT/US2008/008646 Written Opinion.

* cited by examiner

*Primary Examiner* — Sarah Pihonak
(74) *Attorney, Agent, or Firm* — Susan L. Hess; John C. Todaro

(57) ABSTRACT

Disclosed are novel gamma secretase inhibitors of the formula (I): or a pharmaceutically acceptable salt, solvate, or ester thereof, wherein $L^1$, n, X, Ar, Y, Z, Q, and $Q^1$ are as defined herein. Also disclosed are methods for inhibiting gamma secretase, methods for treating Alzheimer's disease, methods of treating one or more neurodegenerative diseases, and methods of inhibiting the deposition of amyloid protein (e.g., amyloid beta protein) in, on or around neurological tissue (e.g., the brain) using the compounds of formula 1.0.

(I)

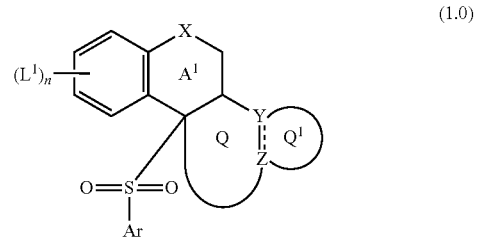

18 Claims, No Drawings

BENZENESULFONYL-CHROMANE, THIOCHROMANE, TETRAHYDRONAPHTHALENE AND RELATED GAMMA SECRETASE INHIBITORS

REFERENCE TO RELATED APPLICATION

This application claims the benefit of U.S. Provisional Application No. 60/950,160 filed Jul. 17, 2007.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

McCombie et al., Tetrahedron Letters, Vol. 34, No. 50, pp. 8033-8036 (1993) describe methods of preparing chromans and thiochromans. However, the chromans and thiochromans described therein are quite different from the compounds of the present invention.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of gamma-secretase (also termed "γ-secretase") and have the Formula (1.0):

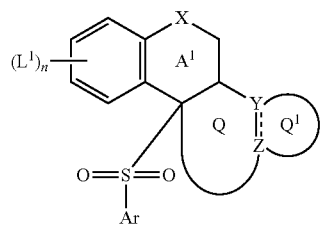

(1.0)

or a pharmaceutically acceptable salt, solvate, or ester thereof, wherein $L^1$, n, X, Ar, Y, Z, Q, and $Q^1$ are as defined below.

This invention also provides the compounds of formula (1.0) in pure and isolated form.

This invention also provides the compounds of formula (1.0) in pure form.

This invention also provides the compounds of formula (1.0) in isolated form.

This invention also provides compounds of formula selected from the group consisting of: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

This invention also provides a compound of formula (1.0) selected from the group consisting of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, $1.9^{41}$, $1.9^{42}$, 1.10, $1.10^{41}$, $1.10^{42}$, 2.10, $2.10^{41}$, $2.10^{42}$, 3.10, 1.10A, 2.10A, 3.10A, $3.10^{41}$, $3.10^{42}$, 1.11, $1.11^{41}$, $1.11^{42}$, 2.11, $2.11^{41}$, $2.11^{42}$, 3.11, $3.11^{41}$, $3.11^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

This invention also provides a pharmaceutically acceptable salt of the compound of formula (1.0) selected from the group consisting of the pharmaceutically acceptable salts of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, $1.9^{41}$, $1.9^{42}$, 1.10, $1.10^{41}$, $1.10^{42}$, 2.10, $2.10^{41}$, $2.10^{42}$, 3.10, 1.10A, 2.10A, 3.10A, $3.10^{41}$, $3.10^{42}$, 1.11, $1.11^{41}$, $1.11^{42}$, 2.11, $2.11^{41}$, $2.11^{42}$, 3.11, $3.11^{41}$, $3.11^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

This invention also provides a solvate of the compound of formula (1.0) selected from the group consisting of the solvates of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, $1.9^{41}$, $1.9^{42}$, 1.10, $1.10^{41}$, $1.10^{42}$, 2.10, $2.10^{41}$, $2.10^{42}$, 3.10, 1.10A, 2.10A, 3.10A, $3.10^{41}$, $3.10^{42}$, 1.11, $1.11^{41}$, $1.11^{42}$, 2.11, $2.11^{41}$, $2.11^{42}$, 3.11, $3.11^{41}$, $3.11^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

This invention also provides a pharmaceutically acceptable ester of the compound of formula (1.0) selected from the group consisting of the pharmaceutically acceptable esters of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, $1.9^{41}$, $1.9^{42}$, 1.10, $1.10^{41}$, $1.10^{42}$, 2.10, $2.10^{41}$, $2.10^{42}$, 3.10, 1.10A, 2.10A, 3.10A, 3.10$^{41}$, 3.10$^{42}$, 1.11, 1.11$^{41}$, 1.11$^{42}$, 2.11, 2.11$^{41}$, 2.11$^{42}$, 3.11, 3.11$^{41}$, 3.11$^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

This invention also provides a pharmaceutical composition comprising an effective amount of one or more (e.g., 1, 2 or 3, or 1 or 2, or 1) compounds of Formula (1.0) and at least one pharmaceutically acceptable carrier.

This invention also provides a pharmaceutical composition comprising an effective amount a compound of Formula (1.0) and at least one pharmaceutically acceptable carrier.

This invention also provides a pharmaceutically acceptable salt of a compound of formula (1.0).

This invention also provides a solvate of a compound of formula (1.0).

This invention also provides a pharmaceutically acceptable ester of a compound of formula (1.0).

This invention also provides a method for inhibiting gamma-secretase in a patient in need of such treatment, said method comprising administering to said patient an effective amount (i.e., a therapeutically effective amount) of one or more (e.g., 1, 2 or 3, or 1 or 2, or 1) compounds of formula (1.0).

This invention also provides a method for inhibiting gamma-secretase in a patient in need of such treatment, said method comprising administering to said patient an effective amount (i.e., a therapeutically effective amount) of a compound of formula (1.0).

This invention also provides a method of treating one or more neurodegenerative diseases in a patient in need of such treatment, said method comprising administering to said patient an effective amount (i.e., a therapeutically effective amount) of one or more (e.g., 1, 2 or 3, or 1 or 2, or 1) compounds of formula (1.0).

This invention also provides a method of treating one or more neurodegenerative diseases in a patient in need of such treatment, said method comprising administering to said patient an effective amount (i.e., a therapeutically effective amount) of a compound of formula (1.0).

This invention also provides a method of inhibiting the deposition of amyloid protein (e.g., amyloid beta protein) in, on or around neurological tissue (e.g., the brain) in a patient in need of such treatment, said method comprising administering to said patient an effective amount (i.e., a therapeutically effective amount) of one or more (e.g., 1, 2 or 3, or 1 or 2, or 1) compounds of formula (1.0).

This invention also provides a method of inhibiting the deposition of amyloid protein (e.g., amyloid beta protein) in, on or around neurological tissue (e.g., the brain) in a patient in need of such treatment, said method comprising administering to said patient an effective amount (i.e., a therapeutically effective amount) of a compound of formula (1.0).

This invention also provides a method of treating Alzheimer's disease in a patient in need of such treatment, said method comprising administering to said patient an effective amount (i.e., a therapeutically effective amount) of one or more (e.g., 1, 2 or 3, or 1 or 2, or 1) compounds of formula (1.0).

This invention also provides a method of treating Alzheimer's disease in a patient in need of such treatment, said method comprising administering to said patient an effective amount (i.e., a therapeutically effective amount) of one or more (e.g., 1, 2 or 3, or 1 or 2, or 1) compounds of formula (1.0).

This invention also provides combination therapies for (1) inhibiting gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (1.0) and the administration of one or more (e.g., one) other pharmaceutical active ingredients (e.g., drugs). The compounds of formula (1.0) and the other drugs can be administered separately (i.e., each is in its own separate dosage form), or the compounds of formula (1.0) can be combined with the other drugs in the same dosage form.

This invention provides any of the above methods wherein the compound of formula (1.0) is a pharmaceutically acceptable salt of the compound of formula (1.0).

This invention provides any of the above methods wherein the compound of formula (1.0) is a solvate of the compound of formula (1.0).

This invention provides any of the above methods wherein the compound of formula (1.0) is a pharmaceutically acceptable ester of the compound of formula (1.0).

This invention also provides any of the above methods wherein the compound of formula (1.0) is selected from the group consisting of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.9$^{41}$, 1.9$^{42}$, 1.10, 1.10$^{41}$, 1.10$^{42}$, 2.10, 2.10$^{41}$, 2.10$^{42}$, 3.10, 1.10A, 2.10A, 3.10A, 3.10$^{41}$, 3.10$^{42}$, 1.11, 1.11$^{41}$, 1.11$^{42}$, 2.11, 2.11$^{41}$, 2.11$^{42}$, 3.11, 3.11$^{41}$, 3.11$^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

This invention also provides any one of the above methods wherein the compound of formula (1.0) is selected from the group consisting of: Compounds 4a, 4b, 5a, 5b, 5b2, 5b3, 5b4, 5b5, 5c, 6a, 6b, 7a, 7b, 7d, 7e, 7f, 7g, 8a, 8a1, 8b, 8b1, 8c1, 8d, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42b, 43, 44, 45, 46, 47, 48, 49, 50, and 51.

DETAILED DESCRIPTION OF THE INVENTION

This invention provides compounds that are inhibitors (e.g., antagonists) of gamma-secretase (also termed "γ-secretase") and have the Formula (1.0):

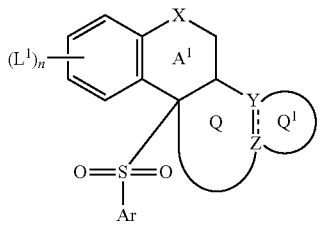

(1.0)

or a pharmaceutically acceptable salt, solvate, or ester thereof, wherein:

$L^1$, n, X, Y, Z, Q, $Q^1$ and Ar are each independently selected;

X is selected from the group consisting of —C($R^1$)$_2$—, —O—, —S—, —S(O$_2$)—, —N$R^1$—, and —N(C(O)$R^1$)—;

The dotted line (----) represents an optional bond between Y and Z;

Y is selected from the group consisting of N and CH and C, and when Y is N the optional bond is absent, when Y is CH the optional bond is absent, and when Y is C the optional bond is present;

Z is selected from the group consisting of: CH, C, and N, provided that both Y and Z are not N (i.e., only one of Y and Z can be N), and when Z is N the optional bond is absent, when Z is CH the optional bond is absent, and when Z is C the optional bond is present (those skilled in the art will appreciate that when Y is N then Z is CH, and when Z is N then Y is CH);

Q represents a 5 to 8 membered ring fused to Rings $A^1$ and $Q^1$, wherein Y and Z are as defined above and the remaining Q ring members are —CH$_2$— groups, and in one example Q is a 5 to 7 membered ring, and in another example Q is a 5 to 6 membered ring, and in another example Q is a 5 membered ring, and in another example Q is a 6 membered ring, and preferably Q is a 6 membered ring;

$Q^1$ is a 5 to 7 membered ring (including Y and Z) fused to Ring Q, said $Q^1$ ring comprising at least one heteroatom (e.g., 1 to 3, or 1 to 2, or 1) selected from the group consisting of N, O, S, S(O), and S(O)$_2$; or $Q^1$ is a 5 to 7 membered ring (including Y and Z) fused to Ring Q, said $Q^1$ ring comprising at least one heteroatom (e.g., 1 to 3, or 1 to 2, or 1) selected from the group consisting of N, O, S, S(O), and S(O)$_2$; and said $Q^1$ ring being substituted with 1 to 3 substituents independently selected from the group consisting of: $R^3$ substituents (wherein each $R^3$ can be bound to any substitutable atom in the $Q^1$ ring, such as any substitutable carbon atom and/or any substitutable nitrogen atom, and (a) in one example at least one carbon atom of said $Q^1$ ring is substituted with one $R^3$ group, and (b) in another example one carbon atom of said $Q^1$ ring is substituted with one $R^3$ group, and (c) in another example one carbon atom of said $Q^1$ ring is substituted with two independently selected $R^3$ groups and the remaining carbon atoms of said $Q^1$ ring are unsubstituted, and (d) in another example one carbon atom of said $Q^1$ ring is substituted with two independently selected $R^3$ groups, and one or more of the remaining carbon atoms are substituted with one $R^3$ group wherein each $R^3$ group is independently selected when more than one remaining carbon atom is substituted with an $R^3$ group, and (e) in other examples the $Q^1$ ring is as described in any one of the examples described in (a) to (d) wherein said $Q^1$ ring comprises at least one nitrogen atom that is substituted with an $R^3$ group, and wherein each $R^3$ group is independently selected for each nitrogen atom when more than one nitrogen is substituted with an $R^3$ group);

Each $R^1$ is independently selected from the group consisting of H and alkyl;

$R^2$ is selected from the group consisting of: H, and alkyl (e.g., $C_1$ to $C_6$ alkyl, such as, for example, methyl, ethyl and isopropyl);

Each $R^3$ substituent is independently selected from the group consisting of:

(1) alkyl (e.g., $C_1$ to $C_6$ alkyl, such as, for example, methyl, ethyl, and isopropyl), (2) alkoxyalkyl- (such as, for example, —($C_1$ to $C_6$)alkoxy-($C_1$ to $C_6$)alkyl-, such as, for example, —($C_1$ to $C_4$)alkoxy-($C_1$ to $C_4$)alkyl-, such as, for example, —($C_1$ to $C_2$)alkoxy-($C_1$ to $C_2$)alkyl-, such as, for example, —CH$_2$OCH$_3$), (3) hydroxyalkyl (such as, for example, hydroxy($C_1$ to $C_6$)alkyl-, such as, for example, hydroxy($C_1$ to $C_4$)alkyl-, such as, for example, hydroxy($C_1$ to $C_2$)alkyl-, such as, for example, —CH$_2$CH$_2$OH, and in another example, —CH$_2$CH$_2$CH$_2$OH), (4) —O$R^2$ (e.g., —OH, —OCH$_3$, —OC$_2$H$_5$, and —OCH(CH$_3$)$_2$), (5) arylalkyl- (e.g., aryl($C_1$ to $C_6$)alkyl-, such as, for example, benzyl and —(CH$_2$)$_3$-phenyl), (6) =O, (7) substituted arylalkyl- (e.g., substituted aryl($C_1$ to $C_6$)alkyl-, such as substituted benzyl) substituted with 1 to 3 substituents each independently selected from the group consisting of: —O$R^2$ (e.g., p-methoxybenzyl), (8) alkenyl (e.g., $C_2$ to $C_6$ alkenyl, such as, for example, $C_2$ to $C_4$ alkenyl), and wherein examples of said alkenyl include —CH$_2$CH=CH$_2$ and —CH$_2$CH=CHCH$_3$, (9) heterocycloalkylalkyl- (e.g., a ($C_5$ to $C_7$)heterocycloalkyl-($C_1$ to $C_6$)alkyl-, such as a ($C_5$ to $C_7$)heterocycloalkyl-($C_1$ to $C_4$)alkyl-, such as a ($C_5$ to $C_7$)heterocycloalkyl-($C_1$ to $C_2$)alkyl-, such as for example, pyrrolidinyl-($C_1$ to $C_2$)alkyl-, such as for example, pyrrolidinyl-CH$_2$—CH$_2$—, and in another example, morpholinyl-($C_1$ to $C_2$)alkyl-, such as, for example, morpholinyl-CH$_2$—CH$_2$—),

(10) -alkyl-C(O)OH (e.g., —($C_1$ to $C_6$)alkyl-C(O)OH, such as, for example, —($C_1$ to $C_4$)alkyl-C(O)OH, such as, for example, —($C_1$ to $C_2$)alkyl-C(O)OH, such as, for example, —CH$_2$CH$_2$—C(O)OH, and in another example —CH$_2$—C(O)OH),

(11) -alkyl-N$R^5R^6$ (e.g., —($C_1$ to $C_6$)alkyl-N$R^5R^6$, such as, for example, —($C_1$ to $C_4$)alkyl-N$R^5R^6$, such as, for example, —($C_1$ to $C_2$)alkyl N$R^5R^6$), wherein $R^5$ and $R^6$ are each independently selected from the group consisting of: H and alkyl (e.g., $C_1$ to $C_6$ alkyl, such as, for example, $C_1$ to $C_4$ alkyl, such as, for example, methyl, ethyl, and isopropyl), and wherein examples of said -alkyl-N$R^5R^6$ group include, for example, —CH$_2$CH$_2$CH$_2$N(CH$_3$)$_2$,

(12) -alkyl-C(O)N$R^5R^6$ (e.g., —($C_1$ to $C_6$)alkyl-C(O)N$R^5R^6$, such as, for example, —($C_1$ to $C_4$)alkyl-C(O)N$R^5R^6$, such as, for example, —($C_1$ to $C_2$)alkyl-C(O)N$R^5R^6$, wherein $R^5$ and $R^6$ are as defined in (11) above, and wherein in one example said -alkyl-C(O)N$R^5R^6$ group is —CH$_2$—C(O)NH$_2$,

(13) arylalkenyl- (e.g., aryl($C_2$ to $C_6$)alkenyl-, such as, for example, aryl($C_2$ to $C_4$)alkenyl-, such as, for example, phenyl($C_2$ to $C_6$)alkenyl-, such as, for example, phenyl($C_2$ to $C_4$)alkenyl-, such as, for example, —CH$_2$CH=CH-phenyl),

(14) -alkyl-C(O)O$R^7$ wherein $R^7$ is a $C_1$ to $C_6$ alkyl group (and in one example, $R^7$ is a $C_1$ to $C_4$ alkyl group, and in another example $R^7$ is a $C_1$ to $C_2$ alkyl group), and wherein in one example said -alkyl-C(O)OR$^7$ moiety is —(C$_1$ to C$_6$)alkyl-C(O)O—(C$_1$ to C$_6$)alkyl, and in another example said -alkyl-C(O)OR$^7$ moiety is —(C$_1$ to C$_4$)alkyl-C(O)O—(C$_1$ to C$_4$)alkyl, and in another example said -alkyl-C(O)OR$^7$ moiety is —(C$_1$ to C$_2$)alkyl-C(O)O—(C$_1$ to C$_2$)alkyl, and

(15) substituted arylalkenyl- (e.g., substituted aryl(C$_2$ to C$_6$)alkenyl-, such as, for example, substituted aryl(C$_2$ to C$_4$)alkenyl-, such as, for example, substituted phenyl(C$_2$ to C$_6$)alkenyl-, such as, for example, substituted phenyl (C$_2$ to C$_4$)alkenyl-, such as, for example, substituted —CH$_2$CH=CH-phenyl), wherein said substituted arylalkenyl- is substituted with 1 to 3 substituents independently selected from the group consisting of: —OR$^5$, —NR$^5$R$^6$, —CF$_3$, —CN, —C(O)$_2$R$^5$, and —C(O)NR$^5$R$^6$, and wherein R$^5$ and R$^6$ are as defined in (11) above; or two R$^3$ groups bound to the same carbon, taken together with the carbon to which they are bound, form a cycloalkyl ring (e.g., a C$_5$ to C$_7$ cycloalkyl ring, such as, for example, cyclopentyl) or form a cycloalkenyl ring (e.g., a C$_5$ to C$_7$ cycloalkenyl ring, such as, for example, cyclopentenyl);

Ar is selected from the group consisting of: (a) unsubstituted aryl, (b) aryl substituted with one or more L$^1$ groups, (c) unsubstituted heteroaryl (e.g., pyridyl), and (d) substituted heteroaryl (e.g., substituted pyridyl) substituted with one or more L$^1$ groups;

each L$^1$ is independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—); and n is 0, 1, 2 or 3.

In one embodiment this invention provides compounds that are inhibitors (e.g., antagonists) of gamma-secretase (also termed "γ-secretase") and have the Formula (1.0):

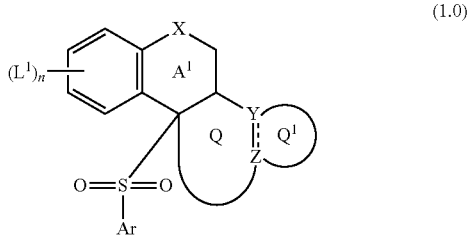

(1.0)

or a pharmaceutically acceptable salt, solvate, or ester thereof, wherein:

X is selected from the group consisting of —C(R$^1$)$_2$—, —O—, —S—, —S(O$_2$)—, —NR$^1$—, and —N(C(O)R$^1$)—;

The dotted line (----) represents an optional bond between Y and Z;

Y is selected from the group consisting of N and CH and C, and when Y is N the optional bond is absent, when Y is CH the optional bond is absent, and when Y is C the optional bond is present;

Z is selected from the group consisting of: CH, C, and N, provided that both Y and Z are not N (i.e., only one of Y and Z can be N), and when Y is N the optional bond is absent, when Z is CH the optional bond is absent, and when Z is C the optional bond is present (those skilled in the art will appreciate that when Y is N then Z is CH, and when Z is N then Y is CH);

Q represents a 5 to 8 membered ring fused to Rings A$^1$ and Q$^1$, wherein Y and Z are as defined above and the remaining Q ring members are —CH$_2$— groups, and in one example Q is a 5 to 7 membered ring, and in another example Q is a 5 to 6 membered ring, and in another example Q is a 5 membered ring, and in another example Q is a 6 membered ring, and preferably Q is a 6 membered ring;

Q$^1$ is a 5 to 7 membered ring (including Y and Z) fused to Ring Q, said Q$^1$ ring comprising at least one heteroatom (e.g., 1 to 3, or 1 to 2, or 1) selected from the group consisting of N, O, S, S(O), and S(O)$_2$; or Q$^1$ is a 5 to 7 membered ring (including Y and Z) fused to Ring Q, said Q$^1$ ring comprising at least one heteroatom (e.g., 1 to 3, or 1 to 2, or 1) selected from the group consisting of N, O, S, S(O), and S(O)$_2$; and said Q$^1$ ring being substituted with 1 to 3 substituents independently selected from the group consisting of: R$^3$ substituents (wherein each R$^3$ can be bound to any substitutable atom in the Q$^1$ ring, such as any substitutable carbon atom and/or any substitutable nitrogen atom, and (a) in one example at least one carbon atom of said Q$^1$ ring is substituted with one R$^3$ group, and (b) in another example one carbon atom of said Q$^1$ ring is substituted with one R$^3$ group, and (c) in another example one carbon atom of said Q$^1$ ring is substituted with two independently selected R$^3$ groups and the remaining carbon atoms of said Q$^1$ ring are unsubstituted, and (d) in another example one carbon atom of said Q$^1$ ring is substituted with two independently selected R$^3$ groups, and one or more of the remaining carbon atoms are substituted with one R$^3$ group wherein each R$^3$ group is independently selected when more than one remaining carbon atom is substituted with an R$^3$ group, and (e) in other examples the Q$^1$ ring is as described in any one of the examples described in (a) to (d) wherein said Q$^1$ ring comprises at least one nitrogen atom that is substituted with an R$^3$ group, and wherein each R$^3$ group is independently selected for each nitrogen atom when more than one nitrogen is substituted with an R$^3$ group);

Each R$^1$ is independently selected from the group consisting of H and alkyl;

R$^2$ is selected from the group consisting of: H, and alkyl (e.g., C$_1$ to C$_6$ alkyl, such as, for example, methyl, ethyl and isopropyl);

Each R$^3$ substituent is independently selected from the group consisting of: (1) alkyl (e.g., C$_1$ to C$_6$ alkyl, such as, for example, methyl and ethyl), (2) alkoxyalkyl-, (3) hydroxyalkyl, (4) —OR$^2$ (e.g., —OH, —OCH$_3$, —OC$_2$H$_5$, and —OCH(CH$_3$)$_2$), (5) arylalkyl- (e.g., aryl(C$_1$ to C$_6$)alkyl-, such as benzyl), (6) =O, and (7) substituted arylalkyl- (e.g., substituted aryl(C$_1$ to C$_6$)alkyl-, such as substituted benzyl) substituted with 1 to 3 substituents each independently selected from the group consisting of: —OR$^2$ (e.g., p-methoxybenzyl);

Ar is selected from the group consisting of: (a) unsubstituted aryl, (b) aryl substituted with one or more L$^1$ groups, (c) unsubstituted heteroaryl (e.g., pyridyl), and (d) substituted heteroaryl (e.g., substituted pyridyl) substituted with one or more L$^1$ groups;

each L$^1$ is independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—); and n is 0, 1, 2 or 3.

In one embodiment of this invention two $R^3$ groups bound to the same carbon atom are taken together with the carbon atom to which they are bound to form a cycloalkyl ring (e.g., a cyclopentyl ring).

In another embodiment of this invention two $R^3$ groups bound to the same carbon atom are taken together with the carbon atom to which they are bound to form a cycloalkenyl ring (e.g., a cyclopentenyl ring).

In another embodiment of this invention $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkyl ring (e.g., a cyclopentyl ring).

In another embodiment of this invention $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkenyl ring (e.g., a cyclopentenyl ring).

In another embodiment of this invention Q is a 6 membered ring, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkyl ring (e.g., a cyclopentyl ring).

In another embodiment of this invention Q is a 6 membered ring, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkenyl ring (e.g., a cyclopentenyl ring).

In another embodiment of this invention Y is CH, Z is CH, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkyl ring (e.g., a cyclopentyl ring).

In another embodiment of this invention Y is CH, Z is CH, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkenyl ring (e.g., a cyclopentenyl ring).

In another embodiment of this invention Y is CH, Z is CH, Q is a 6 membered ring, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkyl ring (e.g., a cyclopentyl ring).

In another embodiment of this invention Y is CH, Z is CH, Q is a 6 membered ring, $Q^1$ is a 6 membered ring comprising a —N—$SO_2$— moiety in the ring, and two $R^3$ groups bound to the carbon adjacent to the —$SO_2$— moiety are taken together with the carbon atom to which they are bound to form a cycloalkenyl ring (e.g., a cyclopentenyl ring).

In one embodiment of this invention Y is CH, Z is CH, and $Q^1$ is a 6 membered ring comprising a nitrogen atom and a —$S(O)_2$— group.

In another embodiment of this invention Y is CH, Z is CH, Q is a 6 membered ring, and $Q^1$ is a 6 membered ring comprising a nitrogen atom and a —$S(O)_2$— group.

In one embodiment of this invention Y is CH, Z is CH, $Q^1$ is a 6 membered ring comprising a nitrogen atom and a —$S(O)_2$— group, and said $Q^1$ ring substituted with 1 to 3 substituents as defined in formula 1.0.

In another embodiment of this invention Y is CH, Z is CH, Q is a 6 membered ring, $Q^1$ is a 6 membered ring comprising a nitrogen atom and a —$S(O)_2$— group, and said $Q^1$ ring substituted with 1 to 3 substituents as defined in formula 1.0.

In another embodiment of this invention Y is CH, Z is CH, $Q^1$ is a 5 membered ring comprising an oxygen atom.

In another embodiment of this invention Y is CH, Z is CH, Q is a 6 membered ring, and $Q^1$ is a 5 membered ring comprising an oxygen atom.

In another embodiment of this invention Y is CH, Z is CH, $Q^1$ is a 5 membered ring comprising an oxygen atom, and said $Q^1$ ring substituted with 1 to 3 substituents as defined in formula 1.0.

In another embodiment of this invention Y is CH, Z is CH, Q is a 6 membered ring, $Q^1$ is a 5 membered ring comprising an oxygen atom, and said $Q^1$ ring substituted with 1 to 3 substituents as defined in formula 1.0.

In another embodiment of this invention Y is CH, Z is CH, and $Q^1$ is a 5 membered ring comprising a nitrogen atom.

In another embodiment of this invention Y is CH, Z is CH, Q is a 6 membered ring, and $Q^1$ is a 5 membered ring comprising a nitrogen atom.

In another embodiment of this invention Y is CH, Z is CH, $Q^1$ is a 5 membered ring comprising a nitrogen atom, and said $Q^1$ ring substituted with 1 to 3 substituents as defined in formula 1.0.

In another embodiment of this invention Y is CH, Z is CH, Q is a 6 membered ring, $Q^1$ is a 5 membered ring comprising a nitrogen atom, and said $Q^1$ ring substituted with 1 to 3 substituents as defined in formula 1.0.

In another embodiment of this invention Y is C, Z is C, the optional bond between Y and Z is present, and $Q^1$ is a 5 membered ring comprising a nitrogen atom.

In another embodiment of this invention Y is C, Z is C, the optional bond between Y and Z is present, Q is a 6 membered ring, and $Q^1$ is a 5 membered ring comprising a nitrogen atom.

In another embodiment of this invention Y is C, Z is C, the optional bond between Y and Z is present, $Q^1$ is a 5 membered ring comprising a nitrogen atom, and said $Q^1$ ring substituted with 1 to 3 substituents as defined in formula 1.0.

In another embodiment of this invention Y is C, Z is C, the optional bond between Y and Z is present, Q is a 6 membered ring, $Q^1$ is a 5 membered ring comprising a nitrogen atom, and said $Q^1$ ring substituted with 1 to 3 substituents as defined in formula 1.0.

In another embodiment of this invention Y is CH, Z is CH, and $Q^1$ is a 6 membered ring comprising a nitrogen atom.

In another embodiment of this invention Y is CH, Z is CH, Q is a 6 membered ring, and $Q^1$ is a 6 membered ring comprising a nitrogen atom.

In another embodiment of this invention Y is CH, Z is CH, $Q^1$ is a 6 membered ring comprising a nitrogen atom, and said $Q^1$ ring substituted with 1 to 3 substituents as defined in formula 1.0.

In another embodiment of this invention Y is CH, Z is CH, Q is a 6 membered ring, $Q^1$ is a 6 membered ring comprising a nitrogen atom, and said $Q^1$ ring substituted with 1 to 3 substituents as defined in formula 1.0.

In another embodiment of this invention Y is N, Z is CH, and $Q^1$ is a 6 membered ring comprising a nitrogen atom in addition to the nitrogen atom at Y.

In another embodiment of this invention Y is N, Z is CH, Q is a 6 membered ring, and $Q^1$ is a 6 membered ring comprising a nitrogen atom in addition to the nitrogen atom at Y.

In another embodiment of this invention Y is N, Z is CH, $Q^1$ is a 6 membered ring comprising a nitrogen atom in addition to the nitrogen atom at Y, and said $Q^1$ ring substituted with 1 to 3 substituents as defined in formula 1.0.

In another embodiment of this invention Y is N, Z is CH, Q is a 6 membered ring, $Q^1$ is a 6 membered ring comprising a nitrogen atom in addition to the nitrogen atom at Y, and said $Q^1$ ring substituted with 1 to 3 substituents as defined in formula 1.0.

In another embodiment of this invention each $R^3$ is independently selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, —$OR^2$, phenyl($C_1$ to $C_4$)alkyl-, =O, phenyl($C_1$ to $C_2$)alkyl-, $C_2$ to $C_4$ alkenyl, ($C_5$ to $C_7$)heterocycloalkyl-($C_1$ to $C_2$)alkyl-, —($C_1$ to $C_2$)alkyl-C(O)OH, —($C_1$ to $C_4$)alkyl-$NR^5R^6$, —($C_1$ to $C_4$)alkyl-C(O)$NR^5R^6$, phenyl($C_2$ to $C_4$)alkenyl-, —($C_1$ to $C_4$)alkyl-C(O)O—($C_1$ to $C_4$)alkyl, and substituted phenyl($C_2$ to $C_4$)alkenyl-.

In another embodiment of this invention each $R^3$ is independently selected from the group consisting of: methyl, ethyl, isopropyl, —$CH_2CH_2OH$, —$CH_2CH_2CH_2OH$, —OH, —$OCH_3$, —$OC_2H_5$, —$OCH(CH_3)_2$, benzyl, —$(CH_2)_3$-phenyl, =O, p-methoxybenzyl, —$CH_2CH=CH_2$, —$CH_2CH=CHCH_3$, pyrrolidinyl-$CH_2$—$CH_2$—, morpholinyl-$CH_2$—$CH_2$—, —$CH_2CH_2$—C(O)OH, —$CH_2$—C(O)OH, —$CH_2CH_2CH_2N(CH_3)_2$, —$CH_2$—C(O)$NH_2$ and —$CH_2CH$=CH-phenyl.

In another embodiment of this invention $R^3$ is alkyl.

In another embodiment of this invention $R^3$ is $C_1$ to $C_4$ alkyl.

In another embodiment of this invention $R^3$ is selected from the group consisting of: methyl, ethyl, and isopropyl.

In another embodiment of this invention $R^3$ is methyl.

In another embodiment of this invention $R^3$ is alkoxyalkyl-.

In another embodiment of this invention $R^3$ is ($C_1$ to $C_2$)alkoxy-($C_1$ to $C_2$)alkyl- In another embodiment of this invention $R^3$ is —$CH_2OCH_3$.

In another embodiment of this invention $R^3$ is hydroxyalkyl-.

In another embodiment of this invention $R^3$ is hydroxy($C_1$ to $C_4$)alkyl-.

In another embodiment of this invention $R^3$ is selected from the group consisting of: —$CH_2CH_2OH$ and —$CH_2CH_2CH_2OH$.

In another embodiment of this invention $R^3$ is —$OR^2$.

In another embodiment of this invention $R^3$ is —$OR^2$ wherein $R^2$ is H (i.e., $R^3$ is —OH).

In another embodiment of this invention $R^3$ is —$OR^2$ wherein $R^2$ is alkyl.

In another embodiment of this invention $R^3$ is —$OR^2$ wherein $R^2$ is $C_1$ to $C_4$ alkyl.

In another embodiment of this invention $R^3$ is —$OR^2$ wherein $R^2$ is selected from the group consisting of: —$OCH_3$, —$OC_2H_5$, and —$OCH(CH_3)_2$.

In another embodiment of this invention $R^3$ is arylalkyl-.

In another embodiment of this invention $R^3$ is aryl($C_1$ to $C_4$)alkyl-.

In another embodiment of this invention $R^3$ is phenylalkyl-.

In another embodiment of this invention $R^3$ is phenyl($C_1$ to $C_4$)alkyl-.

In another embodiment of this invention $R^3$ is selected from the group consisting of: benzyl and —$(CH_2)_3$-phenyl.

In another embodiment of this invention $R^3$ is =O.

In another embodiment of this invention $R^3$ is substituted arylalkyl-.

In another embodiment of this invention $R^3$ is substituted aryl($C_1$ to $C_2$)alkyl- In another embodiment of this invention $R^3$ is substituted phenylalkyl-.

In another embodiment of this invention $R^3$ is substituted phenyl($C_1$ to $C_2$)alkyl- In another embodiment of this invention $R^3$ is substituted arylalkyl-.

In another embodiment of this invention $R^3$ is phenyl($C_1$ to $C_2$)alkyl- substituted with —$OR^2$.

In another embodiment of this invention $R^3$ is phenyl($C_1$ to $C_2$)alkyl- substituted with —$OR^2$ wherein $R^2$ is alkyl.

In another embodiment of this invention $R^3$ is benzyl substituted with —$OR^2$ wherein $R^2$ is alkyl.

In another embodiment of this invention $R^3$ is p-methoxybenzyl.

In another embodiment of this invention $R^3$ is alkenyl.

In another embodiment of this invention $R^3$ is $C_2$ to $C_4$ alkenyl.

In another embodiment of this invention $R^3$ is selected from the group consisting of: —$CH_2CH=CH_2$ and —$CH_2CH=CHCH_2$.

In another embodiment of this invention $R^3$ is heterocycloalkylalkyl-.

In another embodiment of this invention $R^3$ is ($C_5$ to $C_7$)heterocycloalkyl-($C_1$ to $C_2$)alkyl-.

In another embodiment of this invention $R^3$ is selected from the group consisting of: pyrrolidinyl-($C_1$ to $C_2$)alkyl- and morphlinyl-($C_1$ to $C_2$)alkyl-.

In another embodiment of this invention $R^3$ is selected from the group consisting of: pyrrolidinyl-$CH_2$—$CH_2$— and morpholinyl-$CH_2$—$CH_2$—.

In another embodiment of this invention $R^3$ is -alkyl-C(O)OH.

In another embodiment of this invention $R^3$ is —($C_1$ to $C_2$)alkyl-C(O)OH.

In another embodiment of this invention $R^3$ is selected from the group consisting of: —$CH_2CH_2$—C(O)OH and —$CH_2$—C(O)OH.

In another embodiment of this invention $R^3$ is -alkyl-$NR^5R^6$.

In another embodiment of this invention $R^3$ is —($C_1$ to $C_4$)alkyl-$NR^5R^6$.

In another embodiment of this invention $R^3$ is —($C_1$ to $C_4$)alkyl-$NR^5R^6$ wherein $R^5$ and $R^6$ are each independently selected from the group consisting of: H, methyl, ethyl, and isopropyl.

In another embodiment of this invention $R^3$ is —$CH_2CH_2CH_2N(CH_3)_2$.

In another embodiment of this invention $R^3$ is -alkyl-C(O)$NR^5R^6$.

In another embodiment of this invention $R^3$ is —($C_1$ to $C_4$)alkyl-C(O)$NR^5R^6$.

In another embodiment of this invention $R^3$ is —($C_1$ to $C_2$)alkyl-C(O)$NR^5R^6$.

In another embodiment of this invention $R^3$ is —($C_1$ to $C_4$)alkyl-C(O)$NR^5R^6$ wherein $R^5$ and $R^6$ are each independently selected from the group consisting of: H, methyl, ethyl, and isopropyl.

In another embodiment of this invention $R^3$ is —($C_1$ to $C_2$)alkyl-C(O)$NR^5R^6$ wherein $R^5$ and $R^6$ are each independently selected from the group consisting of: H, methyl, ethyl, and isopropyl.

In another embodiment of this invention $R^3$ is —$CH_2$—C(O)$NH_2$.

In another embodiment of this invention $R^3$ is arylalkenyl-.

In another embodiment of this invention $R^3$ is aryl($C_2$ to $C_4$)alkenyl-.

In another embodiment of this invention $R^3$ is phenylalkenyl.

In another embodiment of this invention $R^3$ is phenyl($C_2$ to $C_4$)alkenyl-.

In another embodiment of this invention $R^3$ is —$CH_2CH$=$CH$-phenyl.

In another embodiment of this invention $R^3$ is -alkyl-C(O)$OR^7$

In another embodiment of this invention $R^3$ is -alkyl-C(O)$OR^7$ wherein $R^7$ is a $C_1$ to $C_4$ alkyl group.

In another embodiment of this invention $R^3$ is -alkyl-C(O)$OR^7$ wherein $R^7$ is a $C_1$ to $C_2$ alkyl group.

In another embodiment of this invention $R^3$ is —($C_1$ to $C_4$)alkyl-C(O)O—($C_1$ to $C_4$)alkyl.

In another embodiment of this invention $R^3$ is —($C_1$ to $C_2$)alkyl-C(O)O—($C_1$ to $C_2$)alkyl.

In another embodiment of this invention $R^3$ is substituted arylalkenyl-.

In another embodiment of this invention $R^3$ is substituted aryl($C_2$ to $C_6$)alkenyl-.

In another embodiment of this invention $R^3$ is substituted aryl($C_2$ to $C_4$)alkenyl-.

In another embodiment of this invention $R^3$ is substituted phenyl($C_2$ to $C_6$)alkenyl-.

In another embodiment of this invention $R^3$ is substituted phenyl($C_2$ to $C_4$)alkenyl-.

In another embodiment of this invention $R^3$ is substituted —$CH_2CH$=$CH$-phenyl.

In another embodiment of this invention X is O.

In another embodiment of this invention $L^1$ is halo.

In another embodiment of this invention n is 2 and each $L^1$ is the same or different halo.

In another embodiment of this invention n is 2 and $L^1$ is F.

In another embodiment n is 3.

In another embodiment n is 3 and each $L^1$ is the same or different halo.

In another embodiment n is 3 and each $L^1$ is independently selected from the group consisting of F and Cl.

In another embodiment n is 3, two $L^1$ moieties are F, and one $L^1$ is Cl.

In another embodiment n is 3, two $L^1$ moieties are F, one $L^1$ moiety is Cl, and the two F $L^1$ moieties are para to each other.

In another embodiment of this invention Ar is phenyl.

In another embodiment of this invention Ar is phenyl substituted with halo.

In another embodiment of this invention Ar is phenyl substituted with one halo.

In another embodiment of this invention Ar is phenyl substituted with at least one Cl.

In another embodiment of this invention Ar is phenyl substituted with a —$CF_3$ group.

In another embodiment of this invention Ar is phenyl substituted with a cyano group.

In another embodiment of this invention Ar is phenyl substituted with a Cl.

In another embodiment of this invention X is O, each $L^1$ is halo, and Ar is phenyl substituted with at least one —$CF_3$.

In another embodiment of this invention X is O, n is 2, each $L^1$ is the same or different halo, and Ar is phenyl substituted with one —$CF_3$.

In another embodiment of this invention X is O, n is 2, $L^1$ is F, and Ar is phenyl substituted with one —$CF_3$.

In another embodiment of this invention X is O, each $L^1$ is halo, and Ar is phenyl substituted with at least one —CN.

In another embodiment of this invention X is O, n is 2, each $L^1$ is the same or different halo, and Ar is phenyl substituted with one —CN.

In another embodiment of this invention X is O, n is 2, $L^1$ is F, and Ar is phenyl substituted with one —CN.

In another embodiment of this invention X is O, each $L^1$ is halo, and Ar is phenyl substituted with at least one halo.

In another embodiment of this invention X is O, n is 2, each $L^1$ is the same or different halo, and Ar is phenyl substituted with one halo.

In another embodiment of this invention X is O, n is 2, $L^1$ is F, and Ar is phenyl substituted with one Cl.

Another embodiment of this invention is directed to any one of the above embodiments describing Y, Z and $Q^1$, or describing Y, Z Q, and $Q^1$, wherein X is O.

Another embodiment of this invention is directed to any one of the above embodiments describing Y, Z and $Q^1$, or describing Y, Z Q, and $Q^1$, wherein $L^1$ is halo.

Another embodiment of this invention is directed to any one of the above embodiments describing Y, Z and $Q^1$, or describing Y, Z Q, and $Q^1$, wherein n is 2 and each $L^1$ is the same or different halo.

Another embodiment of this invention is directed to any one of the above embodiments describing Y, Z and $Q^1$, or describing Y, Z Q, and $Q^1$, wherein n is 2 and $L^1$ is F.

Another embodiment of this invention is directed to any one of the above embodiments describing Y, Z and $Q^1$, or describing Y, Z Q, and $Q^1$, wherein Ar is phenyl.

Another embodiment of this invention is directed to any one of the above embodiments describing Y, Z and $Q^1$, or describing Y, Z Q, and $Q^1$, wherein Ar is phenyl substituted with halo.

Another embodiment of this invention is directed to any one of the above embodiments describing Y, Z and $Q^1$, or describing Y, Z Q, and $Q^1$, wherein Ar is phenyl substituted with one halo.

Another embodiment of this invention is directed to any one of the above embodiments describing Y, Z and $Q^1$, or describing Y, Z Q, and $Q^1$, wherein Ar is phenyl substituted with at least one Cl.

Another embodiment of this invention is directed to any one of the above embodiments describing Y, Z and $Q^1$, or describing Y, Z Q, and $Q^1$, wherein Ar is phenyl substituted with a Cl.

Another embodiment of this invention is directed to any one of the above embodiments describing Y, Z and $Q^1$, or describing Y, Z Q, and $Q^1$, wherein X is O, each $L^1$ is halo, and Ar is phenyl substituted with at least one halo.

Another embodiment of this invention is directed to any one of the above embodiments describing Y, Z and $Q^1$, or describing Y, Z Q, and $Q^1$, wherein X is O, n is 2, each $L^1$ is the same or different halo, and Ar is phenyl substituted with one halo.

Another embodiment of this invention is directed to any one of the above embodiments describing Y, Z and $Q^1$, or describing Y, Z Q, and $Q^1$, wherein X is O, n is 2, $L^1$ is F, and Ar is phenyl substituted with one Cl.

Another embodiment of this invention is directed to any one of the above embodiments describing Y, Z and $Q^1$, or describing Y, Z Q, and $Q^1$, wherein Ar is phenyl substituted with —$CF_3$.

Another embodiment of this invention is directed to any one of the above embodiments describing Y, Z and $Q^1$, or describing Y, Z Q, and $Q^1$, wherein Ar is phenyl substituted with one —$CF_3$.

Another embodiment of this invention is directed to any one of the above embodiments describing Y, Z and $Q^1$, or describing Y, Z Q, and $Q^1$, wherein Ar is phenyl substituted with at least one —$CF_3$.

Another embodiment of this invention is directed to any one of the above embodiments describing Y, Z and $Q^1$, or describing Y, Z Q, and $Q^1$, wherein Ar is phenyl substituted with a —$CF_3$.

Another embodiment of this invention is directed to any one of the above embodiments describing Y, Z and $Q^1$, or describing Y, Z Q, and $Q^1$, wherein X is O, each $L^1$ is halo, and Ar is phenyl substituted with at least one —$CF_3$.

Another embodiment of this invention is directed to any one of the above embodiments describing Y, Z and $Q^1$, or describing Y, Z Q, and $Q^1$, wherein X is O, n is 2, each $L^1$ is the same or different halo, and Ar is phenyl substituted with one —$CF_3$.

Another embodiment of this invention is directed to any one of the above embodiments describing Y, Z and $Q^1$, or describing Y, Z Q, and $Q^1$, wherein X is O, n is 2, $L^1$ is F, and Ar is phenyl substituted with one —$CF_3$.

Another embodiment of this invention is directed to any one of the above embodiments describing Y, Z and $Q^1$, or describing Y, Z Q, and $Q^1$, wherein Ar is phenyl substituted with —CN.

Another embodiment of this invention is directed to any one of the above embodiments describing Y, Z and $Q^1$, or describing Y, Z Q, and $Q^1$, wherein Ar is phenyl substituted with one —CN.

Another embodiment of this invention is directed to any one of the above embodiments describing Y, Z and $Q^1$, or describing Y, Z Q, and $Q^1$, wherein Ar is phenyl substituted with at least one —CN.

Another embodiment of this invention is directed to any one of the above embodiments describing Y, Z and $Q^1$, or describing Y, Z Q, and $Q^1$, wherein Ar is phenyl substituted with a —CN.

Another embodiment of this invention is directed to any one of the above embodiments describing Y, Z and $Q^1$, or describing Y, Z Q, and $Q^1$, wherein X is O, each $L^1$ is halo, and Ar is phenyl substituted with at least one —CN.

Another embodiment of this invention is directed to any one of the above embodiments describing Y, Z and $Q^1$, or describing Y, Z Q, and $Q^1$, wherein X is O, n is 2, each $L^1$ is the same or different halo, and Ar is phenyl substituted with one —CN.

Another embodiment of this invention is directed to any one of the above embodiments describing Y, Z and $Q^1$, or describing Y, Z Q, and $Q^1$, wherein X is O, n is 2, $L^1$ is F, and Ar is phenyl substituted with —CN.

Another embodiment of this invention is directed to any one of the above embodiments wherein the —$SO_2Ar$ moiety has the stereochemistry:

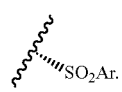

Another embodiment of this invention is directed to any one of the above embodiments wherein the H on the carbon at the ring junction of Rings $A^1$ and Q is cis to the —$SO_2Ar$ moiety:

Another embodiment of this invention is directed to any one of the above embodiments wherein at least one carbon of ring $Q^1$ is substituted with at least one $R^3$ group, and the carbon to $R^3$ bond has the stereochemistry:

In one embodiment of this invention the compounds of formula 1.0 are compounds of the formula 1.1

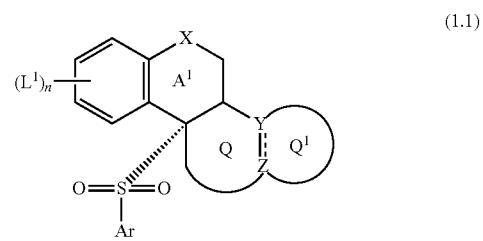

wherein all substituents are as defined for formula 1.0.

In one embodiment of this invention the compounds of formula 1.0 are compounds of the formula 2.1

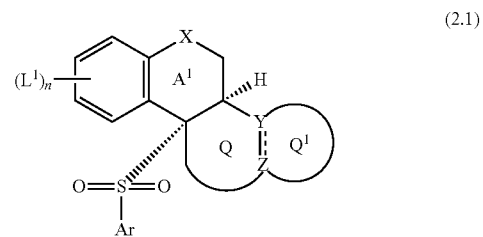

wherein all substituents are as defined for formula 1.0.

In another embodiment this invention is directed to compounds of formula 1.0 having the formula 1.2:

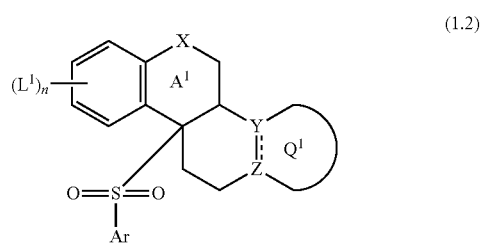

wherein all substituents are as defined for formula 1.0.

In another embodiment this invention is directed to compounds of the formula 1.0 having the formula 1.3:

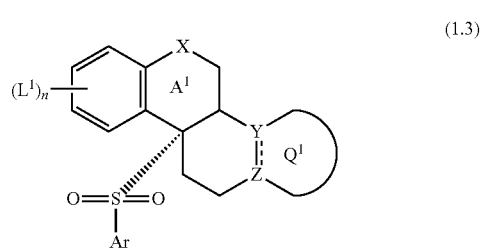

wherein all substituents are as defined for formula 1.0.

In another embodiment this invention is directed to compounds of the formula 1.0 having the formula 2.3:

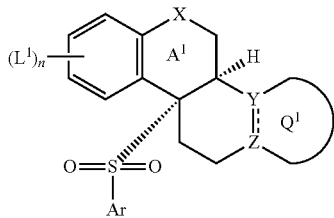
(2.3)

wherein all substituents are as defined for formula 1.0.

In another embodiment this invention directed to compounds of the formula 1.0 having the formula 1.4:

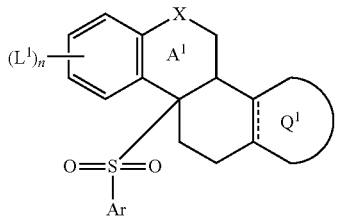
(1.4)

wherein all substituents are as defined for formula 1.0.

In another embodiment this invention directed to compounds of the formula 1.0 having the formula 1.5:

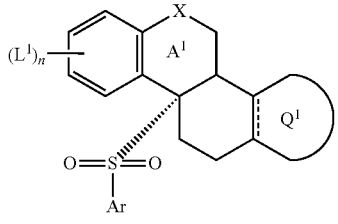
(1.5)

wherein all substituents are as defined for formula 1.0.

In another embodiment this invention directed to compounds of the formula 1.0 having the formula 2.5:

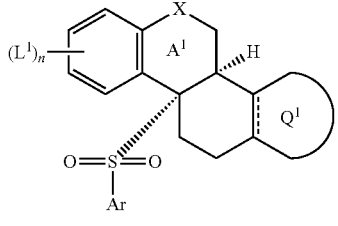
(2.5)

wherein all substituents are as defined for formula 1.0.

In another embodiment this invention directed to compounds of the formula 1.0 having the formula 1.6:

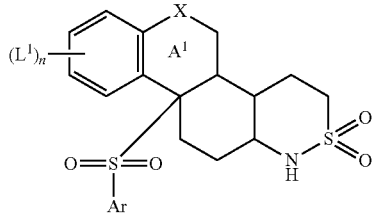
(1.6)

wherein all substituents are as defined for formula 1.0.

In another embodiment this invention directed to compounds of the formula 1.0 having the formula 1.7:

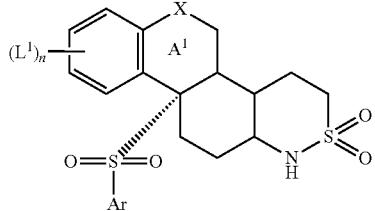
(1.7)

wherein all substituents are as defined for formula 1.0.

In another embodiment this invention directed to compounds of the formula 1.0 having the formula 2.7:

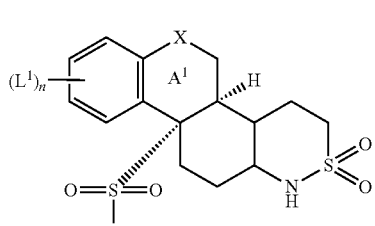
(2.7)

wherein all substituents are as defined for formula 1.0.

In another embodiment this invention directed to compounds of the formula 1.0 having the formula 1.8:

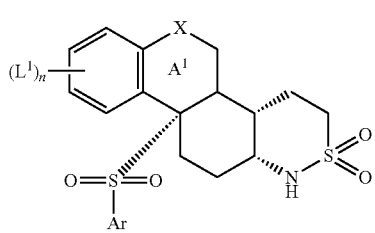
(1.8)

wherein all substituents are as defined for formula 1.0.

In another embodiment this invention directed to compounds of the formula 1.0 having the formula 2.8:

19

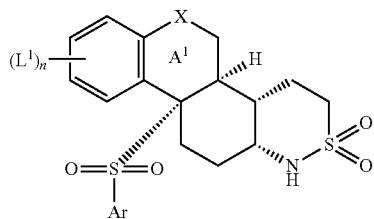

(2.8)

wherein all substituents are as defined for formula 1.0.

In another embodiment this invention directed to compounds of the formula 1.0 having the formula $1.9^{41}$:

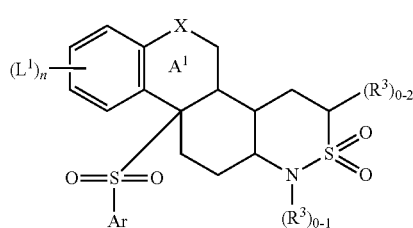

$(1.9^{41})$ wherein all substituents are as defined for formula 1.0. In the substituent "$(R^3)_{0-2}$", the "0-2" means that there is no $R^3$ substituent present (i.e., there would be a H instead of the $R^3$ substituent), or that there is one or two independently selected $R^3$ substituents present at the indicated position. In one embodiment the $=N-(R^3)_{0-1}$ moiety is $=N-H$ (i.e., this N is not substituted). In another embodiment the $=N-(R^3)_{0-1}$ moiety is alkyl (and in one example methyl, and in another example ethyl). In another embodiment, the $=N-(R^3)_{0-1}$ moiety is hydroxyalkyl- (and in one example $-CH_2CH_2OH$). In another embodiment, the $=N-(R^3)_{0-1}$ moiety is substituted arylalkyl- (and in one example, p-methoxybenzyl). In another embodiment the $CH-(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, $-OR^2$, phenyl($C_1$ to $C_4$)alkyl-, $=O$, phenyl($C_1$ to $C_2$)alkyl-, $C_2$ to $C_4$ alkenyl, ($C_5$ to $C_7$)heterocycloalkyl-($C_1$ to $C_2$)alkyl-, $-(C_1$ to $C_2)$alkyl-C(O)OH, $-(C_1$ to $C_4)$alkyl-$NR^5R^6$, $-(C_1$ to $C_4)$alkyl-C(O)$NR^5R^6$, phenyl($C_2$ to $C_4$)alkenyl-, $-(C_1$ to $C_4)$alkyl-C(O)O-($C_1$ to $C_4$)alkyl, and substituted phenyl($C_2$ to $C_4$)alkenyl-. In another embodiment the $CH-(R^3)_{0-2}$ moiety comprises 1-2 $R^3$ groups and each $R^3$ is independently selected from the group consisting of: methyl, ethyl, isopropyl, $-CH_2CH_2OH$, $-CH_2CH_2CH_2OH$, $-OH$, $-OCH_3$, $-OC_2H_5$, $-OCH(CH_3)_2$, benzyl, $-(CH_2)_3$-phenyl, $=O$, p-methoxybenzyl, $-CH_2CH=CH_2$, $-CH_2CH=CHCH_3$, pyrrolidinyl-$CH_2-CH_2-$, morpholinyl-$CH_2-CH_2-$, $-CH_2CH_2-C(O)OH$, $-CH_2-C(O)OH$, $-CH_2CH_2CH_2N(CH_3)_2$, $-CH_2-C(O)NH_2$ and $-CH_2CH=CH$-phenyl. In another embodiment the $CH-(R^3)_{0-2}$ moiety comprises 1-2 $R^3$ groups and each $R^3$ is the same or different $C_1-C_6$ alkyl group. In another embodiment the $CH-(R^3)_{0-2}$ moiety comprises two $R^3$ groups, and said $R^3$ groups are taken together along with the carbon to which they are bound to form a cycloalkyl ring (e.g., a $C_5$ to $C_7$ cycloalkyl ring, such as, for example, cyclopentyl). In another embodiment the $CH-(R^3)_{0-2}$ moiety comprises two $R^3$ groups, and said $R^3$ groups are taken together along with the

20 carbon to which they are bound to form a cycloalkenyl ring (e.g., a $C_5$ to $C_7$ cycloalkenyl ring, such as, for example, cyclopentenyl). In another embodiment X is O.

In another embodiment this invention directed to compounds of the formula 1.0 having the formula 1.9:

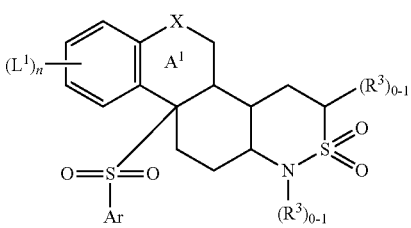

(1.9)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl. Preferably, $X=O$.

In another embodiment this invention directed to compounds of the formula 1.0 having the formula $1.10^{41}$:

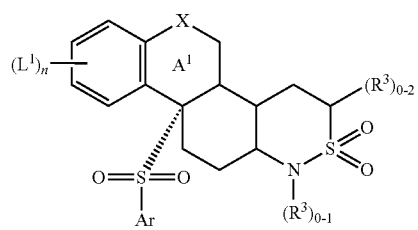

$(1.10^{41})$ wherein all substituents are as defined for formula 1.0. In the substituent "$(R^3)_{0-2}$", the "0-2" means that there is no $R^3$ substituent present (i.e., there would be a H instead of the $R^3$ substituent), or that there is one or two independently selected $R^3$ substituents present at the indicated position. In one embodiment the $=N-(R^3)_{0-1}$ moiety is $=N-H$ (i.e., this N is not substituted). In another embodiment the $=N-(R^3)_{0-1}$ moiety is alkyl (and in one example methyl, and in another example ethyl). In another embodiment, the $=N-(R^3)_{0-1}$ moiety is hydroxyalkyl- (and in one example $-CH_2CH_2OH$). In another embodiment, the $=N-(R^3)_{0-1}$ moiety is substituted arylalkyl- (and in one example, p-methoxybenzyl). In another embodiment the $CH-(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, $-OR^2$, phenyl($C_1$ to $C_4$)alkyl-, $=O$, phenyl($C_1$ to $C_2$)alkyl-, $C_2$ to $C_4$ alkenyl, ($C_5$ to $C_7$)heterocycloalkyl-($C_1$ to $C_2$)alkyl-, $-(C_1$ to $C_2)$alkyl-C(O)OH, $-(C_1$ to $C_4)$alkyl-$NR^5R^6$, $-(C_1$ to $C_4)$alkyl-C(O)$NR^5R^6$, phenyl($C_2$ to $C_4$)alkenyl-, $-(C_1$ to $C_4)$alkyl-C(O)O-($C_1$ to $C_4$)alkyl, and substituted phenyl($C_2$ to $C_4$)alkenyl-. In another embodiment the $CH-(R^3)_{0-2}$ moiety comprises 1-2 $R^3$ groups and each $R^3$ is independently selected from the group consisting of: methyl, ethyl, isopropyl, $-CH_2CH_2OH$, $-CH_2CH_2CH_2OH$, $-OH$, $-OCH_3$, $-OC_2H_5$, $-OCH(CH_3)_2$, benzyl, $-(CH_2)_3$-phenyl, $=O$, p-methoxybenzyl, —CH$_2$CH=CH$_2$, —CH$_2$CH=CHCH$_3$, pyrrolidinyl-CH$_2$—CH$_2$—, morpholinyl-CH$_2$—CH$_2$—, —CH$_2$CH$_2$—C(O)OH, —CH$_2$—C(O)OH, —CH$_2$CH$_2$CH$_2$N(CH$_3$)$_2$, —CH$_2$—C(O)NH$_2$ and —CH$_2$CH=CH-phenyl. In another embodiment the CH—(R$^3$)$_{0-2}$ moiety comprises 1-2 R$^3$ groups and each R$^3$ is the same or different C$_1$-C$_6$ alkyl group. In another embodiment the CH—(R$^3$)$_{0-2}$ moiety comprises two R$^3$ groups, and said R$^3$ groups are taken together along with the carbon to which they are bound to form a cycloalkyl ring (e.g., a C$_5$ to C$_7$ cycloalkyl ring, such as, for example, cyclopentyl). In another embodiment the CH—(R$^3$)$_{0-2}$ moiety comprises two R$^3$ groups, and said R$^3$ groups are taken together along with the carbon to which they are bound to form a cycloalkenyl ring (e.g., a C$_5$ to C$_7$ cycloalkenyl ring, such as, for example, cyclopentenyl). In another embodiment X is O.

In another embodiment this invention directed to compounds of the formula 1.0 having the formula 1.10:

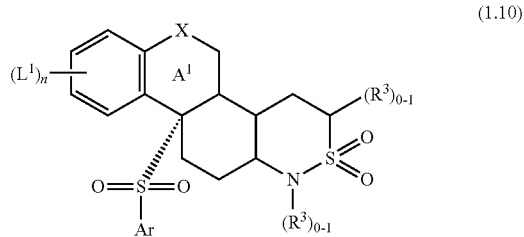

(1.10)

wherein all substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably, the R$^3$ of the CH—R$^3$ moiety is C$_1$-C$_6$ alkyl. Preferably, X=O.

In another embodiment this invention directed to compounds of the formula 1.0 having the formula 2.10$^{A1}$:

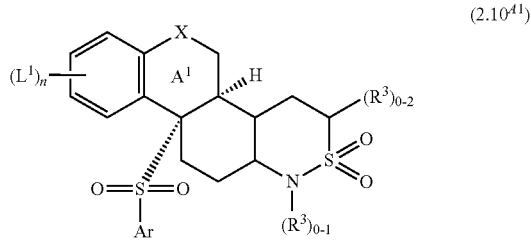

(2.10$^{A1}$)

wherein all substituents are as defined for formula 1.0. In the substituent "(R$^3$)$_{0-2}$", the "0-2" means that there is no R$^3$ substituent present (i.e., there would be a H instead of the R$^3$ substituent), or that there is one or two independently selected R$^3$ substituents present at the indicated position. In one embodiment the =N—(R$^3$)$_{0-1}$ moiety is =N—H (i.e., this N is not substituted). In another embodiment the =N—(R$^3$)$_{0-1}$ moiety is alkyl (and in one example methyl, and in another example ethyl). In another embodiment, the =N—(R$^3$)$_{0-1}$ moiety is hydroxyalkyl- (and in one example —CH$_2$CH$_2$OH). In another embodiment, the =N—(R$^3$)$_{0-1}$ moiety is substituted arylalkyl- (and in one example, p-methoxybenzyl). In another embodiment the CH—(R$^3$)$_{0-2}$ moiety comprises 1-2 R$^3$ groups and each R$^3$ is independently selected from the group consisting of: selected from the group consisting of: C$_1$ to C$_4$ alkyl, (C$_1$ to C$_2$)alkoxy-(C$_1$ to C$_2$)alkyl-, hydroxy(C$_1$ to C$_4$)alkyl-, —OR$^2$, phenyl(C$_1$ to C$_4$)alkyl-, =O, phenyl(C$_1$ to C$_2$)alkyl-, C$_2$ to C$_4$ alkenyl, (C$_5$ to C$_7$)heterocycloalkyl-(C$_1$ to C$_2$)alkyl-, —(C$_1$ to C$_2$)alkyl-C(O)OH, —(C$_1$ to C$_4$)alkyl-NR$^5$R$^6$, —(C$_1$ to C$_4$)alkyl-C(O)NR$^5$R$^6$, phenyl(C$_2$ to C$_4$)alkenyl-, —(C$_1$ to C$_4$)alkyl-C(O)O—(C$_1$ to C$_4$)alkyl, and substituted phenyl(C$_2$ to C$_4$)alkenyl-. In another embodiment the CH—(R$^3$)$_{0-2}$ moiety comprises 1-2 R$^3$ groups and each R$^3$ is independently selected from the group consisting of: methyl, ethyl, isopropyl, —CH$_2$CH$_2$OH, —CH$_2$CH$_2$CH$_2$OH, —OH, —OCH$_3$, —OC$_2$H$_5$, —OCH(CH$_3$)$_2$, benzyl, —(CH$_2$)$_3$-phenyl, =O, p-methoxybenzyl, —CH$_2$CH=CH$_2$, —CH$_2$CH=CHCH$_3$, pyrrolidinyl-CH$_2$—CH$_2$—, morpholinyl-CH$_2$—CH$_2$—, —CH$_2$CH$_2$—C(O)OH, —CH$_2$—C(O)OH, —CH$_2$CH$_2$CH$_2$N(CH$_3$)$_2$, —CH$_2$—C(O)NH$_2$ and —CH$_2$CH=CH-phenyl. In another embodiment the CH—(R$^3$)$_{0-2}$ moiety comprises 1-2 R$^3$ groups and each R$^3$ is the same or different C$_1$-C$_6$ alkyl group. In another embodiment the CH—(R$^3$)$_{0-2}$ moiety comprises two R$^3$ groups, and said R$^3$ groups are taken together along with the carbon to which they are bound to form a cycloalkyl ring (e.g., a C$_5$ to C$_7$ cycloalkyl ring, such as, for example, cyclopentyl). In another embodiment the CH—(R$^3$)$_{0-2}$ moiety comprises two R$^3$ groups, and said R$^3$ groups are taken together along with the carbon to which they are bound to form a cycloalkenyl ring (e.g., a C$_5$ to C$_7$ cycloalkenyl ring, such as, for example, cyclopentenyl). In another embodiment X is O.

In another embodiment this invention directed to compounds of the formula 1.0 having the formula 2.10:

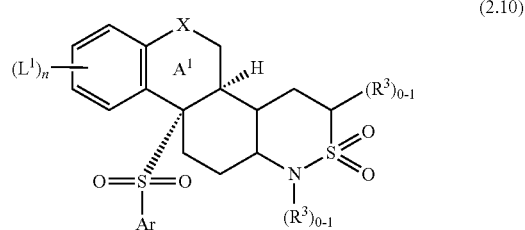

(2.10)

wherein all substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably, the R$^3$ of the CH—R$^3$ moiety is C$_1$-C$_6$ alkyl. Preferably, X=O.

In another embodiment this invention directed to compounds of the formula 1.0 having the formula 3.10$^{A1}$:

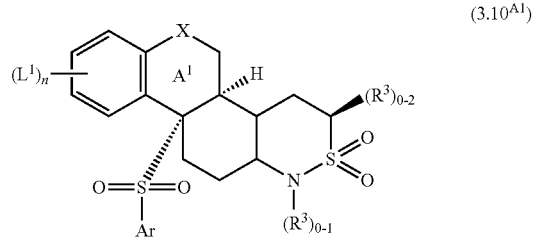

(3.10$^{A1}$)

wherein all substituents are as defined for formula 1.0. In the substituent "(R$^3$)$_{0-2}$", the "0-2" means that there is no R$^3$ substituent present (i.e., there would be a H instead of the $R^3$ substituent), or that there is one or two independently selected $R^3$ substituents present at the indicated position. In one embodiment the =N—$(R^3)_{0-1}$ moiety is =N—H (i.e., this N is not substituted). In another embodiment the =N—$(R^3)_{0-1}$ moiety is alkyl (and in one example methyl, and in another example ethyl). In another embodiment, the =N—$(R^3)_{0-1}$ moiety is hydroxyalkyl- (and in one example —CH$_2$CH$_2$OH). In another embodiment, the =N—$(R^3)_{0-1}$ moiety is substituted arylalkyl- (and in one example, p-methoxybenzyl). In another embodiment the CH—$(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, —OR$^2$, phenyl($C_1$ to $C_4$)alkyl-, =O, phenyl($C_1$ to $C_2$)alkyl-, $C_2$ to $C_4$ alkenyl, ($C_5$ to $C_7$)heterocycloalkyl-($C_1$ to $C_2$)alkyl-, —($C_1$ to $C_2$)alkyl-C(O)OH, —($C_1$ to $C_4$)alkyl-NR$^5$R$^6$, —($C_1$ to $C_4$)alkyl-C(O)NR$^5$R$^6$, phenyl($C_2$ to $C_4$)alkenyl-, —($C_1$ to $C_4$)alkyl-C(O)O—($C_1$ to $C_4$)alkyl, and substituted phenyl($C_2$ to $C_4$)alkenyl-. In another embodiment the CH—$(R^3)_{0-2}$ moiety comprises 1-2 $R^3$ groups and each $R^3$ is independently selected from the group consisting of: methyl, ethyl, isopropyl, —CH$_2$CH$_2$OH, —CH$_2$CH$_2$CH$_2$OH, —OH, —OCH$_3$, —OC$_2$H$_5$, —OCH(CH$_3$)$_2$, benzyl, —(CH$_2$)$_3$-phenyl, =O, p-methoxybenzyl, —CH$_2$CH=CH$_2$, —CH$_2$CH=CHCH$_3$, pyrrolidinyl-CH$_2$—CH$_2$—, morpholinyl-CH$_2$—CH$_2$—, —CH$_2$CH$_2$—C(O)OH, —CH$_2$—C(O)OH, —CH$_2$CH$_2$CH$_2$N(CH$_3$)$_2$, —CH$_2$—C(O)NH$_2$ and —CH$_2$CH=CH-phenyl. In another embodiment the CH—$(R^3)_{0-2}$ moiety comprises 1-2 $R^3$ groups and each $R^3$ is the same or different $C_1$-$C_6$ alkyl group. In another embodiment the CH—$(R^3)_{0-2}$ moiety comprises two $R^3$ groups, and said $R^3$ groups are taken together along with the carbon to which they are bound to form a cycloalkyl ring (e.g., a $C_5$ to $C_7$ cycloalkyl ring, such as, for example, cyclopentyl). In another embodiment the CH—$(R^3)_{0-2}$ moiety comprises two $R^3$ groups, and said $R^3$ groups are taken together along with the carbon to which they are bound to form a cycloalkenyl ring (e.g., a $C_5$ to $C_7$ cycloalkenyl ring, such as, for example, cyclopentenyl). In another embodiment X is O.

In another embodiment this invention directed to compounds of the formula 1.0 having the formula 3.10:

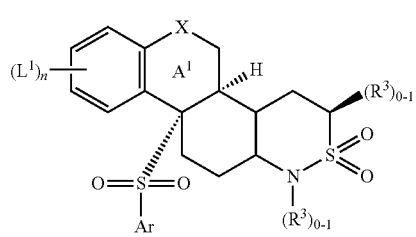

(3.10)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl. Preferably, X=O.

In another embodiment this invention directed to compounds of the formula 1.0 having the formula 1.11$^{41}$:

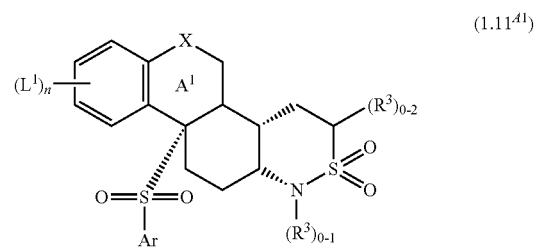

(1.11$^{41}$)

wherein all substituents are as defined for formula 1.0. In the substituent "$(R^3)_{0-2}$", the "0-2" means that there is no $R^3$ substituent present (i.e., there would be a H instead of the $R^3$ substituent), or that there is one or two independently selected $R^3$ substituents present at the indicated position. In one embodiment the =N—$(R^3)_{0-1}$ moiety is =N—H (i.e., this N is not substituted). In another embodiment the =N—$(R^3)_{0-1}$ moiety is alkyl (and in one example methyl, and in another example ethyl). In another embodiment, the =N—$(R^3)_{0-1}$ moiety is hydroxyalkyl- (and in one example —CH$_2$CH$_2$OH). In another embodiment, the =N—$(R^3)_{0-1}$ moiety is substituted arylalkyl- (and in one example, p-methoxybenzyl). In another embodiment the CH—$(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, —OR$^2$, phenyl($C_1$ to $C_4$)alkyl-, =O, phenyl($C_1$ to $C_2$)alkyl-, $C_2$ to $C_4$ alkenyl, ($C_5$ to $C_7$)heterocycloalkyl-($C_1$ to $C_2$)alkyl-, —($C_1$ to $C_2$)alkyl-C(O)OH, —($C_1$ to $C_4$)alkyl-NR$^5$R$^6$, —($C_1$ to $C_4$)alkyl-C(O)NR$^5$R$^6$, phenyl($C_2$ to $C_4$)alkenyl-, —($C_1$ to $C_4$)alkyl-C(O)O—($C_1$ to $C_4$)alkyl, and substituted phenyl($C_2$ to $C_4$)alkenyl-. In another embodiment the CH—$(R^3)_{0-2}$ moiety comprises 1-2 $R^3$ groups and each $R^3$ is independently selected from the group consisting of: methyl, ethyl, isopropyl, —CH$_2$CH$_2$OH, —CH$_2$CH$_2$CH$_2$OH, —OH, —OCH$_3$, —OC$_2$H$_5$, —OCH(CH$_3$)$_2$, benzyl, —(CH$_2$)$_3$-phenyl, =O, p-methoxybenzyl, —CH$_2$CH=CH$_2$, —CH$_2$CH=CHCH$_3$, pyrrolidinyl-CH$_2$—CH$_2$—, morpholinyl-CH$_2$—CH$_2$—, —CH$_2$CH$_2$—C(O)OH, —CH$_2$—C(O)OH, —CH$_2$CH$_2$CH$_2$N(CH$_3$)$_2$, —CH$_2$—C(O)NH$_2$ and —CH$_2$CH=CH-phenyl. In another embodiment the CH—$(R^3)_{0-2}$ moiety comprises 1-2 $R^3$ groups and each $R^3$ is the same or different $C_1$-$C_6$ alkyl group. In another embodiment the CH—$(R^3)_{0-2}$ moiety comprises two $R^3$ groups, and said $R^3$ groups are taken together along with the carbon to which they are bound to form a cycloalkyl ring (e.g., a $C_5$ to $C_7$ cycloalkyl ring, such as, for example, cyclopentyl). In another embodiment the CH—$(R^3)_{0-2}$ moiety comprises two $R^3$ groups, and said $R^3$ groups are taken together along with the carbon to which they are bound to form a cycloalkenyl ring (e.g., a $C_5$ to $C_7$ cycloalkenyl ring, such as, for example, cyclopentenyl). In another embodiment X is O.

In another embodiment this invention directed to compounds of the formula 1.0 having the formula 1.11:

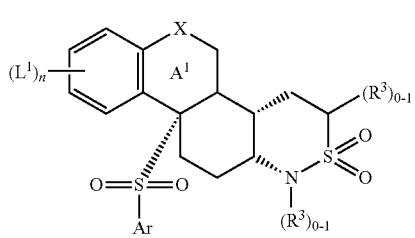

(1.11)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl. Preferably, X=O.

In another embodiment this invention directed to compounds of the formula 1.0 having the formula $2.11^{41}$:

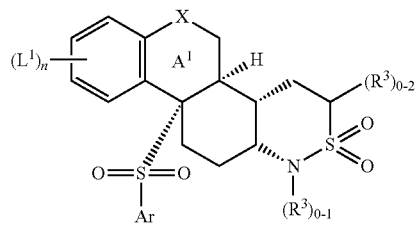

(2.11^{41})

wherein all substituents are as defined for formula 1.0. In the substituent "$(R^3)_{0-2}$", the "0-2" means that there is no $R^3$ substituent present (i.e., there would be a H instead of the $R^3$ substituent), or that there is one or two independently selected $R^3$ substituents present at the indicated position. In one embodiment the =N—$(R^3)_{0-1}$ moiety is =N—H (i.e., this N is not substituted). In another embodiment the =N—$(R^3)_{0-1}$ moiety is alkyl (and in one example methyl, and in another example ethyl). In another embodiment, the =N—$(R^3)_{0-1}$ moiety is hydroxyalkyl- (and in one example —$CH_2CH_2OH$). In another embodiment, the =N—$(R^3)_{0-1}$ moiety is substituted arylalkyl- (and in one example, p-methoxybenzyl). In another embodiment the CH—$(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, —$OR^2$, phenyl($C_1$ to $C_4$)alkyl-, =O, phenyl($C_1$ to $C_2$)alkyl-, $C_2$ to $C_4$ alkenyl, ($C_5$ to $C_7$)heterocycloalkyl-($C_1$ to $C_2$)alkyl-, —($C_1$ to $C_2$)alkyl-C(O)OH, —($C_1$ to $C_4$)alkyl-$NR^5R^6$, —($C_1$ to $C_4$)alkyl-C(O)$NR^5R^6$, phenyl($C_2$ to $C_4$)alkenyl-, —($C_1$ to $C_4$)alkyl-C(O)O—($C_1$ to $C_4$)alkyl, and substituted phenyl($C_2$ to $C_4$)alkenyl-. In another embodiment the CH—$(R^3)_{0-2}$ moiety comprises 1-2 $R^3$ groups and each $R^3$ is independently selected from the group consisting of: methyl, ethyl, isopropyl, —$CH_2CH_2OH$, —$CH_2CH_2CH_2OH$, —OH, —$OCH_3$, —$OC_2H_5$, —$OCH(CH_3)_2$, benzyl, —$(CH_2)_3$-phenyl, =O, p-methoxybenzyl, —$CH_2CH=CH_2$, —$CH_2CH=CHCH_3$, pyrrolidinyl-$CH_2$—$CH_2$—, morpholinyl-$CH_2$—$CH_2$—, —$CH_2CH_2$—C(O)OH, —$CH_2$—C(O)OH, —$CH_2CH_2CH_2N(CH_3)_2$, —$CH_2$—C(O)$NH_2$ and —$CH_2CH$=CH-phenyl. In another embodiment the CH—$(R^3)_{0-2}$ moiety comprises 1-2 $R^3$ groups and each $R^3$ is the same or different $C_1$-$C_6$ alkyl group. In another embodiment the CH—$(R^3)_{0-2}$ moiety comprises two $R^3$ groups, and said $R^3$ groups are taken together along with the carbon to which they are bound to form a cycloalkyl ring (e.g., a $C_5$ to $C_7$ cycloalkyl ring, such as, for example, cyclopentyl). In another embodiment the CH—$(R^3)_{0-2}$ moiety comprises two $R^3$ groups, and said $R^3$ groups are taken together along with the carbon to which they are bound to form a cycloalkenyl ring (e.g., a $C_5$ to $C_7$ cycloalkenyl ring, such as, for example, cyclopentenyl). In another embodiment X is O.

In another embodiment this invention directed to compounds of the formula 1.0 having the formula 2.11:

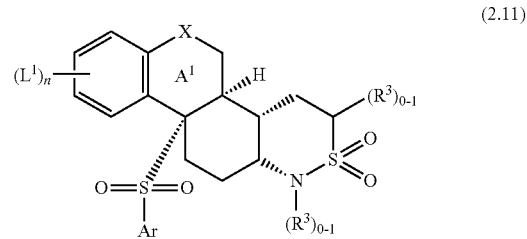

(2.11)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl. Preferably, X=O.

In another embodiment this invention directed to compounds of the formula 1.0 having the formula $3.11^{41}$:

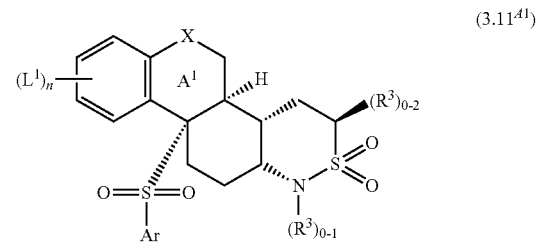

(3.11^{41})

wherein all substituents are as defined for formula 1.0. In the substituent "$(R^3)_{0-2}$", the "0-2" means that there is no $R^3$ substituent present (i.e., there would be a H instead of the $R^3$ substituent), or that there is one or two independently selected $R^3$ substituents present at the indicated position. In one embodiment the =N—$(R^3)_{0-1}$ moiety is =N—H (i.e., this N is not substituted). In another embodiment the =N—$(R^3)_{0-1}$ moiety is alkyl (and in one example methyl, and in another example ethyl). In another embodiment, the =N—$(R^3)_{0-1}$ moiety is hydroxyalkyl- (and in one example —$CH_2CH_2OH$). In another embodiment, the =N—$(R^3)_{0-1}$ moiety is substituted arylalkyl- (and in one example, p-methoxybenzyl). In another embodiment the CH—$(R^3)_{0-2}$ moiety comprises 1-2 $R^3$ groups and each $R^3$ is independently selected from the group consisting of: selected from the group consisting of: $C_1$ to $C_4$ alkyl, ($C_1$ to $C_2$)alkoxy-($C_1$ to $C_2$)alkyl-, hydroxy($C_1$ to $C_4$)alkyl-, —$OR^2$, phenyl($C_1$ to $C_4$)alkyl-, =O, phenyl($C_1$ to $C_2$)alkyl-, $C_2$ to $C_4$ alkenyl, ($C_5$ to $C_7$)heterocycloalkyl-($C_1$ to $C_2$)alkyl-, —($C_1$ to $C_2$)alkyl-C(O)OH, —($C_1$ to $C_4$)alkyl-$NR^5R^6$, —($C_1$ to $C_4$)alkyl-C(O)$NR^5R^6$, phenyl($C_2$ to $C_4$)alkenyl-, —($C_1$ to $C_4$)alkyl-C(O)O—($C_1$ to $C_4$)alkyl, and substituted phenyl($C_2$ to $C_4$)alkenyl-. In another embodiment the CH—$(R^3)_{0-2}$ moiety comprises 1-2 $R^3$ groups and each $R^3$ is independently selected from the group consisting of: methyl, ethyl, isopropyl, —$CH_2CH_2OH$, —$CH_2CH_2CH_2OH$, —OH, —$OCH_3$, —$OC_2H_5$, —$OCH(CH_3)_2$, benzyl, —$(CH_2)_3$-phenyl, =O, p-methoxybenzyl, —$CH_2CH=CH_2$, —$CH_2CH=CHCH_3$, pyrrolidinyl-$CH_2$—$CH_2$—, morpholinyl-$CH_2$—$CH_2$—, —CH₂CH₂—C(O)OH, —CH₂—C(O)OH, —CH₂CH₂CH₂N(CH₃)₂, —CH₂—C(O)NH₂ and —CH₂CH=CH-phenyl. In another embodiment the CH—(R³)₀₋₂ moiety comprises 1-2 R³ groups and each R³ is the same or different C₁-C₆ alkyl group. In another embodiment the CH—(R³)₀₋₂ moiety comprises two R³ groups, and said R³ groups are taken together along with the carbon to which they are bound to form a cycloalkyl ring (e.g., a C₅ to C₇ cycloalkyl ring, such as, for example, cyclopentyl). In another embodiment the CH—(R³)₀₋₂ moiety comprises two R³ groups, and said R³ groups are taken together along with the carbon to which they are bound to form a cycloalkenyl ring (e.g., a C₅ to C₇ cycloalkenyl ring, such as, for example, cyclopentenyl). In another embodiment X is O.

In another embodiment this invention directed to compounds of the formula 1.0 having the formula 3.11:

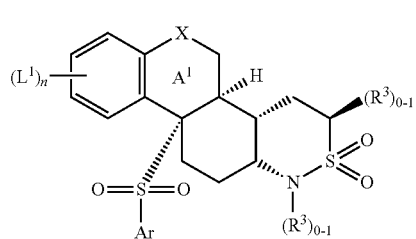
(3.11)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably, the R³ of the CH—R³ moiety is C₁-C₆ alkyl, more preferably ethyl. Preferably, X=O.

In another embodiment this invention directed to compounds of the formula 1.0 having the formula 1.12:

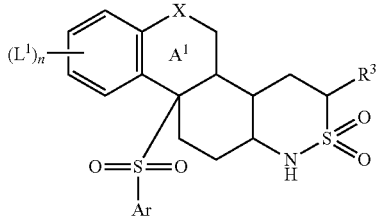
(1.12)

wherein all substituents are as defined for formula 1.0. Preferably, R³ is C₁-C₆ alkyl. Preferably, X=O.

In another embodiment this invention directed to compounds of the formula 1.0 having the formula 1.13:

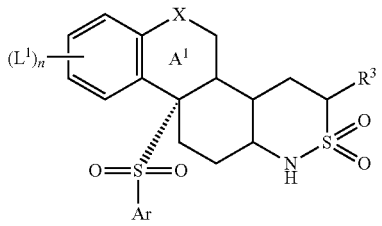
(1.13)

wherein all substituents are as defined for formula 1.0. Preferably, R³ is C₁-C₆ alkyl. Preferably, X=O.

In another embodiment this invention directed to compounds of the formula 1.0 having the formula 2.13:

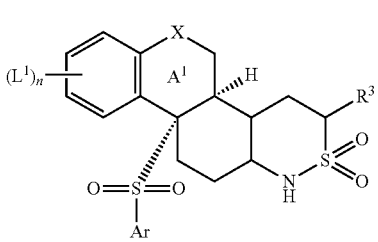
(2.13)

wherein all substituents are as defined for formula 1.0. Preferably, R³ is C₁-C₆ alkyl. Preferably, X=O.

In another embodiment this invention directed to compounds of the formula 1.0 having the formula 3.13:

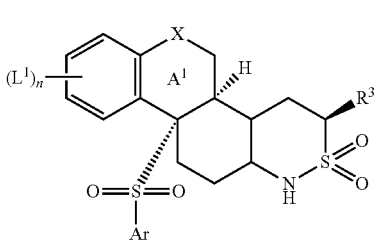
(3.13)

wherein all substituents are as defined for formula 1.0. Preferably, R³ is C₁-C₆ alkyl. Preferably, X=O.

In another embodiment this invention directed to compounds of the formula 1.0 having the formula 1.14:

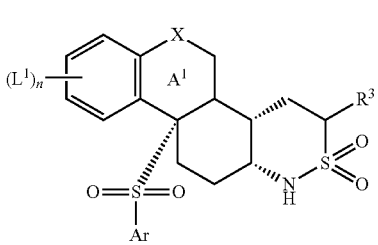
(1.14)

wherein all substituents are as defined for formula 1.0. Preferably, R³ is C₁-C₆ alkyl. Preferably, X=O.

In another embodiment this invention directed to compounds of the formula 1.0 having the formula 2.14:

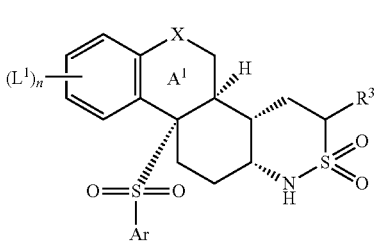
(2.14)

wherein all substituents are as defined for formula 1.0. Preferably, R³ is C₁-C₆ alkyl. Preferably, X=O.

In another embodiment this invention directed to compounds of the formula 1.0 having the formula 3.14:

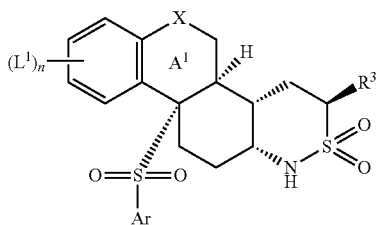

(3.14)

wherein all substituents are as defined for formula 1.0. Preferably, $R^3$ is $C_1$-$C_6$ alkyl. Preferably, X=O.

In another embodiment this invention directed to compounds of the formula 1.0 having the formula 1.15:

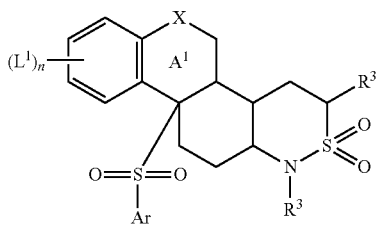

(1.15)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 1.0 having the formula 1.16:

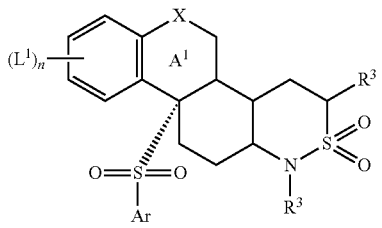

(1.16)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 1.0 having the formula 2.16:

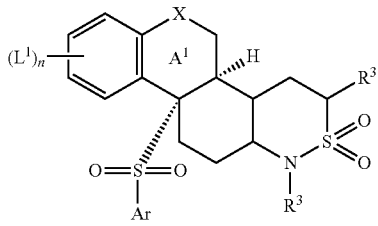

(2.16)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 1.0 having the formula 3.16:

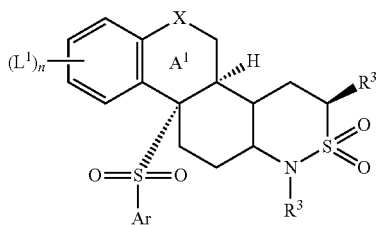

(3.16)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 1.0 having the formula 1.17:

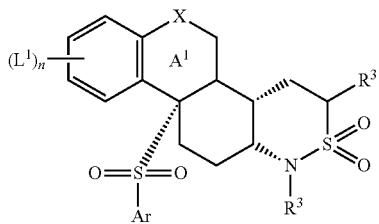

(1.17)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 2.17:

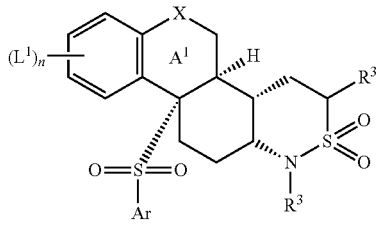

(2.17)

wherein all substituents are as defined for formula 1.0. Each $R^3$ is independently selected. Preferably, $R^3$ of the =N—($R^3$) moiety is H. Preferably, the $R^3$ of the CH—$R^3$ moiety is $C_1$-$C_6$ alkyl. Preferably, X=O.

In another embodiment this invention directed to compounds of the formula 1.0 having the formula 3.17:

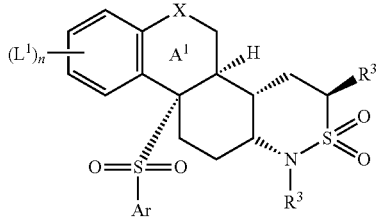

(3.17)

wherein all substituents are as defined for formula 1.0. Each $R^3$ is independently selected. Preferably, $R^3$ of the =N—($R^3$)

moiety is H. Preferably, the $R^3$ of the CH—$R^3$ moiety is $C_1$-$C_6$ alkyl. Preferably, X=O.

In another embodiment this invention directed to compounds of the formula 1.0 having the formula 1.18:

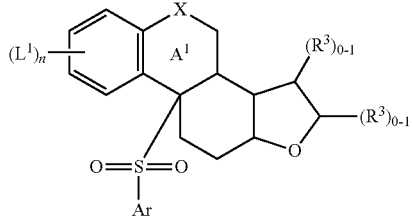

(1.18)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment this invention directed to compounds of the formula 1.0 having the formula 1.19:

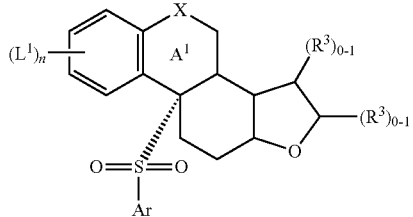

(1.19)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment this invention directed to compounds of the formula 1.0 having the formula 1.20:

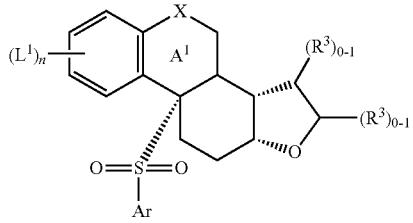

(1.20)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment this invention directed to compounds of the formula 1.0 having the formula 1.18A:

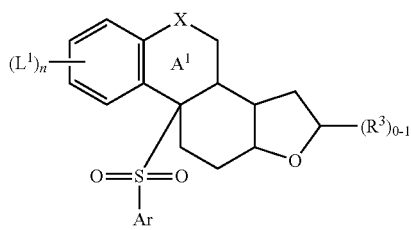

(1.18A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably $R^3$ is selected from the group consisting of —$C_1$-$C_6$ alkyl, hydroxyalkyl, and alkoxyalkyl.

In another embodiment this invention directed to compounds of the formula 1.0 having the formula 1.19A:

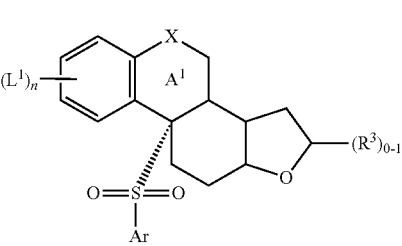

(1.19A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably $R^3$ is selected from the group consisting of —$C_1$-$C_6$ alkyl, hydroxyalkyl, and alkoxyalkyl.

In another embodiment this invention directed to compounds of the formula 1.0 having the formula 1.20A:

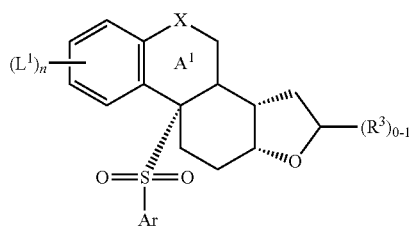

(1.20A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably $R^3$ is selected from the group consisting of —$C_1$-$C_6$ alkyl, hydroxyalkyl, and alkoxyalkyl.

In another embodiment this invention directed to compounds of the formula 1.0 having the formula 1.21:

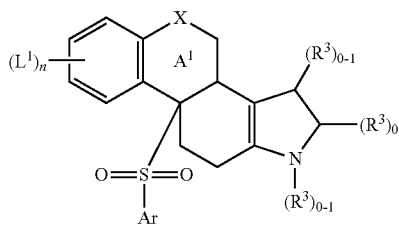

(1.21)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.22:

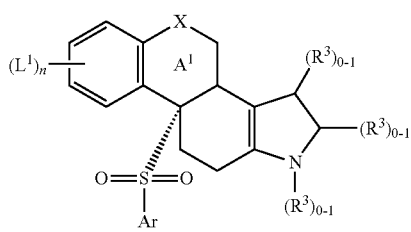

(1.22)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.21A:

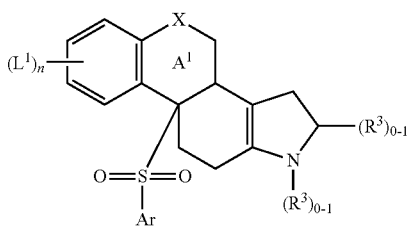

(1.21A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably the $R^3$ of the $CH-R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.22A:

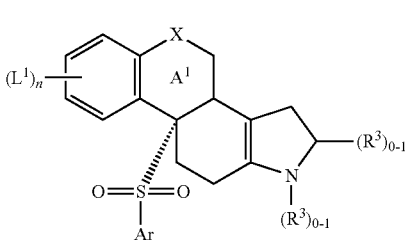

(1.22A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably the $R^3$ of the $CH-R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.23:

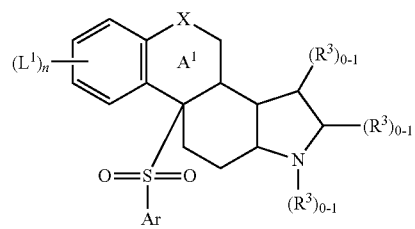

(1.23)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.24:

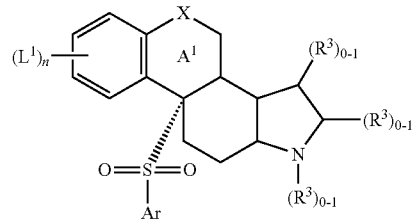

(1.24)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=$N—$(R^3)_{0-1}$ moiety is $=$N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.25:

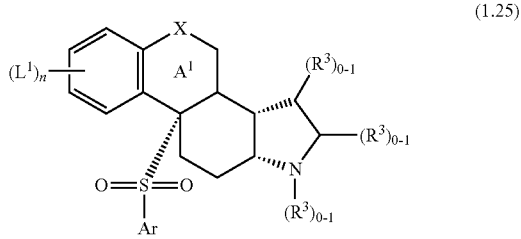

(1.25)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=$N—$(R^3)_{0-1}$ moiety is $=$N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.23A:

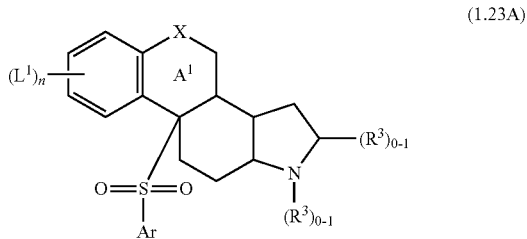

(1.23A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=$N—$(R^3)_{0-1}$ moiety is $=$N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.24A:

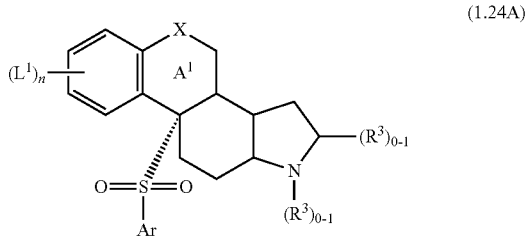

(1.24A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=$N—$(R^3)_{0-1}$ moiety is $=$N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.25A:

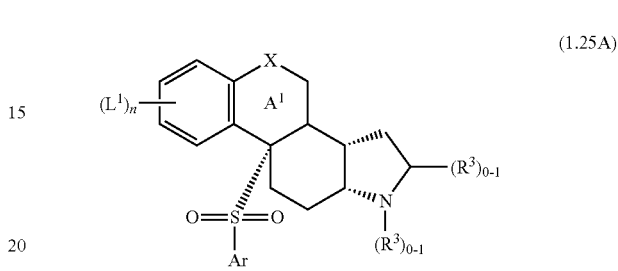

(1.25A)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=$N—$(R^3)_{0-1}$ moiety is $=$N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.26:

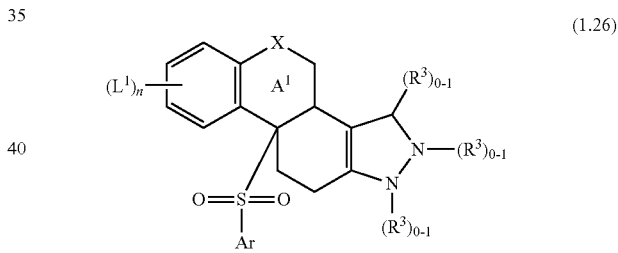

(1.26)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.27:


(1.27)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.28:

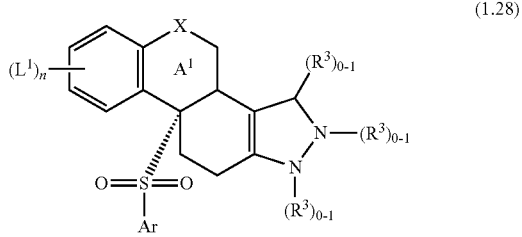

(1.28)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.29:

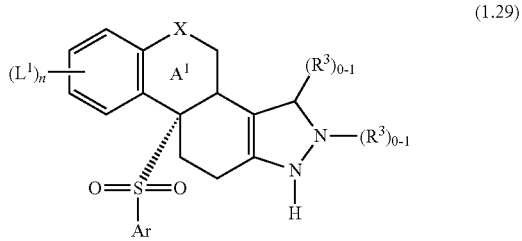

(1.29)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.30:

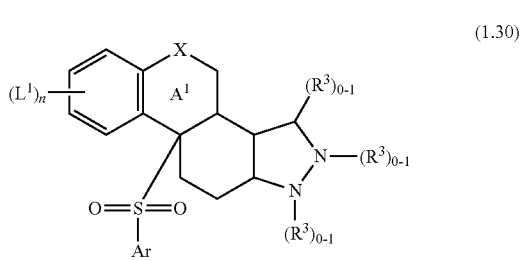

(1.30)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.31:

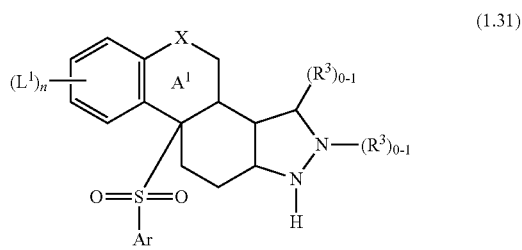

(1.31)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.32:

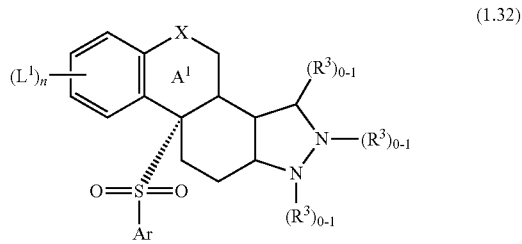

(1.32)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.33:

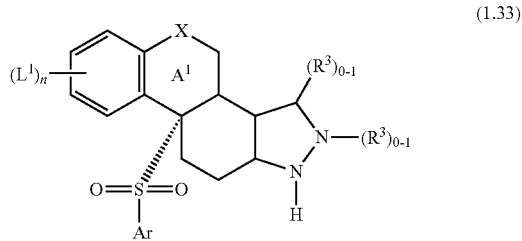

(1.33)

wherein all substituents are as defined for formula 1.0. In the substituent "$(R^3)_{0-1}$", the "0-1" means that there is no $R^3$ substituent present (i.e., there would be a H instead of the $R^3$ substituent present substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment this invention directed to compounds of the formula 1.0 having the formula 1.34:

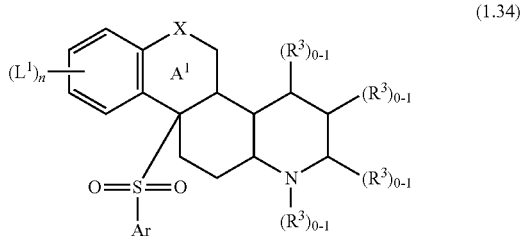

(1.34)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment this invention directed to compounds of the formula 1.0 having the formula 1.35:

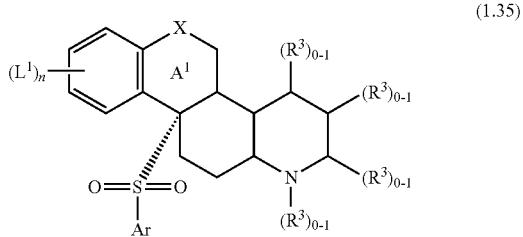

(1.35)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment this invention directed to compounds of the formula 1.0 having the formula 1.36:

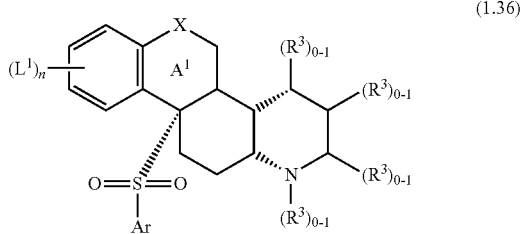

(1.36)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment this invention directed to compounds of the formula 1.0 having the formula 1.37:

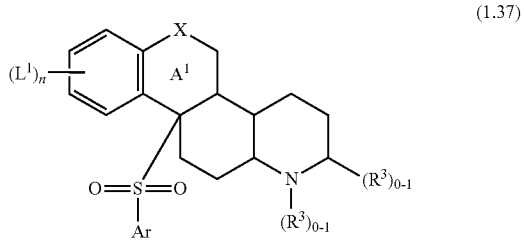

(1.37)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably R³ of the CH—R³ moiety is independently selected from the group consisting of —C₁-C₆ alkyl, hydroxyalkyl, and alkoxyalkyl.

In another embodiment this invention directed to compounds of the formula 1.0 having the formula 1.38:

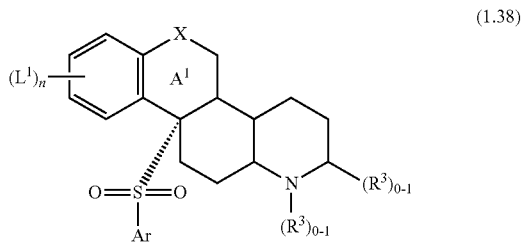

(1.38)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably R³ of the CH—R³ moiety is independently selected from the group consisting of —C₁-C₆ alkyl, hydroxyalkyl, and alkoxyalkyl.

In another embodiment this invention directed to compounds of the formula 1.0 having the formula 1.39:

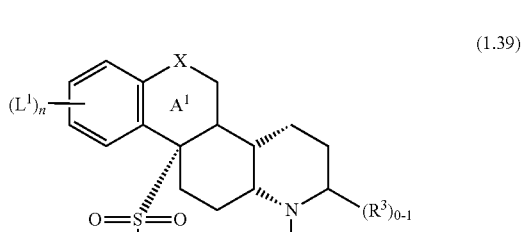

(1.39)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.35C:

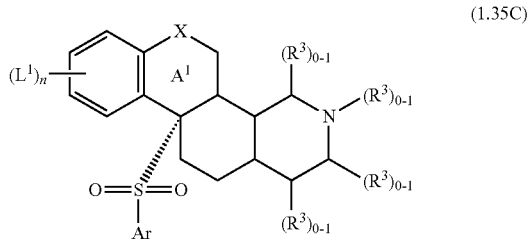

(1.35C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.36C:

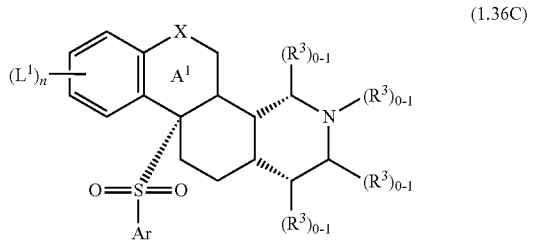

(1.36C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.37C:

(1.37C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{04}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.38C:

(1.38C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.39C:

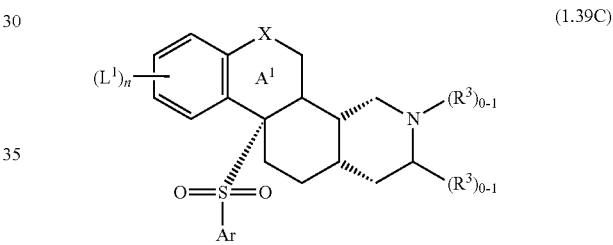

(1.39C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.35D:

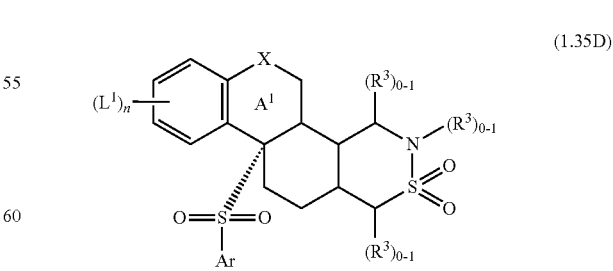

(1.35D)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.36D:

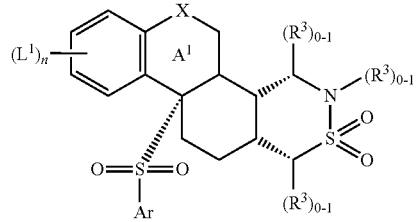

(1.36D)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.37D:

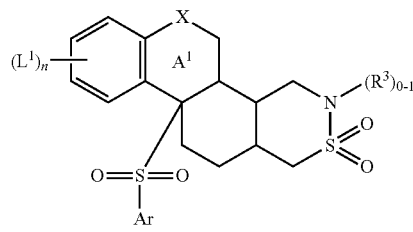

(1.37D)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably, the $=N-(R^3)_{0-1}$ moiety is $=N-H$ (i.e., this N is not substituted).

In another embodiment this invention directed to compounds of the formula 1.0 having the formula 1.38D:

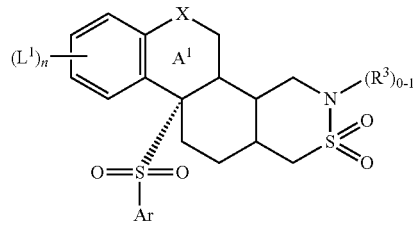

(1.38D)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably, the $=N-(R^3)_{0-1}$ moiety is $=N-H$ (i.e., this N is not substituted).

In another embodiment this invention directed to compounds of the formula 1.0 having the formula 1.39D:

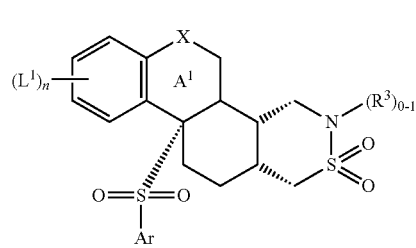

(1.39D)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably, the $=N-(R^3)_{0-1}$ moiety is $=N-H$ (i.e., this N is not substituted).

In another embodiment this invention directed to compounds of the formula 1.0 having the formula 1.35E:

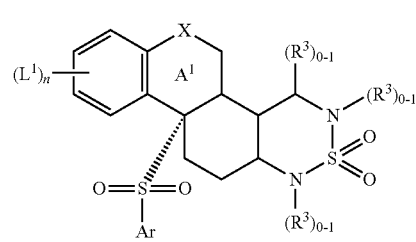

(1.35E)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, each $=N-(R^3)_{0-1}$ moiety is $=N-H$ (i.e., each N is not substituted). Preferably the $R^3$ of the CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.36E:

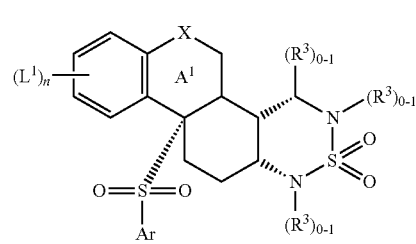

(1.36E)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, each =N—(R³)₀₋₁ moiety is =N—H (i.e., each N is not substituted). Preferably the R³ of the CH—R³ moiety is independently selected from the group consisting of —C₁-C₆ alkyl, hydroxyalkyl, and alkoxyalkyl.

In another embodiment this invention directed to compounds of the formula 1.0 having the formula 1.37E:

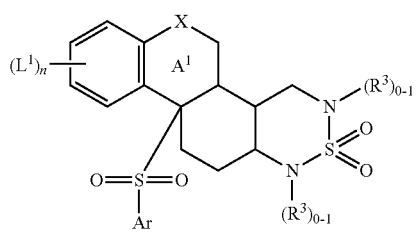

(1.37E)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Preferably, each =N—(R³)₀₋₁ moiety is =N—H (i.e., each N is not substituted).

In another embodiment this invention directed to compounds of the formula 1.0 having the formula 1.38E:

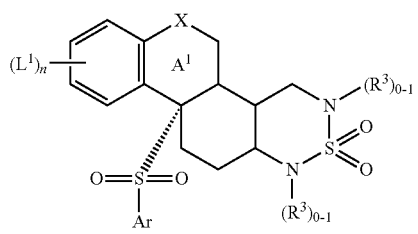

(1.38E)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Preferably, each =N—(R³)₀₋₁ moiety is =N—H (i.e., each N is not substituted).

In another embodiment this invention directed to compounds of the formula 1.0 having the formula 1.39E:

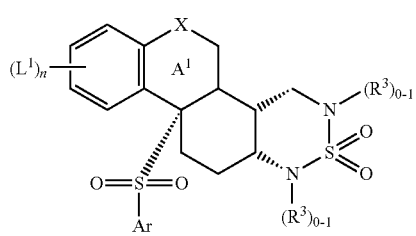

(1.39E)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Preferably, each =N—(R³)₀₋₁ moiety is =N—H (i.e., each N is not substituted).

In another embodiment this invention directed to compounds of the formula 1.0 having the formula 1.40:

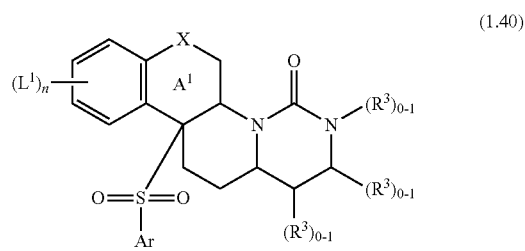

(1.40)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. In one example R³ in the =N—(R)₀₋₁ moiety is a C₁-C₆ alkyl group. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment this invention directed to compounds of the formula 1.0 having the formula 1.41:

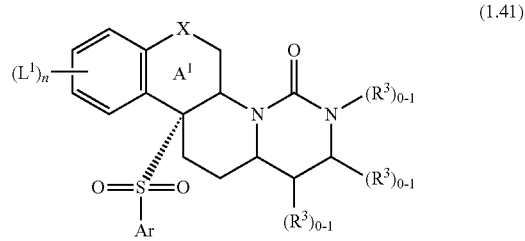

(1.41)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. In one example R³ in the =N—(R)₀₋₁ moiety is a C₁-C₆ alkyl group. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment this invention directed to compounds of the formula 1.0 having the formula 1.42:

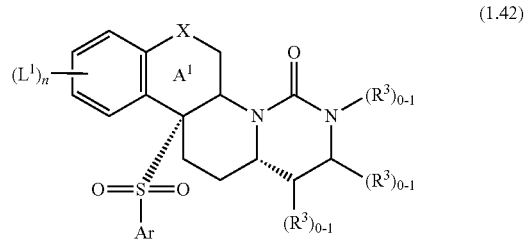

(1.42)

wherein all substituents are as defined for formula 1.0. In the substituent "(R³)₀₋₁", the "0-1" means that there is no R³ substituent present (i.e., there would be a H instead of the R³ substituent), or that there is one R³ substituent present at the indicated position Each R³ is independently selected. In one example R³ in the =N—(R³)₀₋₁ moiety is a C₁-C₆ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.40C:

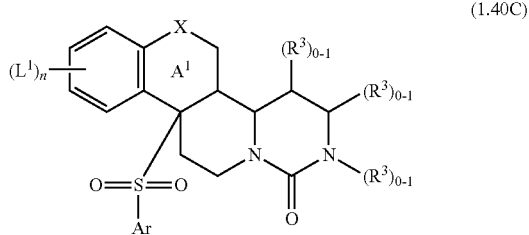

(1.40C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.41C:

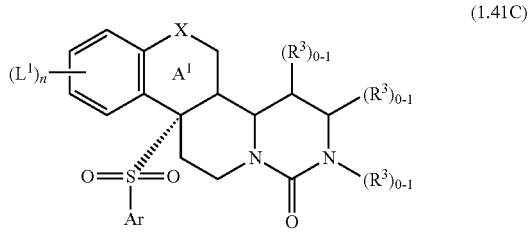

(1.41C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.42C:

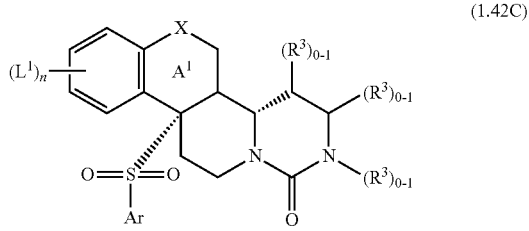

(1.42C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment this invention directed to compounds of the formula 1.0 having the formula 1.43:

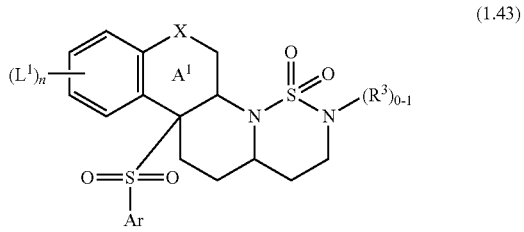

(1.43)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment this invention directed to compounds of the formula 1.0 having the formula 1.44:

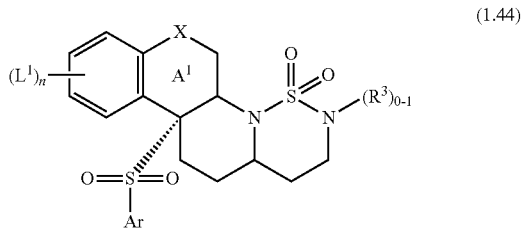

(1.44)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment this invention directed to compounds of the formula 1.0 having the formula 1.45:

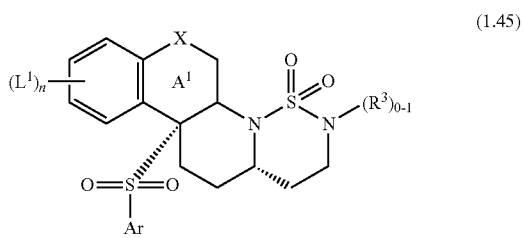

(1.45)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment this invention directed to compounds of the formula 1.0 having the formula 1.43C:

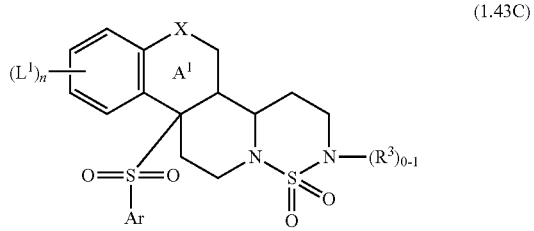

(1.43C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment this invention directed to compounds of the formula 1.0 having the formula 1.44C:

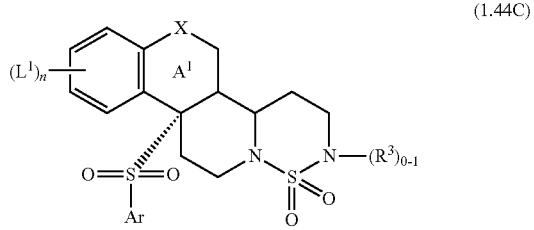

(1.44C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment this invention directed to compounds of the formula 1.0 having the formula 1.45C:

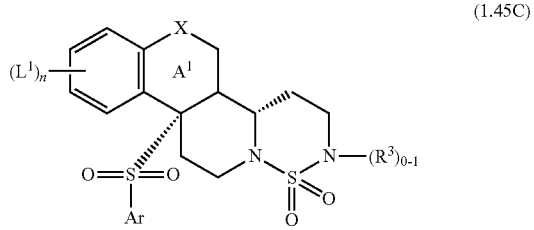

(1.45C)

wherein all substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

Another embodiment of this invention is directed to any one of the embodiments directed to the compounds of formulas: 1.18, 1.19, 1.20, 1.18A, 1.19A, 1.20A, 1.21, 1.22, 1.21A, 1.22A, 1.23, 1.24, 1.25, 1.23A, 1.24A, 1.25A, 1.26, 1.27, 1.28, 1.29, 1.30, 1.31, 1.32, 1.33, 1.34, 1.35, 1.36, 1.37, 1.38, 1.39, 1.35C, 1.36C, 1.37C, 1.38C, 1.39C, 1.35D, 1.36D, 1.37D, 1.38D, 1.39D, 1.35E, 1.36E, 1.37E, 1.38E, 1.39E, 1.40, 1.41, 1.42, 1.40C, 1.41C, 1.42C, 1.43, 1.44, 1.45, 1.43C, 1.44C, and 1.45C wherein the H bound to the carbon at the ring juncture of rings $A^1$ and Q is cis to the —$SO_2Ar$ moiety, that is the —$SO_2Ar$ moiety has the stereochemistry

and the H at the $A^1$ and Q ring juncture has the stereochemistry

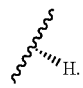

Another embodiment of this invention is directed to any one of the embodiments directed to the compounds of formulas: 1.18, 1.19, 1.20, 1.18A, 1.19A, 1.20A, 1.21, 1.22, 1.21A, 1.22A, 1.23, 1.24, 1.25, 1.23A, 1.24A, 1.25A, 1.26, 1.27, 1.28, 1.29, 1.30, 1.31, 1.32, 1.33, 1.34, 1.35, 1.36, 1.37, 1.38, 1.39, 1.35C, 1.36C, 1.37C, 1.38C, 1.39C, 1.35D, 1.36D, 1.35E, 1.36E, 1.40, 1.41, 1.42, 1.40C, 1.41C, and 1.42C, wherein the H bound to the carbon at the ring juncture of rings $A^1$ and Q is cis to the —$SO_2Ar$ moiety, that is the —$SO_2Ar$ moiety has the stereochemistry

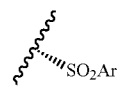

and the H at the $A^1$ and Q ring juncture has the stereochemistry

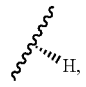

and the $R^3$ groups have the stereochemistry

In another embodiment of this invention the compound of formula 1.0 is a compound of formula 1.1, and X is O.

In another embodiment of this invention the compound of formula 1.0 is a compound of formula 1.1 and $L^1$ is halo.

In another embodiment of this invention the compound of formula 1.0 is a compound of formula 1.1, said compound having the formula (1.1A):

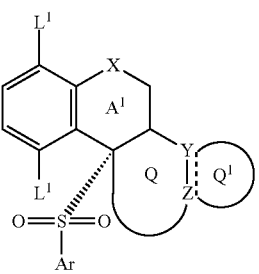

(1.1A)

wherein each $L^1$ is the same or different halo. All other substituents are as defined for formula 1.0.

In another embodiment of this invention the compound of formula 1.0 is a compound of formula 1.1A, wherein each $L^1$ is the same halo. All other substituents are as defined for formula 1.0.

In another embodiment of this invention the compound of formula 1.0 is a compound of formula 1.1, n is 2 and $L^1$ is F.

In another embodiment of this invention the compound of formula 1.0 is a compound of formula 1.1A, wherein each $L^1$ is F. All other substituents are as defined for formula 1.0.

In another embodiment of this invention the compound of formula 1.0 is a compound of formula 1.1 and Ar is phenyl.

In another embodiment of this invention the compound of formula 1.0 is a compound of formula 1.1, Ar is phenyl substituted with halo.

In another embodiment of this invention the compound of formula 1.0 is a compound of formula 1.1 and Ar is phenyl substituted with one halo.

In another embodiment of this invention the compound of formula 1.0 is a compound of formula 1.1 and Ar is:

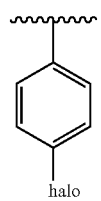
halo

In another embodiment of this invention the compound of formula 1.0 is a compound of formula 1.1 and Ar is phenyl substituted with at least one Cl.

In another embodiment of this invention the compound of formula 1.0 is a compound of formula 1.1 and Ar is phenyl substituted with a Cl.

In another embodiment of this invention the compound of formula 1.0 is a compound of formula 1.1 and Ar is:

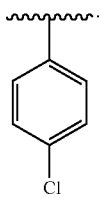
Cl

In another embodiment of this invention the compound of formula 1.0 is a compound of formula 1.1, Ar is phenyl substituted with —$CF_3$.

In another embodiment of this invention the compound of formula 1.0 is a compound of formula 1.1 and Ar is phenyl substituted with one —$CF_3$.

In another embodiment of this invention the compound of formula 1.0 is a compound of formula 1.1 and Ar is:

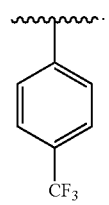
$CF_3$

In another embodiment of this invention the compound of formula 1.0 is a compound of formula 1.1, Ar is phenyl substituted with —CN.

In another embodiment of this invention the compound of formula 1.0 is a compound of formula 1.1 and Ar is phenyl substituted with one —CN.

In another embodiment of this invention the compound of formula 1.0 is a compound of formula 1.1 and Ar is:

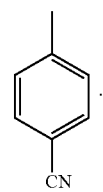
CN

In another embodiment of this invention the compound of formula 1.0 is a compound of formula 1.1, X is O, n is 2, each $L^1$ is halo, and Ar is phenyl substituted with at least one halo.

In another embodiment of this invention the compound of formula 1.0 is a compound of formula 1.1, X is O, n is 2, each $L^1$ is the same or different halo, and Ar is phenyl substituted with one halo.

In another embodiment of this invention the compound of formula 1.0 is a compound of formula 1.1, X is O, n is 2, $L^1$ is F, and Ar is phenyl substituted with one Cl.

In another embodiment of this invention the compound of formula 1.0 is a compound of formula 1.1, X is O, n is 2, each $L^1$ is the same or different halo, and Ar is:

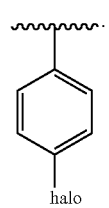
halo

In another embodiment of this invention the compound of formula 1.0 is a compound of formula 1.1, X is O, n is 2, each $L^1$ is the same or different halo, and Ar is:

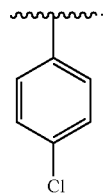

In another embodiment of this invention the compound of formula 1.0 is a compound of formula 1.1, X is O, n is 2, each $L^1$ is halo, and Ar is phenyl substituted with at least one —$CF_3$.

In another embodiment of this invention the compound of formula 1.0 is a compound of formula 1.1, X is O, n is 2, each $L^1$ is the same or different halo, and Ar is phenyl substituted with one —$CF_3$.

In another embodiment of this invention the compound of formula 1.0 is a compound of formula 1.1, X is O, n is 2, $L^1$ is F, and Ar is phenyl substituted with one —$CF_3$.

In another embodiment of this invention the compound of formula 1.0 is a compound of formula 1.1, X is O, n is 2, each $L^1$ is the same or different halo, and Ar is:

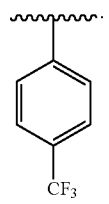

In another embodiment of this invention the compound of formula 1.0 is a compound of formula 1.1, X is O, n is 2 each $L^1$ is halo, and Ar is phenyl substituted with at least one —CN.

In another embodiment of this invention the compound of formula 1.0 is a compound of formula 1.1, X is O, n is 2, each $L^1$ is the same or different halo, and Ar is phenyl substituted with one —CN.

In another embodiment of this invention the compound of formula 1.0 is a compound of formula 1.1, X is O, n is 2, $L^1$ is F, and Ar is phenyl substituted with one —CN.

In another embodiment of this invention the compound of formula 1.0 is a compound of formula 1.1, X is O, n is 2, each $L^1$ is the same or different halo, and Ar is:

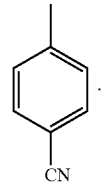

In another embodiment of this invention the compound of formula 1.0 is a compound of formula 1.1, said compound having the formula (1.1A):

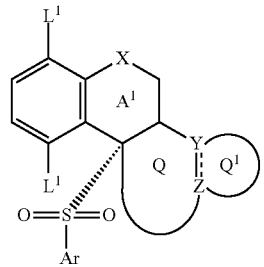

(1.1A)

wherein X is O, each $L^1$ is the same or different halo, and Ar is phenyl substituted with at least one halo.

In another embodiment of this invention the compound of formula 1.0 is a compound of formula 1.1A, wherein X is O, each $L^1$ is the same or different halo, and Ar is phenyl substituted with one halo.

In another embodiment of this invention the compound of formula 1.0 is a compound of formula 1.1A, wherein X is O, each $L^1$ is the same or different halo, and Ar is:

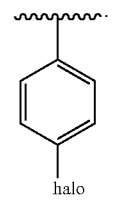

In another embodiment of this invention the compound of formula 1.0 is a compound of formula 1.1A, wherein X is O, each $L^1$ is the same or different halo, and Ar is phenyl substituted with one Cl.

In another embodiment of this invention the compound of formula 1.0 is a compound of formula 1.1A, wherein X is O, each $L^1$ is the same or different halo, and Ar is:

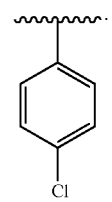

In another embodiment of this invention the compound of formula 1.0 is a compound of formula 1.1A, X is O, each $L^1$ is halo, and Ar is phenyl substituted with at least one —$CF_3$.

In another embodiment of this invention the compound of formula 1.0 is a compound of formula 1.1A, X is O, n is 2, each $L^1$ is the same or different halo, and Ar is phenyl substituted with one —$CF_3$.

In another embodiment of this invention the compound of formula 1.0 is a compound of formula 1.1A, X is O, n is 2, each $L^1$ is the same or different halo, and Ar is:

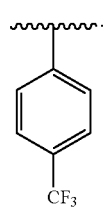

In another embodiment of this invention the compound of formula 1.0 is a compound of formula 1.1A, X is O, each $L^1$ is halo, and Ar is phenyl substituted with at least one —CN.

In another embodiment of this invention the compound of formula 1.0 is a compound of formula 1.1A, X is O, each $L^1$ is the same or different halo, and Ar is phenyl substituted with one —CN.

In another embodiment of this invention the compound of formula 1.0 is a compound of formula 1.1A, X is O, each $L^1$ is the same or different halo, and Ar is:

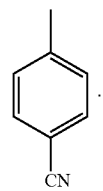

In another embodiment of this invention the compound of formula 1.0 is a compound having the formula (2.1A):

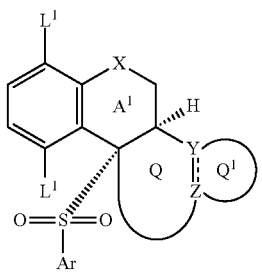

(2.1A)

wherein X is O, each $L^1$ is the same or different halo, and Ar is phenyl substituted with at least one halo.

In another embodiment of this invention the compound of formula 1.0 is a compound of formula (2.1A), wherein X is O, each $L^1$ is the same or different halo, and Ar is phenyl substituted with one halo.

In another embodiment of this invention the compound of formula 1.0 is a compound of formula (2.1A), wherein X is O, each $L^1$ is the same or different halo, and Ar is:

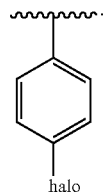

In another embodiment of this invention the compound of formula 1.0 is a compound of formula (2.1A), wherein X is O, each $L^1$ is the same or different halo, and Ar is phenyl substituted with one Cl.

In another embodiment of this invention the compound of formula 1.0 is a compound of formula (2.1A), wherein X is O, each $L^1$ is the same or different halo, and Ar is:

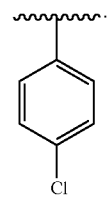

In another embodiment of this invention the compound of formula 1.0 is a compound of formula (2.1A), X is O, each $L^1$ is halo, and Ar is phenyl substituted with at least one —CF$_3$.

In another embodiment of this invention the compound of formula 1.0 is a compound of formula (2.1A), X is O, n is 2, each $L^1$ is the same or different halo, and Ar is phenyl substituted with one —CF$_3$.

In another embodiment of this invention the compound of formula 1.0 is a compound of formula (2.1A), X is O, n is 2, each $L^1$ is the same or different halo, and Ar is:

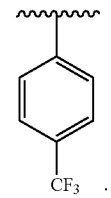

In another embodiment of this invention the compound of formula 1.0 is a compound of formula (2.1A), X is O, each $L^1$ is halo, and Ar is phenyl substituted with at least one —CN.

In another embodiment of this invention the compound of formula 1.0 is a compound of formula (2.1A), X is O, each $L^1$ is the same or different halo, and Ar is phenyl substituted with one —CN.

In another embodiment of this invention the compound of formula 1.0 is a compound of formula (2.1A), X is O, each $L^1$ is the same or different halo, and Ar is:

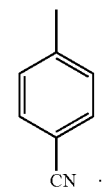

In another embodiment of this invention the compound of formula 1.0 is a compound of formula 1.2, and X is O.

In another embodiment of this invention the compound of formula 1.0 is a compound of formula 1.2 and $L^1$ is halo.

In another embodiment of this invention the compound of formula 1.0 is a compound of formula 1.2, said compound having the formula (1.2A):

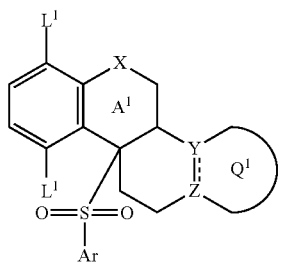
(1.2A)

wherein each $L^1$ is the same or different halo. All other substituents are as defined for formula 1.0.

In another embodiment of this invention the compound of formula 1.0 is a compound of formula 1.2A, wherein each $L^1$ is the same halo. All other substituents are as defined for formula 1.0.

In another embodiment of this invention the compound of formula 1.0 is a compound of formula 1.2, n is 2 and $L^1$ is F.

In another embodiment of this invention the compound of formula 1.0 is a compound of formula 1.2A, wherein each $L^1$ is F. All other substituents are as defined for formula 1.0.

In another embodiment of this invention the compound of formula 1.0 is a compound of formula 1.2 and Ar is phenyl.

In another embodiment of this invention the compound of formula 1.0 is a compound of formula 1.2, Ar is phenyl substituted with halo.

In another embodiment of this invention the compound of formula 1.0 is a compound of formula 1.2 and Ar is phenyl substituted with one halo.

In another embodiment of this invention the compound of formula 1.0 is a compound of formula 1.2 and Ar is:

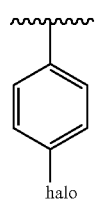

In another embodiment of this invention the compound of formula 1.0 is a compound of formula 1.2 and Ar is phenyl substituted with at least one Cl.

In another embodiment of this invention the compound of formula 1.0 is a compound of formula 1.2 and Ar is phenyl substituted with a Cl.

In another embodiment of this invention the compound of formula 1.0 is a compound of formula 1.2 and Ar is:

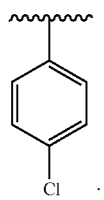

In another embodiment of this invention the compound of formula 1.0 is a compound of formula 1.2, Ar is phenyl substituted with —$CF_3$.

In another embodiment of this invention the compound of formula 1.0 is a compound of formula 1.2 and Ar is phenyl substituted with one —$CF_3$.

In another embodiment of this invention the compound of formula 1.0 is a compound of formula 1.2 and Ar is:

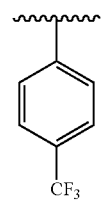

In another embodiment of this invention the compound of formula 1.0 is a compound of formula 1.2, Ar is phenyl substituted with —CN.

In another embodiment of this invention the compound of formula 1.0 is a compound of formula 1.2 and Ar is phenyl substituted with one —CN.

In another embodiment of this invention the compound of formula 1.0 is a compound of formula 1.2 and Ar is:

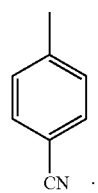

In another embodiment of this invention the compound of formula 1.0 is a compound of formula 1.2, X is O, each $L^1$ is halo, and Ar is phenyl substituted with at least one halo.

In another embodiment of this invention the compound of formula 1.0 is a compound of formula 1.2, X is O, n is 2, each $L^1$ is the same or different halo, and Ar is phenyl substituted with one halo.

In another embodiment of this invention the compound of formula 1.0 is a compound of formula 1.2, X is O, n is 2, $L^1$ is F, and Ar is phenyl substituted with one Cl.

In another embodiment of this invention the compound of formula 1.0 is a compound of formula 1.2, X is O, n is 2, each $L^1$ is the same or different halo, and Ar is:

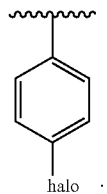

In another embodiment of this invention the compound of formula 1.0 is a compound of formula 1.2, X is O, n is 2, each $L^1$ is the same or different halo, and Ar is:

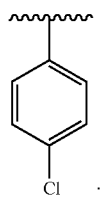

In another embodiment of this invention the compound of formula 1.0 is a compound of formula 1.2, X is O, n is 2, each $L^1$ is halo, and Ar is phenyl substituted with at least one —$CF_3$.

In another embodiment of this invention the compound of formula 1.0 is a compound of formula 1.2, X is O, n is 2, each $L^1$ is the same or different halo, and Ar is phenyl substituted with one —$CF_3$.

In another embodiment of this invention the compound of formula 1.0 is a compound of formula 1.2, X is O, n is 2, $L^1$ is F, and Ar is phenyl substituted with one —$CF_3$.

In another embodiment of this invention the compound of formula 1.0 is a compound of formula 1.2, X is O, n is 2, each $L^1$ is the same or different halo, and Ar is:

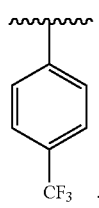 [SMILES: *c1ccc(C(F)(F)F)cc1]

In another embodiment of this invention the compound of formula 1.0 is a compound of formula 1.2, X is O, n is 2 each $L^1$ is halo, and Ar is phenyl substituted with at least one —CN.

In another embodiment of this invention the compound of formula 1.0 is a compound of formula 1.2, X is O, n is 2, each $L^1$ is the same or different halo, and Ar is phenyl substituted with one —CN.

In another embodiment of this invention the compound of formula 1.0 is a compound of formula 1.2, X is O, n is 2, $L^1$ is F, and Ar is phenyl substituted with one —CN.

In another embodiment of this invention the compound of formula 1.0 is a compound of formula 1.2, X is O, n is 2, each $L^1$ is the same or different halo, and Ar is:

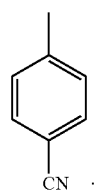

In another embodiment of this invention the compound of formula 1.0 is a compound of formula 1.2, said compound having the formula (1.2A):

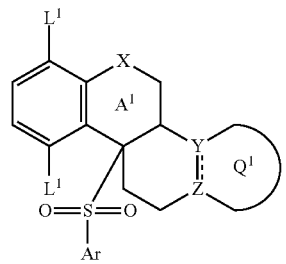

(1.2A)

wherein X is O, n is 2, each $L^1$ is the same or different halo, and Ar is phenyl substituted with at least one halo.

In another embodiment of this invention the compound of formula 1.0 is a compound of formula 1.2A, wherein X is O, each $L^1$ is the same or different halo, and Ar is phenyl substituted with one halo.

In another embodiment of this invention the compound of formula 1.0 is a compound of formula 1.2A, wherein X is O, each $L^1$ is the same or different halo, and Ar is:

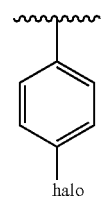

In another embodiment of this invention the compound of formula 1.0 is a compound of formula 1.2A, wherein X is O, each $L^1$ is the same or different halo, and Ar is phenyl substituted with one Cl.

In another embodiment of this invention the compound of formula 1.0 is a compound of formula 1.2A, wherein X is O, each $L^1$ is the same or different halo, and Ar is:

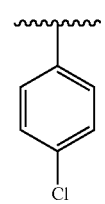

In another embodiment of this invention the compound of formula 1.0 is a compound of formula 1.2A, X is O, each $L^1$ is halo, and Ar is phenyl substituted with at least one —$CF_3$.

In another embodiment of this invention the compound of formula 1.0 is a compound of formula 1.2A, X is O, n is 2, each $L^1$ is the same or different halo, and Ar is phenyl substituted with one —$CF_3$.

In another embodiment of this invention the compound of formula 1.0 is a compound of formula 1.2A, X is O, n is 2, each $L^1$ is the same or different halo, and Ar is:

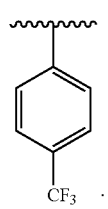

In another embodiment of this invention the compound of formula 1.0 is a compound of formula 1.2A, X is O, each $L^1$ is halo, and Ar is phenyl substituted with at least one —CN.

In another embodiment of this invention the compound of formula 1.0 is a compound of formula 1.2A, X is O, each $L^1$ is the same or different halo, and Ar is phenyl substituted with one —CN.

In another embodiment of this invention the compound of formula 1.0 is a compound of formula 1.2A, X is O, each $L^1$ is the same or different halo, and Ar is:

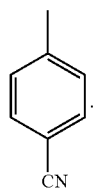

In another embodiment of this invention the compound of formula 1.0 is a compound of formula 1.3, and X is O.

In another embodiment of this invention the compound of formula 1.0 is a compound of formula 1.3 and $L^1$ is halo.

In another embodiment of this invention the compound of formula 1.0 is a compound of formula 1.3, said compound having the formula (1.3A):

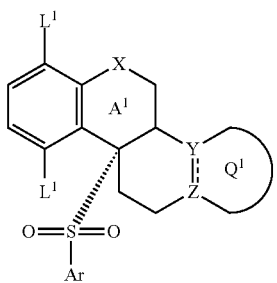

(1.3A)

wherein each $L^1$ is the same or different halo. All other substituents are as defined for formula 1.0.

In another embodiment of this invention the compound of formula 1.0 is a compound of formula 1.3A, wherein each $L^1$ is the same halo. All other substituents are as defined for formula 1.0.

In another embodiment of this invention the compound of formula 1.0 is a compound of formula 1.3, n is 2 and $L^1$ is F.

In another embodiment of this invention the compound of formula 1.0 is a compound of formula 1.3A, wherein each $L^1$ is F. All other substituents are as defined for formula 1.0.

In another embodiment of this invention the compound of formula 1.0 is a compound of formula 1.3 and Ar is phenyl.

In another embodiment of this invention the compound of formula 1.0 is a compound of formula 1.3, Ar is phenyl substituted with halo.

In another embodiment of this invention the compound of formula 1.0 is a compound of formula 1.3 and Ar is phenyl substituted with one halo.

In another embodiment of this invention the compound of formula 1.0 is a compound of formula 1.3 and Ar is:

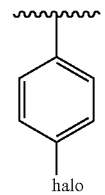

In another embodiment of this invention the compound of formula 1.0 is a compound of formula 1.3 and Ar is phenyl substituted with at least one Cl.

In another embodiment of this invention the compound of formula 1.0 is a compound of formula 1.3 and Ar is phenyl substituted with a Cl.

In another embodiment of this invention the compound of formula 1.0 is a compound of formula 1.3 and Ar is:

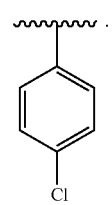

In another embodiment of this invention the compound of formula 1.0 is a compound of formula 1.3, Ar is phenyl substituted with —$CF_3$.

In another embodiment of this invention the compound of formula 1.0 is a compound of formula 1.3 and Ar is phenyl substituted with one —$CF_3$.

In another embodiment of this invention the compound of formula 1.0 is a compound of formula 1.3 and Ar is:

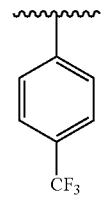 [SMILES: *c1ccc(C(F)(F)F)cc1]

In another embodiment of this invention the compound of formula 1.0 is a compound of formula 1.3, Ar is phenyl substituted with —CN.

In another embodiment of this invention the compound of formula 1.0 is a compound of formula 1.3 and Ar is phenyl substituted with one —CN.

In another embodiment of this invention the compound of formula 1.0 is a compound of formula 1.3 and Ar is:

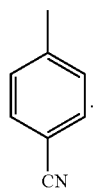

In another embodiment of this invention the compound of formula 1.0 is a compound of formula 1.3, X is O, each $L^1$ is halo, and Ar is phenyl substituted with at least one halo.

In another embodiment of this invention the compound of formula 1.0 is a compound of formula 1.3, X is O, n is 2, each $L^1$ is the same or different halo, and Ar is phenyl substituted with one halo.

In another embodiment of this invention the compound of formula 1.0 is a compound of formula 1.3, X is O, n is 2, $L^1$ is F, and Ar is phenyl substituted with one Cl.

In another embodiment of this invention the compound of formula 1.0 is a compound of formula 1.3, X is O, n is 2, each $L^1$ is the same or different halo, and Ar is:

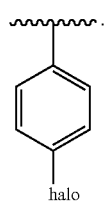

In another embodiment of this invention the compound of formula 1.0 is a compound of formula 1.3, X is O, n is 2, each $L^1$ is the same or different halo, and Ar is:

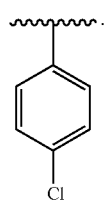

In another embodiment of this invention the compound of formula 1.0 is a compound of formula 1.3, X is O, n is 2, each $L^1$ is halo, and Ar is phenyl substituted with at least one —$CF_3$.

In another embodiment of this invention the compound of formula 1.0 is a compound of formula 1.3, X is O, n is 2, each $L^1$ is the same or different halo, and Ar is phenyl substituted with one —$CF_3$.

In another embodiment of this invention the compound of formula 1.0 is a compound of formula 1.2, X is O, n is 2, $L^1$ is F, and Ar is phenyl substituted with one —$CF_3$.

In another embodiment of this invention the compound of formula 1.0 is a compound of formula 1.3, X is O, n is 2, each $L^1$ is the same or different halo, and Ar is:

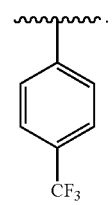

In another embodiment of this invention the compound of formula 1.0 is a compound of formula 1.3, X is O, n is 2 each $L^1$ is halo, and Ar is phenyl substituted with at least one —CN.

In another embodiment of this invention the compound of formula 1.0 is a compound of formula 1.3, X is O, n is 2, each $L^1$ is the same or different halo, and Ar is phenyl substituted with one —CN.

In another embodiment of this invention the compound of formula 1.0 is a compound of formula 1.3, X is O, n is 2, $L^1$ is F, and Ar is phenyl substituted with one —CN.

In another embodiment of this invention the compound of formula 1.0 is a compound of formula 1.3, X is O, n is 2, each $L^1$ is the same or different halo, and Ar is:

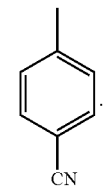

In another embodiment of this invention the compound of formula 1.0 is a compound of formula 1.3, said compound having the formula (1.3A):

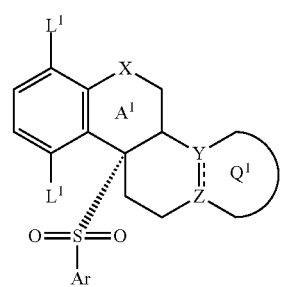

(1.3A)

wherein X is O, each $L^1$ is the same or different halo, and Ar is phenyl substituted with at least one halo.

In another embodiment of this invention the compound of formula 1.0 is a compound of formula 1.3A, wherein X is O, each $L^1$ is the same or different halo, and Ar is phenyl substituted with one halo.

In another embodiment of this invention the compound of formula 1.0 is a compound of formula 1.3A, wherein X is O, each $L^1$ is the same or different halo, and Ar is:

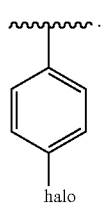
halo

In another embodiment of this invention the compound of formula 1.0 is a compound of formula 1.3A, wherein X is O, each $L^1$ is the same or different halo, and Ar is phenyl substituted with one Cl.

In another embodiment of this invention the compound of formula 1.0 is a compound of formula 1.3A, wherein X is O, each $L^1$ is the same or different halo, and Ar is:

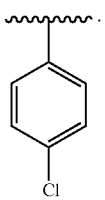 [SMILES: *c1ccc(Cl)cc1]
Cl

In another embodiment of this invention the compound of formula 1.0 is a compound of formula 1.3A, X is O, each $L^1$ is halo, and Ar is phenyl substituted with at least one —$CF_3$.

In another embodiment of this invention the compound of formula 1.0 is a compound of formula 1.3A, X is O, each $L^1$ is the same or different halo, and Ar is phenyl substituted with one —$CF_3$.

In another embodiment of this invention the compound of formula 1.0 is a compound of formula 1.3A, X is O, each $L^1$ is the same or different halo, and Ar is:

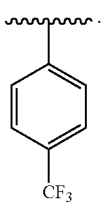 [SMILES: *c1ccc(C(F)(F)F)cc1]
$CF_3$

In another embodiment of this invention the compound of formula 1.0 is a compound of formula 1.3A, X is O, each $L^1$ is halo, and Ar is phenyl substituted with at least one —CN.

In another embodiment of this invention the compound of formula 1.0 is a compound of formula 1.3A, X is O, each $L^1$ is the same or different halo, and Ar is phenyl substituted with one —CN.

In another embodiment of this invention the compound of formula 1.0 is a compound of formula 1.3A, X is O, each $L^1$ is the same or different halo, and Ar is:

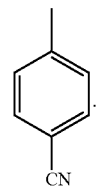
CN

In another embodiment of this invention the compound of formula 1.0 is a compound of the formula (2.3A):

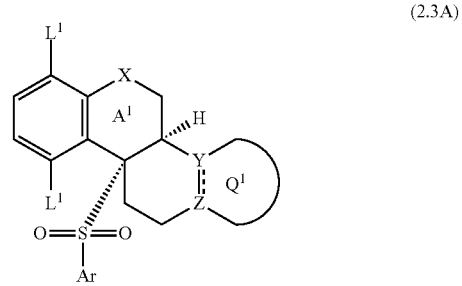

(2.3A)

wherein X is O, each $L^1$ is the same or different halo, and Ar is phenyl substituted with at least one halo.

In another embodiment of this invention the compound of formula 1.0 is a compound of formula 2.3A, wherein X is O, each $L^1$ is the same or different halo, and Ar is phenyl substituted with one halo.

In another embodiment of this invention the compound of formula 1.0 is a compound of formula 2.3A, wherein X is O, each $L^1$ is the same or different halo, and Ar is:

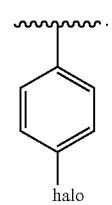
halo

In another embodiment of this invention the compound of formula 1.0 is a compound of formula 2.3A, wherein X is O, each $L^1$ is the same or different halo, and Ar is phenyl substituted with one Cl.

In another embodiment of this invention the compound of formula 1.0 is a compound of formula 2.3A, wherein X is O, each $L^1$ is the same or different halo, and Ar is:

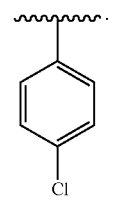
Cl

In another embodiment of this invention the compound of formula 1.0 is a compound of formula 2.3A, X is O, each $L^1$ is halo, and Ar is phenyl substituted with at least one —$CF_3$.

In another embodiment of this invention the compound of formula 1.0 is a compound of formula 2.3A, X is O, each $L^1$ is the same or different halo, and Ar is phenyl substituted with one —$CF_3$.

In another embodiment of this invention the compound of formula 1.0 is a compound of formula 2.3A, X is O, each $L^1$ is the same or different halo, and Ar is:

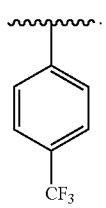

In another embodiment of this invention the compound of formula 1.0 is a compound of formula 2.3A, X is O, each $L^1$ is halo, and Ar is phenyl substituted with at least one —CN.

In another embodiment of this invention the compound of formula 1.0 is a compound of formula 2.3A, X is O, each $L^1$ is the same or different halo, and Ar is phenyl substituted with one —CN.

In another embodiment of this invention the compound of formula 1.0 is a compound of formula 2.3A, X is O, each $L^1$ is the same or different halo, and Ar is:

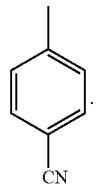

In another embodiment of this invention the compound of formula 1.0 is a compound of formula 1.4, and X is O.

In another embodiment of this invention the compound of formula 1.0 is a compound of formula 1.4 and $L^1$ is halo.

In another embodiment of this invention the compound of formula 1.0 is a compound of formula 1.4, said compound having the formula (1.4A):

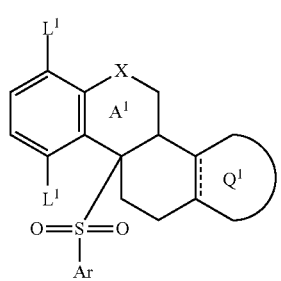

(1.4A)

wherein each $L^1$ is the same or different halo. All other substituents are as defined for formula 1.0.

In another embodiment of this invention the compound of formula 1.0 is a compound of formula 1.4A, wherein each $L^1$ is the same halo. All other substituents are as defined for formula 1.0.

In another embodiment of this invention the compound of formula 1.0 is a compound of formula 1.4, n is 2 and $L^1$ is F.

In another embodiment of this invention the compound of formula 1.0 is a compound of formula 1.4A, wherein each $L^1$ is F. All other substituents are as defined for formula 1.0.

In another embodiment of this invention the compound of formula 1.0 is a compound of formula 1.4 and Ar is phenyl.

In another embodiment of this invention the compound of formula 1.0 is a compound of formula 1.4, Ar is phenyl substituted with halo.

In another embodiment of this invention the compound of formula 1.0 is a compound of formula 1.4 and Ar is phenyl substituted with one halo.

In another embodiment of this invention the compound of formula 1.0 is a compound of formula 1.4 and Ar is:

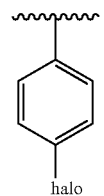

In another embodiment of this invention the compound of formula 1.0 is a compound of formula 1.4 and Ar is phenyl substituted with at least one Cl.

In another embodiment of this invention the compound of formula 1.0 is a compound of formula 1.4 and Ar is phenyl substituted with a Cl.

In another embodiment of this invention the compound of formula 1.0 is a compound of formula 1.4 and Ar is:

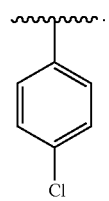

In another embodiment of this invention the compound of formula 1.0 is a compound of formula 1.4, Ar is phenyl substituted with —$CF_3$.

In another embodiment of this invention the compound of formula 1.0 is a compound of formula 1.4 and Ar is phenyl substituted with one —$CF_3$.

In another embodiment of this invention the compound of formula 1.0 is a compound of formula 1.4 and Ar is:

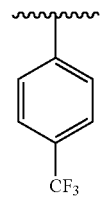 [SMILES: *c1ccc(C(F)(F)F)cc1]

In another embodiment of this invention the compound of formula 1.0 is a compound of formula 1.4, Ar is phenyl substituted with —CN.

In another embodiment of this invention the compound of formula 1.0 is a compound of formula 1.4 and Ar is phenyl substituted with one —CN.

In another embodiment of this invention the compound of formula 1.0 is a compound of formula 1.4 and Ar is:

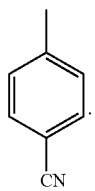

In another embodiment of this invention the compound of formula 1.0 is a compound of formula 1.4, X is O, each L¹ is halo, and Ar is phenyl substituted with at least one halo.

In another embodiment of this invention the compound of formula 1.0 is a compound of formula 1.4, X is O, n is 2, each L¹ is the same or different halo, and Ar is phenyl substituted with one halo.

In another embodiment of this invention the compound of formula 1.0 is a compound of formula 1.4, X is O, n is 2, L¹ is F, and Ar is phenyl substituted with one Cl.

In another embodiment of this invention the compound of formula 1.0 is a compound of formula 1.4, X is O, n is 2, each L¹ is the same or different halo, and Ar is:

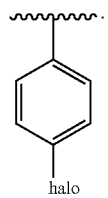

In another embodiment of this invention the compound of formula 1.0 is a compound of formula 1.4, X is O, n is 2, each L¹ is the same or different halo, and Ar is:

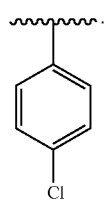

In another embodiment of this invention the compound of formula 1.0 is a compound of formula 1.4, X is O, n is 2, each L¹ is halo, and Ar is phenyl substituted with at least one —CF₃.

In another embodiment of this invention the compound of formula 1.0 is a compound of formula 1.4, X is O, n is 2, each L¹ is the same or different halo, and Ar is phenyl substituted with one —CF₃.

In another embodiment of this invention the compound of formula 1.0 is a compound of formula 1.4, X is O, n is 2, L¹ is F, and Ar is phenyl substituted with one —CF₃.

In another embodiment of this invention the compound of formula 1.0 is a compound of formula 1.4, X is O, n is 2, each L¹ is the same or different halo, and Ar is:

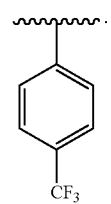

In another embodiment of this invention the compound of formula 1.0 is a compound of formula 1.4, X is O, n is 2 each L¹ is halo, and Ar is phenyl substituted with at least one —CN.

In another embodiment of this invention the compound of formula 1.0 is a compound of formula 1.4, X is O, n is 2, each L¹ is the same or different halo, and Ar is phenyl substituted with one —CN.

In another embodiment of this invention the compound of formula 1.0 is a compound of formula 1.4, X is O, n is 2, L¹ is F, and Ar is phenyl substituted with one —CN.

In another embodiment of this invention the compound of formula 1.0 is a compound of formula 1.4, X is O, n is 2, each L¹ is the same or different halo, and Ar is:

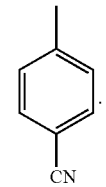

In another embodiment of this invention the compound of formula 1.0 is a compound of formula 1.4, said compound having the formula (1.4A):

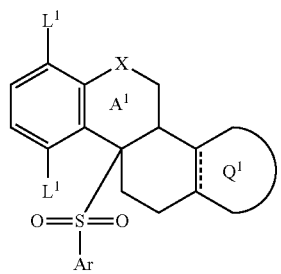

(1.4A)

wherein X is O, each L¹ is the same or different halo, and Ar is phenyl substituted with at least one halo.

In another embodiment of this invention the compound of formula 1.0 is a compound of formula 1.4A, X is O, each L¹ is the same or different halo, and Ar is phenyl substituted with one halo.

In another embodiment of this invention the compound of formula 1.0 is a compound of formula 1.4A, X is O, each L¹ is the same or different halo, and Ar is:

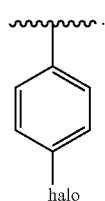

In another embodiment of this invention the compound of formula 1.0 is a compound of formula 1.4A, X is O, each $L^1$ is the same or different halo, and Ar is phenyl substituted with one Cl.

In another embodiment of this invention the compound of formula 1.0 is a compound of formula 1.4A, X is O, each $L^1$ is the same or different halo, and Ar is:

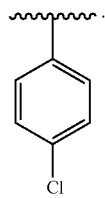

In another embodiment of this invention the compound of formula 1.0 is a compound of formula 1.4A, X is O, each $L^1$ is halo, and Ar is phenyl substituted with at least one —$CF_3$.

In another embodiment of this invention the compound of formula 1.0 is a compound of formula 1.4A, X is O, each $L^1$ is the same or different halo, and Ar is phenyl substituted with one —$CF_3$.

In another embodiment of this invention the compound of formula 1.0 is a compound of formula 1.4A, X is O, each $L^1$ is the same or different halo, and Ar is:

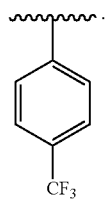

In another embodiment of this invention the compound of formula 1.0 is a compound of formula 1.4A, X is O, each $L^1$ is halo, and Ar is phenyl substituted with at least one —CN.

In another embodiment of this invention the compound of formula 1.0 is a compound of formula 1.4A, X is O, each $L^1$ is the same or different halo, and Ar is phenyl substituted with one —CN.

In another embodiment of this invention the compound of formula 1.0 is a compound of formula 1.4A, X is O, each $L^1$ is the same or different halo, and Ar is:

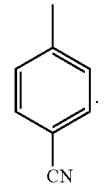

In another embodiment of this invention the compound of formula 1.0 is a compound of formula 1.5, and X is O.

In another embodiment of this invention the compound of formula 1.0 is a compound of formula 1.5 and $L^1$ is halo.

In another embodiment of this invention the compound of formula 1.0 is a compound of formula 1.5, said compound having the formula (1.5A):

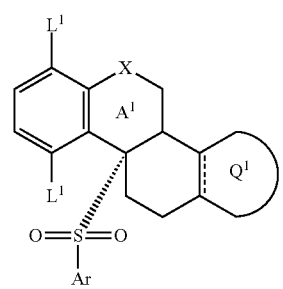

(1.5A)

wherein each $L^1$ is the same or different halo. All other substituents are as defined for formula 1.0.

In another embodiment of this invention the compound of formula 1.0 is a compound of formula 1.5A, wherein each $L^1$ is the same halo. All other substituents are as defined for formula 1.0.

In another embodiment of this invention the compound of formula 1.0 is a compound of formula 1.5, n is 2 and $L^1$ is F.

In another embodiment of this invention the compound of formula 1.0 is a compound of formula 1.5A, wherein each $L^1$ is F. All other substituents are as defined for formula 1.0.

In another embodiment of this invention the compound of formula 1.0 is a compound of formula 1.5 and Ar is phenyl.

In another embodiment of this invention the compound of formula 1.0 is a compound of formula 1.5, Ar is phenyl substituted with halo.

In another embodiment of this invention the compound of formula 1.0 is a compound of formula 1.5 and Ar is phenyl substituted with one halo.

In another embodiment of this invention the compound of formula 1.0 is a compound of formula 1.5 and Ar is:

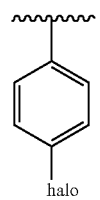

In another embodiment of this invention the compound of formula 1.0 is a compound of formula 1.5 and Ar is phenyl substituted with at least one Cl.

In another embodiment of this invention the compound of formula 1.0 is a compound of formula 1.5 and Ar is phenyl substituted with a Cl.

In another embodiment of this invention the compound of formula 1.0 is a compound of formula 1.5 and Ar is:

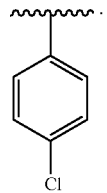

In another embodiment of this invention the compound of formula 1.0 is a compound of formula 1.5, Ar is phenyl substituted with —CF$_3$.

In another embodiment of this invention the compound of formula 1.0 is a compound of formula 1.5 and Ar is phenyl substituted with one —CF$_3$.

In another embodiment of this invention the compound of formula 1.0 is a compound of formula 1.5 and Ar is:

In another embodiment of this invention the compound of formula 1.0 is a compound of formula 1.5, Ar is phenyl substituted with —CN.

In another embodiment of this invention the compound of formula 1.0 is a compound of formula 1.5 and Ar is phenyl substituted with one —CN.

In another embodiment of this invention the compound of formula 1.0 is a compound of formula 1.5 and Ar is:

In another embodiment of this invention the compound of formula 1.0 is a compound of formula 1.5, X is O, each L$^1$ is halo, and Ar is phenyl substituted with at least one halo.

In another embodiment of this invention the compound of formula 1.0 is a compound of formula 1.5, X is O, n is 2, each L$^1$ is the same or different halo, and Ar is phenyl substituted with one halo.

In another embodiment of this invention the compound of formula 1.0 is a compound of formula 1.5, X is O, n is 2, L$^1$ is F, and Ar is phenyl substituted with one Cl.

In another embodiment of this invention the compound of formula 1.0 is a compound of formula 1.5, X is O, n is 2, each L$^1$ is the same or different halo, and Ar is:

In another embodiment of this invention the compound of formula 1.0 is a compound of formula 1.5, X is O, n is 2, each L$^1$ is the same or different halo, and Ar is:

In another embodiment of this invention the compound of formula 1.0 is a compound of formula 1.5, X is O, n is 2, each L$^1$ is halo, and Ar is phenyl substituted with at least one —CF$_3$.

In another embodiment of this invention the compound of formula 1.0 is a compound of formula 1.5, X is O, n is 2, each L$^1$ is the same or different halo, and Ar is phenyl substituted with one —CF$_3$.

In another embodiment of this invention the compound of formula 1.0 is a compound of formula 1.5, X is O, n is 2, L$^1$ is F, and Ar is phenyl substituted with one —CF$_3$.

In another embodiment of this invention the compound of formula 1.0 is a compound of formula 1.5, X is O, n is 2, each L$^1$ is the same or different halo, and Ar is:

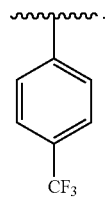

In another embodiment of this invention the compound of formula 1.0 is a compound of formula 1.5, X is O, n is 2 each L$^1$ is halo, and Ar is phenyl substituted with at least one —CN.

In another embodiment of this invention the compound of formula 1.0 is a compound of formula 1.5, X is O, n is 2, each L$^1$ is the same or different halo, and Ar is phenyl substituted with one —CN.

In another embodiment of this invention the compound of formula 1.0 is a compound of formula 1.5, X is O, n is 2, L$^1$ is F, and Ar is phenyl substituted with one —CN.

In another embodiment of this invention the compound of formula 1.0 is a compound of formula 1.5, X is O, n is 2, each L$^1$ is the same or different halo, and Ar is:

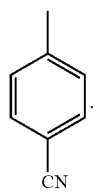

In another embodiment of this invention the compound of formula 1.0 is a compound of formula 1.5, said compound having the formula (1.5A):

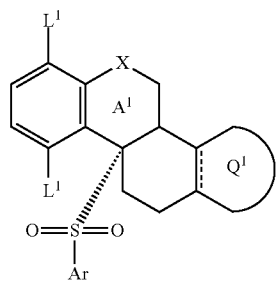

(1.5A)

wherein X is O, each $L^1$ is the same or different halo, and Ar is phenyl substituted with at least one halo.

In another embodiment of this invention the compound of formula 1.0 is a compound of formula 1.5A, X is O, each $L^1$ is the same or different halo, and Ar is phenyl substituted with one halo.

In another embodiment of this invention the compound of formula 1.0 is a compound of formula 1.5A, wherein X is O, each $L^1$ is the same or different halo, and Ar is:

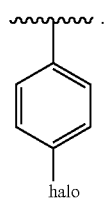

In another embodiment of this invention the compound of formula 1.0 is a compound of formula 1.5A, wherein X is O, each $L^1$ is the same or different halo, and Ar is phenyl substituted with one Cl.

In another embodiment of this invention the compound of formula 1.0 is a compound of formula 1.5A, wherein X is O, each $L^1$ is the same or different halo, and Ar is:

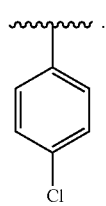

In another embodiment of this invention the compound of formula 1.0 is a compound of formula 1.5A, X is O, each $L^1$ is halo, and Ar is phenyl substituted with at least one —$CF_3$.

In another embodiment of this invention the compound of formula 1.0 is a compound of formula 1.5A, X is O, each $L^1$ is the same or different halo, and Ar is phenyl substituted with one —$CF_3$.

In another embodiment of this invention the compound of formula 1.0 is a compound of formula 1.5A, X is O, each $L^1$ is the same or different halo, and Ar is:

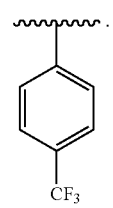

In another embodiment of this invention the compound of formula 1.0 is a compound of formula 1.5A, X is O, each $L^1$ is halo, and Ar is phenyl substituted with at least one —CN.

In another embodiment of this invention the compound of formula 1.0 is a compound of formula 1.5A, X is O, each $L^1$ is the same or different halo, and Ar is phenyl substituted with one —CN.

In another embodiment of this invention the compound of formula 1.0 is a compound of formula 1.5A, X is O, each $L^1$ is the same or different halo, and Ar is:

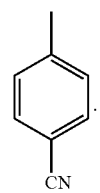

In another embodiment of this invention the compound of formula 1.0 is a compound of formula (2.5A):

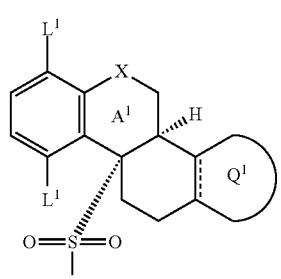

(2.5A)

wherein X is O, each $L^1$ is the same or different halo, and Ar is phenyl substituted with at least one halo.

In another embodiment of this invention the compound of formula 1.0 is a compound of formula 2.5A, X is O, each $L^1$ is the same or different halo, and Ar is phenyl substituted with one halo.

In another embodiment of this invention the compound of formula 1.0 is a compound of formula 2.5A, wherein X is O, each $L^1$ is the same or different halo, and Ar is:

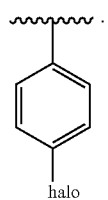

halo

In another embodiment of this invention the compound of formula 1.0 is a compound of formula 2.5A, wherein X is O, each $L^1$ is the same or different halo, and Ar is phenyl substituted with one Cl.

In another embodiment of this invention the compound of formula 1.0 is a compound of formula 2.5A, wherein X is O, each $L^1$ is the same or different halo, and Ar is:

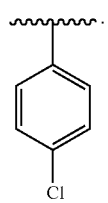

Cl

In another embodiment of this invention the compound of formula 1.0 is a compound of formula 2.5A, X is O, each $L^1$ is halo, and Ar is phenyl substituted with at least one —$CF_3$.

In another embodiment of this invention the compound of formula 1.0 is a compound of formula 2.5A, X is O, each $L^1$ is the same or different halo, and Ar is phenyl substituted with one —$CF_3$.

In another embodiment of this invention the compound of formula 1.0 is a compound of formula 2.5A, X is O, each $L^1$ is the same or different halo, and Ar is:

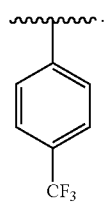

$CF_3$

In another embodiment of this invention the compound of formula 1.0 is a compound of formula 2.5A, X is O, each $L^1$ is halo, and Ar is phenyl substituted with at least one —CN.

In another embodiment of this invention the compound of formula 1.0 is a compound of formula 2.5A, X is O, each $L^1$ is the same or different halo, and Ar is phenyl substituted with one —CN.

In another embodiment of this invention the compound of formula 1.0 is a compound of formula 2.5A, X is O, each $L^1$ is the same or different halo, and Ar is:

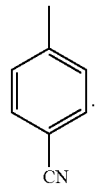

CN

In another embodiment of this invention the compound of formula 1.0 is a compound of formula 1.6, and X is O.

In another embodiment of this invention the compound of formula 1.0 is a compound of formula 1.6 and $L^1$ is halo.

In another embodiment of this invention the compound of formula 1.0 is a compound of formula 1.6, said compound having the formula (1.6A):

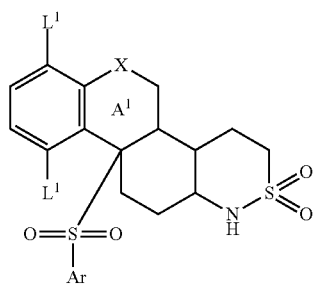

(1.6A)

wherein each $L^1$ is the same or different halo. All other substituents are as defined for formula 1.0.

In another embodiment of this invention the compound of formula 1.0 is a compound of formula 1.6A, wherein each $L^1$ is the same halo. All other substituents are as defined for formula 1.0.

In another embodiment of this invention the compound of formula 1.0 is a compound of formula 1.6, n is 2 and $L^1$ is F.

In another embodiment of this invention the compound of formula 1.0 is a compound of formula 1.6A, wherein each $L^1$ is F. All other substituents are as defined for formula 1.0.

In another embodiment of this invention the compound of formula 1.0 is a compound of formula 1.6 and Ar is phenyl.

In another embodiment of this invention the compound of formula 1.0 is a compound of formula 1.6, Ar is phenyl substituted with halo.

In another embodiment of this invention the compound of formula 1.0 is a compound of formula 1.6 and Ar is phenyl substituted with one halo.

In another embodiment of this invention the compound of formula 1.0 is a compound of formula 1.6 and Ar is:

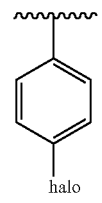

halo

In another embodiment of this invention the compound of formula 1.0 is a compound of formula 1.6 and Ar is phenyl substituted with at least one Cl.

In another embodiment of this invention the compound of formula 1.0 is a compound of formula 1.6 and Ar is phenyl substituted with a Cl.

In another embodiment of this invention the compound of formula 1.0 is a compound of formula 1.6 and Ar is:

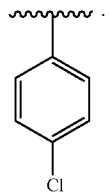

In another embodiment of this invention the compound of formula 1.0 is a compound of formula 1.6, Ar is phenyl substituted with —CF$_3$.

In another embodiment of this invention the compound of formula 1.0 is a compound of formula 1.6 and Ar is phenyl substituted with one —CF$_3$.

In another embodiment of this invention the compound of formula 1.0 is a compound of formula 1.6 and Ar is:

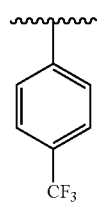

In another embodiment of this invention the compound of formula 1.0 is a compound of formula 1.6, Ar is phenyl substituted with —CN.

In another embodiment of this invention the compound of formula 1.0 is a compound of formula 1.6 and Ar is phenyl substituted with one —CN.

In another embodiment of this invention the compound of formula 1.0 is a compound of formula 1.6 and Ar is:

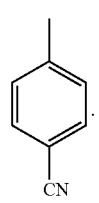

In another embodiment of this invention the compound of formula 1.0 is a compound of formula 1.6, X is O, each L$^1$ is halo, and Ar is phenyl substituted with at least one halo.

In another embodiment of this invention the compound of formula 1.0 is a compound of formula 1.6, X is O, n is 2, each L$^1$ is the same or different halo, and Ar is phenyl substituted with one halo.

In another embodiment of this invention the compound of formula 1.0 is a compound of formula 1.6, X is O, n is 2, L$^1$ is F, and Ar is phenyl substituted with one Cl.

In another embodiment of this invention the compound of formula 1.0 is a compound of formula 1.6, X is O, n is 2, each L$^1$ is the same or different halo, and Ar is:

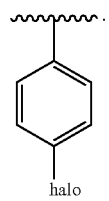

In another embodiment of this invention the compound of formula 1.0 is a compound of formula 1.6, X is O, n is 2, each L$^1$ is the same or different halo, and Ar is:

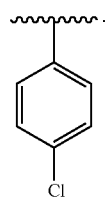

In another embodiment of this invention the compound of formula 1.0 is a compound of formula 1.6, X is O, n is 2, each L$^1$ is halo, and Ar is phenyl substituted with at least one —CF$_3$.

In another embodiment of this invention the compound of formula 1.0 is a compound of formula 1.6, X is O, n is 2, each L$^1$ is the same or different halo, and Ar is phenyl substituted with one —CF$_3$.

In another embodiment of this invention the compound of formula 1.0 is a compound of formula 1.6, X is O, n is 2, L$^1$ is F, and Ar is phenyl substituted with one —CF$_3$.

In another embodiment of this invention the compound of formula 1.0 is a compound of formula 1.6, X is O, n is 2, each L$^1$ is the same or different halo, and Ar is:

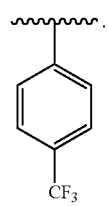

In another embodiment of this invention the compound of formula 1.0 is a compound of formula 1.6, X is O, n is 2 each L$^1$ is halo, and Ar is phenyl substituted with at least one —CN.

In another embodiment of this invention the compound of formula 1.0 is a compound of formula 1.6, X is O, n is 2, each L$^1$ is the same or different halo, and Ar is phenyl substituted with one —CN.

In another embodiment of this invention the compound of formula 1.0 is a compound of formula 1.6, X is O, n is 2, L$^1$ is F, and Ar is phenyl substituted with one —CN.

In another embodiment of this invention the compound of formula 1.0 is a compound of formula 1.6, X is O, n is 2, each L$^1$ is the same or different halo, and Ar is:

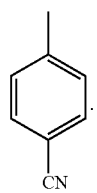

In another embodiment of this invention the compound of formula 1.0 is a compound of formula 1.6, said compound having the formula (1.6A):

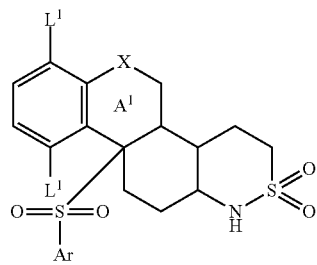
(1.6A)

wherein X is O, each $L^1$ is the same or different halo, and Ar is phenyl substituted with at least one halo.

In another embodiment of this invention the compound of formula 1.0 is a compound of formula 1.6A, wherein X is O, each $L^1$ is the same or different halo, and Ar is phenyl substituted with one halo.

In another embodiment of this invention the compound of formula 1.0 is a compound of formula 1.6A, wherein X is O, each $L^1$ is the same or different halo, and Ar is:

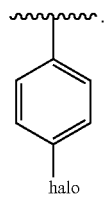

In another embodiment of this invention the compound of formula 1.0 is a compound of formula 1.6A, wherein X is O, each $L^1$ is the same or different halo, and Ar is phenyl substituted with one Cl.

In another embodiment of this invention the compound of formula 1.0 is a compound of formula 1.6A, wherein X is O, each $L^1$ is the same or different halo, and Ar is:

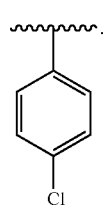

In another embodiment of this invention the compound of formula 1.0 is a compound of formula 1.6A, X is O, each $L^1$ is halo, and Ar is phenyl substituted with at least one —$CF_3$.

In another embodiment of this invention the compound of formula 1.0 is a compound of formula 1.6A, X is O, each $L^1$ is the same or different halo, and Ar is phenyl substituted with one —$CF_3$.

In another embodiment of this invention the compound of formula 1.0 is a compound of formula 1.6A, X is O, each $L^1$ is the same or different halo, and Ar is:

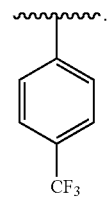

In another embodiment of this invention the compound of formula 1.0 is a compound of formula 1.6A, X is O, each $L^1$ is halo, and Ar is phenyl substituted with at least one —CN.

In another embodiment of this invention the compound of formula 1.0 is a compound of formula 1.6A, X is O, each $L^1$ is the same or different halo, and Ar is phenyl substituted with one —CN.

In another embodiment of this invention the compound of formula 1.0 is a compound of formula 1.6A, X is O, each $L^1$ is the same or different halo, and Ar is:

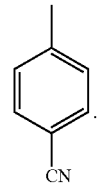

In another embodiment of this invention the compound of formula 1.0 is a compound of formula 1.7, and X is O.

In another embodiment of this invention the compound of formula 1.0 is a compound of formula 1.7 and $L^1$ is halo.

In another embodiment of this invention the compound of formula 1.0 is a compound of formula 1.7, said compound having the formula (1.7A):

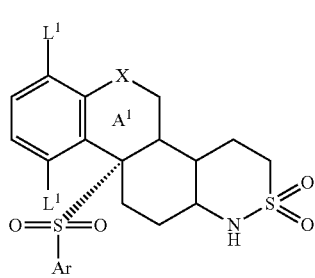
(1.7A)

wherein each $L^1$ is the same or different halo. All other substituents are as defined for formula 1.0.

In another embodiment of this invention the compound of formula 1.0 is a compound of formula 1.7A, wherein each $L^1$ is the same halo. All other substituents are as defined for formula 1.0.

In another embodiment of this invention the compound of formula 1.0 is a compound of formula 1.7, n is 2 and $L^1$ is F.

In another embodiment of this invention the compound of formula 1.0 is a compound of formula 1.7A, wherein each $L^1$ is F. All other substituents are as defined for formula 1.0.

In another embodiment of this invention the compound of formula 1.0 is a compound of formula 1.7 and Ar is phenyl.

In another embodiment of this invention the compound of formula 1.0 is a compound of formula 1.7, Ar is phenyl substituted with halo.

In another embodiment of this invention the compound of formula 1.0 is a compound of formula 1.7 and Ar is phenyl substituted with one halo.

In another embodiment of this invention the compound of formula 1.0 is a compound of formula 1.7 and Ar is:

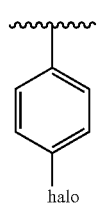

In another embodiment of this invention the compound of formula 1.0 is a compound of formula 1.7 and Ar is phenyl substituted with at least one Cl.

In another embodiment of this invention the compound of formula 1.0 is a compound of formula 1.7 and Ar is phenyl substituted with a Cl.

In another embodiment of this invention the compound of formula 1.0 is a compound of formula 1.7 and Ar is:

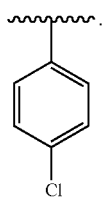

In another embodiment of this invention the compound of formula 1.0 is a compound of formula 1.7, Ar is phenyl substituted with —$CF_3$.

In another embodiment of this invention the compound of formula 1.0 is a compound of formula 1.7 and Ar is phenyl substituted with one —$CF_3$.

In another embodiment of this invention the compound of formula 1.0 is a compound of formula 1.7 and Ar is:

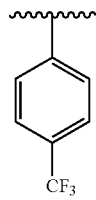

In another embodiment of this invention the compound of formula 1.0 is a compound of formula 1.7, Ar is phenyl substituted with —CN.

In another embodiment of this invention the compound of formula 1.0 is a compound of formula 1.7 and Ar is phenyl substituted with one —CN.

In another embodiment of this invention the compound of formula 1.0 is a compound of formula 1.7 and Ar is:

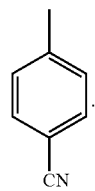

In another embodiment of this invention the compound of formula 1.0 is a compound of formula 1.7, X is O, each $L^1$ is halo, and Ar is phenyl substituted with at least one halo.

In another embodiment of this invention the compound of formula 1.0 is a compound of formula 1.7, X is O, n is 2, each $L^1$ is the same or different halo, and Ar is phenyl substituted with one halo.

In another embodiment of this invention the compound of formula 1.0 is a compound of formula 1.7, X is O, n is 2, $L^1$ is F, and Ar is phenyl substituted with one Cl.

In another embodiment of this invention the compound of formula 1.0 is a compound of formula 1.7, X is O, n is 2, each $L^1$ is the same or different halo, and Ar is:

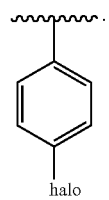

In another embodiment of this invention the compound of formula 1.0 is a compound of formula 1.7, X is O, n is 2, each $L^1$ is the same or different halo, and Ar is:

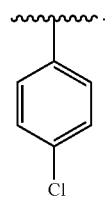 [SMILES: *c1ccc(Cl)cc1]

In another embodiment of this invention the compound of formula 1.0 is a compound of formula 1.7, X is O, n is 2, each $L^1$ is halo, and Ar is phenyl substituted with at least one —$CF_3$.

In another embodiment of this invention the compound of formula 1.0 is a compound of formula 1.7, X is O, n is 2, each $L^1$ is the same or different halo, and Ar is phenyl substituted with one —$CF_3$.

In another embodiment of this invention the compound of formula 1.0 is a compound of formula 1.7, X is O, n is 2, $L^1$ is F, and Ar is phenyl substituted with one —$CF_3$.

In another embodiment of this invention the compound of formula 1.0 is a compound of formula 1.7, X is O, n is 2, each $L^1$ is the same or different halo, and Ar is:

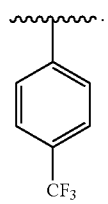

In another embodiment of this invention the compound of formula 1.0 is a compound of formula 1.7, X is O, n is 2 each $L^1$ is halo, and Ar is phenyl substituted with at least one —CN.

In another embodiment of this invention the compound of formula 1.0 is a compound of formula 1.7, X is O, n is 2, each $L^1$ is the same or different halo, and Ar is phenyl substituted with one —CN.

In another embodiment of this invention the compound of formula 1.0 is a compound of formula 1.7, X is O, n is 2, $L^1$ is F, and Ar is phenyl substituted with one —CN.

In another embodiment of this invention the compound of formula 1.0 is a compound of formula 1.7, X is O, n is 2, each $L^1$ is the same or different halo, and Ar is:

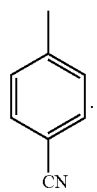

In another embodiment of this invention the compound of formula 1.0 is a compound of formula 1.7, said compound having the formula (1.7A):

(1.7A)

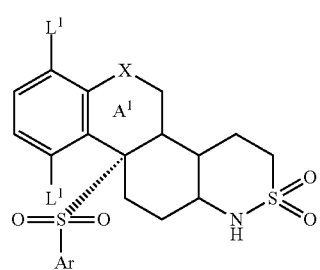

wherein X is O, each $L^1$ is the same or different halo, and Ar is phenyl substituted with at least one halo.

In another embodiment of this invention the compound of formula 1.0 is a compound of formula 1.7A, wherein X is O, each $L^1$ is the same or different halo, and Ar is phenyl substituted with one halo.

In another embodiment of this invention the compound of formula 1.0 is a compound of formula 1.7A, wherein X is O, each $L^1$ is the same or different halo, and Ar is:

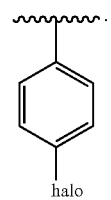

In another embodiment of this invention the compound of formula 1.0 is a compound of formula 1.7A, wherein X is O, each $L^1$ is the same or different halo, and Ar is phenyl substituted with one Cl.

In another embodiment of this invention the compound of formula 1.0 is a compound of formula 1.7A, wherein X is O, each $L^1$ is the same or different halo, and Ar is:

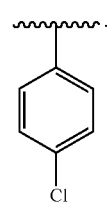 [SMILES: *c1ccc(Cl)cc1]

In another embodiment of this invention the compound of formula 1.0 is a compound of formula 1.7A, X is O, each $L^1$ is halo, and Ar is phenyl substituted with at least one —CF$_3$.

In another embodiment of this invention the compound of formula 1.0 is a compound of formula 1.7A, X is O, each $L^1$ is the same or different halo, and Ar is phenyl substituted with one —CF$_3$.

In another embodiment of this invention the compound of formula 1.0 is a compound of formula 1.7A, X is O, each $L^1$ is the same or different halo, and Ar is:

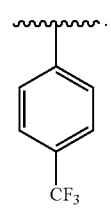 [SMILES: *c1ccc(C(F)(F)F)cc1]

In another embodiment of this invention the compound of formula 1.0 is a compound of formula 1.7A, X is O, each $L^1$ is halo, and Ar is phenyl substituted with at least one —CN.

In another embodiment of this invention the compound of formula 1.0 is a compound of formula 1.7A, X is O, each $L^1$ is the same or different halo, and Ar is phenyl substituted with one —CN.

In another embodiment of this invention the compound of formula 1.0 is a compound of formula 1.7A; X is O, each $L^1$ is the same or different halo, and Ar is:

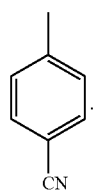

In another embodiment of this invention the compound of formula 1.0 is a compound of the formula (2.7A):

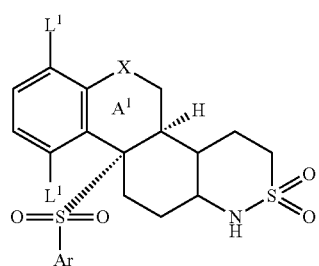
(2.7A)

wherein X is O, each $L^1$ is the same or different halo, and Ar is phenyl substituted with at least one halo.

In another embodiment of this invention the compound of formula 1.0 is a compound of formula 2.7A, wherein X is O, each $L^1$ is the same or different halo, and Ar is phenyl substituted with one halo.

In another embodiment of this invention the compound of formula 1.0 is a compound of formula 2.7A, wherein X is O, each $L^1$ is the same or different halo, and Ar is:

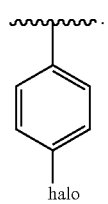

In another embodiment of this invention the compound of formula 1.0 is a compound of formula 2.7A, wherein X is O, each $L^1$ is the same or different halo, and Ar is phenyl substituted with one Cl.

In another embodiment of this invention the compound of formula 1.0 is a compound of formula 2.7A, wherein X is O, each $L^1$ is the same or different halo, and Ar is:

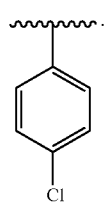 [SMILES: *c1ccc(Cl)cc1]

In another embodiment of this invention the compound of formula 1.0 is a compound of formula 2.7A, X is O, each $L^1$ is halo, and Ar is phenyl substituted with at least one —$CF_3$.

In another embodiment of this invention the compound of formula 1.0 is a compound of formula 2.7A, X is O, each $L^1$ is the same or different halo, and Ar is phenyl substituted with one —$CF_3$.

In another embodiment of this invention the compound of formula 1.0 is a compound of formula 2.7A, X is O, each $L^1$ is the same or different halo, and Ar is:

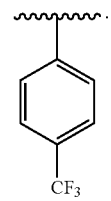 [SMILES: *c1ccc(C(F)(F)F)cc1]

In another embodiment of this invention the compound of formula 1.0 is a compound of formula 2.7A, X is O, each $L^1$ is halo, and Ar is phenyl substituted with at least one —CN.

In another embodiment of this invention the compound of formula 1.0 is a compound of formula 2.7A, X is O, each $L^1$ is the same or different halo, and Ar is phenyl substituted with one —CN.

In another embodiment of this invention the compound of formula 1.0 is a compound of formula 2.7A, X is O, each $L^1$ is the same or different halo, and Ar is:

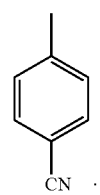

In another embodiment of this invention the compound of formula 1.0 is a compound of formula 1.8, and X is O.

In another embodiment of this invention the compound of formula 1.0 is a compound of formula 1.8 and $L^1$ is halo.

In another embodiment of this invention the compound of formula 1.0 is a compound of formula 1.8, said compound having the formula (1.8A):

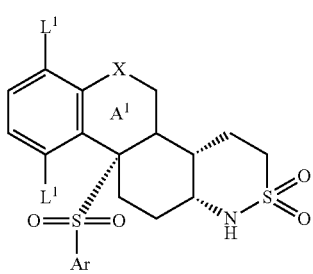
(1.8A)

wherein each $L^1$ is the same or different halo. All other substituents are as defined for formula 1.0.

In another embodiment of this invention the compound of formula 1.0 is a compound of formula 1.8A, wherein each $L^1$ is the same halo. All other substituents are as defined for formula 1.0.

In another embodiment of this invention the compound of formula 1.0 is a compound of formula 1.8, n is 2 and $L^1$ is F.

In another embodiment of this invention the compound of formula 1.0 is a compound of formula 1.8A, wherein each $L^1$ is F. All other substituents are as defined for formula 1.0.

In another embodiment of this invention the compound of formula 1.0 is a compound of formula 1.8 and Ar is phenyl.

In another embodiment of this invention the compound of formula 1.0 is a compound of formula 1.8, Ar is phenyl substituted with halo.

In another embodiment of this invention the compound of formula 1.0 is a compound of formula 1.8 and Ar is phenyl substituted with one halo.

In another embodiment of this invention the compound of formula 1.0 is a compound of formula 1.8 and Ar is:

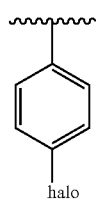

In another embodiment of this invention the compound of formula 1.0 is a compound of formula 1.8 and Ar is phenyl substituted with at least one Cl.

In another embodiment of this invention the compound of formula 1.0 is a compound of formula 1.8 and Ar is phenyl substituted with a Cl.

In another embodiment of this invention the compound of formula 1.0 is a compound of formula 1.8 and Ar is:

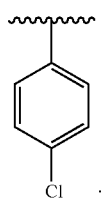

In another embodiment of this invention the compound of formula 1.0 is a compound of formula 1.8, Ar is phenyl substituted with —CF$_3$.

In another embodiment of this invention the compound of formula 1.0 is a compound of formula 1.8 and Ar is phenyl substituted with one —CF$_3$.

In another embodiment of this invention the compound of formula 1.0 is a compound of formula 1.8 and Ar is:

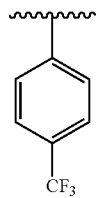

In another embodiment of this invention the compound of formula 1.0 is a compound of formula 1.8, Ar is phenyl substituted with —CN.

In another embodiment of this invention the compound of formula 1.0 is a compound of formula 1.8 and Ar is phenyl substituted with one —CN.

In another embodiment of this invention the compound of formula 1.0 is a compound of formula 1.8 and Ar is:

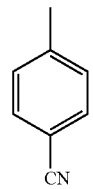

In another embodiment of this invention the compound of formula 1.0 is a compound of formula 1.8, X is O, each $L^1$ is halo, and Ar is phenyl substituted with at least one halo.

In another embodiment of this invention the compound of formula 1.0 is a compound of formula 1.8, X is O, n is 2, each $L^1$ is the same or different halo, and Ar is phenyl substituted with one halo.

In another embodiment of this invention the compound of formula 1.0 is a compound of formula 1.8, X is O, n is 2, $L^1$ is F, and Ar is phenyl substituted with one Cl.

In another embodiment of this invention the compound of formula 1.0 is a compound of formula 1.8, X is O, n is 2, each $L^1$ is the same or different halo, and Ar is:

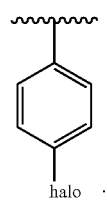

In another embodiment of this invention the compound of formula 1.0 is a compound of formula 1.8, X is O, n is 2, each $L^1$ is the same or different halo, and Ar is:

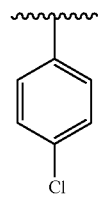

In another embodiment of this invention the compound of formula 1.0 is a compound of formula 1.8, X is O, n is 2, each $L^1$ is halo, and Ar is phenyl substituted with at least one —CF$_3$.

In another embodiment of this invention the compound of formula 1.0 is a compound of formula 1.8, X is O, n is 2, each $L^1$ is the same or different halo, and Ar is phenyl substituted with one —CF$_3$.

In another embodiment of this invention the compound of formula 1.0 is a compound of formula 1.8, X is O, n is 2, $L^1$ is F, and Ar is phenyl substituted with one —CF$_3$.

In another embodiment of this invention the compound of formula 1.0 is a compound of formula 1.8, X is O, n is 2, each $L^1$ is the same or different halo, and Ar is:

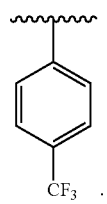

In another embodiment of this invention the compound of formula 1.0 is a compound of formula 1.8, X is O, n is 2 each $L^1$ is halo, and Ar is phenyl substituted with at least one —CN.

In another embodiment of this invention the compound of formula 1.0 is a compound of formula 1.8, X is O, n is 2, each $L^1$ is the same or different halo, and Ar is phenyl substituted with one —CN.

In another embodiment of this invention the compound of formula 1.0 is a compound of formula 1.8, X is O, n is 2, $L^1$ is F, and Ar is phenyl substituted with one —CN.

In another embodiment of this invention the compound of formula 1.0 is a compound of formula 1.8, X is O, n is 2, each $L^1$ is the same or different halo, and Ar is:

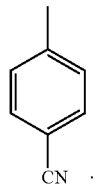

In another embodiment of this invention the compound of formula 1.0 is a compound of formula 1.8, said compound having the formula (1.8A):

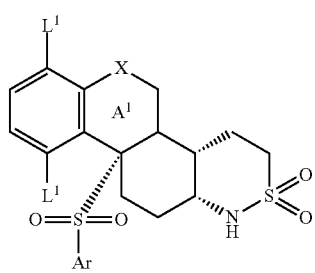

(1.8A)

wherein X is O, each $L^1$ is the same or different halo, and Ar is phenyl substituted with at least one halo.

In another embodiment of this invention the compound of formula 1.0 is a compound of formula 1.8A, wherein X is O, each $L^1$ is the same or different halo, and Ar is phenyl substituted with one halo.

In another embodiment of this invention the compound of formula 1.0 is a compound of formula 1.8A, wherein X is O, each $L^1$ is the same or different halo, and Ar is:

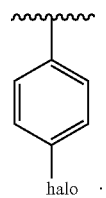

In another embodiment of this invention the compound of formula 1.0 is a compound of formula 1.8A, wherein X is O, each $L^1$ is the same or different halo, and Ar is phenyl substituted with one Cl.

In another embodiment of this invention the compound of formula 1.0 is a compound of formula 1.8A, wherein X is O, each $L^1$ is the same or different halo, and Ar is:

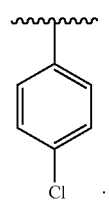

In another embodiment of this invention the compound of formula 1.0 is a compound of formula 1.8A, X is O, each $L^1$ is halo, and Ar is phenyl substituted with at least one —CF$_3$.

In another embodiment of this invention the compound of formula 1.0 is a compound of formula 1.8A, X is O, each $L^1$ is the same or different halo, and Ar is phenyl substituted with one —CF$_3$.

In another embodiment of this invention the compound of formula 1.0 is a compound of formula 1.8A, X is O, each $L^1$ is the same or different halo, and Ar is:

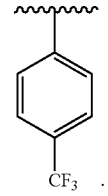

In another embodiment of this invention the compound of formula 1.0 is a compound of formula 1.8A, X is O, each $L^1$ is halo, and Ar is phenyl substituted with at least one —CN.

In another embodiment of this invention the compound of formula 1.0 is a compound of formula 1.8A, X is O, each $L^1$ is the same or different halo, and Ar is phenyl substituted with one —CN.

In another embodiment of this invention the compound of formula 1.0 is a compound of formula 1.8A, X is O, each $L^1$ is the same or different halo, and Ar is:

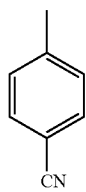

In another embodiment of this invention the compound of formula 1.0 is a compound of the formula (2.8A):

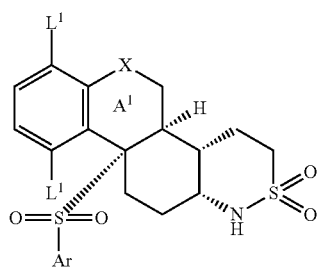

(2.8A)

wherein X is O, each $L^1$ is the same or different halo, and Ar is phenyl substituted with at least one halo.

In another embodiment of this invention the compound of formula 1.0 is a compound of formula 2.8A, wherein X is O, each $L^1$ is the same or different halo, and Ar is phenyl substituted with one halo.

In another embodiment of this invention the compound of formula 1.0 is a compound of formula 2.8A, wherein X is O, each $L^1$ is the same or different halo, and Ar is:

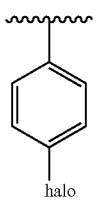

In another embodiment of this invention the compound of formula 1.0 is a compound of formula 2.8A, wherein X is O, each $L^1$ is the same or different halo, and Ar is phenyl substituted with one Cl.

In another embodiment of this invention the compound of formula 1.0 is a compound of formula 2.8A, wherein X is O, each $L^1$ is the same or different halo, and Ar is:

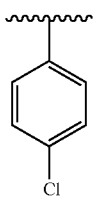

In another embodiment of this invention the compound of formula 1.0 is a compound of formula 2.8A, X is O, each $L^1$ is halo, and Ar is phenyl substituted with at least one —$CF_3$.

In another embodiment of this invention the compound of formula 1.0 is a compound of formula 2.8A, X is O, each $L^1$ is the same or different halo, and Ar is phenyl substituted with one —$CF_3$.

In another embodiment of this invention the compound of formula 1.0 is a compound of formula 2.8A, X is O, each $L^1$ is the same or different halo, and Ar is:

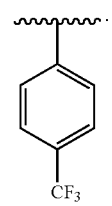

In another embodiment of this invention the compound of formula 1.0 is a compound of formula 2.8A, X is O, each $L^1$ is halo, and Ar is phenyl substituted with at least one —CN.

In another embodiment of this invention the compound of formula 1.0 is a compound of formula 2.8A, X is O, each $L^1$ is the same or different halo, and Ar is phenyl substituted with one —CN.

In another embodiment of this invention the compound of formula 1.0 is a compound of formula 2.8A, X is O, each $L^1$ is the same or different halo, and Ar is:

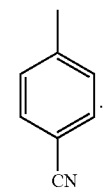

In another embodiment of this invention the compound of formula 1.0 is a compound of formula 1.9, and X is O.

In another embodiment of this invention the compound of formula 1.0 is a compound of formula 1.9 and $L^1$ is halo.

In another embodiment of this invention the compound of formula 1.0 is a compound of formula 1.9, said compound having the formula (1.9A):

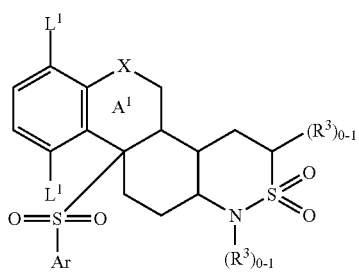

(1.9A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—(R³)₀₋₁ moiety is =N—H (i.e., this N is not substituted). Preferably, the R³ of the CH—R³ moiety is $C_1$-$C_6$ alkyl. Preferably, X=O.

In another embodiment of this invention the compound of formula 1.0 is a compound of formula 1.9A, wherein each $L^1$ is the same halo. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably, the R³ of the CH—R³ moiety is $C_1$-$C_6$ alkyl. Preferably, X=O.

In another embodiment of this invention the compound of formula 1.0 is a compound of formula 1.9, n is 2 and $L^1$ is F.

In another embodiment of this invention the compound of formula 1.0 is a compound of formula 1.9A, wherein each $L^1$ is F. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably, the =N—(R³)₀₋₁ moiety is =N—H (i.e., this N is not substituted). Preferably, the R³ of the CH—R³ moiety is $C_1$-$C_6$ alkyl. Preferably, X=O.

In another embodiment of this invention the compound of formula 1.0 is a compound of formula 1.9 and Ar is phenyl.

In another embodiment of this invention the compound of formula 1.0 is a compound of formula 1.9, Ar is phenyl substituted with halo.

In another embodiment of this invention the compound of formula 1.0 is a compound of formula 1.9 and Ar is phenyl substituted with one halo.

In another embodiment of this invention the compound of formula 1.0 is a compound of formula 1.9 and Ar is:

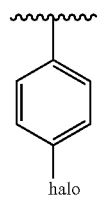

halo

In another embodiment of this invention the compound of formula 1.0 is a compound of formula 1.9 and Ar is phenyl substituted with at least one Cl.

In another embodiment of this invention the compound of formula 1.0 is a compound of formula 1.9 and Ar is phenyl substituted with a Cl.

In another embodiment of this invention the compound of formula 1.0 is a compound of formula 1.9 and Ar is:

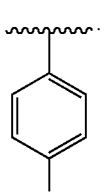

Cl

In another embodiment of this invention the compound of formula 1.0 is a compound of formula 1.9, Ar is phenyl substituted with —$CF_3$.

In another embodiment of this invention the compound of formula 1.0 is a compound of formula 1.9 and Ar is phenyl substituted with one —$CF_3$.

In another embodiment of this invention the compound of formula 1.0 is a compound of formula 1.9 and Ar is:

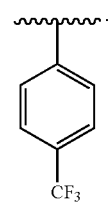

$CF_3$

In another embodiment of this invention the compound of formula 1.0 is a compound of formula 1.9, Ar is phenyl substituted with —CN.

In another embodiment of this invention the compound of formula 1.0 is a compound of formula 1:9 and Ar is phenyl substituted with one —CN.

In another embodiment of this invention the compound of formula 1.0 is a compound of formula 1.9 and Ar is:

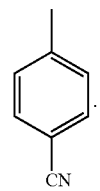

CN

In another embodiment of this invention the compound of formula 1.0 is a compound of formula 1.9, X is O, each $L^1$ is halo, and Ar is phenyl substituted with at least one halo.

In another embodiment of this invention the compound of formula 1.0 is a compound of formula 1.9, X is O, n is 2, each $L^1$ is the same or different halo, and Ar is phenyl substituted with one halo.

In another embodiment of this invention the compound of formula 1.0 is a compound of formula 1.9, X is O, n is 2, $L^1$ is F, and Ar is phenyl substituted with one Cl.

In another embodiment of this invention the compound of formula 1.0 is a compound of formula 1.9, X is O, n is 2, each $L^1$ is the same or different halo, and Ar is:

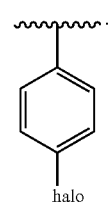

halo

In another embodiment of this invention the compound of formula 1.0 is a compound of formula 1.9, X is O, n is 2, each $L^1$ is the same or different halo, and Ar is:

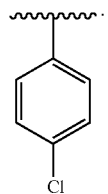 [SMILES: *c1ccc(Cl)cc1]

In another embodiment of this invention the compound of formula 1.0 is a compound of formula 1.9, X is O, n is 2, each $L^1$ is halo, and Ar is phenyl substituted with at least one —$CF_3$.

In another embodiment of this invention the compound of formula 1.0 is a compound of formula 1.9, X is O, n is 2, each $L^1$ is the same or different halo, and Ar is phenyl substituted with one —$CF_3$.

In another embodiment of this invention the compound of formula 1.0 is a compound of formula 1.9, X is O, n is 2, $L^1$ is F, and Ar is phenyl substituted with one —$CF_3$.

In another embodiment of this invention the compound of formula 1.0 is a compound of formula 1.9, X is O, n is 2, each $L^1$ is the same or different halo, and Ar is:

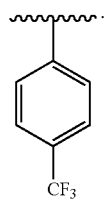

In another embodiment of this invention the compound of formula 1.0 is a compound of formula 1.9, X is O, n is 2 each $L^1$ is halo, and Ar is phenyl substituted with at least one —CN.

In another embodiment of this invention the compound of formula 1.0 is a compound of formula 1.9, X is O, n is 2, each $L^1$ is the same or different halo, and Ar is phenyl substituted with one —CN.

In another embodiment of this invention the compound of formula 1.0 is a compound of formula 1.9, X is O, n is 2, $L^1$ is F, and Ar is phenyl substituted with one —CN.

In another embodiment of this invention the compound of formula 1.0 is a compound of formula 1.9, X is O, n is 2, each $L^1$ is the same or different halo, and Ar is:

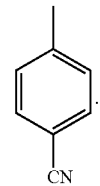

In another embodiment of this invention the compound of formula 1.0 is a compound of formula $1.9^{41}$, said compound having the formula ($1.9^{42}$):

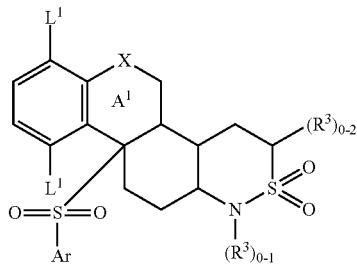

wherein all substituents are as defined for the compounds of formula $1.9^{41}$.

In another embodiment of this invention, for the compounds of formula $1.9^{42}$, X is O, each $L^1$ is the same or different halo, and Ar is phenyl substituted with at least one halo.

In another embodiment of this invention, for the compounds of formula $1.9^{42}$, X is O, each $L^1$ is the same or different halo, and Ar is phenyl substituted with one halo.

In another embodiment of this invention, for the compounds of formula $1.9^{42}$, X is O, each $L^1$ is the same or different halo, and Ar is:

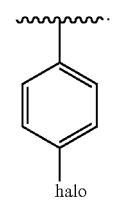

In another embodiment of this invention, for the compounds of formula $1.9^{42}$, X is O, each $L^1$ is the same or different halo, and Ar is phenyl substituted with one Cl.

In another embodiment of this invention, for the compounds of formula $1.9^{42}$, X is O, each $L^1$ is the same or different halo, and Ar is

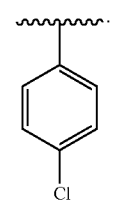 [SMILES: *c1ccc(Cl)cc1]

In another embodiment of this invention, for the compounds of formula $1.9^{42}$, X is O, each $L^1$ is the same or different halo, and Ar is phenyl substituted with at least one —$CF_3$.

In another embodiment of this invention, for the compounds of formula $1.9^{42}$, X is O, each $L^1$ is the same or different halo, and Ar is phenyl substituted with one —$CF_3$.

In another embodiment of this invention, for the compounds of formula $1.9^{42}$, X is O, each $L^1$ is the same or different halo, and Ar is

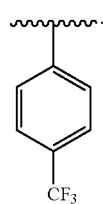

In another embodiment of this invention, for the compounds of formula $1.9^{42}$, X is O, each $L^1$ is the same or different halo, and Ar is phenyl substituted with at least one —CN.

In another embodiment of this invention, for the compounds of formula $1.9^{42}$, X is O, each $L^1$ is the same or different halo, and Ar is phenyl substituted with one —CN.

In another embodiment of this invention, for the compounds of formula $1.9^{42}$, X is O, each $L^1$ is the same or different halo, and Ar is

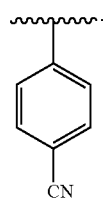

Other embodiments of the invention are directed to any one of the embodiments directed to formula $1.9^{42}$ wherein each $L^1$ is F.

In another embodiment of this invention the compound of formula 1.0 is a compound of formula 1.9, said compound having the formula (1.9A):

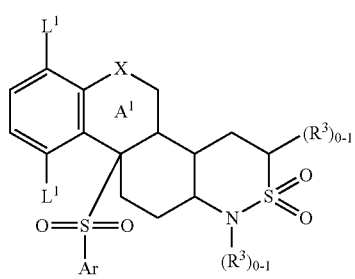

(1.9A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.9A, wherein X is O, each $L^1$ is the same or different halo, and Ar is:

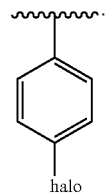

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is:

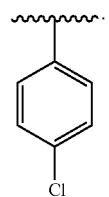 [SMILES: *c1ccc(Cl)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is:

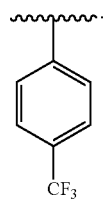

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.9A, wherein X is O, each $L^1$ is the same or different halo, and Ar is:

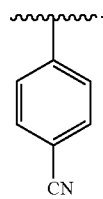

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10, and X is O.

In another embodiment of this invention the compound of formula 1.0 is a compound of formula 1.10 and $L^1$ is halo.

In another embodiment of this invention the compound of formula 1.0 is a compound of formula 1.10, said compound having the formula (1.10A):

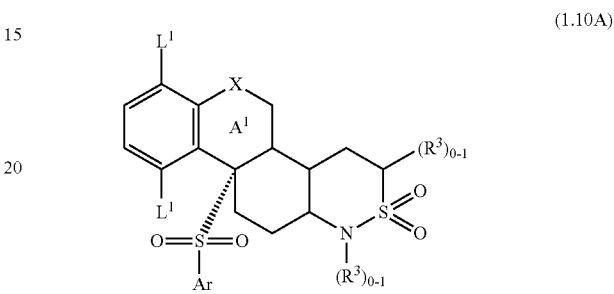

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl. Preferably, X=O.

In another embodiment of this invention the compound of formula 1.0 is a compound of formula 1.10A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl. Preferably, X=O.

In another embodiment of this invention the compound of formula 1.0 is a compound of formula 1.10, n is 2 and $L^1$ is F.

In another embodiment of this invention the compound of formula 1.0 is a compound of formula 1.10A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl. Preferably, X=O.

In another embodiment of this invention the compound of formula 1.0 is a compound of formula 1.10 and Ar is phenyl.

In another embodiment of this invention the compound of formula 1.0 is a compound of formula 1.10, Ar is phenyl substituted with halo.

In another embodiment of this invention the compound of formula 1.0 is a compound of formula 1.10 and Ar is phenyl substituted with one halo.

In another embodiment of this invention the compound of formula 1.0 is a compound of formula 1.10 and Ar is:

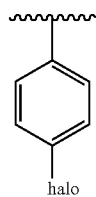

In another embodiment of this invention the compound of formula 1.0 is a compound of formula 1.10 and Ar is phenyl substituted with at least one Cl.

In another embodiment of this invention the compound of formula 1.0 is a compound of formula 1.10 and Ar is phenyl substituted with a Cl.

In another embodiment of this invention the compound of formula 1.0 is a compound of formula 1.10 and Ar is:

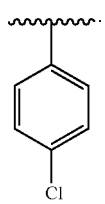

In another embodiment of this invention the compound of formula 1.0 is a compound of formula 1.10 and Ar is phenyl substituted with at least one —CF$_3$.

In another embodiment of this invention the compound of formula 1.0 is a compound of formula 1.10 and Ar is phenyl substituted with a —CF$_3$.

In another embodiment of this invention the compound of formula 1.0 is a compound of formula 1.10 and Ar is:

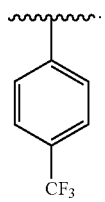

In another embodiment of this invention the compound of formula 1.0 is a compound of formula 1.10 and Ar is phenyl substituted with at least one —CN.

In another embodiment of this invention the compound of formula 1.0 is a compound of formula 1.10 and Ar is phenyl substituted with a —CN.

In another embodiment of this invention the compound of formula 1.0 is a compound of formula 1.10 and Ar is:

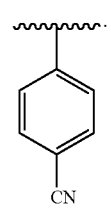

In another embodiment of this invention the compound of formula 1.0 is a compound of formula 1.10, X is O, each L$^1$ is halo, and Ar is phenyl substituted with at least one halo.

In another embodiment of this invention the compound of formula 1.0 is a compound of formula 1.10, X is O, n is 2, each L$^1$ is the same or different halo, and Ar is phenyl substituted with one halo.

In another embodiment of this invention the compound of formula 1.0 is a compound of formula 1.10, X is O, n is 2, L$^1$ is F, and Ar is phenyl substituted with one Cl.

In another embodiment of this invention the compound of formula 1.0 is a compound of formula 1.10, X is O, n is 2, each L$^1$ is the same or different halo, and Ar is:

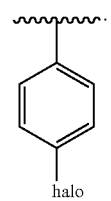

In another embodiment of this invention the compound of formula 1.0 is a compound of formula 1.10, X is O, n is 2, each L$^1$ is the same or different halo, and Ar is:

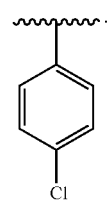

In another embodiment of this invention the compound of formula 1.0 is a compound of formula 1.10, X is O, n is 2, each L$^1$ is the same or different halo, and Ar is phenyl substituted with at least one —CF$_3$.

In another embodiment of this invention the compound of formula 1.0 is a compound of formula 1.10, X is O, n is 2, L$^1$ is F, and Ar is phenyl substituted with one —CF$_3$.

In another embodiment of this invention the compound of formula 1.0 is a compound of formula 1.10, X is O, n is 2, L$^1$ is F, and Ar is phenyl substituted with one —CF$_3$.

In another embodiment of this invention the compound of formula 1.0 is a compound of formula 1.10, X is O, n is 2, each L$^1$ is the same or different halo, and Ar is:

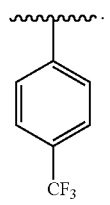

In another embodiment of this invention the compound of formula 1.0 is a compound of formula 1.10, X is O, n is 2, each $L^1$ is the same or different halo, and Ar is phenyl substituted with at least one —CN.

In another embodiment of this invention the compound of formula 1.0 is a compound of formula 1.10, X is O, n is 2, $L^1$ is F, and Ar is phenyl substituted with one —CN.

In another embodiment of this invention the compound of formula 1.0 is a compound of formula 1.10, X is O, n is 2, $L^1$ is F, and Ar is phenyl substituted with one —CN.

In another embodiment of this invention the compound of formula 1.0 is a compound of formula 1.10, X is O, n is 2, each $L^1$ is the same or different halo, and Ar is:

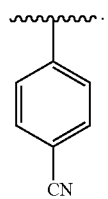

In another embodiment of this invention the compound of formula 1.0 is a compound of formula $1.10^{41}$, said compound having the formula ($1.10^{42}$):

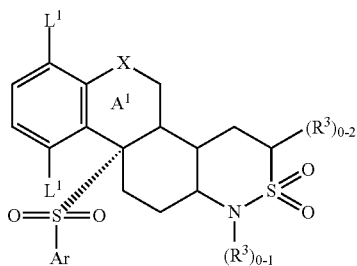

($1.10^{42}$)

wherein all substituents are as defined for the compounds of formula $1.10^{41}$.

In another embodiment of this invention, for the compounds of formula $1.10^{42}$, X is O, each $L^1$ is the same or different halo, and Ar is phenyl substituted with at least one halo.

In another embodiment of this invention, for the compounds of formula $1.10^{42}$, X is O, each $L^1$ is the same or different halo, and Ar is phenyl substituted with one halo.

In another embodiment of this invention, for the compounds of formula $1.10^{42}$, X is O, each $L^1$ is the same or different halo, and Ar is:

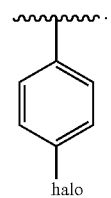

In another embodiment of this invention, for the compounds of formula $1.10^{42}$, X is O, each $L^1$ is the same or different halo, and Ar is phenyl substituted with one Cl.

In another embodiment of this invention, for the compounds of formula $1.10^{42}$, X is O, each $L^1$ is the same or different halo, and Ar is

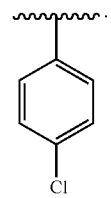

In another embodiment of this invention, for the compounds of formula $1.10^{42}$, X is O, each $L^1$ is the same or different halo, and Ar is phenyl substituted with at least one —$CF_3$.

In another embodiment of this invention, for the compounds of formula $1.10^{42}$, X is O, each $L^1$ is the same or different halo, and Ar is phenyl substituted with one —$CF_3$.

In another embodiment of this invention, for the compounds of formula $1.10^{42}$, X is O, each $L^1$ is the same or different halo, and Ar is

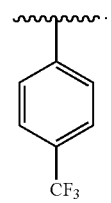

In another embodiment of this invention, for the compounds of formula $1.10^{42}$, X is O, each $L^1$ is the same or different halo, and Ar is phenyl substituted with at least one —CN.

In another embodiment of this invention, for the compounds of formula $1.10^{42}$, X is O, each $L^1$ is the same or different halo, and Ar is phenyl substituted with one —CN.

In another embodiment of this invention, for the compounds of formula $1.10^{42}$, X is O, each $L^1$ is the same or different halo, and Ar is

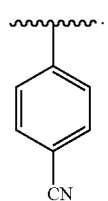

Other embodiments of the invention are directed to any one of the embodiments directed to formula 1.10[42] wherein each $L^1$ is F.

In another embodiment of this invention the compound of formula 1.0 is a compound of formula 1.10, said compound having the formula (1.10A):

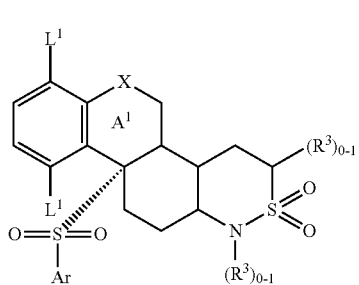

(1.10A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is:

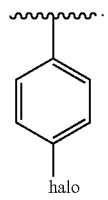

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.10A, X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is:

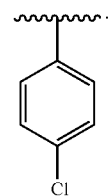

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is:

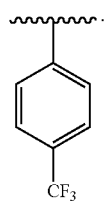

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.10A, wherein X is O, each $L^1$ is the same or different halo, and Ar is:

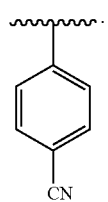

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula $2.10^{41}$, said compound having the formula ($2.10^{42}$):

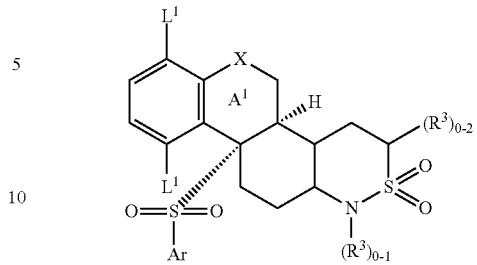

wherein all substituents are as defined for the compounds of formula $2.10^{41}$.

In another embodiment of this invention, for the compounds of formula $2.10^{42}$, X is O, each $L^1$ is the same or different halo, and Ar is phenyl substituted with at least one halo.

In another embodiment of this invention, for the compounds of formula $2.10^{42}$, X is O, each $L^1$ is the same or different halo, and Ar is phenyl substituted with one halo.

In another embodiment of this invention, for the compounds of formula $2.10^{42}$, X is O, each $L^1$ is the same or different halo, and Ar is:

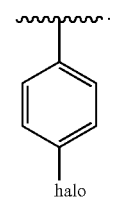

In another embodiment of this invention, for the compounds of formula $2.10^{42}$, X is O, each $L^1$ is the same or different halo, and Ar is phenyl substituted with one Cl.

In another embodiment of this invention, for the compounds of formula $2.10^{42}$, X is O, each $L^1$ is the same or different halo, and Ar is

In another embodiment of this invention, for the compounds of formula $2.10^{42}$, X is O, each $L^1$ is the same or different halo, and Ar is phenyl substituted with at least one —$CF_3$.

In another embodiment of this invention, for the compounds of formula $2.10^{42}$, X is O, each $L^1$ is the same or different halo, and Ar is phenyl substituted with one —$CF_3$.

In another embodiment of this invention, for the compounds of formula $2.10^{42}$, X is O, each $L^1$ is the same or different halo, and Ar is

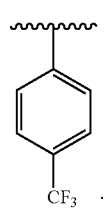

In another embodiment of this invention, for the compounds of formula 2.10$^{42}$, X is O, each $L^1$ is the same or different halo, and Ar is phenyl substituted with at least one —CN.

In another embodiment of this invention, for the compounds of formula 2.10$^{42}$, X is O, each $L^1$ is the same or different halo, and Ar is phenyl substituted with one —CN.

In another embodiment of this invention, for the compounds of formula 2.10$^{42}$, X is O, each $L^1$ is the same or different halo, and Ar is

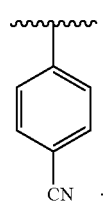

Other embodiments of the invention are directed to any one of the embodiments directed to formula 2.10$^{42}$ wherein each $L^1$ is F.

In another embodiment of this invention the compound of formula 1.0 is a compound of the formula (2.10A):

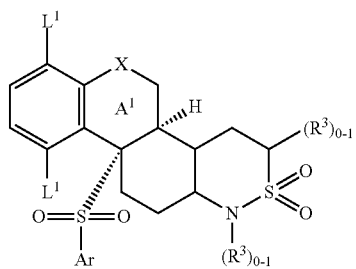

(2.10A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 2.10A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 2.10A, wherein X is O, each $L^1$ is the same or different halo, and Ar is:

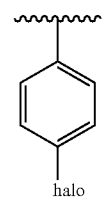

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 2.10A, X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 2.10A, wherein X is O, each $L^1$ is the same or different halo, and Ar is:

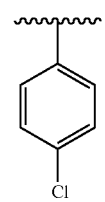

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 2.10A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 2.10A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl.

In another embodiment of this invention the compound of formula 1.0 is a compound of formula 2.10A, wherein X is O, each $L^1$ is the same or different halo, and Ar is:

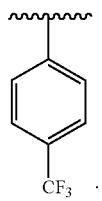

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl.

In another embodiment of this invention the compound of formula 1.0 is a compound of formula 2.10A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl.

In another embodiment of this invention the compound of formula 1.0 is a compound of formula 2.10A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl.

In another embodiment of this invention the compound of formula 1.0 is a compound of formula 2.10A, wherein X is O, each $L^1$ is the same or different halo, and Ar is:

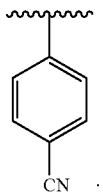

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably, the $R^3$ of the $CH-R^3$ moiety is $C_1-C_6$ alkyl.

In another embodiment of this invention the compound of formula 1.0 is a compound of formula $3.10^{41}$, said compound having the formula ($3.10^{42}$):

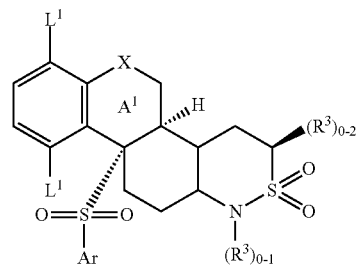

(3.10⁴²)

wherein all substituents are as defined for the compounds of formula $3.10^{41}$.

In another embodiment of this invention, for the compounds of formula $3.10^{42}$, X is O, each $L^1$ is the same or different halo, and Ar is phenyl substituted with at least one halo.

In another embodiment of this invention, for the compounds of formula $3.10^{42}$, X is O, each $L^1$ is the same or different halo, and Ar is phenyl substituted with one halo.

In another embodiment of this invention, for the compounds of formula $3.10^{42}$, X is O, each $L^1$ is the same or different halo, and Ar is:

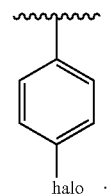

In another embodiment of this invention, for the compounds of formula $3.10^{42}$, X is O, each $L^1$ is the same or different halo, and Ar is phenyl substituted with one Cl.

In another embodiment of this invention, for the compounds of formula $3.10^{42}$, X is O, each $L^1$ is the same or different halo, and Ar is

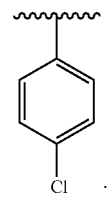 [SMILES: *c1ccc(Cl)cc1]

In another embodiment of this invention, for the compounds of formula $3.10^{42}$, X is O, each $L^1$ is the same or different halo, and Ar is phenyl substituted with at least one —CF$_3$.

In another embodiment of this invention, for the compounds of formula $3.10^{42}$, X is O, each $L^1$ is the same or different halo, and Ar is phenyl substituted with one —CF$_3$.

In another embodiment of this invention, for the compounds of formula $3.10^{42}$, X is O, each $L^1$ is the same or different halo, and Ar is

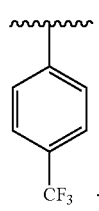 [SMILES: *c1ccc(C(F)(F)F)cc1]

In another embodiment of this invention, for the compounds of formula $3.10^{42}$, X is O, each $L^1$ is the same or different halo, and Ar is phenyl substituted with at least one —CN.

In another embodiment of this invention, for the compounds of formula $3.10^{42}$, X is O, each $L^1$ is the same or different halo, and Ar is phenyl substituted with one —CN.

In another embodiment of this invention, for the compounds of formula $3.10^{42}$, X is O, each $L^1$ is the same or different halo, and Ar is

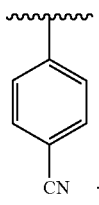

Other embodiments of the invention are directed to any one of the embodiments directed to formula $3.10^{42}$ wherein each $L^1$ is F.

In another embodiment of this invention the compound of formula 1.0 is a compound of the formula (3.10A):

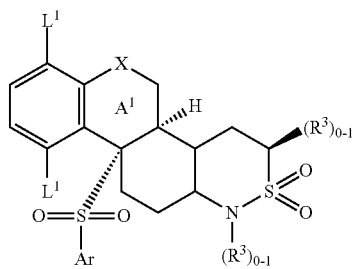

(3.10A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is:

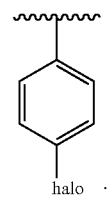

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 3.10A, X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is:

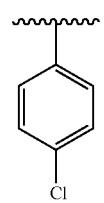

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is phenyl substituted with one —$CF_3$. In the substituent "$(R^3)_{0-1}$", the "0-1"

means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is:

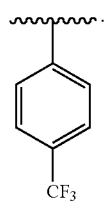

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 3.10A, wherein X is O, each $L^1$ is the same or different halo, and Ar is:

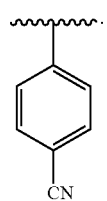 [SMILES: *c1ccc(C#N)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl.

In another embodiment of this invention the compound of formula 1.0 is a compound of formula 1.11, and X is O.

In another embodiment of this invention the compound of formula 1.0 is a compound of formula 1.11 and $L^1$ is halo.

In another embodiment of this invention the compound of formula 1.0 is a compound of formula 1.11, said compound having the formula:

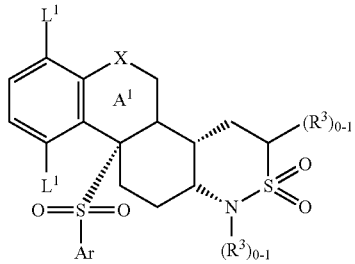

(1.11A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferable ethyl. Preferably, X=O.

In another embodiment of this invention the compound of formula 1.0 is a compound of formula 1.11A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferable ethyl. Preferably, X=O.

In another embodiment of this invention the compound of formula 1.0 is a compound of formula 1.11, n is 2 and $L^1$ is F.

In another embodiment of this invention the compound of formula 1.0 is a compound of formula 1.11A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferable ethyl. Preferably, X=O.

In another embodiment of this invention the compound of formula 1.0 is a compound of formula 1.11 and Ar is phenyl.

In another embodiment of this invention the compound of formula 1.0 is a compound of formula 1.11, Ar is phenyl substituted with halo.

In another embodiment of this invention the compound of formula 1.0 is a compound of formula 1.11 and Ar is phenyl substituted with one halo.

In another embodiment of this invention the compound of formula 1.0 is a compound of formula 1.11 and Ar is:

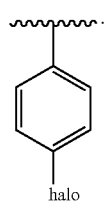

In another embodiment of this invention the compound of formula 1.0 is a compound of formula 1.11 and Ar is phenyl substituted with at least one Cl.

In another embodiment of this invention the compound of formula 1.0 is a compound of formula 1.11 and Ar is phenyl substituted with a Cl.

In another embodiment of this invention the compound of formula 1.0 is a compound of formula 1.11 and Ar is:

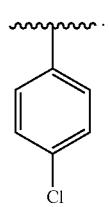

In another embodiment of this invention the compound of formula 1.0 is a compound of formula 1.11 and Ar is phenyl substituted with at least one —$CF_3$.

In another embodiment of this invention the compound of formula 1.0 is a compound of formula 1.11 and Ar is phenyl substituted with one —$CF_3$.

In another embodiment of this invention the compound of formula 1.0 is a compound of formula 1.11 and Ar is:

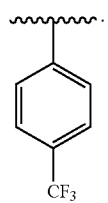

In another embodiment of this invention the compound of formula 1.0 is a compound of formula 1.11, Ar is phenyl substituted with at least one —CN.

In another embodiment of this invention the compound of formula 1.0 is a compound of formula 1.11 and Ar is phenyl substituted with one —CN.

In another embodiment of this invention the compound of formula 1.0 is a compound of formula 1.11 and Ar is:

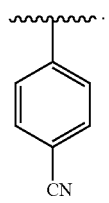

In another embodiment of this invention the compound of formula 1.0 is a compound of formula 1.11, X is O, each $L^1$ is halo, and Ar is phenyl substituted with at least one halo.

In another embodiment of this invention the compound of formula 1.0 is a compound of formula 1.11, X is O, n is 2, each $L^1$ is the same or different halo, and Ar is phenyl substituted with one halo.

In another embodiment of this invention the compound of formula 1.0 is a compound of formula 1.11, X is O, n is 2, $L^1$ is F, and Ar is phenyl substituted with one Cl.

In another embodiment of this invention the compound of formula 1.0 is a compound of formula 1.11, X is O, n is 2, each $L^1$ is the same or different halo, and Ar is:

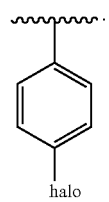

In another embodiment of this invention the compound of formula 1.0 is a compound of formula 1.11, X is O, n is 2, each $L^1$ is the same or different halo, and Ar is:

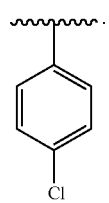 [SMILES: *c1ccc(Cl)cc1]

In another embodiment of this invention the compound of formula 1.0 is a compound of formula 1.11, X is O, each $L^1$ is halo, and Ar is phenyl substituted with at least one —$CF_3$.

In another embodiment of this invention the compound of formula 1.0 is a compound of formula 1.11, X is O, n is 2, each $L^1$ is the same or different halo, and Ar is phenyl substituted with one —$CF_3$.

In another embodiment of this invention the compound of formula 1.0 is a compound of formula 1.11, X is O, n is 2, $L^1$ is F, and Ar is phenyl substituted with one —$CF_3$.

In another embodiment of this invention the compound of formula 1.0 is a compound of formula 1.11, X is O, n is 2, $L^1$ is F, and Ar is phenyl substituted with one —$CF_3$.

In another embodiment of this invention the compound of formula 1.0 is a compound of formula 1.11, X is O, n is 2, each $L^1$ is the same or different halo, and Ar is:

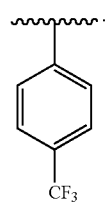

In another embodiment of this invention the compound of formula 1.0 is a compound of formula 1.11, X is O, each $L^1$ is halo, and Ar is phenyl substituted with at least one —CN.

In another embodiment of this invention the compound of formula 1.0 is a compound of formula 1.11, X is O, n is 2, each $L^1$ is the same or different halo, and Ar is phenyl substituted with one —CN.

In another embodiment of this invention the compound of formula 1.0 is a compound of formula 1.11, X is O, n is 2, $L^1$ is F, and Ar is phenyl substituted with one —CN.

In another embodiment of this invention the compound of formula 1.0 is a compound of formula 1.11, X is O, n is 2, $L^1$ is F, and Ar is phenyl substituted with one —CN.

In another embodiment of this invention the compound of formula 1.0 is a compound of formula 1.11, X is O, n is 2, each $L^1$ is the same or different halo, and Ar is:

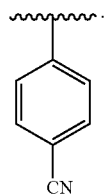

In another embodiment of this invention the compound of formula 1.0 is a compound of formula $1.11^{41}$, said compound having the formula ($1.11^{42}$):

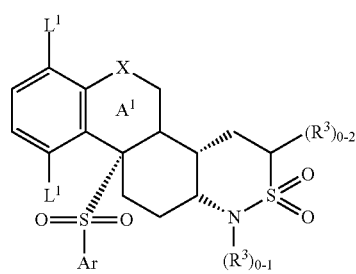

(1.11$^{42}$)

wherein all substituents are as defined for the compounds of formula $1.11^{41}$.

In another embodiment of this invention, for the compounds of formula $1.11^{42}$, X is O, each $L^1$ is the same or different halo, and Ar is phenyl substituted with at least one halo.

In another embodiment of this invention, for the compounds of formula $1.11^{42}$, X is O, each $L^1$ is the same or different halo, and Ar is phenyl substituted with one halo.

In another embodiment of this invention, for the compounds of formula $1.11^{42}$, X is O, each $L^1$ is the same or different halo, and Ar is:

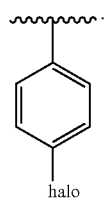

In another embodiment of this invention, for the compounds of formula $1.11^{42}$, X is O, each $L^1$ is the same or different halo, and Ar is phenyl substituted with one Cl.

In another embodiment of this invention, for the compounds of formula $1.11^{42}$, X is O, each $L^1$ is the same or different halo, and Ar is

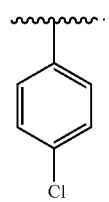

In another embodiment of this invention, for the compounds of formula $1.11^{42}$, X is O, each $L^1$ is the same or different halo, and Ar is phenyl substituted with at least one —$CF_3$.

In another embodiment of this invention, for the compounds of formula $1.11^{42}$, X is O, each $L^1$ is the same or different halo, and Ar is phenyl substituted with one —$CF_3$.

In another embodiment of this invention, for the compounds of formula $1.11^{42}$, X is O, each $L^1$ is the same or different halo, and Ar is

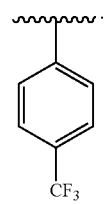

In another embodiment of this invention, for the compounds of formula $1.11^{42}$, X is O, each $L^1$ is the same or different halo, and Ar is phenyl substituted with at least one —CN.

In another embodiment of this invention, for the compounds of formula $1.11^{42}$, X is O, each $L^1$ is the same or different halo, and Ar is phenyl substituted with one —CN.

In another embodiment of this invention, for the compounds of formula $1.11^{42}$, X is O, each $L^1$ is the same or different halo, and Ar is

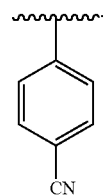 [SMILES: *c1ccc(C#N)cc1]

Other embodiments of the invention are directed to any one of the embodiments directed to formula $1.11^{42}$ wherein each $L^1$ is F.

In another embodiment of this invention the compound of formula 1.0 is a compound of formula 1.11, said compound having the formula (1.11A):

(1.11A)

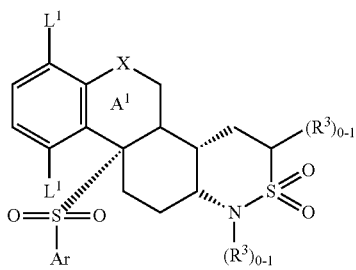

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 1.11A, X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 1.11A, wherein X is O, each $L^1$ is the same or different halo, and Ar is:

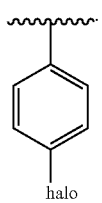
halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 1.11A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 1.11A, wherein X is O, each $L^1$ is the same or different halo, and Ar is:

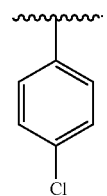
Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula $2.11^{41}$, said compound having the formula ($2.11^{42}$):

($2.11^{42}$)

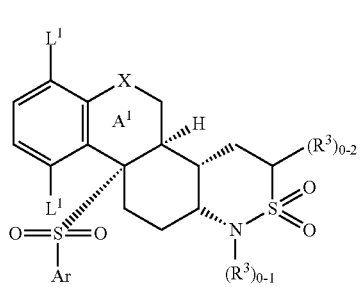

wherein all substituents are as defined for the compounds of formula $2.11^{41}$.

In another embodiment of this invention, for the compounds of formula $2.11^{42}$, X is O, each $L^1$ is the same or different halo, and Ar is phenyl substituted with at least one halo.

In another embodiment of this invention, for the compounds of formula $2.11^{42}$, X is O, each $L^1$ is the same or different halo, and Ar is phenyl substituted with one halo.

In another embodiment of this invention, for the compounds of formula $2.11^{42}$, X is O, each $L^1$ is the same or different halo, and Ar is:

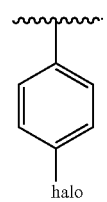
halo

In another embodiment of this invention, for the compounds of formula $2.11^{42}$, X is O, each $L^1$ is the same or different halo, and Ar is phenyl substituted with one Cl.

In another embodiment of this invention, for the compounds of formula $2.11^{42}$, X is O, each $L^1$ is the same or different halo, and Ar is In another embodiment of this invention, for the compounds of formula $2.11^{42}$, X is O, each $L^1$ is the same or different halo, and Ar is phenyl substituted with at least one —$CF_3$.

In another embodiment of this invention, for the compounds of formula $2.11^{42}$, X is O, each $L^1$ is the same or different halo, and Ar is phenyl substituted with one —$CF_3$.

In another embodiment of this invention, for the compounds of formula $2.11^{42}$, X is O, each $L^1$ is the same or different halo, and Ar is

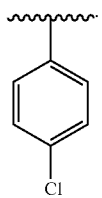

In another embodiment of this invention, for the compounds of formula $2.11^{42}$, X is O, each $L^1$ is the same or different halo, and Ar is phenyl substituted with at least one —CN.

In another embodiment of this invention, for the compounds of formula $2.11^{42}$, X is O, each $L^1$ is the same or different halo, and Ar is phenyl substituted with one —CN.

In another embodiment of this invention, for the compounds of formula $2.11^{42}$, X is O, each $L^1$ is the same or different halo, and Ar is

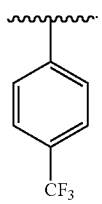

Other embodiments of the invention are directed to any one of the embodiments directed to formula $2.11^{42}$ wherein each $L^1$ is F.

In another embodiment of this invention the compound of formula 1.0 is a compound of the formula (2.11A):

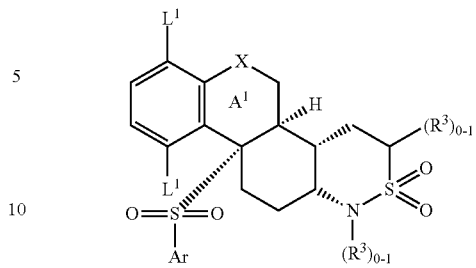

(2.11A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 2.11A, X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 2.11A, wherein X is O, each $L^1$ is the same or different halo, and Ar is:

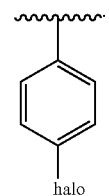

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 2.11A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 2.11A, wherein X is O, each $L^1$ is the same or different halo, and Ar is:

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula $3.11^{41}$, said compound having the formula ($3.11^{42}$):

($3.11^{42}$)

wherein all substituents are as defined for the compounds of formula $3.11^{41}$.

In another embodiment of this invention, for the compounds of formula $3.11^{42}$, X is O, each $L^1$ is the same or different halo, and Ar is phenyl substituted with at least one halo.

In another embodiment of this invention, for the compounds of formula $3.11^{42}$, X is O, each $L^1$ is the same or different halo, and Ar is phenyl substituted with one halo.

In another embodiment of this invention, for the compounds of formula $3.11^{42}$, X is O, each $L^1$ is the same or different halo, and Ar is:

(halo-substituted phenyl structure)

In another embodiment of this invention, for the compounds of formula $3.11^{42}$, X is O, each $L^1$ is the same or different halo, and Ar is phenyl substituted with one Cl.

In another embodiment of this invention, for the compounds of formula $3.11^{42}$, X is O, each $L^1$ is the same or different halo, and Ar is (Cl-substituted phenyl structure)

In another embodiment of this invention, for the compounds of formula $3.11^{42}$, X is O, each $L^1$ is the same or different halo, and Ar is phenyl substituted with at least one —$CF_3$.

In another embodiment of this invention, for the compounds of formula $3.11^{42}$, X is O, each $L^1$ is the same or different halo, and Ar is phenyl substituted with one —$CF_3$.

In another embodiment of this invention, for the compounds of formula $3.11^{42}$, X is O, each $L^1$ is the same or different halo, and Ar is ($CF_3$-substituted phenyl structure)

In another embodiment of this invention, for the compounds of formula $3.11^{42}$, X is O, each $L^1$ is the same or different halo, and Ar is phenyl substituted with at least one —CN.

In another embodiment of this invention, for the compounds of formula $3.11^{42}$, X is O, each $L^1$ is the same or different halo, and Ar is phenyl substituted with one —CN.

In another embodiment of this invention, for the compounds of formula $3.11^{42}$, X is O, each $L^1$ is the same or different halo, and Ar is (CN-substituted phenyl structure)

Other embodiments of the invention are directed to any one of the embodiments directed to formula $3.11^{42}$ wherein each $L^1$ is F.

In another embodiment of this invention the compound of formula 1.0 is a compound of the formula (3.11A):

(3.11A)

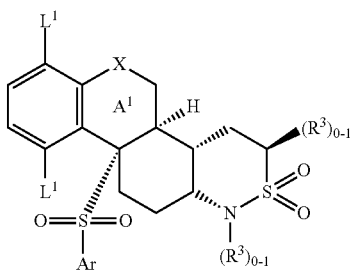

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 3.11A, X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 3.11A, wherein X is O, each $L^1$ is the same or different halo, and Ar is:

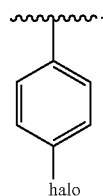
halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 3.11A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 3.11A, wherein X is O, each $L^1$ is the same or different halo, and Ar is:

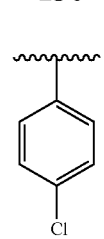
Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably, the $R^3$ of the CH—$R^3$ moiety is $C_1$-$C_6$ alkyl, more preferably ethyl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein $L^1$ is halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein n is 2 and each $L^1$ is the same or different halo, and wherein each $L^1$ is para to each other (i.e., the compound has the formula:

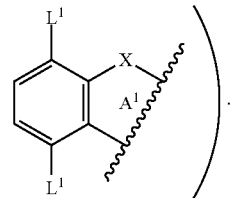

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein n is 2 and each $L^1$ is the same halo, and wherein each $L^1$ is para to each other (i.e., the compound has the formula:

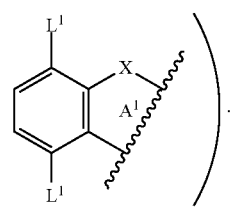

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein n is 2 and $L^1$ is F.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein n is 2 and each $L^1$ is F, and wherein each $L^1$ is para to each other (i.e., the compound has the formula:

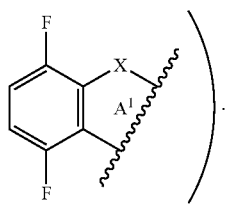

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with one halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is:

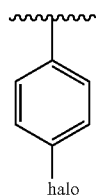

halo

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with at least one Cl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with a Cl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is:

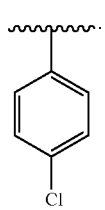 [SMILES: *c1ccc(Cl)cc1]

Cl

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with at least one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with a —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is:

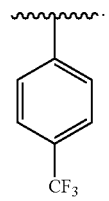

$CF_3$

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with at least one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is phenyl substituted with a —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein Ar is:

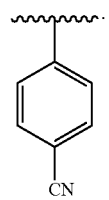

CN

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, each $L^1$ is halo, and Ar is phenyl substituted with at least one halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is phenyl substituted with one halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, $L^1$ is F, and Ar is phenyl substituted with one Cl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is:

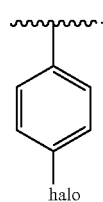

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is:

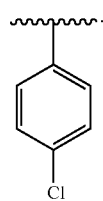 [SMILES: *c1ccc(Cl)cc1]

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, each $L^1$ is halo, and Ar is phenyl substituted with at least one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is phenyl substituted with one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, $L^1$ is F, and Ar is phenyl substituted with one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is:

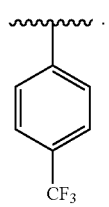

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, each $L^1$ is halo, and Ar is phenyl substituted with at least one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is phenyl substituted with one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, $L^1$ is F, and Ar is phenyl substituted with one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and Ar is:

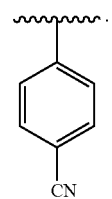

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

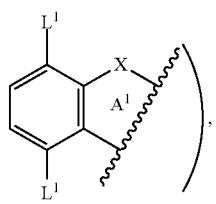

and Ar is phenyl substituted with at least one halo.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

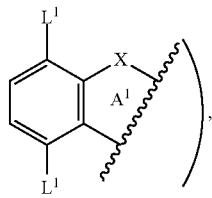

and Ar is phenyl substituted with one halo.

In another embodiment of this invention the compound of formula 1.0 is a compound of formula 11.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

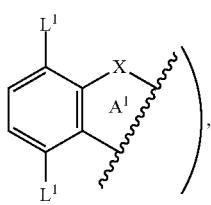

and Ar is:

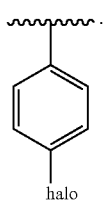
halo

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

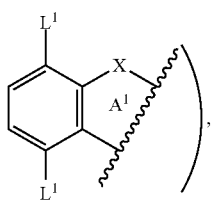

and Ar is phenyl substituted with one Cl.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

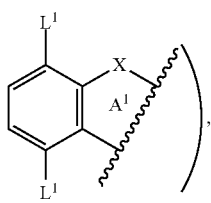

and Ar is:

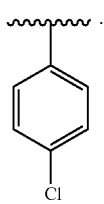
Cl

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

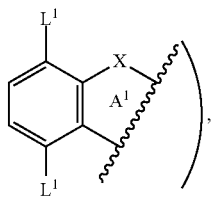

and Ar is phenyl substituted with at least one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

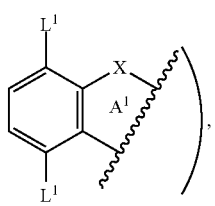

and Ar is phenyl substituted with one —$CF_3$.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

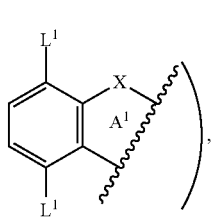

and Ar is:

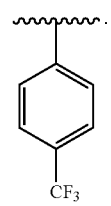
$CF_3$

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

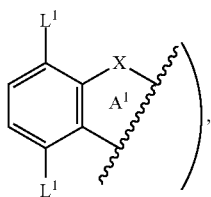

and Ar is phenyl substituted with at least one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

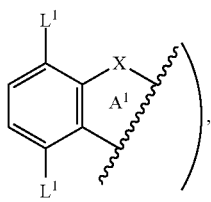

and Ar is phenyl substituted with one —CN.

In another embodiment of this invention the compound of formula 1.0 is a compound of formula 1.12, 1.13, 2.13, 3.13, 1.14, 2.14, 3.14, 1.15, 1.16, 2.16, 3.16, 1.17, 2.17 or 3.17 wherein X is O, n is 2, each $L^1$ is the same or different halo, and wherein each $L^1$ is para to each other (i.e., the compound has the formula:

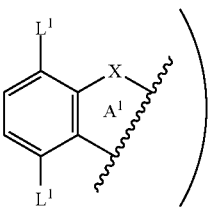

and Ar is:

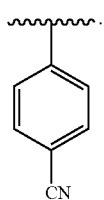

In another embodiment of this invention the compound of formula 1.0 is a compound of formula 1.18, and X is O.

In another embodiment of this invention the compound of formula 1.0 is a compound of formula 1.18 and $L^1$ is halo.

In another embodiment of this invention the compound of formula 1.0 is a compound of formula 1.18, said compound having the formula (1.18B):

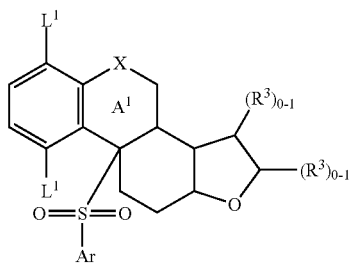

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18, n is 2 and $L^1$ is F.

In another embodiment of this invention the compound of formula 1.0 is a compound of formula 1.18B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18 and Ar is phenyl.

In another embodiment of this invention the compound of formula 1.0 is a compound of formula 1.18, Ar is phenyl substituted with halo.

In another embodiment of this invention the compound of formula 1.0 is a compound of formula 1.18 and Ar is phenyl substituted with one halo.

In another embodiment of this invention the compound of formula 1.0 is a compound of formula 1.18 and Ar is:

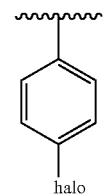

In another embodiment of this invention the compound of formula 1.0 is a compound of formula 1.18 and Ar is phenyl substituted with at least one Cl.

In another embodiment of this invention the compound of formula 1.0 is a compound of formula 1.18 and Ar is phenyl substituted with a Cl.

In another embodiment of this invention the compound of formula 1.0 is a compound of formula 1.18 and Ar is:

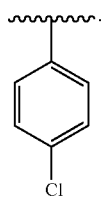

In another embodiment of this invention the compound of formula 1.0 is a compound of formula 1.18 and Ar is phenyl substituted with at least one —CF₃.

In another embodiment of this invention the compound of formula 1.0 is a compound of formula 1.18 and Ar is phenyl substituted with a —CF₃.

In another embodiment of this invention the compound of formula 1.0 is a compound of formula 1.18 and Ar is:

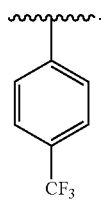 [SMILES: *c1ccc(C(F)(F)F)cc1]

In another embodiment of this invention the compound of formula 1.0 is a compound of formula 1.18 and Ar is phenyl substituted with at least one CN.

In another embodiment of this invention the compound of formula 1.0 is a compound of formula 1.18 and Ar is phenyl substituted with a —CN.

In another embodiment of this invention the compound of formula 1.0 is a compound of formula 1.18 and Ar is:

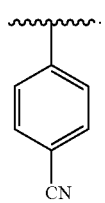

In another embodiment of this invention the compound of formula 1.0 is a compound of formula 1.18, X is O, each $L^1$ is halo, and Ar is phenyl substituted with at least one halo.

In another embodiment of this invention the compound of formula 1.0 is a compound of formula 1.18, X is O, n is 2, each $L^1$ is the same or different halo, and Ar is phenyl substituted with one halo.

In another embodiment of this invention the compound of formula 1.0 is a compound of formula 1.18, X is O, n is 2, $L^1$ is F, and Ar is phenyl substituted with one Cl.

In another embodiment of this invention the compound of formula 1.0 is a compound of formula 1.18, X is O, n is 2, each $L^1$ is the same or different halo, and Ar is:

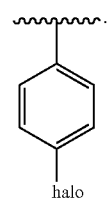

In another embodiment of this invention the compound of formula 1.0 is a compound of formula 1.18, X is O, n is 2, each $L^1$ is the same or different halo, and Ar is:

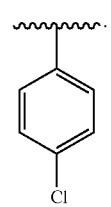

In another embodiment of this invention the compound of formula 1.0 is a compound of formula 1.18, X is O, each $L^1$ is halo, and Ar is phenyl substituted with at least one —CF₃.

In another embodiment of this invention the compound of formula 1.0 is a compound of formula 1.18, X is O, n is 2, each $L^1$ is the same or different halo, and Ar is phenyl substituted with one —CF₃.

In another embodiment of this invention the compound of formula 1.0 is a compound of formula 1.18, X is O, n is 2, $L^1$ is F, and Ar is phenyl substituted with one —CF₃.

In another embodiment of this invention the compound of formula 1.0 is a compound of formula 1.18, X is O, n is 2, each $L^1$ is the same or different halo, and Ar is:

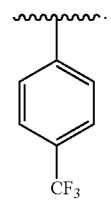

In another embodiment of this invention the compound of formula 1.0 is a compound of formula 1.18, X is O, each $L^1$ is halo, and Ar is phenyl substituted with at least one —CN.

In another embodiment of this invention the compound of formula 1.0 is a compound of formula 1.18, X is O, n is 2, each $L^1$ is the same or different halo, and Ar is phenyl substituted with one CN.

In another embodiment of this invention the compound of formula 1.0 is a compound of formula 1.18, X is O, n is 2, $L^1$ is F, and Ar is phenyl substituted with one —CN.

In another embodiment of this invention the compound of formula 1.0 is a compound of formula 1.18, X is O, n is 2, each $L^1$ is the same or different halo, and Ar is:

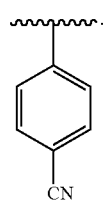

In another embodiment of this invention the compound of formula 1.0 is a compound of formula 1.18, said compound having the formula (1.18B):

(1.18B)

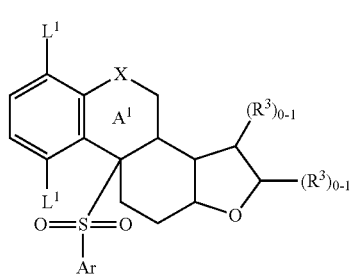

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O each $L^1$ is the same or different halo, and Ar is:

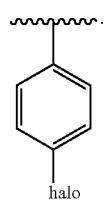

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, n is 2, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, each $L^1$ is the same or different halo, and Ar is:

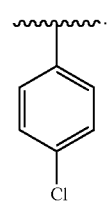

In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, n is 2, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.18B, wherein X is O, each $L^1$ is the same or different halo, and Ar is:

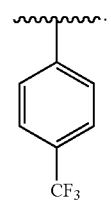

In the substituent "$(R^3)_{0-1}$", the "0-1" means that there is no $R^3$ substituent present (i.e., there would be a H instead of the $R^3$ substituent), or that there is one $R^3$ substituent present at the indicated position. Preferably each $R^3$ is independently selected from the group consisting of —C$_1$-C$_6$ alkyl, hydroxyalkyl, and alkoxyalkyl.

In another embodiment of this invention the compound of formula 1.0 is a compound of formula 1.18B, wherein X is O, each L$^1$ is the same or different halo, and Ar is phenyl substituted with at least one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.18B, wherein X is O, n is 2, each L$^1$ is the same or different halo, and Ar is phenyl substituted with one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.18B, wherein X is O, each L$^1$ is the same or different halo, and Ar is:

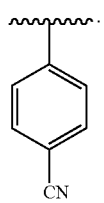

In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.19, and X is O.

In another embodiment of this invention the compound of formula 1.0 is a compound of formula 1.19 and L$^1$ is halo.

In another embodiment of this invention the compound of formula 1.0 is a compound of formula 1.19, said compound having the formula (1.19B):

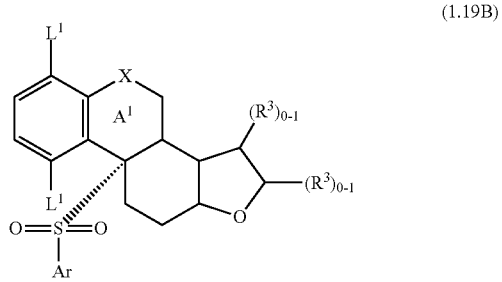

(1.19B)

wherein each L$^1$ is the same or different halo. All other substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.19B, wherein each L$^1$ is the same halo. All other substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.19, n is 2 and L$^1$ is F.

In another embodiment of this invention the compound of formula 1.0 is a compound of formula 1.19B, wherein each L$^1$ is F. All other substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably each R$^3$ is independently selected from the group consisting of —C$_1$-C$_6$ alkyl, hydroxyalkyl, and alkoxyalkyl.

In another embodiment of this invention the compound of formula 1.0 is a compound of formula 1.19 and Ar is phenyl.

In another embodiment of this invention the compound of formula 1.0 is a compound of formula 1.19, Ar is phenyl substituted with halo.

In another embodiment of this invention the compound of formula 1.0 is a compound of formula 1.19 and Ar is phenyl substituted with one halo.

In another embodiment of this invention the compound of formula 1.0 is a compound of formula 1.19 and Ar is:

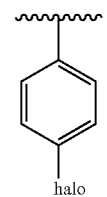

In another embodiment of this invention the compound of formula 1.0 is a compound of formula 1.19 and Ar is phenyl substituted with at least one Cl.

In another embodiment of this invention the compound of formula 1.0 is a compound of formula 1.19 and Ar is phenyl substituted with a Cl.

In another embodiment of this invention the compound of formula 1.0 is a compound of formula 1.19 and Ar is:

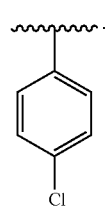 [SMILES: *c1ccc(Cl)cc1]

In another embodiment of this invention the compound of formula 1.0 is a compound of formula 1.19 and Ar is phenyl substituted with at least one —CF$_3$.

In another embodiment of this invention the compound of formula 1.0 is a compound of formula 1.19 and Ar is phenyl substituted with a —CF₃.

In another embodiment of this invention the compound of formula 1.0 is a compound of formula 1.19 and Ar is:

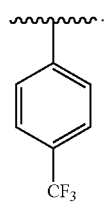

In another embodiment of this invention the compound of formula 1.0 is a compound of formula 1.19 and Ar is phenyl substituted with at least one —CN.

In another embodiment of this invention the compound of formula 1.0 is a compound of formula 1.19 and Ar is phenyl substituted with a —CN.

In another embodiment of this invention the compound of formula 1.0 is a compound of formula 1.19 and Ar is:

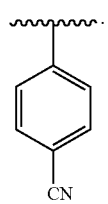

In another embodiment of this invention the compound of formula 1.0 is a compound of formula 1.19, X is O, each $L^1$ is halo, and Ar is phenyl substituted with at least one halo.

In another embodiment of this invention the compound of formula 1.0 is a compound of formula 1.19, X is O, n is 2, each $L^1$ is the same or different halo, and Ar is phenyl substituted with one halo.

In another embodiment of this invention the compound of formula 1.0 is a compound of formula 1.19, X is O, n is 2, $L^1$ is F, and Ar is phenyl substituted with one Cl.

In another embodiment of this invention the compound of formula 1.0 is a compound of formula 1.19, X is O, n is 2, each $L^1$ is the same or different halo, and Ar is:

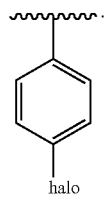

In another embodiment of this invention the compound of formula 1.0 is a compound of formula 1.19, X is O, n is 2, each $L^1$ is the same or different halo, and Ar is:

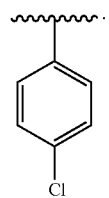 [SMILES: *c1ccc(Cl)cc1]

In another embodiment of this invention the compound of formula 1.0 is a compound of formula 1.19, X is O, each $L^1$ is halo, and Ar is phenyl substituted with at least one —CF₃.

In another embodiment of this invention the compound of formula 1.0 is a compound of formula 1.19, X is O, n is 2, each $L^1$ is the same or different halo, and Ar is phenyl substituted with one —CF₃.

In another embodiment of this invention the compound of formula 1.0 is a compound of formula 1.19, X is O, n is 2, $L^1$ is F, and Ar is phenyl substituted with one —CF₃.

In another embodiment of this invention the compound of formula 1.0 is a compound of formula 1.19, X is O, n is 2, each $L^1$ is the same or different halo, and Ar is:

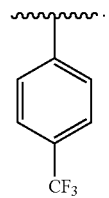 [SMILES: *c1ccc(C(F)(F)F)cc1]

In another embodiment of this invention the compound of formula 1.0 is a compound of formula 1.19, X is O, each $L^1$ is halo, and Ar is phenyl substituted with at least one —CN.

In another embodiment of this invention the compound of formula 1.0 is a compound of formula 1.19, X is O, n is 2, each $L^1$ is the same or different halo, and Ar is phenyl substituted with one —CN.

In another embodiment of this invention the compound of formula 1.0 is a compound of formula 1.19, X is O, n is 2, $L^1$ is F, and Ar is phenyl substituted with one —CN.

In another embodiment of this invention the compound of formula 1.0 is a compound of formula 1.19, X is O, n is 2, each $L^1$ is the same or different halo, and Ar is:

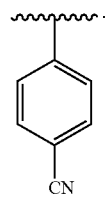

In another embodiment of this invention the compound of formula 1.0 is a compound of formula 1.19, said compound having the formula (1.19B):

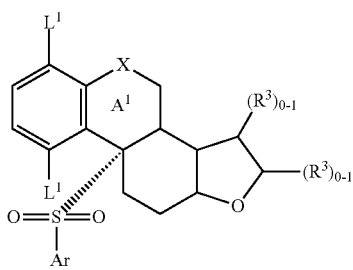

(1.19B)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is:

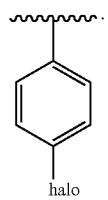

halo

In the substituent "$(R^3)_{0-1}$", the "0-1" means that there is no $R^3$ substituent present (i.e., there would be a H instead of the $R^3$ substituent), or that there is one $R^3$ Preferably each $R^3$ is independently selected from the group consisting of —$C_1$-$C_6$ alkyl, hydroxyalkyl, and alkoxyalkyl substituent present at the indicated position. Each $R^3$ is independently selected.

In another embodiment of this invention the compound of formula 1.0 is a compound of formula 1.19B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is:

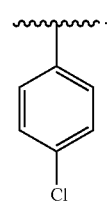 [SMILES: *c1ccc(Cl)cc1]

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.19B, wherein X is O, each $L^1$ is the same or different halo, and Ar is:

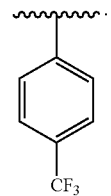

$CF_3$

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.20, and X is O.

In another embodiment of this invention the compound of formula 1.0 is a compound of formula 1.20 and $L^1$ is halo.

In another embodiment of this invention the compound of formula 1.0 is a compound of formula 1.20, said compound having the formula:

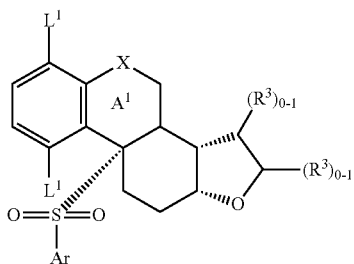
(1.20B)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.20B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.20, n is 2 and $L^1$ is F.

In another embodiment of this invention the compound of formula 1.0 is a compound of formula 1.20B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably each $R^3$ is independently selected from the group consisting of —$C_1$-$C_6$ alkyl, hydroxyalkyl, and alkoxyalkyl.

In another embodiment of this invention the compound of formula 1.0 is a compound of formula 1.20 and Ar is phenyl.

In another embodiment of this invention the compound of formula 1.0 is a compound of formula 1.20, Ar is phenyl substituted with halo.

In another embodiment of this invention the compound of formula 1.0 is a compound of formula 1.20 and Ar is phenyl substituted with one halo.

In another embodiment of this invention the compound of formula 1.0 is a compound of formula 1.20 and Ar is:

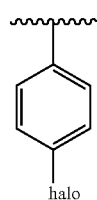
halo

In another embodiment of this invention the compound of formula 1.0 is a compound of formula 1.20 and Ar is phenyl substituted with at least one Cl.

In another embodiment of this invention the compound of formula 1.0 is a compound of formula 1.20 and Ar is phenyl substituted with a Cl.

In another embodiment of this invention the compound of formula 1.0 is a compound of formula 1.20 and Ar is:

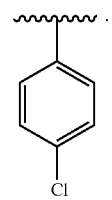
Cl

In another embodiment of this invention the compound of formula 1.0 is a compound of formula 1.20 and Ar is phenyl substituted with at least one —CN.

In another embodiment of this invention the compound of formula 1.0 is a compound of formula 1.20 and Ar is phenyl substituted with a —CN.

In another embodiment of this invention the compound of formula 1.0 is a compound of formula 1.20 and Ar is:

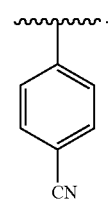
CN

In another embodiment of this invention the compound of formula 1.0 is a compound of formula 1.20 and Ar is phenyl substituted with at least one —$CF_3$.

In another embodiment of this invention the compound of formula 1.0 is a compound of formula 1.20 and Ar is phenyl substituted with a —$CF_3$.

In another embodiment of this invention the compound of formula 1.0 is a compound of formula 1.20 and Ar is:

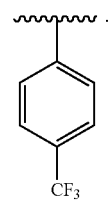
$CF_3$

In another embodiment of this invention the compound of formula 1.0 is a compound of formula 1.20, X is O, each $L^1$ is halo, and Ar is phenyl substituted with at least one halo.

In another embodiment of this invention the compound of formula 1.0 is a compound of formula 1.20, X is O, n is 2, each $L^1$ is the same or different halo, and Ar is phenyl substituted with one halo.

In another embodiment of this invention the compound of formula 1.0 is a compound of formula 1.20, X is O, n is 2, $L^1$ is F, and Ar is phenyl substituted with one Cl.

In another embodiment of this invention the compound of formula 1.0 is a compound of formula 1.20, X is O, n is 2, each $L^1$ is the same or different halo, and Ar is:

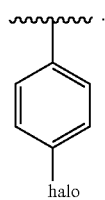

halo

In another embodiment of this invention the compound of formula 1.0 is a compound of formula 1.20, X is O, n is 2, each $L^1$ is the same or different halo, and Ar is:

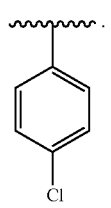

Cl

In another embodiment of this invention the compound of formula 1.0 is a compound of formula 1.20, X is O, each $L^1$ is halo, and Ar is phenyl substituted with at least one —$CF_3$.

In another embodiment of this invention the compound of formula 1.0 is a compound of formula 1.20, X is O, n is 2, each $L^1$ is the same or different halo, and Ar is phenyl substituted with one —$CF_3$.

In another embodiment of this invention the compound of formula 1.0 is a compound of formula 1.20, X is O, n is 2, $L^1$ is F, and Ar is phenyl substituted with one —$CF_3$.

In another embodiment of this invention the compound of formula 1.0 is a compound of formula 1.20, X is O, n is 2, each $L^1$ is the same or different halo, and Ar is:

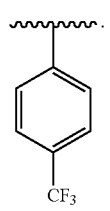

$CF_3$

In another embodiment of this invention the compound of formula 1.0 is a compound of formula 1.20, X is O, each $L^1$ is halo, and Ar is phenyl substituted with at least one —CN.

In another embodiment of this invention the compound of formula 1.0 is a compound of formula 1.20, X is O, n is 2, each $L^1$ is the same or different halo, and Ar is phenyl substituted with one —CN.

In another embodiment of this invention the compound of formula 1.0 is a compound of formula 1.20, X is O, n is 2, $L^1$ is F, and Ar is phenyl substituted with one —CN.

In another embodiment of this invention the compound of formula 1.0 is a compound of formula 1.20, X is O, n is 2, each $L^1$ is the same or different halo, and Ar is:

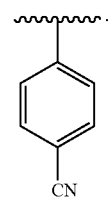

CN

In another embodiment of this invention the compound of formula 1.0 is a compound of formula 1.20, said compound having the formula (1.20B):

(1.20B)

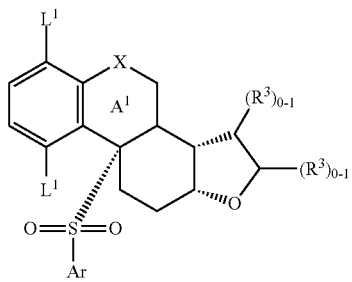

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is:

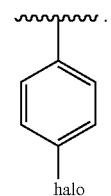

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is:

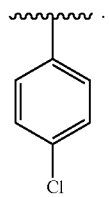 [SMILES: *c1ccc(Cl)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.208, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is:

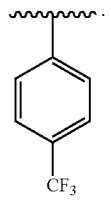 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ is selected from the group consisting of —$C_1$-$C_6$ alkyl, hydroxyalkyl, and alkoxyalkyl.

In another embodiment of this invention the compound of formula 1.0 is a compound of formula 1.20B, wherein X is O, each $L^1$ is the same or different halo, and Ar is:

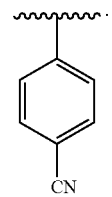

Another embodiment of this invention is directed to any one of the above embodiments directed to compounds of formula 1.18 except that the compound of formula 1.18A is used instead of the compound of formula 1.18, and the compound of formula 1.18C is instead of the compound of formula 1.18B. The compound of formula 1.18C is:

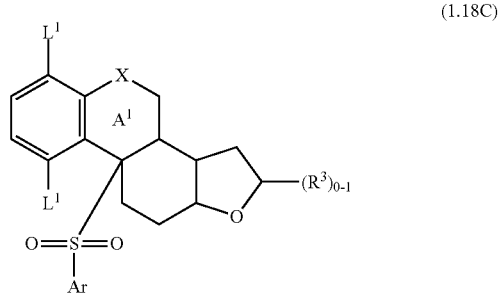

(1.18C)

Thus, for example, other embodiments of this invention are directed to each one of the embodiments described above for the compound of formula 1.18 except that the compound of formula 1.18A is used instead of the compound of 1.18, and the compound of formula 1.18C is used instead of the compound of formula 1.18B.

Another embodiment of this invention is directed to any one of the above embodiments directed to compounds of formula 1.19 except that the compound of formula 1.19A is used instead of the compound of formula 1.19, and the compound of formula 1.19C is instead of the compound of formula 1.19B. The compound of formal 1.19C is:

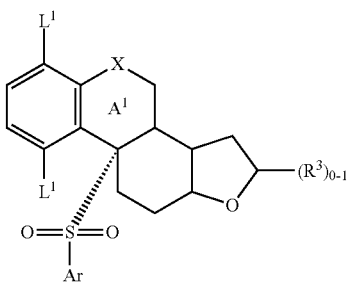

(1.19C)

Thus, for example, other embodiments of this invention are directed to each one of the embodiments described above for the compound of formula 1.19 except that the compound of formula 1.19A is used instead of the compound of 1.19, and the compound of formula 1.19C is used instead of the compound of formula 1.19B.

Another embodiment of this invention is directed to any one of the above embodiments directed to compounds of formula 1.20 except that the compound of formula 1.20A is used instead of the compound of formula 1.20, and the compound of formula 1.20C is instead of the compound of formula 1.20B. The compound of formal 1.20C is:

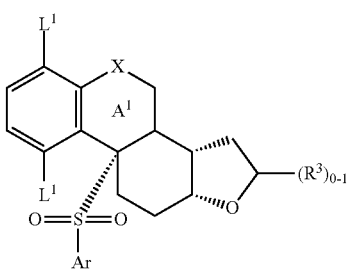

(1.20C)

Thus, for example, other embodiments of this invention are directed to each one of the embodiments described above for the compound of formula 1.20 except that the compound of formula 1.20A is used instead of the compound of 1.20, and the compound of formula 1.20C is used instead of the compound of formula 1.20B.

In another embodiment of this invention the compound of formula 1.0 is a compound of formula 1.21, and X is O.

In another embodiment of this invention the compound of formula 1.0 is a compound of formula 1.21 and $L^1$ is halo.

In another embodiment of this invention the compound of formula 1.0 is a compound of formula 1.21, said compound having the formula (1.21B):

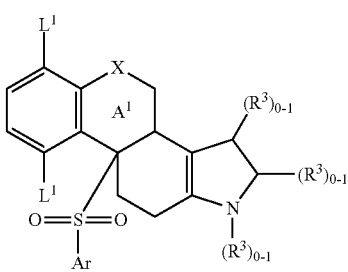

(1.21B)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21, n is 2 and $L^1$ is F.

In another embodiment of this invention the compound of formula 1.0 is a compound of formula 1.21B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21 and Ar is phenyl.

In another embodiment of this invention the compound of formula 1.0 is a compound of formula 1.21, Ar is phenyl substituted with halo.

In another embodiment of this invention the compound of formula 1.0 is a compound of formula 1.21 and Ar is phenyl substituted with one halo.

In another embodiment of this invention the compound of formula 1.0 is a compound of formula 1.21 and Ar is:

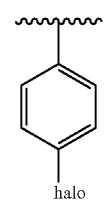

halo

In another embodiment of this invention the compound of formula 1.0 is a compound of formula 1.21 and Ar is phenyl substituted with at least one Cl.

In another embodiment of this invention the compound of formula 1.0 is a compound of formula 1.21 and Ar is phenyl substituted with a Cl.

In another embodiment of this invention the compound of formula 1.0 is a compound of formula 1.21 and Ar is:

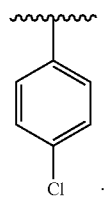

In another embodiment of this invention the compound of formula 1.0 is a compound of formula 1.21 and Ar is phenyl substituted with at least one —CF$_3$.

In another embodiment of this invention the compound of formula 1.0 is a compound of formula 1.21 and Ar is phenyl substituted with a —CF$_3$.

In another embodiment of this invention the compound of formula 1.0 is a compound of formula 1.21 and Ar is:

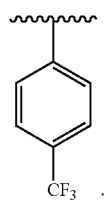

In another embodiment of this invention the compound of formula 1.0 is a compound of formula 1.21 and Ar is phenyl substituted with at least one —CN.

In another embodiment of this invention the compound of formula 1.0 is a compound of formula 1.21 and Ar is phenyl substituted with a —CN.

In another embodiment of this invention the compound of formula 1.0 is a compound of formula 1.21 and Ar is:

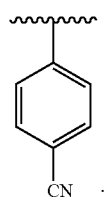

In another embodiment of this invention the compound of formula 1.0 is a compound of formula 1.21, X is O, each L$^1$ is halo, and Ar is phenyl substituted with at least one halo.

In another embodiment of this invention the compound of formula 1.0 is a compound of formula 1.21, X is O, n is 2, each L$^1$ is the same or different halo, and Ar is phenyl substituted with one halo.

In another embodiment of this invention the compound of formula 1.0 is a compound of formula 1.11, X is O, n is 2, L$^1$ is F, and Ar is phenyl substituted with one Cl.

In another embodiment of this invention the compound of formula 1.0 is a compound of formula 1.21, X is O, n is 2, each L$^1$ is the same or different halo, and Ar is:

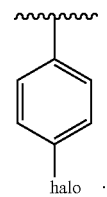

In another embodiment of this invention the compound of formula 1.0 is a compound of formula 1.21, X is O, n is 2, each L$^1$ is the same or different halo, and Ar is:

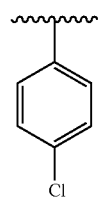

In another embodiment of this invention the compound of formula 1.0 is a compound of formula 1.21, X is O, each L$^1$ is halo, and Ar is phenyl substituted with at least one —CF$_3$.

In another embodiment of this invention the compound of formula 1.0 is a compound of formula 1.21, X is O, n is 2, each L$^1$ is the same or different halo, and Ar is phenyl substituted with one —CF$_3$.

In another embodiment of this invention the compound of formula 1.0 is a compound of formula 1.21, X is O, n is 2, L$^1$ is F, and Ar is phenyl substituted with one —CF$_3$.

In another embodiment of this invention the compound of formula 1.0 is a compound of formula 1.21, X is O, n is 2, each L$^1$ is the same or different halo, and Ar is:

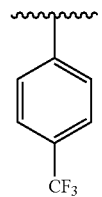

In another embodiment of this invention the compound of formula 1.0 is a compound of formula 1.21, X is O, each L$^1$ is halo, and Ar is phenyl substituted with at least one —CN.

In another embodiment of this invention the compound of formula 1.0 is a compound of formula 1.21, X is O, n is 2, each L$^1$ is the same or different halo, and Ar is phenyl substituted with one —CN.

In another embodiment of this invention the compound of formula 1.0 is a compound of formula 1.21, X is O, n is 2, L$^1$ is F, and Ar is phenyl substituted with one —CN.

In another embodiment of this invention the compound of formula 1.0 is a compound of formula 1.21, X is O, n is 2, each L$^1$ is the same or different halo, and Ar is:

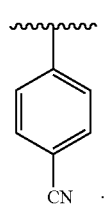

In another embodiment of this invention the compound of formula 1.0 is a compound of formula 1.21, said compound having the formula (1.21B):

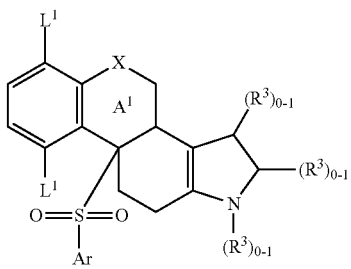

(1.21B)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is:

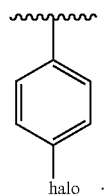

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is:

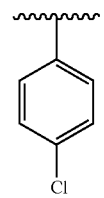

In the substituent "$(R^3)_{3-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is:

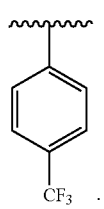

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.21B, wherein X is O, each $L^1$ is the same or different halo, and Ar is:

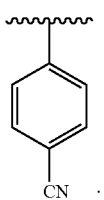

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.22, and X is O.

In another embodiment of this invention the compound of formula 1.0 is a compound of formula 1.22 and $L^1$ is halo.

In another embodiment of this invention the compound of formula 1.0 is a compound of formula 1.22, said compound having the formula (1.22B):

(1.22B)

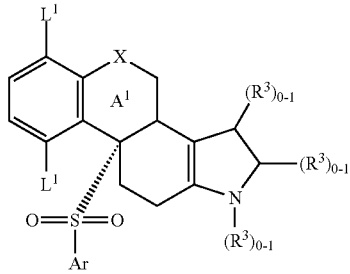

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.22B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.22, n is 2 and $L^1$ is F.

In another embodiment of this invention the compound of formula 1.0 is a compound of formula 1.22B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.22 and Ar is phenyl.

In another embodiment of this invention the compound of formula 1.0 is a compound of formula 1.22, Ar is phenyl substituted with halo.

In another embodiment of this invention the compound of formula 1.0 is a compound of formula 1.22 and Ar is phenyl substituted with one halo.

In another embodiment of this invention the compound of formula 1.0 is a compound of formula 1.22 and Ar is:

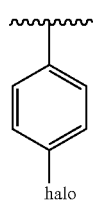

In another embodiment of this invention the compound of formula 1.0 is a compound of formula 1.22 and Ar is phenyl substituted with at least one Cl.

In another embodiment of this invention the compound of formula 1.0 is a compound of formula 1.22 and Ar is phenyl substituted with a Cl.

In another embodiment of this invention the compound of formula 1.0 is a compound of formula 1.22 and Ar is:

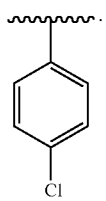

In another embodiment of this invention the compound of formula 1.0 is a compound of formula 1.22 and Ar is phenyl substituted with at least one —$CF_3$.

In another embodiment of this invention the compound of formula 1.0 is a compound of formula 1.22 and Ar is phenyl substituted with a —$CF_3$.

In another embodiment of this invention the compound of formula 1.0 is a compound of formula 1.22 and Ar is:

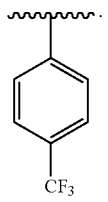

In another embodiment of this invention the compound of formula 1.0 is a compound of formula 1.22 and Ar is phenyl substituted with at least one —CN.

In another embodiment of this invention the compound of formula 1.0 is a compound of formula 1.22 and Ar is phenyl substituted with a —CN.

In another embodiment of this invention the compound of formula 1.0 is a compound of formula 1.22 and Ar is:

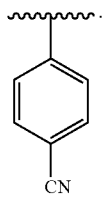

In another embodiment of this invention the compound of formula 1.0 is a compound of formula 1.22, X is O, each $L^1$ is halo, and Ar is phenyl substituted with at least one halo.

In another embodiment of this invention the compound of formula 1.0 is a compound of formula 1.22, X is O, n is 2, each $L^1$ is the same or different halo, and Ar is phenyl substituted with one halo.

In another embodiment of this invention the compound of formula 1.0 is a compound of formula 1.22, X is O, n is 2, $L^1$ is F, and Ar is phenyl substituted with one Cl.

In another embodiment of this invention the compound of formula 1.0 is a compound of formula 1.22, X is O, n is 2, each $L^1$ is the same or different halo, and Ar is:

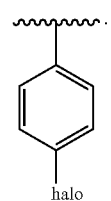

In another embodiment of this invention the compound of formula 1.0 is a compound of formula 1.22, X is O, n is 2, each $L^1$ is the same or different halo, and Ar is:

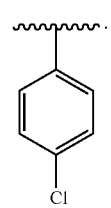 [SMILES: *c1ccc(Cl)cc1]

In another embodiment of this invention the compound of formula 1.0 is a compound of formula 1.22, X is O, each $L^1$ is halo, and Ar is phenyl substituted with at least one —$CF_3$.

In another embodiment of this invention the compound of formula 1.0 is a compound of formula 1.22, X is O, n is 2, each $L^1$ is the same or different halo, and Ar is phenyl substituted with one —$CF_3$.

In another embodiment of this invention the compound of formula 1.0 is a compound of formula 1.22, X is O, n is 2, $L^1$ is F, and Ar is phenyl substituted with one —$CF_3$.

In another embodiment of this invention the compound of formula 1.0 is a compound of formula 1.22, X is O, n is 2, each $L^1$ is the same or different halo, and Ar is:

In another embodiment of this invention the compound of formula 1.0 is a compound of formula 1.22, X is O, each $L^1$ is halo, and Ar is phenyl substituted with at least one —CN.

In another embodiment of this invention the compound of formula 1.0 is a compound of formula 1.22, X is O, n is 2, each $L^1$ is the same or different halo, and Ar is phenyl substituted with one —CN.

In another embodiment of this invention the compound of formula 1.0 is a compound of formula 1.22, X is O, n is 2, $L^1$ is F, and Ar is phenyl substituted with one —CN.

In another embodiment of this invention the compound of formula 1.0 is a compound of formula 1.22, X is O, n is 2, each $L^1$ is the same or different halo, and Ar is:

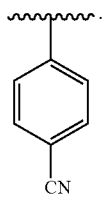

In another embodiment of this invention the compound of formula 1.0 is a compound of formula 1.22, said compound having the formula (1.22B):

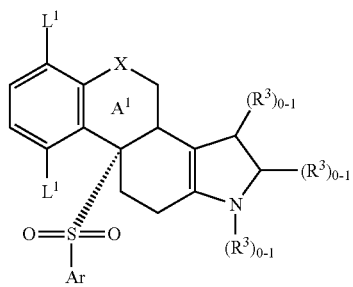

(1.22B)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.22B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.22B, wherein X is O, each $L^1$ is the same or different halo, and Ar is:

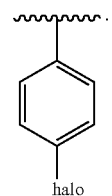

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.22B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.228, wherein X is O, each $L^1$ is the same or different halo, and Ar is:

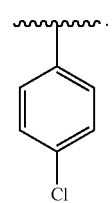

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.228, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.228, wherein X is O, each $L^1$ is the same or different halo, and Ar is phenyl substituted with one —CF$_3$. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.22B, wherein X is O, each L$^1$ is the same or different halo, and Ar is:

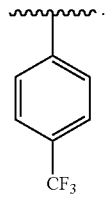

In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.22B, wherein X is O, each L$^1$ is the same or different halo, and Ar is phenyl substituted with one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.22B, wherein X is O, each L$^1$ is the same or different halo, and Ar is phenyl substituted with one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.22B, wherein X is O, each L$^1$ is the same or different halo, and Ar is:

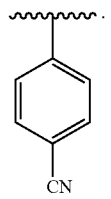

In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

Another embodiment of this invention is directed to any one of the above embodiments directed to compounds of formula 1.21 except that the compound of formula 1.21A is used instead of the compound of formula 1.21, and the compound of formula 1.21C is instead of the compound of formula 1.21B. The compound of formula 1.21C is:

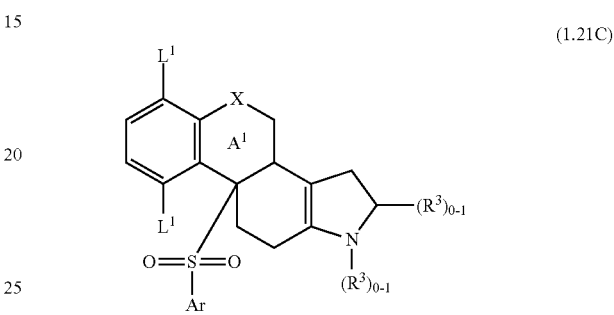

Thus, for example, other embodiments of this invention are directed to each one of the embodiments described above for the compound of formula 1.21 except that the compound of formula 1.21A is used instead of the compound of 1.218, and the compound of formula 1.21C is used instead of the compound of formula 1.21B.

Another embodiment of this invention is directed to any one of the above embodiments directed to compounds of formula 1.22 except that the compound of formula 1.22A is used instead of the compound of formula 1.22, and the compound of formula 1.22C is instead of the compound of formula 1.21B. The compound of formula 1.22C is:

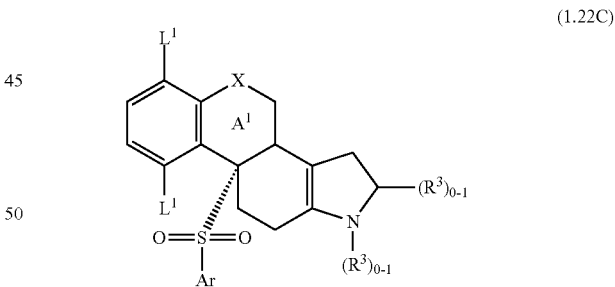

Thus, for example, other embodiments of this invention are directed to each one of the embodiments described above for the compound of formula 1.22 except that the compound of formula 1.22A is used instead of the compound of 1.22, and the compound of formula 1.22C is used instead of the compound of formula 1.22B.

In another embodiment of this invention the compound of formula 1.0 is a compound of formula 1.23, and X is O.

In another embodiment of this invention the compound of formula 1.0 is a compound of formula 1.23 and L$^1$ is halo.

In another embodiment of this invention the compound of formula 1.0 is a compound of formula 1.23, said compound having the formula (1.23B):

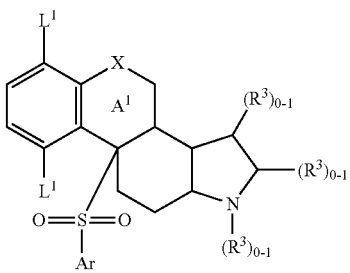

(1.23B)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23, n is 2 and $L^1$ is F.

In another embodiment of this invention the compound of formula 1.0 is a compound of formula 1.23B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23 and Ar is phenyl.

In another embodiment of this invention the compound of formula 1.0 is a compound of formula 1.23, Ar is phenyl substituted with halo.

In another embodiment of this invention the compound of formula 1.0 is a compound of formula 1.23 and Ar is phenyl substituted with one halo.

In another embodiment of this invention the compound of formula 1.0 is a compound of formula 1.23 and Ar is:

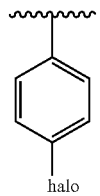

In another embodiment of this invention the compound of formula 1.0 is a compound of formula 1.23 and Ar is phenyl substituted with at least one Cl.

In another embodiment of this invention the compound of formula 1.0 is a compound of formula 1.23 and Ar is phenyl substituted with a Cl.

In another embodiment of this invention the compound of formula 1.0 is a compound of formula 1.23 and Ar is:

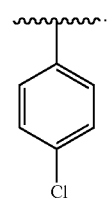

In another embodiment of this invention the compound of formula 1.0 is a compound of formula 1.23 and Ar is phenyl substituted with at least one —$CF_3$.

In another embodiment of this invention the compound of formula 1.0 is a compound of formula 1.23 and Ar is phenyl substituted with a —$CF_3$.

In another embodiment of this invention the compound of formula 1.0 is a compound of formula 1.23 and Ar is:

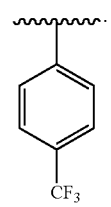

In another embodiment of this invention the compound of formula 1.0 is a compound of formula 1.23 and Ar is phenyl substituted with at least one —CN.

In another embodiment of this invention the compound of formula 1.0 is a compound of formula 1.23 and Ar is phenyl substituted with a —CN.

In another embodiment of this invention the compound of formula 1.0 is a compound of formula 1.23 and Ar is:

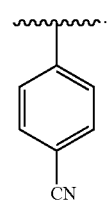

In another embodiment of this invention the compound of formula 1.0 is a compound of formula 1.23, X is O, each $L^1$ is halo, and Ar is phenyl substituted with at least one halo.

In another embodiment of this invention the compound of formula 1.0 is a compound of formula 1.23, X is O, n is 2, each $L^1$ is the same or different halo, and Ar is phenyl substituted with one halo.

In another embodiment of this invention the compound of formula 1.0 is a compound of formula 1.23, X is O, n is 2, $L^1$ is F, and Ar is phenyl substituted with one Cl.

In another embodiment of this invention the compound of formula 1.0 is a compound of formula 1.23, X is O, n is 2, each $L^1$ is the same or different halo, and Ar is:

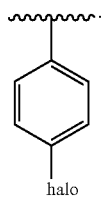

In another embodiment of this invention the compound of formula 1.0 is a compound of formula 1.23, X is O, n is 2, each $L^1$ is the same or different halo, and Ar is:

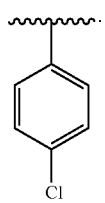

In another embodiment of this invention the compound of formula 1.0 is a compound of formula 1.23, X is O, each $L^1$ is halo, and Ar is phenyl substituted with at least one —$CF_3$.

In another embodiment of this invention the compound of formula 1.0 is a compound of formula 1.23, X is O, n is 2, each $L^1$ is the same or different halo, and Ar is phenyl substituted with one —$CF_3$.

In another embodiment of this invention the compound of formula 1.0 is a compound of formula 1.23, X is O, n is 2, $L^1$ is F, and Ar is phenyl substituted with one —$CF_3$.

In another embodiment of this invention the compound of formula 1.0 is a compound of formula 1.23, X is O, n is 2, each $L^1$ is the same or different halo, and Ar is:

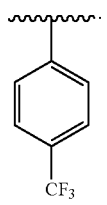

In another embodiment of this invention the compound of formula 1.0 is a compound of formula 1.23, X is O, each $L^1$ is halo, and Ar is phenyl substituted with at least one —CN.

In another embodiment of this invention the compound of formula 1.0 is a compound of formula 1.23, X is O, n is 2, each $L^1$ is the same or different halo, and Ar is phenyl substituted with one —CN.

In another embodiment of this invention the compound of formula 1.0 is a compound of formula 1.23, X is O, n is 2, $L^1$ is F, and Ar is phenyl substituted with one —CN.

In another embodiment of this invention the compound of formula 1.0 is a compound of formula 1.23, X is O, n is 2, each $L^1$ is the same or different halo, and Ar is:

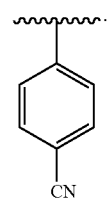

In another embodiment of this invention the compound of formula 1.0 is a compound of formula 1.23, said compound having the formula (1.23B):

(1.23B)

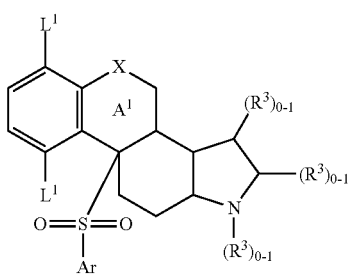

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is:

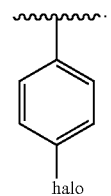

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is:

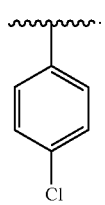

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.23B, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is:

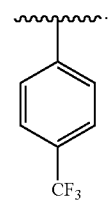 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.23B, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.23B, wherein X is O, each $L^1$ is the same or different halo, and Ar is:

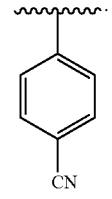

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.24, and X is O.

In another embodiment of this invention the compound of formula 1.0 is a compound of formula 1.24 and $L^1$ is halo.

In another embodiment of this invention the compound of formula 1.0 is a compound of formula 1.24, said compound having the formula (1.24B):

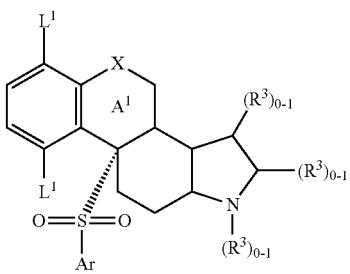

(1.24B)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.248, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.24, n is 2 and $L^1$ is F.

In another embodiment of this invention the compound of formula 1.0 is a compound of formula 1.248, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.24 and Ar is phenyl.

In another embodiment of this invention the compound of formula 1.0 is a compound of formula 1.24, Ar is phenyl substituted with halo.

In another embodiment of this invention the compound of formula 1.0 is a compound of formula 1.24 and Ar is phenyl substituted with one halo.

In another embodiment of this invention the compound of formula 1.0 is a compound of formula 1.24 and Ar is:

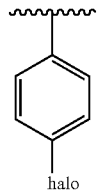
halo

In another embodiment of this invention the compound of formula 1.0 is a compound of formula 1.24 and Ar is phenyl substituted with at least one Cl.

In another embodiment of this invention the compound of formula 1.0 is a compound of formula 1.24 and Ar is phenyl substituted with a Cl.

In another embodiment of this invention the compound of formula 1.0 is a compound of formula 1.24 and Ar is:

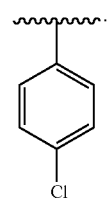
Cl

In another embodiment of this invention the compound of formula 1.0 is a compound of formula 1.24 and Ar is phenyl substituted with at least one —$CF_3$.

In another embodiment of this invention the compound of formula 1.0 is a compound of formula 1.24 and Ar is phenyl substituted with a —$CF_3$.

In another embodiment of this invention the compound of formula 1.0 is a compound of formula 1.24 and Ar is:

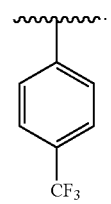
$CF_3$

In another embodiment of this invention the compound of formula 1.0 is a compound of formula 1.24 and Ar is phenyl substituted with at least one —CN.

In another embodiment of this invention the compound of formula 1.0 is a compound of formula 1.24 and Ar is phenyl substituted with a —CN.

In another embodiment of this invention the compound of formula 1.0 is a compound of formula 1.24 and Ar is:

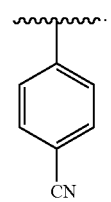
CN

In another embodiment of this invention the compound of formula 1.0 is a compound of formula 1.24, X is O, each $L^1$ is halo, and Ar is phenyl substituted with at least one halo.

In another embodiment of this invention the compound of formula 1.0 is a compound of formula 1.24, X is O, n is 2, each $L^1$ is the same or different halo, and Ar is phenyl substituted with one halo.

In another embodiment of this invention the compound of formula 1.0 is a compound of formula 1.24, X is O, n is 2, $L^1$ is F, and Ar is phenyl substituted with one Cl.

In another embodiment of this invention the compound of formula 1.0 is a compound of formula 1.24, X is O, n is 2, each $L^1$ is the same or different halo, and Ar is:

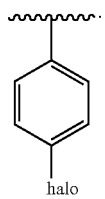
halo

In another embodiment of this invention the compound of formula 1.0 is a compound of formula 1.24, X is O, n is 2, each $L^1$ is the same or different halo, and Ar is:

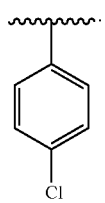
Cl

In another embodiment of this invention the compound of formula 1.0 is a compound of formula 1.24, X is O, each $L^1$ is halo, and Ar is phenyl substituted with at least one —$CF_3$.

In another embodiment of this invention the compound of formula 1.0 is a compound of formula 1.24, X is O, n is 2, each $L^1$ is the same or different halo, and Ar is phenyl substituted with one —$CF_3$.

In another embodiment of this invention the compound of formula 1.0 is a compound of formula 1.24, X is O, n is 2, $L^1$ is F, and Ar is phenyl substituted with one —$CF_3$.

In another embodiment of this invention the compound of formula 1.0 is a compound of formula 1.24, X is O, n is 2, each $L^1$ is the same or different halo, and Ar is:

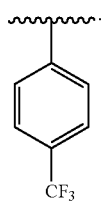
$CF_3$

In another embodiment of this invention the compound of formula 1.0 is a compound of formula 1.24, X is O, each $L^1$ is halo, and Ar is phenyl substituted with at least one —CN.

In another embodiment of this invention the compound of formula 1.0 is a compound of formula 1.24, X is O, n is 2, each $L^1$ is the same or different halo, and Ar is phenyl substituted with one —CN.

In another embodiment of this invention the compound of formula 1.0 is a compound of formula 1.24, X is O, n is 2, $L^1$ is F, and Ar is phenyl substituted with one —CN.

In another embodiment of this invention the compound of formula 1.0 is a compound of formula 1.24, X is O, n is 2, each $L^1$ is the same or different halo, and Ar is:

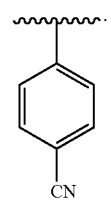
CN

In another embodiment of this invention the compound of formula 1.0 is a compound of formula 1.24, said compound having the formula (1.24B):

(1.24B)

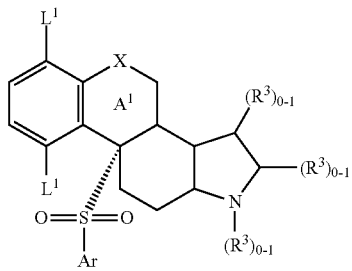

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.248, wherein X is O, each $L^1$ is the same or different halo, and Ar is:

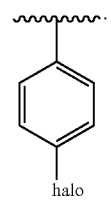
halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.248, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.248, wherein X is O, each $L^1$ is the same or different halo, and Ar is:

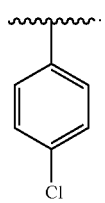

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is phenyl substituted with at least one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is phenyl substituted with one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is:

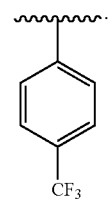

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is phenyl substituted with at least one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is phenyl substituted with one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.24B, wherein X is O, each $L^1$ is the same or different halo, and Ar is:

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1$-$C_6$ alkyl, hydroxyalkyl, and alkoxyalkyl.

In another embodiment of this invention the compound of formula 1.0 is a compound of formula 1.25, and X is O.

In another embodiment of this invention the compound of formula 1.0 is a compound of formula 1.25 and L¹ is halo.

In another embodiment of this invention the compound of formula 1.0 is a compound of formula 1.25, said compound having the formula (1.25B):

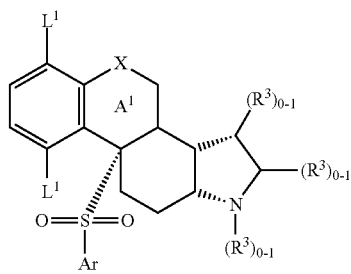

(1.25B)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25, n is 2 and L¹ is F.

In another embodiment of this invention the compound of formula 1.0 is a compound of formula 1.25B, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25 and Ar is phenyl.

In another embodiment of this invention the compound of formula 1.0 is a compound of formula 1.25, Ar is phenyl substituted with halo.

In another embodiment of this invention the compound of formula 1.0 is a compound of formula 1.25 and Ar is phenyl substituted with one halo.

In another embodiment of this invention the compound of formula 1.0 is a compound of formula 1.25 and Ar is:

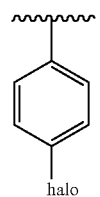

In another embodiment of this invention the compound of formula 1.0 is a compound of formula 1.25 and Ar is phenyl substituted with at least one Cl.

In another embodiment of this invention the compound of formula 1.0 is a compound of formula 1.25 and Ar is phenyl substituted with a Cl.

In another embodiment of this invention the compound of formula 1.0 is a compound of formula 1.25 and Ar is:

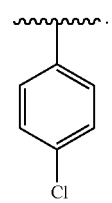

In another embodiment of this invention the compound of formula 1.0 is a compound of formula 1.25 and Ar is phenyl substituted with at least one —$CF_3$.

In another embodiment of this invention the compound of formula 1.0 is a compound of formula 1.25 and Ar is phenyl substituted with a —$CF_3$.

In another embodiment of this invention the compound of formula 1.0 is a compound of formula 1.25 and Ar is:

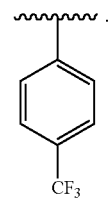

In another embodiment of this invention the compound of formula 1.0 is a compound of formula 1.25 and Ar is phenyl substituted with at least one —CN.

In another embodiment of this invention the compound of formula 1.0 is a compound of formula 1.25 and Ar is phenyl substituted with a —CN.

In another embodiment of this invention the compound of formula 1.0 is a compound of formula 1.25 and Ar is:

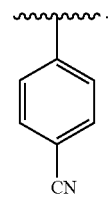

In another embodiment of this invention the compound of formula 1.0 is a compound of formula 1.25, X is O, each $L^1$ is halo, and Ar is phenyl substituted with at least one halo.

In another embodiment of this invention the compound of formula 1.0 is a compound of formula 1.25, X is O, n is 2, each $L^1$ is the same or different halo, and Ar is phenyl substituted with one halo.

In another embodiment of this invention the compound of formula 1.0 is a compound of formula 1.25, X is O, n is 2, $L^1$ is F, and Ar is phenyl substituted with one Cl.

In another embodiment of this invention the compound of formula 1.0 is a compound of formula 1.25, X is O, n is 2, each $L^1$ is the same or different halo, and Ar is:

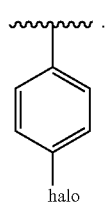

halo

In another embodiment of this invention the compound of formula 1.0 is a compound of formula 1.25, X is O, n is 2, each $L^1$ is the same or different halo, and Ar is:

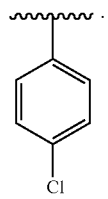

Cl

In another embodiment of this invention the compound of formula 1.0 is a compound of formula 1.25, X is O, each $L^1$ is halo, and Ar is phenyl substituted with at least one —$CF_3$.

In another embodiment of this invention the compound of formula 1.0 is a compound of formula 1.25, X is O, n is 2, each $L^1$ is the same or different halo, and Ar is phenyl substituted with one —$CF_3$.

In another embodiment of this invention the compound of formula 1.0 is a compound of formula 1.25, X is O, n is 2, $L^1$ is F, and Ar is phenyl substituted with one —$CF_3$.

In another embodiment of this invention the compound of formula 1.0 is a compound of formula 1.25, X is O, n is 2, each $L^1$ is the same or different halo, and Ar is:

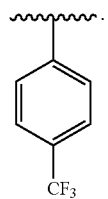

$CF_3$

In another embodiment of this invention the compound of formula 1.0 is a compound of formula 1.25, X is O, each $L^1$ is halo, and Ar is phenyl substituted with at least one —CN.

In another embodiment of this invention the compound of formula 1.0 is a compound of formula 1.25, X is O, n is 2, each $L^1$ is the same or different halo, and Ar is phenyl substituted with one —CN.

In another embodiment of this invention the compound of formula 1.0 is a compound of formula 1.25, X is O, n is 2, $L^1$ is F, and Ar is phenyl substituted with one —CN.

In another embodiment of this invention the compound of formula 1.0 is a compound of formula 1.25, X is O, n is 2, each $L^1$ is the same or different halo, and Ar is:

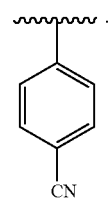

CN

In another embodiment of this invention the compound of formula 1.0 is a compound of formula 1.25, said compound having the formula (1.25B):

(1.25B)

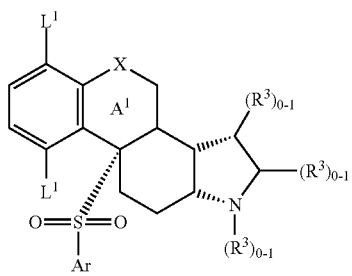

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is:

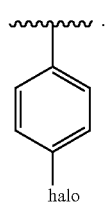

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is:

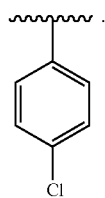

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is:

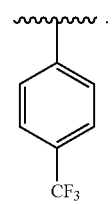

$CF_3$

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.25B, wherein X is O, each $L^1$ is the same or different halo, and Ar is:

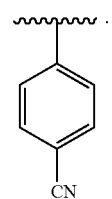

CN

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

Another embodiment of this invention is directed to any one of the above embodiments directed to compounds of formula 1.23 except that the compound of formula 1.23A is used instead of the compound of formula 1.23, and the compound of formula 1.23C is instead of the compound of formula 1.23B. The compound of formula 1.23C is:

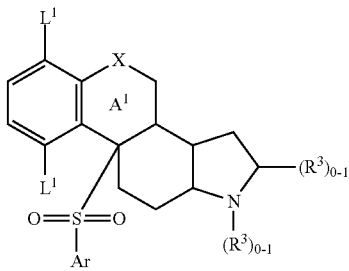

(1.23C)

Thus, for example, other embodiments of this invention are directed to each one of the embodiments described above for the compound of formula 1.23 except that the compound of formula 1.23A is used instead of the compound of 1.23, and the compound of formula 1.23C is used instead of the compound of formula 1.23B.

Another embodiment of this invention is directed to any one of the above embodiments directed to compounds of formula 1.24 except that the compound of formula 1.24A is used instead of the compound of formula 1.24, and the compound of formula 1.24C is instead of the compound of formula 1.24B. The compound of formula 1.24C is:

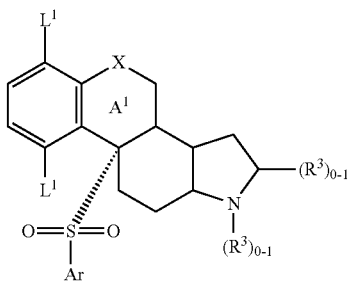

(1.24C)

Thus, for example, other embodiments of this invention are directed to each one of the embodiments described above for the compound of formula 1.24 except that the compound of formula 1.24A is used instead of the compound of 1.24, and the compound of formula 1.24C is used instead of the compound of formula 1.24B.

Another embodiment of this invention is directed to any one of the above embodiments directed to compounds of formula 1.25 except that the compound of formula 1.25A is used instead of the compound of formula 1.25, and the compound of formula 1.25C is instead of the compound of formula 1.25B. The compound of formula 1.25C is:

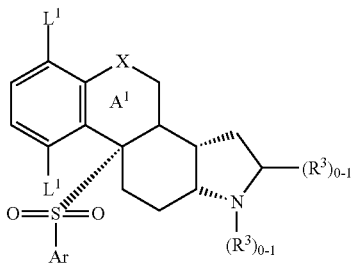

(1.25C)

Thus, for example, other embodiments of this invention are directed to each one of the embodiments described above for the compound of formula 1.25 except that the compound of formula 1.25A is used instead of the compound of 1.25, and the compound of formula 1.25C is used instead of the compound of formula 1.25B.

In another embodiment of this invention the compound of formula 1.0 is a compound of formula 1.26, and X is O.

In another embodiment of this invention the compound of formula 1.0 is a compound of formula 1.26 and $L^1$ is halo.

In another embodiment of this invention the compound of formula 1.0 is a compound of formula 1.26, said compound having the formula (1.26A):

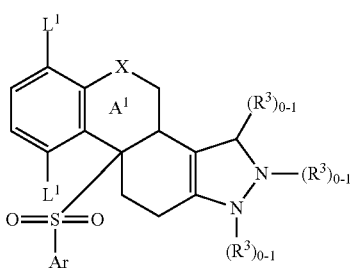

(1.26A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26, n is 2 and $L^1$ is F.

In another embodiment of this invention the compound of formula 1.0 is a compound of formula 1.26A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26 and Ar is phenyl.

In another embodiment of this invention the compound of formula 1.0 is a compound of formula 1.26, Ar is phenyl substituted with halo.

In another embodiment of this invention the compound of formula 1.0 is a compound of formula 1.26 and Ar is phenyl substituted with one halo.

In another embodiment of this invention the compound of formula 1.0 is a compound of formula 1.26 and Ar is:

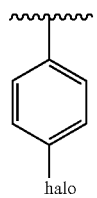

In another embodiment of this invention the compound of formula 1.0 is a compound of formula 1.26 and Ar is phenyl substituted with at least one Cl.

In another embodiment of this invention the compound of formula 1.0 is a compound of formula 1.26 and Ar is phenyl substituted with a Cl.

In another embodiment of this invention the compound of formula 1.0 is a compound of formula 1.26 and Ar is:

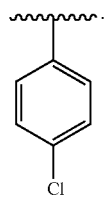

In another embodiment of this invention the compound of formula 1.0 is a compound of formula 1.26 and Ar is phenyl substituted with at least one —$CF_3$.

In another embodiment of this invention the compound of formula 1.0 is a compound of formula 1.26 and Ar is phenyl substituted with a —$CF_3$.

In another embodiment of this invention the compound of formula 1.0 is a compound of formula 1.26 and Ar is:

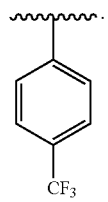

In another embodiment of this invention the compound of formula 1.0 is a compound of formula 1.26 and Ar is phenyl substituted with at least one —CN.

In another embodiment of this invention the compound of formula 1.0 is a compound of formula 1.26 and Ar is phenyl substituted with a —CN.

In another embodiment of this invention the compound of formula 1.0 is a compound of formula 1.26 and Ar is:

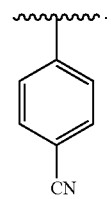

In another embodiment of this invention the compound of formula 1.0 is a compound of formula 1.26, X is O, each $L^1$ is halo, and Ar is phenyl substituted with at least one halo.

In another embodiment of this invention the compound of formula 1.0 is a compound of formula 1.26, X is O, n is 2, each $L^1$ is the same or different halo, and Ar is phenyl substituted with one halo.

In another embodiment of this invention the compound of formula 1.0 is a compound of formula 1.26, X is O, n is 2, $L^1$ is F, and Ar is phenyl substituted with one Cl.

In another embodiment of this invention the compound of formula 1.0 is a compound of formula 1.26, X is O, n is 2, each $L^1$ is the same or different halo, and Ar is:

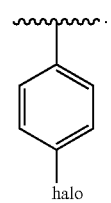

In another embodiment of this invention the compound of formula 1.0 is a compound of formula 1.26, X is O, n is 2, each $L^1$ is the same or different halo, and Ar is:

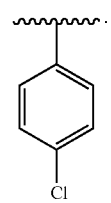

In another embodiment of this invention the compound of formula 1.0 is a compound of formula 1.26, X is O, each $L^1$ is halo, and Ar is phenyl substituted with at least one —$CF_3$.

In another embodiment of this invention the compound of formula 1.0 is a compound of formula 1.26, X is O, n is 2, each $L^1$ is the same or different halo, and Ar is phenyl substituted with one —$CF_3$.

In another embodiment of this invention the compound of formula 1.0 is a compound of formula 1.26, X is O, n is 2, $L^1$ is F, and Ar is phenyl substituted with one —$CF_3$.

In another embodiment of this invention the compound of formula 1.0 is a compound of formula 1.26, X is O, n is 2, each $L^1$ is the same or different halo, and Ar is:

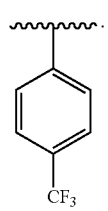

In another embodiment of this invention the compound of formula 1.0 is a compound of formula 1.26, X is O, each $L^1$ is halo, and Ar is phenyl substituted with at least one —CN.

In another embodiment of this invention the compound of formula 1.0 is a compound of formula 1.26, X is O, n is 2, each $L^1$ is the same or different halo, and Ar is phenyl substituted with one —CN.

In another embodiment of this invention the compound of formula 1.0 is a compound of formula 1.26, X is O, n is 2, $L^1$ is F, and Ar is phenyl substituted with one —CN.

In another embodiment of this invention the compound of formula 1.0 is a compound of formula 1.26, X is O, n is 2, each $L^1$ is the same or different halo, and Ar is:

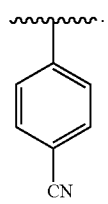

In another embodiment of this invention the compound of formula 1.0 is a compound of formula 1.26, said compound having the formula (1.26A):

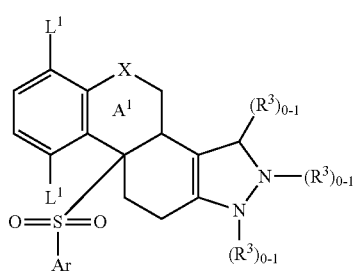

(1.26A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is:

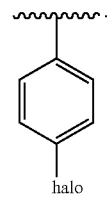

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is:

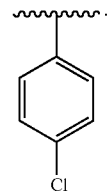

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is:

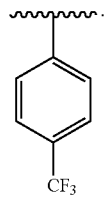

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.26A, wherein X is O, each $L^1$ is the same or different halo, and Ar is:

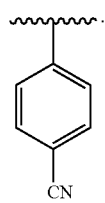

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27, and X is O.

In another embodiment of this invention the compound of formula 1.0 is a compound of formula 1.27 and $L^1$ is halo.

In another embodiment of this invention the compound of formula 1.0 is a compound of formula 1.27, said compound having the formula (1.27A):

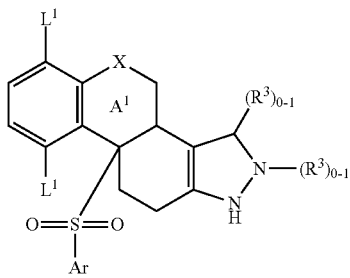

(1.27A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27, n is 2 and $L^1$ is F.

In another embodiment of this invention the compound of formula 1.0 is a compound of formula 1.27A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27 and Ar is phenyl.

In another embodiment of this invention the compound of formula 1.0 is a compound of formula 1.27, Ar is phenyl substituted with halo.

In another embodiment of this invention the compound of formula 1.0 is a compound of formula 1.27 and Ar is phenyl substituted with one halo.

In another embodiment of this invention the compound of formula 1.0 is a compound of formula 1.27 and Ar is:

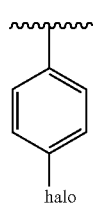

In another embodiment of this invention the compound of formula 1.0 is a compound of formula 1.27 and Ar is phenyl substituted with at least one Cl.

In another embodiment of this invention the compound of formula 1.0 is a compound of formula 1.27 and Ar is phenyl substituted with a Cl.

In another embodiment of this invention the compound of formula 1.0 is a compound of formula 1.27 and Ar is:

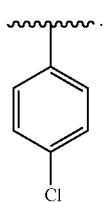

In another embodiment of this invention the compound of formula 1.0 is a compound of formula 1.27 and Ar is phenyl substituted with at least one —$CF_3$.

In another embodiment of this invention the compound of formula 1.0 is a compound of formula 1.27 and Ar is phenyl substituted with a —$CF_3$.

In another embodiment of this invention the compound of formula 1.0 is a compound of formula 1.27 and Ar is:

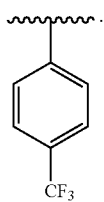

In another embodiment of this invention the compound of formula 1.0 is a compound of formula 1.27 and Ar is phenyl substituted with at least one —CN.

In another embodiment of this invention the compound of formula 1.0 is a compound of formula 1.27 and Ar is phenyl substituted with a —CN.

In another embodiment of this invention the compound of formula 1.0 is a compound of formula 1.27 and Ar is:

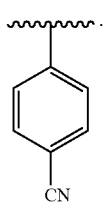 [SMILES: *c1ccc(C#N)cc1]

In another embodiment of this invention the compound of formula 1.0 is a compound of formula 1.27, X is O, each $L^1$ is halo, and Ar is phenyl substituted with at least one halo.

In another embodiment of this invention the compound of formula 1.0 is a compound of formula 1.27, X is O, n is 2, each $L^1$ is the same or different halo, and Ar is phenyl substituted with one halo.

In another embodiment of this invention the compound of formula 1.0 is a compound of formula 1.27, X is O, n is 2, $L^1$ is F, and Ar is phenyl substituted with one Cl.

In another embodiment of this invention the compound of formula 1.0 is a compound of formula 1.27, X is O, n is 2, each $L^1$ is the same or different halo, and Ar is:

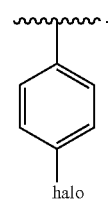

In another embodiment of this invention the compound of formula 1.0 is a compound of formula 1.27, X is O, n is 2, each $L^1$ is the same or different halo, and Ar is:

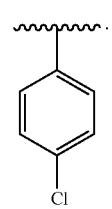

In another embodiment of this invention the compound of formula 1.0 is a compound of formula 1.27, X is O, each $L^1$ is halo, and Ar is phenyl substituted with at least one —$CF_3$.

In another embodiment of this invention the compound of formula 1.0 is a compound of formula 1.27, X is O, n is 2, each $L^1$ is the same or different halo, and Ar is phenyl substituted with one —$CF_3$.

In another embodiment of this invention the compound of formula 1.0 is a compound of formula 1.27, X is O, n is 2, $L^1$ is F, and Ar is phenyl substituted with one —$CF_3$.

In another embodiment of this invention the compound of formula 1.0 is a compound of formula 1.27, X is O, n is 2, each $L^1$ is the same or different halo, and Ar is:

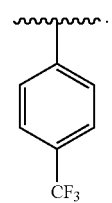

In another embodiment of this invention the compound of formula 1.0 is a compound of formula 1.27, X is O, each $L^1$ is halo, and Ar is phenyl substituted with at least one —CN.

In another embodiment of this invention the compound of formula 1.0 is a compound of formula 1.27, X is O, n is 2, each $L^1$ is the same or different halo, and Ar is phenyl substituted with one —CN.

In another embodiment of this invention the compound of formula 1.0 is a compound of formula 1.27, X is O, n is 2, $L^1$ is F, and Ar is phenyl substituted with one —CN In another embodiment of this invention the compound of formula 1.0 is a compound of formula 1.27, X is O, n is 2, each $L^1$ is the same or different halo, and Ar is:

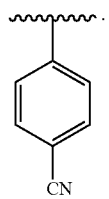 [SMILES: *c1ccc(C#N)cc1]

In another embodiment of this invention the compound of formula 1.0 is a compound of formula 1.27, said compound having the formula:

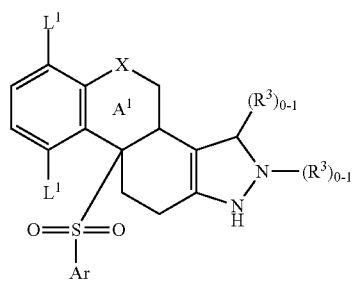

(1.27A)

wherein X is O, $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is:

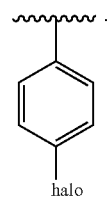

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is:

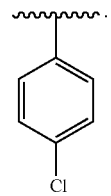

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is:

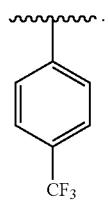

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.27A, wherein X is O, each $L^1$ is the same or different halo, and Ar is:

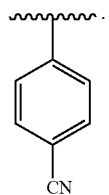 [SMILES: *c1ccc(C#N)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28, and X is O.

In another embodiment of this invention the compound of formula 1.0 is a compound of formula 1.28 and $L^1$ is halo.

In another embodiment of this invention the compound of formula 1.0 is a compound of formula 1.28, said compound having the formula (1.28A):

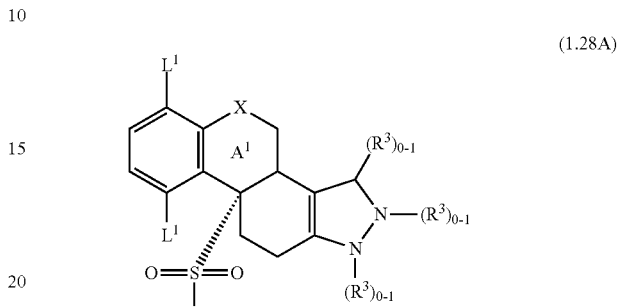

(1.28A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28, n is 2 and $L^1$ is F.

In another embodiment of this invention the compound of formula 1.0 is a compound of formula 1.28A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28 and Ar is phenyl.

In another embodiment of this invention the compound of formula 1.0 is a compound of formula 1.28, Ar is phenyl substituted with halo.

In another embodiment of this invention the compound of formula 1.0 is a compound of formula 1.28 and Ar is phenyl substituted with one halo.

In another embodiment of this invention the compound of formula 1.0 is a compound of formula 1.28 and Ar is:

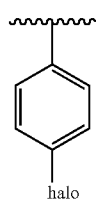
halo

In another embodiment of this invention the compound of formula 1.0 is a compound of formula 1.28 and Ar is phenyl substituted with at least one Cl.

In another embodiment of this invention the compound of formula 1.0 is a compound of formula 1.28 and Ar is phenyl substituted with a Cl.

In another embodiment of this invention the compound of formula 1.0 is a compound of formula 1.28 and Ar is:

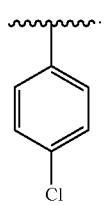
Cl

In another embodiment of this invention the compound of formula 1.0 is a compound of formula 1.28 and Ar is phenyl substituted with at least one —$CF_3$.

In another embodiment of this invention the compound of formula 1.0 is a compound of formula 1.28 and Ar is phenyl substituted with a —$CF_3$.

In another embodiment of this invention the compound of formula 1.0 is a compound of formula 1.28 and Ar is:

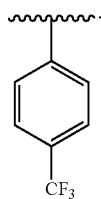
$CF_3$

In another embodiment of this invention the compound of formula 1.0 is a compound of formula 1.28 and Ar is phenyl substituted with at least one —CN.

In another embodiment of this invention the compound of formula 1.0 is a compound of formula 1.28 and Ar is phenyl substituted with a —CN.

In another embodiment of this invention the compound of formula 1.0 is a compound of formula 1.28 and Ar is:

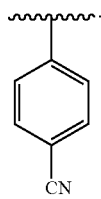 [SMILES: *c1ccc(C#N)cc1]
CN

In another embodiment of this invention the compound of formula 1.0 is a compound of formula 1.28, X is O, each $L^1$ is halo, and Ar is phenyl substituted with at least one halo.

In another embodiment of this invention the compound of formula 1.0 is a compound of formula 1.28, X is O, n is 2, each $L^1$ is the same or different halo, and Ar is phenyl substituted with one halo.

In another embodiment of this invention the compound of formula 1.0 is a compound of formula 1.28, X is O, n is 2, $L^1$ is F, and Ar is phenyl substituted with one Cl.

In another embodiment of this invention the compound of formula 1.0 is a compound of formula 1.28, X is O, n is 2, each $L^1$ is the same or different halo, and Ar is:

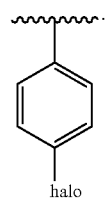
halo

In another embodiment of this invention the compound of formula 1.0 is a compound of formula 1.28, X is O, n is 2, each $L^1$ is the same or different halo, and Ar is:

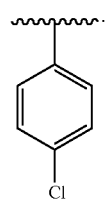
Cl

In another embodiment of this invention the compound of formula 1.0 is a compound of formula 1.28, X is O, each $L^1$ is halo, and Ar is phenyl substituted with at least one —$CF_3$.

In another embodiment of this invention the compound of formula 1.0 is a compound of formula 1.28, X is O, n is 2, each $L^1$ is the same or different halo, and Ar is phenyl substituted with one —$CF_3$.

In another embodiment of this invention the compound of formula 1.0 is a compound of formula 1.28, X is O, n is 2, $L^1$ is F, and Ar is phenyl substituted with one —$CF_3$ In another embodiment of this invention the compound of formula 1.0 is a compound of formula 1.28, X is O, n is 2, each $L^1$ is the same or different halo, and Ar is:

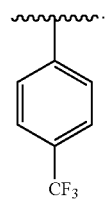 [SMILES: *c1ccc(C(F)(F)F)cc1]
$CF_3$

In another embodiment of this invention the compound of formula 1.0 is a compound of formula 1.28, X is O, each $L^1$ is halo, and Ar is phenyl substituted with at least one —CN.

In another embodiment of this invention the compound of formula 1.0 is a compound of formula 1.28, X is O, n is 2, each $L^1$ is the same or different halo, and Ar is phenyl substituted with one —CN.

In another embodiment of this invention the compound of formula 1.0 is a compound of formula 1.28, X is O, n is 2, $L^1$ is F, and Ar is phenyl substituted with one —CN In another embodiment of this invention the compound of formula 1.0 is a compound of formula 1.28, X is O, n is 2, each $L^1$ is the same or different halo, and Ar is:

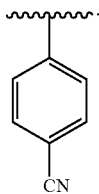

In another embodiment of this invention the compound of formula 1.0 is a compound of formula 1.28, said compound having the formula (1.28A):

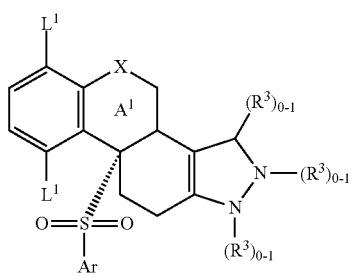

(1.28A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is:

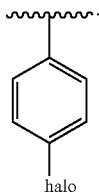

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is:

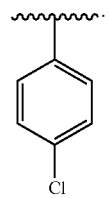 [SMILES: *c1ccc(Cl)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is:

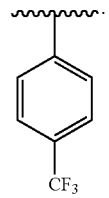 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.28A, wherein X is O, each $L^1$ is the same or different halo, and Ar is:

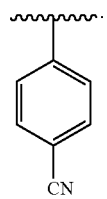

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29, and X is O.

In another embodiment of this invention the compound of formula 1.0 is a compound of formula 1.29 and $L^1$ is halo.

In another embodiment of this invention the compound of formula 1.0 is a compound of formula 1.29, said compound having the formula (1.29A):

(1.29A)

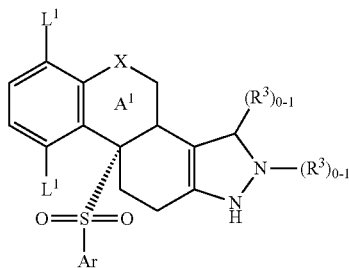

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29, n is 2 and $L^1$ is F.

In another embodiment of this invention the compound of formula 1.0 is a compound of formula 1.29A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29 and Ar is phenyl.

In another embodiment of this invention the compound of formula 1.0 is a compound of formula 1.29, Ar is phenyl substituted with halo.

In another embodiment of this invention the compound of formula 1.0 is a compound of formula 1.29 and Ar is phenyl substituted with one halo.

In another embodiment of this invention the compound of formula 1.0 is a compound of formula 1.29 and Ar is:

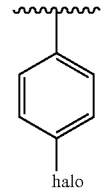

In another embodiment of this invention the compound of formula 1.0 is a compound of formula 1.29 and Ar is phenyl substituted with at least one Cl.

In another embodiment of this invention the compound of formula 1.0 is a compound of formula 1.29 and Ar is phenyl substituted with a Cl.

In another embodiment of this invention the compound of formula 1.0 is a compound of formula 1.29 and Ar is:

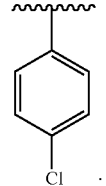

In another embodiment of this invention the compound of formula 1.0 is a compound of formula 1.29 and Ar is phenyl substituted with at least one —CF$_3$.

In another embodiment of this invention the compound of formula 1.0 is a compound of formula 1.29 and Ar is phenyl substituted with a —CF$_3$.

In another embodiment of this invention the compound of formula 1.0 is a compound of formula 1.29 and Ar is:

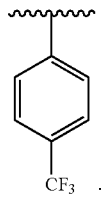

In another embodiment of this invention the compound of formula 1.0 is a compound of formula 1.29 and Ar is phenyl substituted with at least one —CN.

In another embodiment of this invention the compound of formula 1.0 is a compound of formula 1.29 and Ar is phenyl substituted with a —CN.

In another embodiment of this invention the compound of formula 1.0 is a compound of formula 1.29 and Ar is:

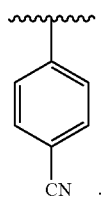

In another embodiment of this invention the compound of formula 1.0 is a compound of formula 1.29, X is O, each L$^1$ is halo, and Ar is phenyl substituted with at least one halo.

In another embodiment of this invention the compound of formula 1.0 is a compound of formula 1.29, X is O, n is 2, each L$^1$ is the same or different halo, and Ar is phenyl substituted with one halo.

In another embodiment of this invention the compound of formula 1.0 is a compound of formula 1.29, X is O, n is 2, L$^1$ is F, and Ar is phenyl substituted with one Cl.

In another embodiment of this invention the compound of formula 1.0 is a compound of formula 1.29, X is O, n is 2, each L$^1$ is the same or different halo, and Ar is:

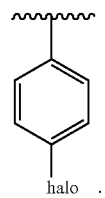

In another embodiment of this invention the compound of formula 1.0 is a compound of formula 1.29, X is O, n is 2, each L$^1$ is the same or different halo, and Ar is:

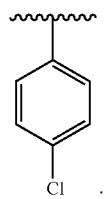

In another embodiment of this invention the compound of formula 1.0 is a compound of formula 1.29, X is O, each L$^1$ is halo, and Ar is phenyl substituted with at least one —CF$_3$.

In another embodiment of this invention the compound of formula 1.0 is a compound of formula 1.29, X is O, n is 2, each L$^1$ is the same or different halo, and Ar is phenyl substituted with one —CF$_3$.

In another embodiment of this invention the compound of formula 1.0 is a compound of formula 1.29, X is O, n is 2, L$^1$ is F, and Ar is phenyl substituted with one —CF$_3$ In another embodiment of this invention the compound of formula 1.0 is a compound of formula 1.29, X is O, n is 2, each L$^1$ is the same or different halo, and Ar is:

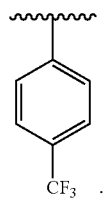

In another embodiment of this invention the compound of formula 1.0 is a compound of formula 1.29, X is O, each L$^1$ is halo, and Ar is phenyl substituted with at least one —CN.

In another embodiment of this invention the compound of formula 1.0 is a compound of formula 1.29, X is O, n is 2, each L$^1$ is the same or different halo, and Ar is phenyl substituted with one —CN.

In another embodiment of this invention the compound of formula 1.0 is a compound of formula 1.29, X is O, n is 2, L$^1$ is F, and Ar is phenyl substituted with one —CF$_3$ In another embodiment of this invention the compound of formula 1.0 is a compound of formula 1.29, X is O, n is 2, each L$^1$ is the same or different halo, and Ar is:

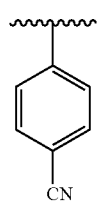

In another embodiment of this invention the compound of formula 1.0 is a compound of formula 1.29, said compound having the formula (1.29A):

(1.29A)

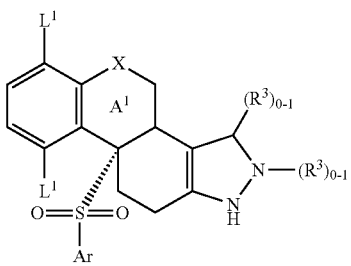

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is:

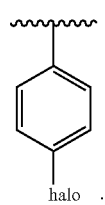

halo .

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is:

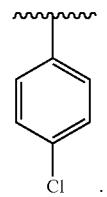

Cl .

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is:

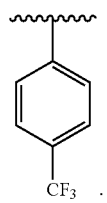 [SMILES: *c1ccc(C(F)(F)F)cc1]

$CF_3$ .

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.29A, wherein X is O, each $L^1$ is the same or different halo, and Ar is:

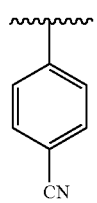

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30, and X is O.

In another embodiment of this invention the compound of formula 1.0 is a compound of formula 1.30 and $L^1$ is halo.

In another embodiment of this invention the compound of formula 1.0 is a compound of formula 1.30, said compound having the formula (1.30A):

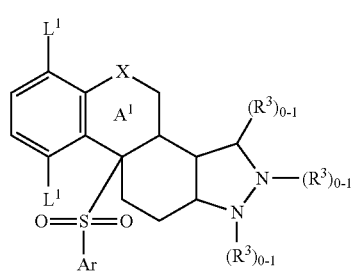

(1.30A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30, n is 2 and $L^1$ is F.

In another embodiment of this invention the compound of formula 1.0 is a compound of formula 1.30A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30 and Ar is phenyl.

In another embodiment of this invention the compound of formula 1.0 is a compound of formula 1.30, Ar is phenyl substituted with halo.

In another embodiment of this invention the compound of formula 1.0 is a compound of formula 1.30 and Ar is phenyl substituted with one halo.

In another embodiment of this invention the compound of formula 1.0 is a compound of formula 1.30 and Ar is:

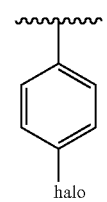

In another embodiment of this invention the compound of formula 1.0 is a compound of formula 1.30 and Ar is phenyl substituted with at least one Cl.

In another embodiment of this invention the compound of formula 1.0 is a compound of formula 1.30 and Ar is phenyl substituted with a Cl.

In another embodiment of this invention the compound of formula 1.0 is a compound of formula 1.30 and Ar is:

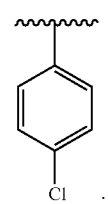

In another embodiment of this invention the compound of formula 1.0 is a compound of formula 1.30 and Ar is phenyl substituted with at least one —$CF_3$.

In another embodiment of this invention the compound of formula 1.0 is a compound of formula 1.30 and Ar is phenyl substituted with a —$CF_3$.

In another embodiment of this invention the compound of formula 1.0 is a compound of formula 1.30 and Ar is:

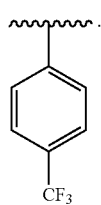 [SMILES: *c1ccc(C(F)(F)F)cc1]

In another embodiment of this invention the compound of formula 1.0 is a compound of formula 1.30 and Ar is phenyl substituted with at least one —CN.

In another embodiment of this invention the compound of formula 1.0 is a compound of formula 1.30 and Ar is phenyl substituted with a —CN.

In another embodiment of this invention the compound of formula 1.0 is a compound of formula 1.30 and Ar is:

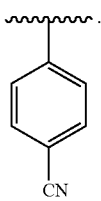

In another embodiment of this invention the compound of formula 1.0 is a compound of formula 1.30, X is O, each $L^1$ is halo, and Ar is phenyl substituted with at least one halo.

In another embodiment of this invention the compound of formula 1.0 is a compound of formula 1.30, X is O, n is 2, each $L^1$ is the same or different halo, and Ar is phenyl substituted with one halo.

In another embodiment of this invention the compound of formula 1.0 is a compound of formula 1.30, X is O, n is 2, $L^1$ is F, and Ar is phenyl substituted with one Cl.

In another embodiment of this invention the compound of formula 1.0 is a compound of formula 1.30, X is O, n is 2, each $L^1$ is the same or different halo, and Ar is:

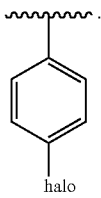

In another embodiment of this invention the compound of formula 1.0 is a compound of formula 1.30, X is O, n is 2, each $L^1$ is the same or different halo, and Ar is:

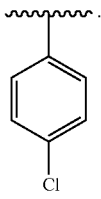 [SMILES: *c1ccc(Cl)cc1]

In another embodiment of this invention the compound of formula 1.0 is a compound of formula 1.30, X is O, each $L^1$ is halo, and Ar is phenyl substituted with at least one —CF₃.

In another embodiment of this invention the compound of formula 1.0 is a compound of formula 1.30, X is O, n is 2, each $L^1$ is the same or different halo, and Ar is phenyl substituted with one —CF₃.

In another embodiment of this invention the compound of formula 1.0 is a compound of formula 1.30, X is O, n is 2, $L^1$ is F, and Ar is phenyl substituted with one —CF₃.

In another embodiment of this invention the compound of formula 1.0 is a compound of formula 1.30, X is O, n is 2, each $L^1$ is the same or different halo, and Ar is:

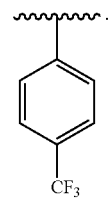

In another embodiment of this invention the compound of formula 1.0 is a compound of formula 1.30, X is O, each $L^1$ is halo, and Ar is phenyl substituted with at least one —CN.

In another embodiment of this invention the compound of formula 1.0 is a compound of formula 1.30, X is O, n is 2, each $L^1$ is the same or different halo, and Ar is phenyl substituted with one —CN.

In another embodiment of this invention the compound of formula 1.0 is a compound of formula 1.30, X is O, n is 2, $L^1$ is F, and Ar is phenyl substituted with one —CN.

In another embodiment of this invention the compound of formula 1.0 is a compound of formula 1.30, X is O, n is 2, each $L^1$ is the same or different halo, and Ar is:

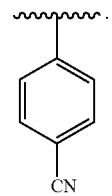

In another embodiment of this invention the compound of formula 1.0 is a compound of formula 1.30, said compound having the formula (1.30A):

(1.30A)

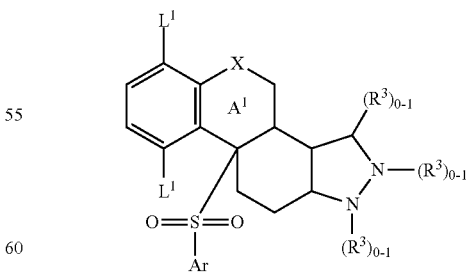

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is:

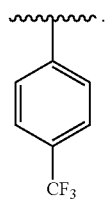 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is:

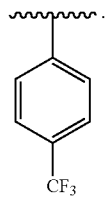

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.30A, wherein X is O, each $L^1$ is the same or different halo, and Ar is:

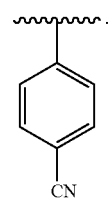

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31, and X is O.

In another embodiment of this invention the compound of formula 1.0 is a compound of formula 1.31 and $L^1$ is halo.

In another embodiment of this invention the compound of formula 1.0 is a compound of formula 1.31, said compound having the formula (1.31A):

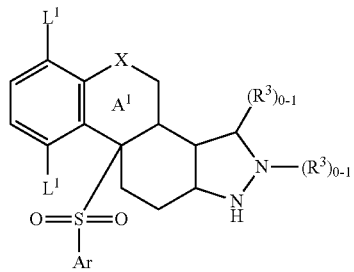

(1.31A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31, n is 2 and $L^1$ is F.

In another embodiment of this invention the compound of formula 1.0 is a compound of formula 1.31A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31 and Ar is phenyl.

In another embodiment of this invention the compound of formula 1.0 is a compound of formula 1.31, Ar is phenyl substituted with halo.

In another embodiment of this invention the compound of formula 1.0 is a compound of formula 1.31 and Ar is phenyl substituted with one halo.

In another embodiment of this invention the compound of formula 1.0 is a compound of formula 1.31 and Ar is:

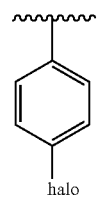

In another embodiment of this invention the compound of formula 1.0 is a compound of formula 1.31 and Ar is phenyl substituted with at least one Cl.

In another embodiment of this invention the compound of formula 1.0 is a compound of formula 1.31 and Ar is phenyl substituted with a Cl.

In another embodiment of this invention the compound of formula 1.0 is a compound of formula 1.31 and Ar is:

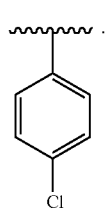 [SMILES: *c1ccc(Cl)cc1]

In another embodiment of this invention the compound of formula 1.0 is a compound of formula 1.31 and Ar is phenyl substituted with at least one —$CF_3$.

In another embodiment of this invention the compound of formula 1.0 is a compound of formula 1.31 and Ar is phenyl substituted with a —$CF_3$.

In another embodiment of this invention the compound of formula 1.0 is a compound of formula 1.31 and Ar is:

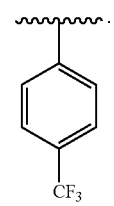

In another embodiment of this invention the compound of formula 1.0 is a compound of formula 1.31 and Ar is phenyl substituted with at least one —CN.

In another embodiment of this invention the compound of formula 1.0 is a compound of formula 1.31 and Ar is phenyl substituted with a —CN.

In another embodiment of this invention the compound of formula 1.0 is a compound of formula 1.31 and Ar is:

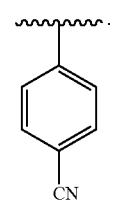

In another embodiment of this invention the compound of formula 1.0 is a compound of formula 1.31, X is O, each $L^1$ is halo, and Ar is phenyl substituted with at least one halo.

In another embodiment of this invention the compound of formula 1.0 is a compound of formula 1.31, X is O, n is 2, each $L^1$ is the same or different halo, and Ar is phenyl substituted with one halo.

In another embodiment of this invention the compound of formula 1.0 is a compound of formula 1.31, X is O, n is 2, $L^1$ is F, and Ar is phenyl substituted with one Cl.

In another embodiment of this invention the compound of formula 1.0 is a compound of formula 1.31, X is O, n is 2, each $L^1$ is the same or different halo, and Ar is:

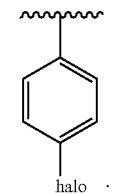

In another embodiment of this invention the compound of formula 1.0 is a compound of formula 1.31, X is O, n is 2, each $L^1$ is the same or different halo, and Ar is:

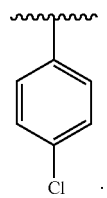

In another embodiment of this invention the compound of formula 1.0 is a compound of formula 1.31, X is O, each $L^1$ is halo, and Ar is phenyl substituted with at least one —$CF_3$.

In another embodiment of this invention the compound of formula 1.0 is a compound of formula 1.31, X is O, n is 2, each $L^1$ is the same or different halo, and Ar is phenyl substituted with one —$CF_3$.

In another embodiment of this invention the compound of formula 1.0 is a compound of formula 1.31, X is O, n is 2, $L^1$ is F, and Ar is phenyl substituted with one —$CF_3$.

In another embodiment of this invention the compound of formula 1.0 is a compound of formula 1.31, X is O, n is 2, each $L^1$ is the same or different halo, and Ar is:

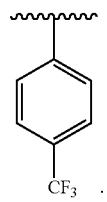

In another embodiment of this invention the compound of formula 1.0 is a compound of formula 1.31, X is O, each $L^1$ is halo, and Ar is phenyl substituted with at least one —CN.

In another embodiment of this invention the compound of formula 1.0 is a compound of formula 1.31, X is O, n is 2, each $L^1$ is the same or different halo, and Ar is phenyl substituted with one —CN.

In another embodiment of this invention the compound of formula 1.0 is a compound of formula 1.31, X is O, n is 2, $L^1$ is F, and Ar is phenyl substituted with one —CN.

In another embodiment of this invention the compound of formula 1.0 is a compound of formula 1.31, X is O, n is 2, each $L^1$ is the same or different halo, and Ar is:

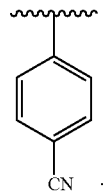

In another embodiment of this invention the compound of formula 1.0 is a compound of formula 1.31, said compound having the formula (1.31A):

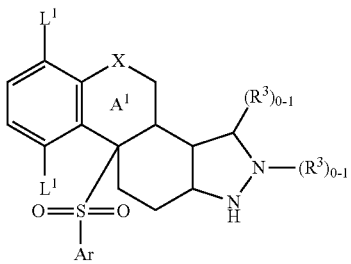

(1.31A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is:

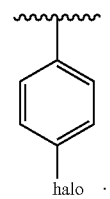

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is:

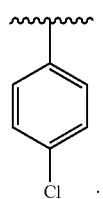

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is:

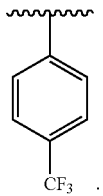 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.31A, wherein X is O, each $L^1$ is the same or different halo, and Ar is:

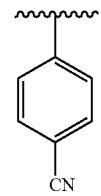

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32, and X is O.

In another embodiment of this invention the compound of formula 1.0 is a compound of formula 1.32 and $L^1$ is halo.

In another embodiment of this invention the compound of formula 1.0 is a compound of formula 1.32, said compound having the formula (1.32A):

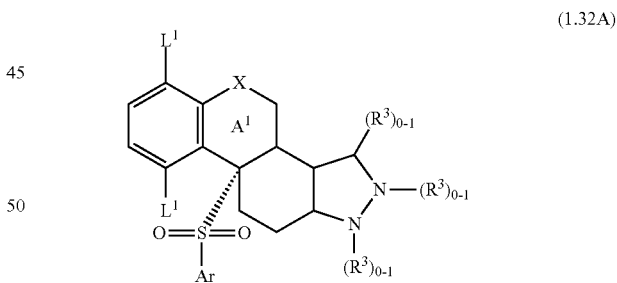

(1.32A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32, n is 2 and L¹ is F.

In another embodiment of this invention the compound of formula 1.0 is a compound of formula 1.32A, wherein each L¹ is F. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32 and Ar is phenyl.

In another embodiment of this invention the compound of formula 1.0 is a compound of formula 1.32, Ar is phenyl substituted with halo.

In another embodiment of this invention the compound of formula 1.0 is a compound of formula 1.32 and Ar is phenyl substituted with one halo.

In another embodiment of this invention the compound of formula 1.0 is a compound of formula 1.32 and Ar is:

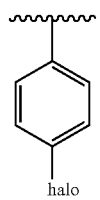

In another embodiment of this invention the compound of formula 1.0 is a compound of formula 1.32 and Ar is phenyl substituted with at least one Cl.

In another embodiment of this invention the compound of formula 1.0 is a compound of formula 1.32 and Ar is phenyl substituted with a Cl.

In another embodiment of this invention the compound of formula 1.0 is a compound of formula 1.32 and Ar is:

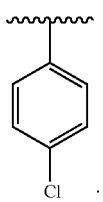

In another embodiment of this invention the compound of formula 1.0 is a compound of formula 1.32 and Ar is phenyl substituted with at least one —CF₃.

In another embodiment of this invention the compound of formula 1.0 is a compound of formula 1.32 and Ar is phenyl substituted with a —CF₃.

In another embodiment of this invention the compound of formula 1.0 is a compound of formula 1.32 and Ar is:

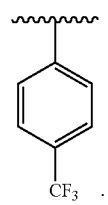 [SMILES: *c1ccc(C(F)(F)F)cc1]

In another embodiment of this invention the compound of formula 1.0 is a compound of formula 1.32 and Ar is phenyl substituted with at least one —CN.

In another embodiment of this invention the compound of formula 1.0 is a compound of formula 1.32 and Ar is phenyl substituted with a —CN.

In another embodiment of this invention the compound of formula 1.0 is a compound of formula 1.32 and Ar is:

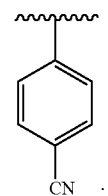

In another embodiment of this invention the compound of formula 1.0 is a compound of formula 1.32, X is O, each L¹ is halo, and Ar is phenyl substituted with at least one halo.

In another embodiment of this invention the compound of formula 1.0 is a compound of formula 1.32, X is O, n is 2, each L¹ is the same or different halo, and Ar is phenyl substituted with one halo.

In another embodiment of this invention the compound of formula 1.0 is a compound of formula 1.32, X is O, n is 2, L¹ is F, and Ar is phenyl substituted with one Cl.

In another embodiment of this invention the compound of formula 1.0 is a compound of formula 1.32, X is O, n is 2, each L¹ is the same or different halo, and Ar is:

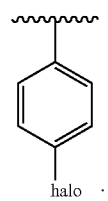

In another embodiment of this invention the compound of formula 1.0 is a compound of formula 1.32, X is O, n is 2, each L¹ is the same or different halo, and Ar is:

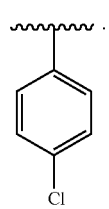

In another embodiment of this invention the compound of formula 1.0 is a compound of formula 1.32, X is O, each $L^1$ is halo, and Ar is phenyl substituted with at least one —$CF_3$.

In another embodiment of this invention the compound of formula 1.0 is a compound of formula 1.32, X is O, n is 2, each $L^1$ is the same or different halo, and Ar is phenyl substituted with one —$CF_3$.

In another embodiment of this invention the compound of formula 1.0 is a compound of formula 1.32, X is O, n is 2, $L^1$ is F, and Ar is phenyl substituted with one —$CF_3$.

In another embodiment of this invention the compound of formula 1.0 is a compound of formula 1.32, X is O, n is 2, each $L^1$ is the same or different halo, and Ar is:

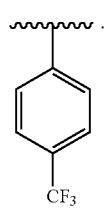

In another embodiment of this invention the compound of formula 1.0 is a compound of formula 1.32, X is O, each $L^1$ is halo, and Ar is phenyl substituted with at least one —CN.

In another embodiment of this invention the compound of formula 1.0 is a compound of formula 1.32, X is O, n is 2, each $L^1$ is the same or different halo, and Ar is phenyl substituted with one —CN.

In another embodiment of this invention the compound of formula 1.0 is a compound of formula 1.32, X is O, n is 2, $L^1$ is F, and Ar is phenyl substituted with one —CN.

In another embodiment of this invention the compound of formula 1.0 is a compound of formula 1.32, X is O, n is 2, each $L^1$ is the same or different halo, and Ar is:

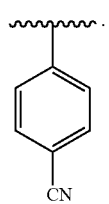 [SMILES: *c1ccc(C#N)cc1]

In another embodiment of this invention the compound of formula 1.0 is a compound of formula 1.32, said compound having the formula (1.32A):

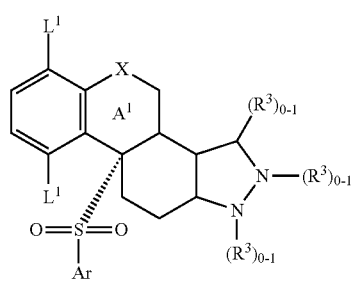

(1.32A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32A, wherein X is O, each $L^1$ is the same or different halo, and Ar is:

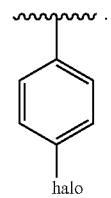

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.32A, wherein X is O, each $L^1$ is the same or different halo, and Ar is:

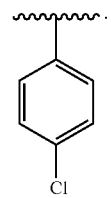

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected.

Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is phenyl substituted with at least one —CF₃. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is phenyl substituted with one —CF₃. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is:

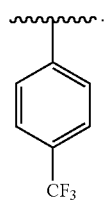

In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is phenyl substituted with at least one —CN. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is phenyl substituted with one —CN. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.32A, wherein X is O, each L¹ is the same or different halo, and Ar is:

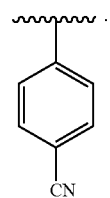

In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.33, and X is O.

In another embodiment of this invention the compound of formula 1.0 is a compound of formula 1.33 and L¹ is halo.

In another embodiment of this invention the compound of formula 1.0 is a compound of formula 1.33, said compound having the formula (1.33A):

(1.33A)

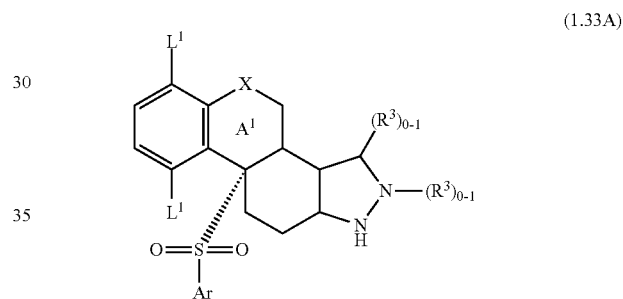

wherein each L¹ is the same or different halo. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.33A, wherein each L¹ is the same halo. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably R³ of the CH—R³ moiety is independently selected from the group consisting of —C₁-C₆ alkyl, hydroxyalkyl, and alkoxyalkyl.

In another embodiment of this invention the compound of formula 1.0 is a compound of formula 1.33, n is 2 and L¹ is F.

In another embodiment of this invention the compound of formula 1.0 is a compound of formula 1.33A, wherein each L¹ is F. All other substituents are as defined for formula 1.0. In the substituent "(R³)₀₋₁", the "0-1" means that there is no R³ substituent present (i.e., there would be a H instead of the R³ substituent), or that there is one R³ substituent present at the indicated position. Each R³ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33 and Ar is phenyl.

In another embodiment of this invention the compound of formula 1.33, Ar is phenyl substituted with halo.

In another embodiment of this invention the compound of formula 1.0 is a compound of formula 1.33 and Ar is phenyl substituted with one halo.

In another embodiment of this invention the compound of formula 1.0 is a compound of formula 1.33 and Ar is:

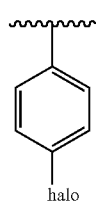

In another embodiment of this invention the compound of formula 1.0 is a compound of formula 1.33 and Ar is phenyl substituted with at least one Cl.

In another embodiment of this invention the compound of formula 1.0 is a compound of formula 1.33 and Ar is phenyl substituted with a Cl.

In another embodiment of this invention the compound of formula 1.0 is a compound of formula 1.33 and Ar is:

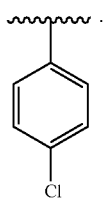

In another embodiment of this invention the compound of formula 1.0 is a compound of formula 1.33 and Ar is phenyl substituted with at least one —$CF_3$.

In another embodiment of this invention the compound of formula 1.0 is a compound of formula 1.33 and Ar is phenyl substituted with a —$CF_3$.

In another embodiment of this invention the compound of formula 1.0 is a compound of formula 1.33 and Ar is:

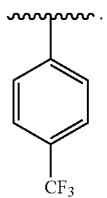 [SMILES: *c1ccc(C(F)(F)F)cc1]

In another embodiment of this invention the compound of formula 1.0 is a compound of formula 1.33 and Ar is phenyl substituted with at least one —CN.

In another embodiment of this invention the compound of formula 1.0 is a compound of formula 1.33 and Ar is phenyl substituted with a —CN.

In another embodiment of this invention the compound of formula 1.0 is a compound of formula 1.33 and Ar is:

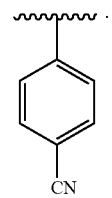

In another embodiment of this invention the compound of formula 1.0 is a compound of formula 1.33, X is O, each $L^1$ is halo, and Ar is phenyl substituted with at least one halo.

In another embodiment of this invention the compound of formula 1.0 is a compound of formula 1.33, X is O, n is 2, each $L^1$ is the same or different halo, and Ar is phenyl substituted with one halo.

In another embodiment of this invention the compound of formula 1.0 is a compound of formula 1.33, X is O, n is 2, $L^1$ is F, and Ar is phenyl substituted with one Cl.

In another embodiment of this invention the compound of formula 1.0 is a compound of formula 1.33, X is O, n is 2, each $L^1$ is the same or different halo, and Ar is:

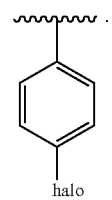

In another embodiment of this invention the compound of formula 1.0 is a compound of formula 1.33, X is O, n is 2, each $L^1$ is the same or different halo, and Ar is:

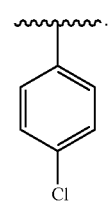

In another embodiment of this invention the compound of formula 1.0 is a compound of formula 1.33, X is O, each $L^1$ is halo, and Ar is phenyl substituted with at least one —$CF_3$.

In another embodiment of this invention the compound of formula 1.0 is a compound of formula 1.33, X is O, n is 2, each $L^1$ is the same or different halo, and Ar is phenyl substituted with one —$CF_3$.

In another embodiment of this invention the compound of formula 1.0 is a compound of formula 1.33, X is O, n is 2, $L^1$ is F, and Ar is phenyl substituted with one —$CF_3$.

In another embodiment of this invention the compound of formula 1.0 is a compound of formula 1.33, X is O, n is 2, each $L^1$ is the same or different halo, and Ar is:

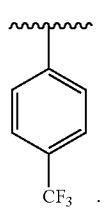

In another embodiment of this invention the compound of formula 1.0 is a compound of formula 1.33, X is O, each $L^1$ is halo, and Ar is phenyl substituted with at least one —CN.

In another embodiment of this invention the compound of formula 1.0 is a compound of formula 1.33, X is O, n is 2, each $L^1$ is the same or different halo, and Ar is phenyl substituted with one —CN.

In another embodiment of this invention the compound of formula 1.0 is a compound of formula 1.33, X is O, n is 2, $L^1$ is F, and Ar is phenyl substituted with one —CN.

In another embodiment of this invention the compound of formula 1.0 is a compound of formula 1.33, X is O, n is 2, each $L^1$ is the same or different halo, and Ar is:

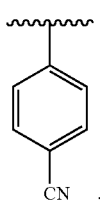 [SMILES: *c1ccc(C#N)cc1]

In another embodiment of this invention the compound of formula 1.0 is a compound of formula 1.33, said compound having the formula (1.33A):

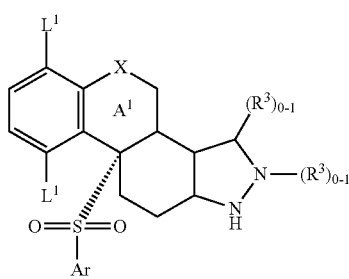

(1.33A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is:

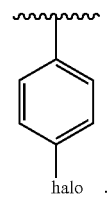

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is:

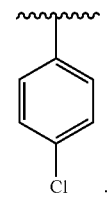

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is:

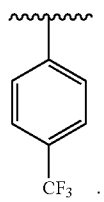

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.33A, wherein X is O, each $L^1$ is the same or different halo, and Ar is:

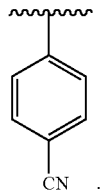

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34, and X is O.

In another embodiment of this invention the compound of formula 1.0 is a compound of formula 1.34 and $L^1$ is halo.

In another embodiment of this invention the compound of formula 1.0 is a compound of formula 1.34, said compound having the formula (1.34A):

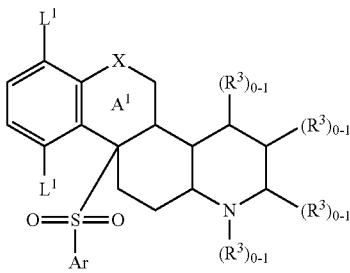

(1.34A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34, n is 2 and $L^1$ is F.

In another embodiment of this invention the compound of formula 1.0 is a compound of formula 1.34A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34 and Ar is phenyl.

In another embodiment of this invention the compound of formula 1.0 is a compound of formula 1.34, Ar is phenyl substituted with halo.

In another embodiment of this invention the compound of formula 1.0 is a compound of formula 1.34 and Ar is phenyl substituted with one halo.

In another embodiment of this invention the compound of formula 1.0 is a compound of formula 1.34 and Ar is:

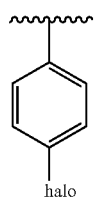
halo

In another embodiment of this invention the compound of formula 1.0 is a compound of formula 1.34 and Ar is phenyl substituted with at least one Cl.

In another embodiment of this invention the compound of formula 1.0 is a compound of formula 1.34 and Ar is phenyl substituted with a Cl.

In another embodiment of this invention the compound of formula 1.0 is a compound of formula 1.34 and Ar is:

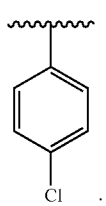
Cl

In another embodiment of this invention the compound of formula 1.0 is a compound of formula 1.34 and Ar is phenyl substituted with at least one —CF$_3$.

In another embodiment of this invention the compound of formula 1.0 is a compound of formula 1.34 and Ar is phenyl substituted with a —CF$_3$.

In another embodiment of this invention the compound of formula 1.0 is a compound of formula 1.34 and Ar is:

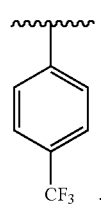 [SMILES: *c1ccc(C(F)(F)F)cc1]
CF$_3$

In another embodiment of this invention the compound of formula 1.0 is a compound of formula 1.34 and Ar is phenyl substituted with at least one —CN.

In another embodiment of this invention the compound of formula 1.0 is a compound of formula 1.34 and Ar is phenyl substituted with a —CN.

In another embodiment of this invention the compound of formula 1.0 is a compound of formula 1.34 and Ar is:

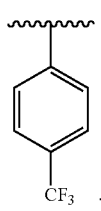 [SMILES: *c1ccc(C(F)(F)F)cc1]
CF$_3$

In another embodiment of this invention the compound of formula 1.0 is a compound of formula 1.34, X is O, each L$^1$ is halo, and Ar is phenyl substituted with at least one halo.

In another embodiment of this invention the compound of formula 1.0 is a compound of formula 1.34, X is O, n is 2, each L$^1$ is the same or different halo, and Ar is phenyl substituted with one halo.

In another embodiment of this invention the compound of formula 1.0 is a compound of formula 1.34, X is O, n is 2, L$^1$ is F, and Ar is phenyl substituted with one Cl.

In another embodiment of this invention the compound of formula 1.0 is a compound of formula 1.34, X is O, n is 2, each L$^1$ is the same or different halo, and Ar is:

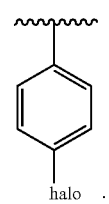
halo

In another embodiment of this invention the compound of formula 1.0 is a compound of formula 1.34, X is O, n is 2, each L$^1$ is the same or different halo, and Ar is:

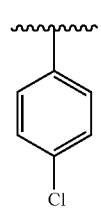
Cl

In another embodiment of this invention the compound of formula 1.0 is a compound of formula 1.34, X is O, each L$^1$ is halo, and Ar is phenyl substituted with at least one —CF$_3$.

In another embodiment of this invention the compound of formula 1.0 is a compound of formula 1.34, X is O, n is 2, each L$^1$ is the same or different halo, and Ar is phenyl substituted with one —CF$_3$.

In another embodiment of this invention the compound of formula 1.0 is a compound of formula 1.34, X is O, n is 2, L$^1$ is F, and Ar is phenyl substituted with one —CF$_3$.

In another embodiment of this invention the compound of formula 1.0 is a compound of formula 1.34, X is O, n is 2, each L$^1$ is the same or different halo, and Ar is:

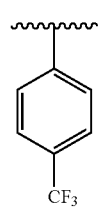
CF$_3$

In another embodiment of this invention the compound of formula 1.0 is a compound of formula 1.34, X is O, each L$^1$ is halo, and Ar is phenyl substituted with at least one —CN.

In another embodiment of this invention the compound of formula 1.0 is a compound of formula 1.34, X is O, n is 2, each L$^1$ is the same or different halo, and Ar is phenyl substituted with one —CN.

In another embodiment of this invention the compound of formula 1.0 is a compound of formula 1.34, X is O, n is 2, L$^1$ is F, and Ar is phenyl substituted with one —CN.

In another embodiment of this invention the compound of formula 1.0 is a compound of formula 1.34, X is O, n is 2, each $L^1$ is the same or different halo, and Ar is:

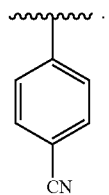

In another embodiment of this invention the compound of formula 1.0 is a compound of formula 1.34, said compound having the formula (1.34A):

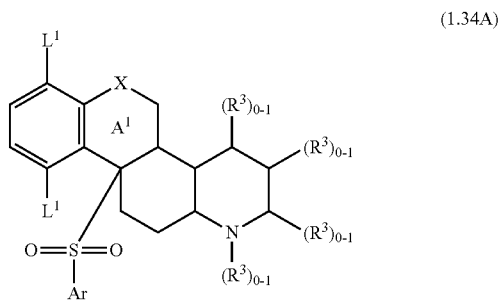

(1.34A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is:

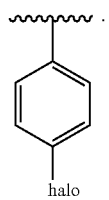

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is:

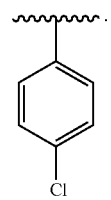

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is:

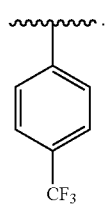

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.34A, wherein X is O, each $L^1$ is the same or different halo, and Ar is:

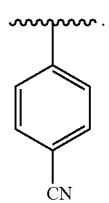 [SMILES: *c1ccc(C#N)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35, and X is O.

In another embodiment of this invention the compound of formula 1.0 is a compound of formula 1.35 and $L^1$ is halo.

In another embodiment of this invention the compound of formula 1.0 is a compound of formula 1.35, said compound having the formula (1.35A):

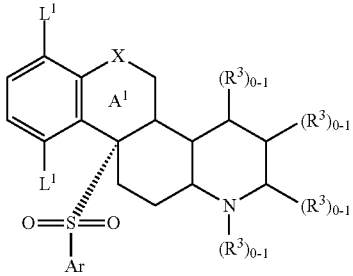

(1.35A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35, n is 2 and $L^1$ is F.

In another embodiment of this invention the compound of formula 1.0 is a compound of formula 1.35A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35 and Ar is phenyl.

In another embodiment of this invention the compound of formula 1.0 is a compound of formula 1.35, Ar is phenyl substituted with halo.

In another embodiment of this invention the compound of formula 1.0 is a compound of formula 1.35 and Ar is phenyl substituted with one halo.

In another embodiment of this invention the compound of formula 1.0 is a compound of formula 1.35 and Ar is:

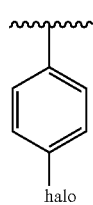

In another embodiment of this invention the compound of formula 1.0 is a compound of formula 1.35 and Ar is phenyl substituted with at least one Cl.

In another embodiment of this invention the compound of formula 1.0 is a compound of formula 1.35 and Ar is phenyl substituted with a Cl.

In another embodiment of this invention the compound of formula 1.0 is a compound of formula 1.35 and Ar is:

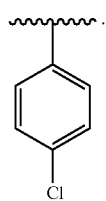 [SMILES: *c1ccc(Cl)cc1]

In another embodiment of this invention the compound of formula 1.0 is a compound of formula 1.35 and Ar is phenyl substituted with at least one —$CF_3$.

In another embodiment of this invention the compound of formula 1.0 is a compound of formula 1.35 and Ar is phenyl substituted with a —$CF_3$.

In another embodiment of this invention the compound of formula 1.0 is a compound of formula 1.35 and Ar is:

In another embodiment of this invention the compound of formula 1.0 is a compound of formula 1.35 and Ar is phenyl substituted with at least one —CN.

In another embodiment of this invention the compound of formula 1.0 is a compound of formula 1.35 and Ar is phenyl substituted with a —CN.

In another embodiment of this invention the compound of formula 1.0 is a compound of formula 1.35 and Ar is:

In another embodiment of this invention the compound of formula 1.0 is a compound of formula 1.35, X is O, each $L^1$ is halo, and Ar is phenyl substituted with at least one halo.

In another embodiment of this invention the compound of formula 1.0 is a compound of formula 1.35, X is O, n is 2, each $L^1$ is the same or different halo, and Ar is phenyl substituted with one halo.

In another embodiment of this invention the compound of formula 1.0 is a compound of formula 1.35, X is O, n is 2, $L^1$ is F, and Ar is phenyl substituted with one Cl.

In another embodiment of this invention the compound of formula 1.0 is a compound of formula 1.35, X is O, n is 2, each $L^1$ is the same or different halo, and Ar is:

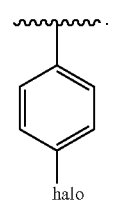

In another embodiment of this invention the compound of formula 1.0 is a compound of formula 1.35, X is O, n is 2, each $L^1$ is the same or different halo, and Ar is:

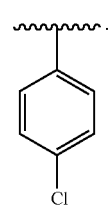

In another embodiment of this invention the compound of formula 1.0 is a compound of formula 1.35, X is O, each $L^1$ is halo, and Ar is phenyl substituted with at least one —$CF_3$.

In another embodiment of this invention the compound of formula 1.0 is a compound of formula 1.35, X is O, n is 2, each $L^1$ is the same or different halo, and Ar is phenyl substituted with one —$CF_3$.

In another embodiment of this invention the compound of formula 1.0 is a compound of formula 1.35, X is O, n is 2, $L^1$ is F, and Ar is phenyl substituted with one —$CF_3$.

In another embodiment of this invention the compound of formula 1.0 is a compound of formula 1.35, X is O, n is 2, each $L^1$ is the same or different halo, and Ar is:

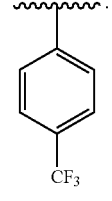

In another embodiment of this invention the compound of formula 1.0 is a compound of formula 1.35, X is O, each $L^1$ is halo, and Ar is phenyl substituted with at least one —CN.

In another embodiment of this invention the compound of formula 1.0 is a compound of formula 1.35, X is O, n is 2, each $L^1$ is the same or different halo, and Ar is phenyl substituted with one —CN.

In another embodiment of this invention the compound of formula 1.0 is a compound of formula 1.350, X is O, n is 2, $L^1$ is F, and Ar is phenyl substituted with one —CN.

In another embodiment of this invention the compound of formula 1.0 is a compound of formula 1.35, X is O, n is 2, each $L^1$ is the same or different halo, and Ar is:

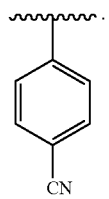

In another embodiment of this invention the compound of formula 1.0 is a compound of formula 1.35, said compound having the formula (1.35A):

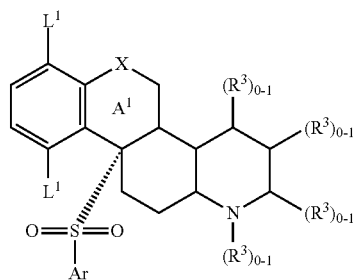

(1.35A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is:

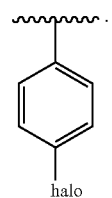

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is:

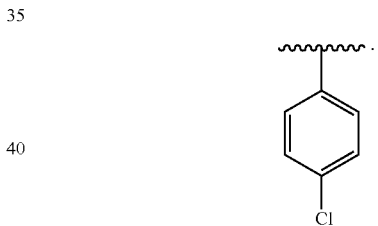

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is:

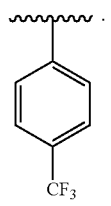 [SMILES: *c1ccc(C(F)(F)F)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.35A, wherein X is O, each $L^1$ is the same or different halo, and Ar is:

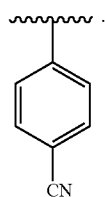 [SMILES: *c1ccc(C#N)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36, and X is O.

In another embodiment of this invention the compound of formula 1.0 is a compound of formula 1.36 and $L^1$ is halo.

In another embodiment of this invention the compound of formula 1.0 is a compound of formula 1.36, said compound having the formula (1.36A):

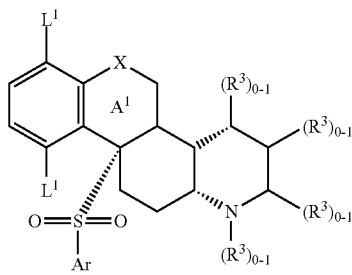

(1.36A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36, n is 2 and $L^1$ is F.

In another embodiment of this invention the compound of formula 1.0 is a compound of formula 1.36A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36 and Ar is phenyl.

In another embodiment of this invention the compound of formula 1.0 is a compound of formula 1.36, Ar is phenyl substituted with halo.

In another embodiment of this invention the compound of formula 1.0 is a compound of formula 1.36 and Ar is phenyl substituted with one halo.

In another embodiment of this invention the compound of formula 1.0 is a compound of formula 1.36 and Ar is:

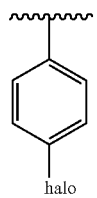
halo

In another embodiment of this invention the compound of formula 1.0 is a compound of formula 1.36 and Ar is phenyl substituted with at least one Cl.

In another embodiment of this invention the compound of formula 1.0 is a compound of formula 1.36 and Ar is phenyl substituted with a Cl.

In another embodiment of this invention the compound of formula 1.0 is a compound of formula 1.36 and Ar is:

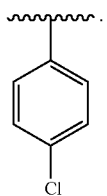 [SMILES: *c1ccc(Cl)cc1]
Cl

In another embodiment of this invention the compound of formula 1.0 is a compound of formula 1.36 and Ar is phenyl substituted with at least one —$CF_3$.

In another embodiment of this invention the compound of formula 1.0 is a compound of formula 1.36 and Ar is phenyl substituted with a —$CF_3$.

In another embodiment of this invention the compound of formula 1.0 is a compound of formula 1.36 and Ar is:

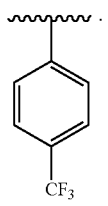
$CF_3$

In another embodiment of this invention the compound of formula 1.0 is a compound of formula 1.36 and Ar is phenyl substituted with at least one —CN.

In another embodiment of this invention the compound of formula 1.0 is a compound of formula 1.36 and Ar is phenyl substituted with a —CN.

In another embodiment of this invention the compound of formula 1.0 is a compound of formula 1.36 and Ar is:

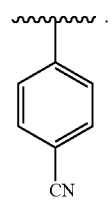
CN

In another embodiment of this invention the compound of formula 1.0 is a compound of formula 1.36, X is O, each $L^1$ is halo, and Ar is phenyl substituted with at least one halo.

In another embodiment of this invention the compound of formula 1.0 is a compound of formula 1.36, X is O, n is 2, each $L^1$ is the same or different halo, and Ar is phenyl substituted with one halo.

In another embodiment of this invention the compound of formula 1.0 is a compound of formula 1.36, X is O, n is 2, $L^1$ is F, and Ar is phenyl substituted with one Cl.

In another embodiment of this invention the compound of formula 1.0 is a compound of formula 1.36, X is O, n is 2, each $L^1$ is the same or different halo, and Ar is:

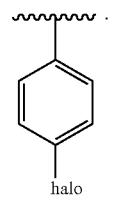
halo

In another embodiment of this invention the compound of formula 1.0 is a compound of formula 1.36, X is O, n is 2, each $L^1$ is the same or different halo, and Ar is:

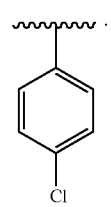
Cl

In another embodiment of this invention the compound of formula 1.0 is a compound of formula 1.36, X is O, each $L^1$ is halo, and Ar is phenyl substituted with at least one —$CF_3$.

In another embodiment of this invention the compound of formula 1.0 is a compound of formula 1.36, X is O, n is 2, each $L^1$ is the same or different halo, and Ar is phenyl substituted with one —$CF_3$.

In another embodiment of this invention the compound of formula 1.0 is a compound of formula 1.36, X is O, n is 2, $L^1$ is F, and Ar is phenyl substituted with one —$CF_3$.

In another embodiment of this invention the compound of formula 1.0 is a compound of formula 1.36, X is O, n is 2, each $L^1$ is the same or different halo, and Ar is:

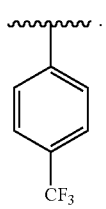

In another embodiment of this invention the compound of formula 1.0 is a compound of formula 1.36, X is O, each $L^1$ is halo, and Ar is phenyl substituted with at least one —CN.

In another embodiment of this invention the compound of formula 1.0 is a compound of formula 1.36, X is O, n is 2, each $L^1$ is the same or different halo, and Ar is phenyl substituted with one —CN.

In another embodiment of this invention the compound of formula 1.0 is a compound of formula 1.36, X is O, n is 2, $L^1$ is F, and Ar is phenyl substituted with one —CN.

In another embodiment of this invention the compound of formula 1.0 is a compound of formula 1.36, X is O, n is 2, each $L^1$ is the same or different halo, and Ar is:

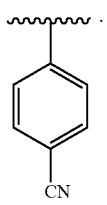

In another embodiment of this invention the compound of formula 1.0 is a compound of formula 1.36, said compound having the formula (1.36A):

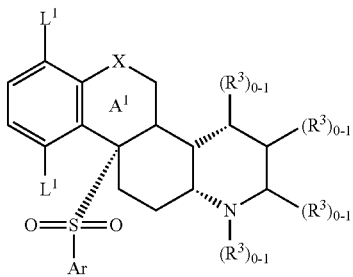

(1.36A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein X is O, n is 2, each $L^1$ is the same or different halo, and Ar is:

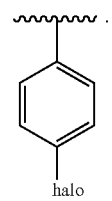

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein X is O, n is 2, each $L^1$ is the same or different halo, and Ar is:

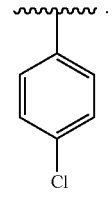

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.36A, wherein X is O, n is 2, each $L^1$ is the same or different halo, and Ar is:

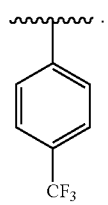

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with at least one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.36A, wherein X is O, each $L^1$ is the same or different halo, and Ar is phenyl substituted with one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.36A, wherein X is O, n is 2, each $L^1$ is the same or different halo, and Ar is:

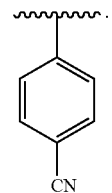

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37, and X is O.

In another embodiment of this invention the compound of formula 1.0 is a compound of formula 1.37 and $L^1$ is halo.

In another embodiment of this invention the compound of formula 1.0 is a compound of formula 1.37, said compound having the formula (1.37A):

(1.37A)

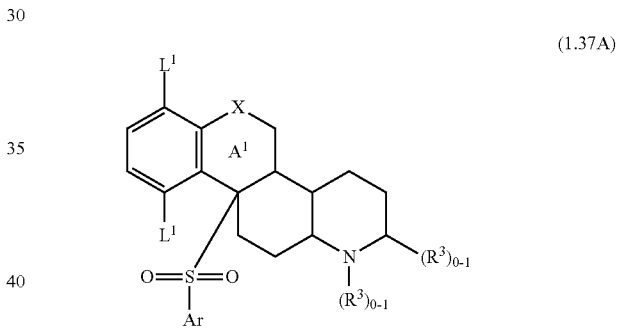

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37, n is 2 and $L^1$ is F.

In another embodiment of this invention the compound of formula 1.0 is a compound of formula 1.37A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37 and Ar is phenyl.

In another embodiment of this invention the compound of formula 1.0 is a compound of formula 1.37, Ar is phenyl substituted with halo.

In another embodiment of this invention the compound of formula 1.0 is a compound of formula 1.37 and Ar is phenyl substituted with one halo.

In another embodiment of this invention the compound of formula 1.0 is a compound of formula 1.37 and Ar is:

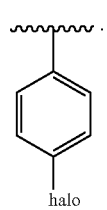

In another embodiment of this invention the compound of formula 1.0 is a compound of formula 1.37 and Ar is phenyl substituted with at least one Cl.

In another embodiment of this invention the compound of formula 1.0 is a compound of formula 1.37 and Ar is phenyl substituted with a Cl.

In another embodiment of this invention the compound of formula 1.0 is a compound of formula 1.37 and Ar is:

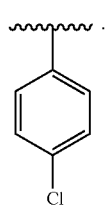

In another embodiment of this invention the compound of formula 1.0 is a compound of formula 1.37 and Ar is phenyl substituted with at least one —$CF_3$.

In another embodiment of this invention the compound of formula 1.0 is a compound of formula 1.37 and Ar is phenyl substituted with a —$CF_3$.

In another embodiment of this invention the compound of formula 1.0 is a compound of formula 1.37 and Ar is:

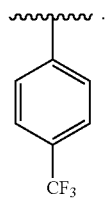

In another embodiment of this invention the compound of formula 1.0 is a compound of formula 1.37 and Ar is phenyl substituted with at least one —CN.

In another embodiment of this invention the compound of formula 1.0 is a compound of formula 1.37 and Ar is phenyl substituted with a —CN.

In another embodiment of this invention the compound of formula 1.0 is a compound of formula 1.37 and Ar is:

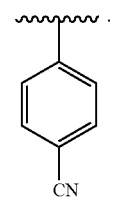

In another embodiment of this invention the compound of formula 1.0 is a compound of formula 1.37, X is O, each $L^1$ is halo, and Ar is phenyl substituted with at least one halo.

In another embodiment of this invention the compound of formula 1.0 is a compound of formula 1.37, X is O, n is 2, each $L^1$ is the same or different halo, and Ar is phenyl substituted with one halo.

In another embodiment of this invention the compound of formula 1.0 is a compound of formula 1.37, X is O, n is 2, $L^1$ is F, and Ar is phenyl substituted with one Cl.

In another embodiment of this invention the compound of formula 1.0 is a compound of formula 1.37, X is O, n is 2, each $L^1$ is the same or different halo, and Ar is:

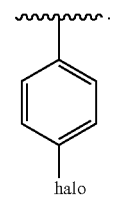

In another embodiment of this invention the compound of formula 1.0 is a compound of formula 1.37, X is O, n is 2, each $L^1$ is the same or different halo, and Ar is:

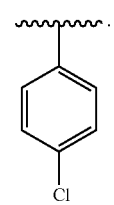 [SMILES: *c1ccc(Cl)cc1]

In another embodiment of this invention the compound of formula 1.0 is a compound of formula 1.37, X is O, each $L^1$ is halo, and Ar is phenyl substituted with at least one —$CF_3$.

In another embodiment of this invention the compound of formula 1.0 is a compound of formula 1.37, X is O, n is 2, each $L^1$ is the same or different halo, and Ar is phenyl substituted with one —$CF_3$.

In another embodiment of this invention the compound of formula 1.0 is a compound of formula 1.37, X is O, n is 2, $L^1$ is F, and Ar is phenyl substituted with one —$CF_3$.

In another embodiment of this invention the compound of formula 1.0 is a compound of formula 1.37, X is O, n is 2, each $L^1$ is the same or different halo, and Ar is:

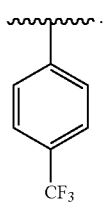 [SMILES: *c1ccc(C(F)(F)F)cc1]

In another embodiment of this invention the compound of formula 1.0 is a compound of formula 1.37, X is O, each $L^1$ is halo, and Ar is phenyl substituted with at least one —CN.

In another embodiment of this invention the compound of formula 1.0 is a compound of formula 1.37, X is O, n is 2, each $L^1$ is the same or different halo, and Ar is phenyl substituted with one —CN.

In another embodiment of this invention the compound of formula 1.0 is a compound of formula 1.37, X is O, n is 2, $L^1$ is F, and Ar is phenyl substituted with one —CN.

In another embodiment of this invention the compound of formula 1.0 is a compound of formula 1.37, X is O, n is 2, each $L^1$ is the same or different halo, and Ar is:

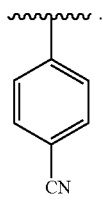

In another embodiment of this invention the compound of formula 1.0 is a compound of formula 1.37, said compound having the formula (1.37A):

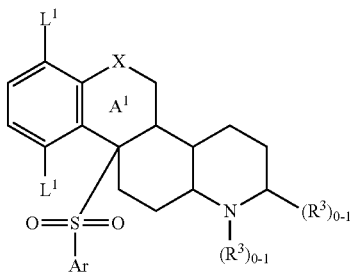

(1.37A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is:

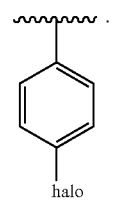

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37A, wherein X is O, n is 2, each $L^1$ is the same or different halo, and Ar is:

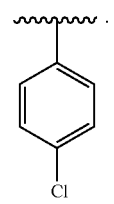

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein X is O, n is 2, each $L^1$ is the same or different halo, and Ar is:

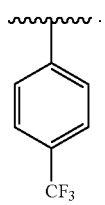

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with at least one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein X is O, each $L^1$ is the same or different halo, and Ar is phenyl substituted with one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.37A, wherein X is O, n is 2, each $L^1$ is the same or different halo, and Ar is:

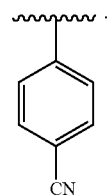

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.38, and X is O.

In another embodiment of this invention the compound of formula 1.0 is a compound of formula 1.38 and $L^1$ is halo.

In another embodiment of this invention the compound of formula 1.0 is a compound of formula 1.38, said compound having the formula (1.38A):

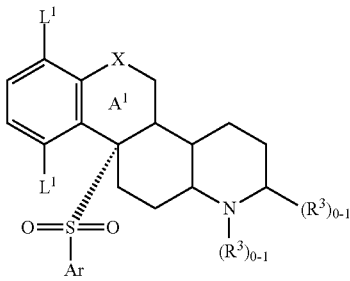

(1.38A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.38A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.38, n is 2 and $L^1$ is F.

In another embodiment of this invention the compound of formula 1.0 is a compound of formula 1.38A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted).

In another embodiment of this invention the compound of formula 1.0 is a compound of formula 1.38 and Ar is phenyl.

In another embodiment of this invention the compound of formula 1.0 is a compound of formula 1.38, Ar is phenyl substituted with halo.

In another embodiment of this invention the compound of formula 1.0 is a compound of formula 1.38 and Ar is phenyl substituted with one halo.

In another embodiment of this invention the compound of formula 1.0 is a compound of formula 1.38 and Ar is:

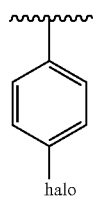

In another embodiment of this invention the compound of formula 1.0 is a compound of formula 1.38 and Ar is phenyl substituted with at least one Cl.

In another embodiment of this invention the compound of formula 1.0 is a compound of formula 1.38 and Ar is phenyl substituted with a Cl.

In another embodiment of this invention the compound of formula 1.0 is a compound of formula 1.38 and Ar is:

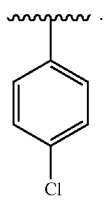 [SMILES: *c1ccc(Cl)cc1]

In another embodiment of this invention the compound of formula 1.0 is a compound of formula 1.38 and Ar is phenyl substituted with at least one —$CF_3$.

In another embodiment of this invention the compound of formula 1.0 is a compound of formula 1.38 and Ar is phenyl substituted with a —$CF_3$.

In another embodiment of this invention the compound of formula 1.0 is a compound of formula 1.38 and Ar is:

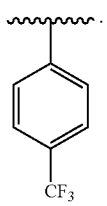

In another embodiment of this invention the compound of formula 1.0 is a compound of formula 1.38 and Ar is phenyl substituted with at least one —CN.

In another embodiment of this invention the compound of formula 1.0 is a compound of formula 1.38 and Ar is phenyl substituted with a —CN.

In another embodiment of this invention the compound of formula 1.0 is a compound of formula 1.38 and Ar is:

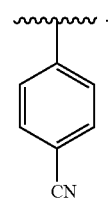

In another embodiment of this invention the compound of formula 1.0 is a compound of formula 1.38, X is O, each $L^1$ is halo, and Ar is phenyl substituted with at least one halo.

In another embodiment of this invention the compound of formula 1.0 is a compound of formula 1.38, X is O, n is 2, each $L^1$ is the same or different halo, and Ar is phenyl substituted with one halo.

In another embodiment of this invention the compound of formula 1.0 is a compound of formula 1.38, X is O, n is 2, $L^1$ is F, and Ar is phenyl substituted with one Cl.

In another embodiment of this invention the compound of formula 1.0 is a compound of formula 1.38, X is O, n is 2, each $L^1$ is the same or different halo, and Ar is:

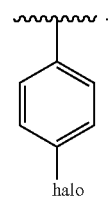

In another embodiment of this invention the compound of formula 1.0 is a compound of formula 1.38, X is O, n is 2, each $L^1$ is the same or different halo, and Ar is:

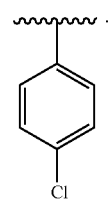

In another embodiment of this invention the compound of formula 1.0 is a compound of formula 1.38, X is O, each $L^1$ is halo, and Ar is phenyl substituted with at least one —$CF_3$.

In another embodiment of this invention the compound of formula 1.0 is a compound of formula 1.38, X is O, n is 2, each $L^1$ is the same or different halo, and Ar is phenyl substituted with one —$CF_3$.

In another embodiment of this invention the compound of formula 1.0 is a compound of formula 1.38, X is O, n is 2, $L^1$ is F, and Ar is phenyl substituted with one —$CF_3$.

In another embodiment of this invention the compound of formula 1.0 is a compound of formula 1.38, X is O, n is 2, each $L^1$ is the same or different halo, and Ar is:

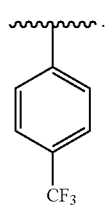

In another embodiment of this invention the compound of formula 1.0 is a compound of formula 1.38, X is O, each $L^1$ is halo, and Ar is phenyl substituted with at least one —CN.

In another embodiment of this invention the compound of formula 1.0 is a compound of formula 1.38, X is O, n is 2, each $L^1$ is the same or different halo, and Ar is phenyl substituted with one —CN.

In another embodiment of this invention the compound of formula 1.0 is a compound of formula 1.38, X is O, n is 2, $L^1$ is F, and Ar is phenyl substituted with one —CN.

In another embodiment of this invention the compound of formula 1.0 is a compound of formula 1.38, X is O, n is 2, each $L^1$ is the same or different halo, and Ar is:

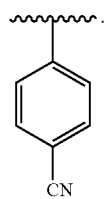

In another embodiment of this invention the compound of formula 1.0 is a compound of formula 1.38, said compound having the formula (1.38A):

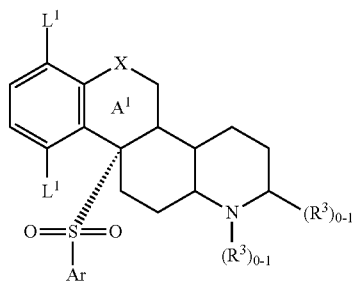

(1.38A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is:

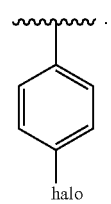

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_5$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is:

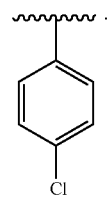

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is:

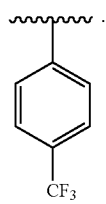

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.38A, wherein X is O, each $L^1$ is the same or different halo, and Ar is:

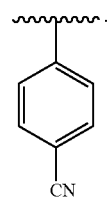

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39, and X is O.

In another embodiment of this invention the compound of formula 1.0 is a compound of formula 1.39 and $L^1$ is halo.

In another embodiment of this invention the compound of formula 1.0 is a compound of formula 1.39, said compound having the formula (1.39A):

(1.39A)

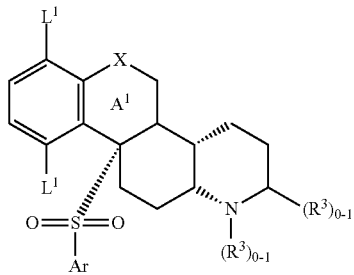

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the $=N-(R^3)_{0-1}$ moiety is $=N-H$ (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39, n is 2 and $L^1$ is F.

In another embodiment of this invention the compound of formula 1.0 is a compound of formula 1.39A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39 and Ar is phenyl.

In another embodiment of this invention the compound of formula 1.0 is a compound of formula 1.39, Ar is phenyl substituted with halo.

In another embodiment of this invention the compound of formula 1.0 is a compound of formula 1.39 and Ar is phenyl substituted with one halo.

In another embodiment of this invention the compound of formula 1.0 is a compound of formula 1.39 and Ar is:

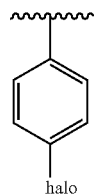

In another embodiment of this invention the compound of formula 1.0 is a compound of formula 1.39 and Ar is phenyl substituted with at least one Cl.

In another embodiment of this invention the compound of formula 1.0 is a compound of formula 1.39 and Ar is phenyl substituted with a Cl.

In another embodiment of this invention the compound of formula 1.0 is a compound of formula 1.39 and Ar is:

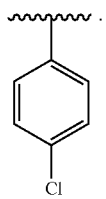

In another embodiment of this invention the compound of formula 1.0 is a compound of formula 1.39 and Ar is phenyl substituted with at least one —$CF_3$.

In another embodiment of this invention the compound of formula 1.0 is a compound of formula 1.39 and Ar is phenyl substituted with a —$CF_3$.

In another embodiment of this invention the compound of formula 1.0 is a compound of formula 1.39 and Ar is:

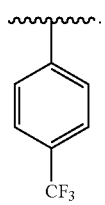

In another embodiment of this invention the compound of formula 1.0 is a compound of formula 1.39 and Ar is phenyl substituted with at least one —CN.

In another embodiment of this invention the compound of formula 1.0 is a compound of formula 1.39 and Ar is phenyl substituted with a —CN.

In another embodiment of this invention the compound of formula 1.0 is a compound of formula 1.39 and Ar is:

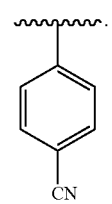

In another embodiment of this invention the compound of formula 1.0 is a compound of formula 1.39, X is O, each $L^1$ is halo, and Ar is phenyl substituted with at least one halo.

In another embodiment of this invention the compound of formula 1.0 is a compound of formula 1.39, X is O, n is 2, each $L^1$ is the same or different halo, and Ar is phenyl substituted with one halo.

In another embodiment of this invention the compound of formula 1.0 is a compound of formula 1.39, X is O, n is 2, $L^1$ is F, and Ar is phenyl substituted with one Cl.

In another embodiment of this invention the compound of formula 1.0 is a compound of formula 1.39, X is O, n is 2, each $L^1$ is the same or different halo, and Ar is:

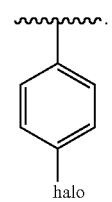

In another embodiment of this invention the compound of formula 1.0 is a compound of formula 1.39, X is O, n is 2, each $L^1$ is the same or different halo, and Ar is:

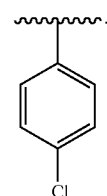

In another embodiment of this invention the compound of formula 1.0 is a compound of formula 1.39, X is O, each $L^1$ is halo, and Ar is phenyl substituted with at least one —$CF_3$.

In another embodiment of this invention the compound of formula 1.0 is a compound of formula 1.39, X is O, n is 2, each $L^1$ is the same or different halo, and Ar is phenyl substituted with one —$CF_3$.

In another embodiment of this invention the compound of formula 1.0 is a compound of formula 1.39, X is O, n is 2, $L^1$ is F, and Ar is phenyl substituted with one —$CF_3$.

In another embodiment of this invention the compound of formula 1.0 is a compound of formula 1.39, X is O, n is 2, each $L^1$ is the same or different halo, and Ar is:

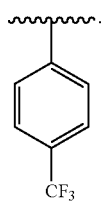

In another embodiment of this invention the compound of formula 1.0 is a compound of formula 1.39, X is O, each $L^1$ is halo, and Ar is phenyl substituted with at least one —CN.

In another embodiment of this invention the compound of formula 1.0 is a compound of formula 1.39, X is O, n is 2, each $L^1$ is the same or different halo, and Ar is phenyl substituted with one —CN.

In another embodiment of this invention the compound of formula 1.0 is a compound of formula 1.39, X is O, n is 2, $L^1$ is F, and Ar is phenyl substituted with one —CN.

In another embodiment of this invention the compound of formula 1.0 is a compound of formula 1.39, X is O, n is 2, each $L^1$ is the same or different halo, and Ar is:

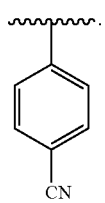

In another embodiment of this invention the compound of formula 1.0 is a compound of formula 1.39, said compound having the formula (1.39A):

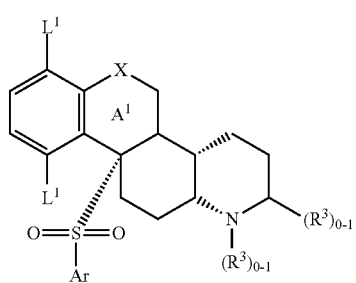

(1.39A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein X is O, each $L^1$ is the same or different halo, and Ar is:

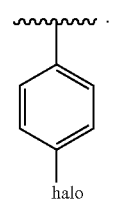

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein X is O, each $L^1$ is the same or different halo, and Ar is:

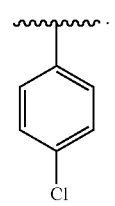

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. Preferably, the =N—$(R^3)_{0-1}$ moiety is =N—H (i.e., this N is not substituted). Preferably $R^3$ of the CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.39A, wherein X is O, each $L^1$ is the same or different halo, and Ar is phenyl substituted with at least one —CF$_3$. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.39A, wherein X is O, each L$^1$ is the same or different halo, and Ar is phenyl substituted with one —CF$_3$. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.39A, wherein X is O, each L$^1$ is the same or different halo, and Ar is:

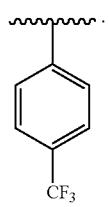

In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.39A, wherein X is O, each L$^1$ is the same or different halo, and Ar is phenyl substituted with at least one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.39A, wherein X is O, each L$^1$ is the same or different halo, and Ar is phenyl substituted with one —CN. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.39A, wherein X is O, each L$^1$ is the same or different halo, and Ar is:

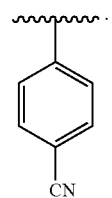

In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. Preferably, the =N—(R$^3$)$_{0-1}$ moiety is =N—H (i.e., this N is not substituted). Preferably R$^3$ of the CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.40, and X is O.

In another embodiment of this invention the compound of formula 1.0 is a compound of formula 1.40 and L$^1$ is halo.

In another embodiment of this invention the compound of formula 1.0 is a compound of formula 1.40, said compound having the formula (1.40A):

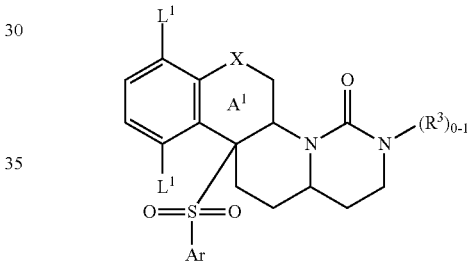

(1.40A)

wherein each L$^1$ is the same or different halo. All other substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. In one example R$^3$ in the =N—(R$^3$)$_{0-1}$ moiety is a C$_1$-C$_6$ alkyl group. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.40A, wherein each L$^1$ is the same halo. All other substituents are as defined for formula 1.0. In the substituent "(R$^3$)$_{0-1}$", the "0-1" means that there is no R$^3$ substituent present (i.e., there would be a H instead of the R$^3$ substituent), or that there is one R$^3$ substituent present at the indicated position. Each R$^3$ is independently selected. In one example R$^3$ in the =N—(R$^3$)$_{0-1}$ moiety is a C$_1$-C$_6$ alkyl group. Preferably, the =N—(R$^3$)$_{0-1}$ moiety is =N—H (i.e., this N is not substituted). Preferably each R$^3$ of each CH—R$^3$ moiety is independently selected from the group consisting of —C$_1$-C$_6$ alkyl, hydroxyalkyl, and alkoxyalkyl.

In another embodiment of this invention the compound of formula 1.0 is a compound of formula 1.40, n is 2 and L$^1$ is F.

In another embodiment of this invention the compound of formula 1.0 is a compound of formula 1.40A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40 and Ar is phenyl.

In another embodiment of this invention the compound of formula 1.0 is a compound of formula 1.40, Ar is phenyl substituted with halo.

In another embodiment of this invention the compound of formula 1.0 is a compound of formula 1.40 and Ar is phenyl substituted with one halo.

In another embodiment of this invention the compound of formula 1.0 is a compound of formula 1.40 and Ar is:

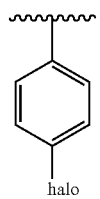

In another embodiment of this invention the compound of formula 1.0 is a compound of formula 1.40 and Ar is phenyl substituted with at least one Cl.

In another embodiment of this invention the compound of formula 1.0 is a compound of formula 1.40 and Ar is phenyl substituted with a Cl.

In another embodiment of this invention the compound of formula 1.0 is a compound of formula 1.40 and Ar is:

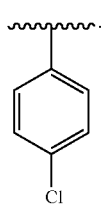

In another embodiment of this invention the compound of formula 1.0 is a compound of formula 1.40 and Ar is phenyl substituted with at least one —$CF_3$.

In another embodiment of this invention the compound of formula 1.0 is a compound of formula 1.40 and Ar is phenyl substituted with a —$CF_3$.

In another embodiment of this invention the compound of formula 1.0 is a compound of formula 1.40 and Ar is:

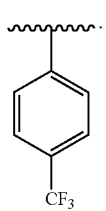

In another embodiment of this invention the compound of formula 1.0 is a compound of formula 1.40 and Ar is phenyl substituted with at least one —CN.

In another embodiment of this invention the compound of formula 1.0 is a compound of formula 1.40 and Ar is phenyl substituted with a —CN.

In another embodiment of this invention the compound of formula 1.0 is a compound of formula 1.40 and Ar is:

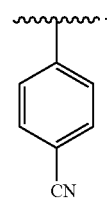 [SMILES: *c1ccc(C#N)cc1]

In another embodiment of this invention the compound of formula 1.0 is a compound of formula 1.40, X is O, each $L^1$ is halo, and Ar is phenyl substituted with at least one halo.

In another embodiment of this invention the compound of formula 1.0 is a compound of formula 1.40, X is O, n is 2, each $L^1$ is the same or different halo, and Ar is phenyl substituted with one halo.

In another embodiment of this invention the compound of formula 1.0 is a compound of formula 1.40, X is O, n is 2, $L^1$ is F, and Ar is phenyl substituted with one Cl.

In another embodiment of this invention the compound of formula 1.0 is a compound of formula 1.40, X is O, n is 2, each $L^1$ is the same or different halo, and Ar is:

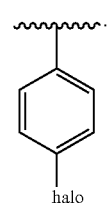

In another embodiment of this invention the compound of formula 1.0 is a compound of formula 1.40, X is O, n is 2, each $L^1$ is the same or different halo, and Ar is:

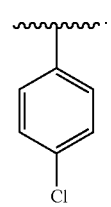

In another embodiment of this invention the compound of formula 1.0 is a compound of formula 1.40, X is O, each $L^1$ is halo, and Ar is phenyl substituted with at least one —$CF_3$.

In another embodiment of this invention the compound of formula 1.0 is a compound of formula 1.40, X is O, n is 2, each $L^1$ is the same or different halo, and Ar is phenyl substituted with one —$CF_3$.

In another embodiment of this invention the compound of formula 1.0 is a compound of formula 1.40, X is O, n is 2, $L^1$ is F, and Ar is phenyl substituted with one —$CF_3$.

In another embodiment of this invention the compound of formula 1.0 is a compound of formula 1.40, X is O, n is 2, each $L^1$ is the same or different halo, and Ar is:

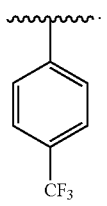

In another embodiment of this invention the compound of formula 1.0 is a compound of formula 1.40, X is O, each $L^1$ is halo, and Ar is phenyl substituted with at least one —CN.

In another embodiment of this invention the compound of formula 1.0 is a compound of formula 1.40, X is O, n is 2, each $L^1$ is the same or different halo, and Ar is phenyl substituted with one —CN.

In another embodiment of this invention the compound of formula 1.0 is a compound of formula 1.40, X is O, n is 2, $L^1$ is F, and Ar is phenyl substituted with one —CN.

In another embodiment of this invention the compound of formula 1.0 is a compound of formula 1.40, X is O, n is 2, each $L^1$ is the same or different halo, and Ar is:

In another embodiment of this invention the compound of formula 1.0 is a compound of formula 1.40, said compound having the formula (1.40A):

(1.40A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is:

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, n is 2, each $L^1$ is the same or different halo, and Ar is:

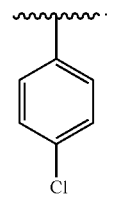

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, n is 2, each $L^1$ is the same or different halo, and Ar is:

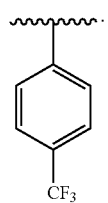

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.40A, wherein X is O, n is 2, each $L^1$ is the same or different halo, and Ar is:

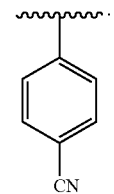

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41, and X is O.

In another embodiment of this invention the compound of formula 1.0 is a compound of formula 1.41 and $L^1$ is halo.

In another embodiment of this invention the compound of formula 1.0 is a compound of formula 1.41, said compound having the formula:

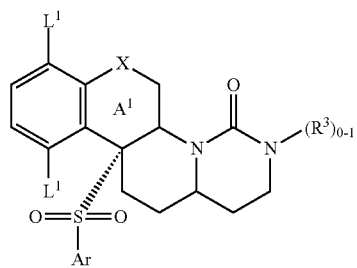

(1.41A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41, n is 2 and $L^1$ is F.

In another embodiment of this invention the compound of formula 1.0 is a compound of formula 1.41A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41 and Ar is phenyl.

In another embodiment of this invention the compound of formula 1.0 is a compound of formula 1.41, Ar is phenyl substituted with halo.

In another embodiment of this invention the compound of formula 1.0 is a compound of formula 1.41 and Ar is phenyl substituted with one halo.

In another embodiment of this invention the compound of formula 1.0 is a compound of formula 1.41 and Ar is:

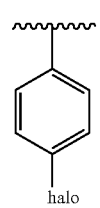

In another embodiment of this invention the compound of formula 1.0 is a compound of formula 1.41 and Ar is phenyl substituted with at least one Cl.

In another embodiment of this invention the compound of formula 1.0 is a compound of formula 1.41 and Ar is phenyl substituted with a Cl.

In another embodiment of this invention the compound of formula 1.0 is a compound of formula 1.41 and Ar is:

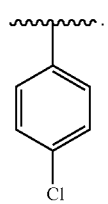

In another embodiment of this invention the compound of formula 1.0 is a compound of formula 1.41 and Ar is phenyl substituted with at least one —$CF_3$.

In another embodiment of this invention the compound of formula 1.0 is a compound of formula 1.41 and Ar is phenyl substituted with a —$CF_3$.

In another embodiment of this invention the compound of formula 1.0 is a compound of formula 1.41 and Ar is:

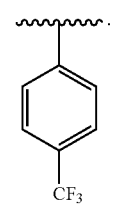 [SMILES: *c1ccc(C(F)(F)F)cc1]

In another embodiment of this invention the compound of formula 1.0 is a compound of formula 1.41 and Ar is phenyl substituted with at least one —CN.

In another embodiment of this invention the compound of formula 1.0 is a compound of formula 1.41 and Ar is phenyl substituted with a —CN.

In another embodiment of this invention the compound of formula 1.0 is a compound of formula 1.41 and Ar is:

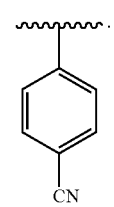 [SMILES: *c1ccc(C#N)cc1]

In another embodiment of this invention the compound of formula 1.0 is a compound of formula 1.41, X is O, each $L^1$ is halo, and Ar is phenyl substituted with at least one halo.

In another embodiment of this invention the compound of formula 1.0 is a compound of formula 1.41, X is O, n is 2, each $L^1$ is the same or different halo, and Ar is phenyl substituted with one halo.

In another embodiment of this invention the compound of formula 1.0 is a compound of formula 1.41, X is O, n is 2, $L^1$ is F, and Ar is phenyl substituted with one Cl.

In another embodiment of this invention the compound of formula 1.0 is a compound of formula 1.41, X is O, n is 2, each $L^1$ is the same or different halo, and Ar is:

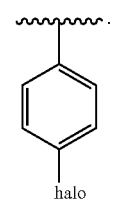

In another embodiment of this invention the compound of formula 1.0 is a compound of formula 1.41, X is O, n is 2, each $L^1$ is the same or different halo, and Ar is:

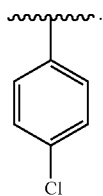

In another embodiment of this invention the compound of formula 1.0 is a compound of formula 1.41, X is O, each $L^1$ is halo, and Ar is phenyl substituted with at least one —$CF_3$.

In another embodiment of this invention the compound of formula 1.0 is a compound of formula 1.41, X is O, n is 2, each $L^1$ is the same or different halo, and Ar is phenyl substituted with one —$CF_3$.

In another embodiment of this invention the compound of formula 1.0 is a compound of formula 1.41, X is O, n is 2, $L^1$ is F, and Ar is phenyl substituted with one —$CF_3$.

In another embodiment of this invention the compound of formula 1.0 is a compound of formula 1.41, X is O, n is 2, each $L^1$ is the same or different halo, and Ar is:

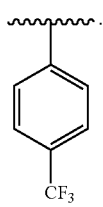

In another embodiment of this invention the compound of formula 1.0 is a compound of formula 1.41, X is O, each $L^1$ is halo, and Ar is phenyl substituted with at least one —CN.

In another embodiment of this invention the compound of formula 1.0 is a compound of formula 1.41, X is O, n is 2, each $L^1$ is the same or different halo, and Ar is phenyl substituted with one —CN.

In another embodiment of this invention the compound of formula 1.0 is a compound of formula 1.41, X is O, n is 2, $L^1$ is F, and Ar is phenyl substituted with one —CN.

In another embodiment of this invention the compound of formula 1.0 is a compound of formula 1.41, X is O, n is 2, each $L^1$ is the same or different halo, and Ar is:

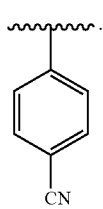

In another embodiment of this invention the compound of formula 1.0 is a compound of formula 1.41, said compound having the formula (1.41A):

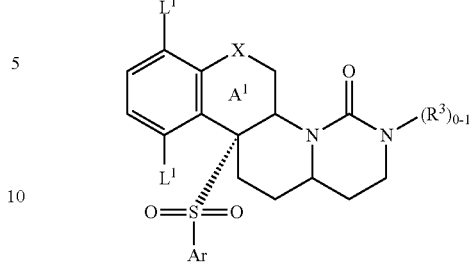

(1.41A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is:

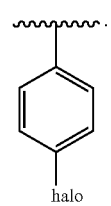

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is:

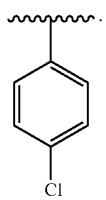

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—(R)$_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is:

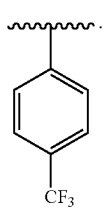

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.41A, wherein X is O, each $L^1$ is the same or different halo, and Ar is:

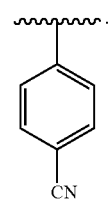

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42, and X is O.

In another embodiment of this invention the compound of formula 1.0 is a compound of formula 1.42 and $L^1$ is halo.

In another embodiment of this invention the compound of formula 1.0 is a compound of formula 1.42, said compound having the formula (1.42A):

(1.42A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42, n is 2 and $L^1$ is F.

In another embodiment of this invention the compound of formula 1.0 is a compound of formula 1.42A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42 and Ar is phenyl.

In another embodiment of this invention the compound of formula 1.0 is a compound of formula 1.42, Ar is phenyl substituted with halo.

In another embodiment of this invention the compound of formula 1.0 is a compound of formula 1.42 and Ar is phenyl substituted with one halo.

In another embodiment of this invention the compound of formula 1.0 is a compound of formula 142 and Ar is:

In another embodiment of this invention the compound of formula 1.0 is a compound of formula 1.42 and Ar is phenyl substituted with at least one Cl.

In another embodiment of this invention the compound of formula 1.0 is a compound of formula 1.42 and Ar is phenyl substituted with a Cl.

In another embodiment of this invention the compound of formula 1.0 is a compound of formula 1.42 and Ar is:

In another embodiment of this invention the compound of formula 1.0 is a compound of formula 1.42 and Ar is phenyl substituted with at least one —$CF_3$.

In another embodiment of this invention the compound of formula 1.0 is a compound of formula 1.42 and Ar is phenyl substituted with a —$CF_3$.

In another embodiment of this invention the compound of formula 1.0 is a compound of formula 1.42 and Ar is:

In another embodiment of this invention the compound of formula 1.0 is a compound of formula 1.42 and Ar is phenyl substituted with at least one —CN.

In another embodiment of this invention the compound of formula 1.0 is a compound of formula 1.42 and Ar is phenyl substituted with a —CN.

In another embodiment of this invention the compound of formula 1.0 is a compound of formula 1.42 and Ar is:

In another embodiment of this invention the compound of formula 1.0 is a compound of formula 1.42, X is O, each L¹ is halo, and Ar is phenyl substituted with at least one halo.

In another embodiment of this invention the compound of formula 1.0 is a compound of formula 1.42, X is O, n is 2, each L¹ is the same or different halo, and Ar is phenyl substituted with one halo.

In another embodiment of this invention the compound of formula 1.0 is a compound of formula 1.42, X is O, n is 2, L¹ is F, and Ar is phenyl substituted with one Cl.

In another embodiment of this invention the compound of formula 1.0 is a compound of formula 1.42, X is O, n is 2, each L¹ is the same or different halo, and Ar is:

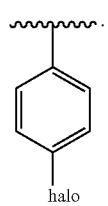

halo

In another embodiment of this invention the compound of formula 1.0 is a compound of formula 1.42, X is O, n is 2, each L¹ is the same or different halo, and Ar is:

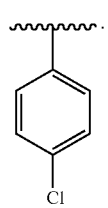

Cl

In another embodiment of this invention the compound of formula 1.0 is a compound of formula 1.42, X is O, each L¹ is halo, and Ar is phenyl substituted with at least one —CF₃.

In another embodiment of this invention the compound of formula 1.0 is a compound of formula 1.42, X is O, n is 2, each L¹ is the same or different halo, and Ar is phenyl substituted with one —CF₃.

In another embodiment of this invention the compound of formula 1.0 is a compound of formula 1.42, X is O, n is 2, L¹ is F, and Ar is phenyl substituted with one —CF₃.

In another embodiment of this invention the compound of formula 1.0 is a compound of formula 1.42, X is O, n is 2, each L¹ is the same or different halo, and Ar is:

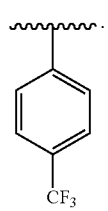

CF₃

In another embodiment of this invention the compound of formula 1.0 is a compound of formula 1.42, X is O, each L¹ is halo, and Ar is phenyl substituted with at least one —CN.

In another embodiment of this invention the compound of formula 1.0 is a compound of formula 1.42, X is O, n is 2, each L¹ is the same or different halo, and Ar is phenyl substituted with one CN.

In another embodiment of this invention the compound of formula 1.0 is a compound of formula 1.42, X is O, n is 2, L¹ is F, and Ar is phenyl substituted with one —CN.

In another embodiment of this invention the compound of formula 1.0 is a compound of formula 1.42, X is O, n is 2, each L¹ is the same or different halo, and Ar is:

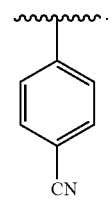

CN

In another embodiment of this invention the compound of formula 1.0 is a compound of formula 1.42, said compound having the formula (1.42A):

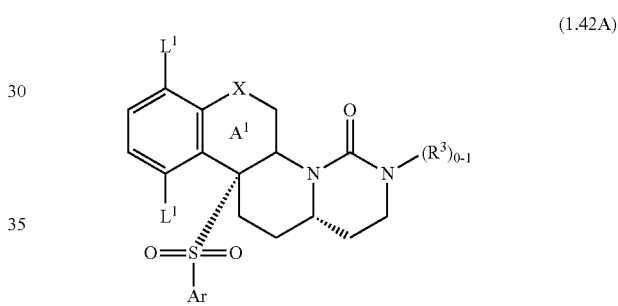

(1.42A)

wherein X is O, each L¹ is the same or different halo, and Ar is phenyl substituted with at least one halo. In the substituent "(R³)₀₋₁", the "0-1" means that there is no R³ substituent present (i.e., there would be a H instead of the R³ substituent), or that there is one R³ substituent present at the indicated position. Each R³ is independently selected. In one example R³ in the =N—(R³)₀₋₁ moiety is a C₁-C₆ alkyl group. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment of this invention the compound of formula 1.0 is a compound of formula 1.42A, wherein X is O, each L¹ is the same or different halo, and Ar is phenyl substituted with one halo. In the substituent "(R³)₀₋₁", the "0-1" means that there is no R³ substituent present (i.e., there would be a H instead of the R³ substituent), or that there is one R³ substituent present at the indicated position. Each R³ is independently selected. In one example R³ in the =N—(R³)₀₋₁ moiety is a C₁-C₆ alkyl group. Preferably, the =N—(R³)₀₋₁ moiety is =N—H (i.e., this N is not substituted). Preferably each R³ of each CH—R³ moiety is independently selected from the group consisting of —C₁-C₆ alkyl, hydroxyalkyl, and alkoxyalkyl.

In another embodiment of this invention the compound of formula 1.0 is a compound of formula 1.42A, wherein X is O, each L¹ is the same or different halo, and Ar is:

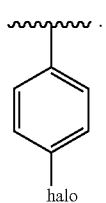
halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is:

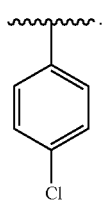
Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is:

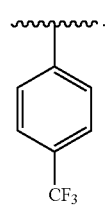
$CF_3$

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted). Preferably each $R^3$ of each CH—$R^3$ moiety is independently selected from the group consisting of —$C_1$-$C_6$ alkyl, hydroxyalkyl, and alkoxyalkyl.

In another embodiment of this invention the compound of formula 1.0 is a compound of formula 1.42A, wherein X is O, each $L^1$ is the same or different halo, and Ar is:

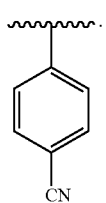

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{04}$ moiety is a $C_1-C_6$ alkyl group. Preferably, the $=N-(R^3)_{0-1}$ moiety is $=N-H$ (i.e., this N is not substituted). Preferably each $R^3$ of each $CH-R^3$ moiety is independently selected from the group consisting of $-C_1-C_6$ alkyl, hydroxyalkyl, and alkoxyalkyl.

In another embodiment of this invention the compound of formula 1.0 is a compound of formula 1.43, and X is O.

In another embodiment of this invention the compound of formula 1.0 is a compound of formula 1.43 and $L^1$ is halo.

In another embodiment of this invention the compound of formula 1.0 is a compound of formula 1.43, said compound having the formula (1.43A):

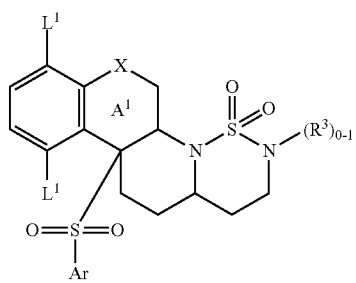

(1.43A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.43A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.43, n is 2 and $L^1$ is F.

In another embodiment of this invention the compound of formula 1.0 is a compound of formula 1.43A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.43 and Ar is phenyl.

In another embodiment of this invention the compound of formula 1.0 is a compound of formula 1.43, Ar is phenyl substituted with halo.

In another embodiment of this invention the compound of formula 1.0 is a compound of formula 1.43 and Ar is phenyl substituted with one halo.

In another embodiment of this invention the compound of formula 1.0 is a compound of formula 1.43 and Ar is:

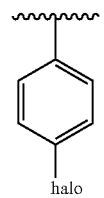

In another embodiment of this invention the compound of formula 1.0 is a compound of formula 1.43 and Ar is phenyl substituted with at least one Cl.

In another embodiment of this invention the compound of formula 1.0 is a compound of formula 1.43 and Ar is phenyl substituted with a Cl.

In another embodiment of this invention the compound of formula 1.0 is a compound of formula 1.43 and Ar is:

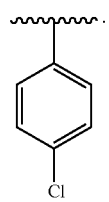

In another embodiment of this invention the compound of formula 1.0 is a compound of formula 1.43 and Ar is phenyl substituted with at least one $-CF_3$.

In another embodiment of this invention the compound of formula 1.0 is a compound of formula 1.43 and Ar is phenyl substituted with a $-CF_3$.

In another embodiment of this invention the compound of formula 1.0 is a compound of formula 1.43 and Ar is:

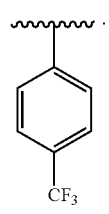 [SMILES: *c1ccc(C(F)(F)F)cc1]

In another embodiment of this invention the compound of formula 1.0 is a compound of formula 1.43 and Ar is phenyl substituted with at least one $-CN$.

In another embodiment of this invention the compound of formula 1.0 is a compound of formula 1.43 and Ar is phenyl substituted with a —CN.

In another embodiment of this invention the compound of formula 1.0 is a compound of formula 1.43 and Ar is:

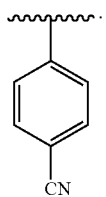

In another embodiment of this invention the compound of formula 1.0 is a compound of formula 1.43, X is O, each $L^1$ is halo, and Ar is phenyl substituted with at least one halo.

In another embodiment of this invention the compound of formula 1.0 is a compound of formula 1.43, X is O, n is 2, each $L^1$ is the same or different halo, and Ar is phenyl substituted with one halo.

In another embodiment of this invention the compound of formula 1.0 is a compound of formula 1.43, X is O, n is 2, $L^1$ is F, and Ar is phenyl substituted with one Cl.

In another embodiment of this invention the compound of formula 1.0 is a compound of formula 1.43, X is O, n is 2, each $L^1$ is the same or different halo, and Ar is:

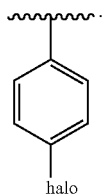

In another embodiment of this invention the compound of formula 1.0 is a compound of formula 1.43, X is O, n is 2, each $L^1$ is the same or different halo, and Ar is:

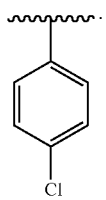

In another embodiment of this invention the compound of formula 1.0 is a compound of formula 1.43, X is O, each $L^1$ is halo, and Ar is phenyl substituted with at least one —$CF_3$.

In another embodiment of this invention the compound of formula 1.0 is a compound of formula 1.43, X is O, n is 2, each $L^1$ is the same or different halo, and Ar is phenyl substituted with one —$CF_3$.

In another embodiment of this invention the compound of formula 1.0 is a compound of formula 1.43, X is O, n is 2, $L^1$ is F, and Ar is phenyl substituted with one —$CF_3$.

In another embodiment of this invention the compound of formula 1.0 is a compound of formula 1.43, X is O, n is 2, each $L^1$ is the same or different halo, and Ar is:

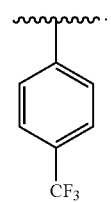 [SMILES: *c1ccc(C(F)(F)F)cc1]

In another embodiment of this invention the compound of formula 1.0 is a compound of formula 1.43, X is O, each $L^1$ is halo, and Ar is phenyl substituted with at least one —CN.

In another embodiment of this invention the compound of formula 1.0 is a compound of formula 1.43, X is O, n is 2, each $L^1$ is the same or different halo, and Ar is phenyl substituted with one —CN.

In another embodiment of this invention the compound of formula 1.0 is a compound of formula 1.43, X is O, n is 2, $L^1$ is F, and Ar is phenyl substituted with one —CN.

In another embodiment of this invention the compound of formula 1.0 is a compound of formula 1.43, X is O, n is 2, each $L^1$ is the same or different halo, and Ar is:

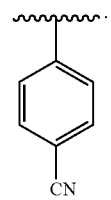

In another embodiment of this invention the compound of formula 1.0 is a compound of formula 1.43, said compound having the formula (1.43A):

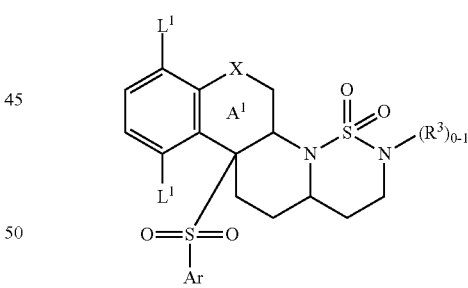

(1.43A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.43A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is:

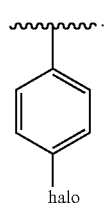

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is:

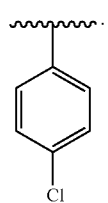

Cl

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is phenyl substituted with at least one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is phenyl substituted with one —$CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is:

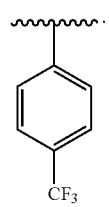 [SMILES: *c1ccc(C(F)(F)F)cc1]

$CF_3$

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is phenyl substituted with at least one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is phenyl substituted with one —CN. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=\!\!N\!-\!(R^3)_{0-1}$ moiety is a $C_1$-$C_6$ alkyl group. Preferably, the $=\!\!N\!-\!(R^3)_{0-1}$ moiety is $=\!\!N\!-\!H$ (i.e., this N is not substituted).

In another embodiment of this invention the compound of formula 1.0 is a compound of formula 1.43A, wherein X is O, each $L^1$ is the same or different halo, and Ar is:

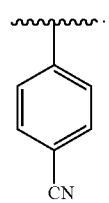 [SMILES: *c1ccc(C#N)cc1]

CN

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44, and X is O.

In another embodiment of this invention the compound of formula 1.0 is a compound of formula 1.44 and $L^1$ is halo.

In another embodiment of this invention the compound of formula 1.0 is a compound of formula 1.44, said compound having the formula (1.44A):

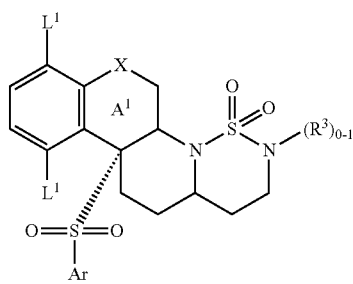

(1.44A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44, n is 2 and $L^1$ is F.

In another embodiment of this invention the compound of formula 1.0 is a compound of formula 1.44A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44 and Ar is phenyl.

In another embodiment of this invention the compound of formula 1.0 is a compound of formula 1.44, Ar is phenyl substituted with halo.

In another embodiment of this invention the compound of formula 1.0 is a compound of formula 1.44 and Ar is phenyl substituted with one halo.

In another embodiment of this invention the compound of formula 1.0 is a compound of formula 1.44 and Ar is:

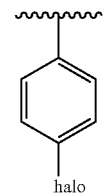

halo

In another embodiment of this invention the compound of formula 1.0 is a compound of formula 1.44 and Ar is phenyl substituted with at least one Cl.

In another embodiment of this invention the compound of formula 1.0 is a compound of formula 1.44 and Ar is phenyl substituted with a Cl.

In another embodiment of this invention the compound of formula 1.0 is a compound of formula 1.44 and Ar is:

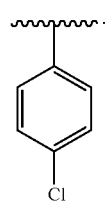

Cl

In another embodiment of this invention the compound of formula 1.0 is a compound of formula 1.44 and Ar is phenyl substituted with at least one $-CF_3$.

In another embodiment of this invention the compound of formula 1.0 is a compound of formula 1.44 and Ar is phenyl substituted with a $-CF_3$.

In another embodiment of this invention the compound of formula 1.0 is a compound of formula 1.44 and Ar is:

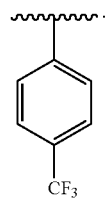 [SMILES: *c1ccc(C(F)(F)F)cc1]

$CF_3$

In another embodiment of this invention the compound of formula 1.0 is a compound of formula 1.44 and Ar is phenyl substituted with at least one $-CN$.

In another embodiment of this invention the compound of formula 1.0 is a compound of formula 1.44 and Ar is phenyl substituted with a $-CN$.

In another embodiment of this invention the compound of formula 1.0 is a compound of formula 1.44 and Ar is:

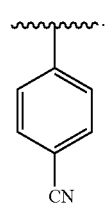

CN

In another embodiment of this invention the compound of formula 1.0 is a compound of formula 1.44, X is O, each $L^1$ is halo, and Ar is phenyl substituted with at least one halo.

In another embodiment of this invention the compound of formula 1.0 is a compound of formula 1.44, X is O, n is 2, each $L^1$ is the same or different halo, and Ar is phenyl substituted with one halo.

In another embodiment of this invention the compound of formula 1.0 is a compound of formula 1.44, X is O, n is 2, $L^1$ is F, and Ar is phenyl substituted with one Cl.

In another embodiment of this invention the compound of formula 1.0 is a compound of formula 1.44, X is O, n is 2, each $L^1$ is the same or different halo, and Ar is:

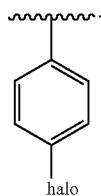

halo

In another embodiment of this invention the compound of formula 1.0 is a compound of formula 1.44, X is O, n is 2, each $L^1$ is the same or different halo, and Ar is:

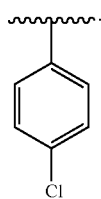 [SMILES: *c1ccc(Cl)cc1]

Cl

In another embodiment of this invention the compound of formula 1.0 is a compound of formula 1.44, X is O, each $L^1$ is halo, and Ar is phenyl substituted with at least one —$CF_3$.

In another embodiment of this invention the compound of formula 1.0 is a compound of formula 1.44, X is O, n is 2, each $L^1$ is the same or different halo, and Ar is phenyl substituted with one —$CF_3$.

In another embodiment of this invention the compound of formula 1.0 is a compound of formula 1.44, X is O, n is 2, $L^1$ is F, and Ar is phenyl substituted with one —$CF_3$.

In another embodiment of this invention the compound of formula 1.0 is a compound of formula 1.44, X is O, n is 2, each $L^1$ is the same or different halo, and Ar is:

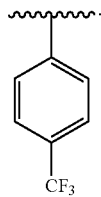

$CF_3$

In another embodiment of this invention the compound of formula 1.0 is a compound of formula 1.44, X is O, each $L^1$ is halo, and Ar is phenyl substituted with at least one —CN.

In another embodiment of this invention the compound of formula 1.0 is a compound of formula 1.44, X is O, n is 2, each $L^1$ is the same or different halo, and Ar is phenyl substituted with one —CN.

In another embodiment of this invention the compound of formula 1.0 is a compound of formula 1.44, X is O, n is 2, $L^1$ is F, and Ar is phenyl substituted with one —CN.

In another embodiment of this invention the compound of formula 1.0 is a compound of formula 1.44, X is O, n is 2, each $L^1$ is the same or different halo, and Ar is:

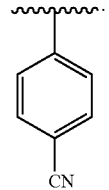

CN

In another embodiment of this invention the compound of formula 1.0 is a compound of formula 1.44, said compound having the formula (1.44A):

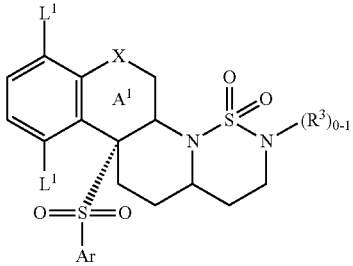

(1.44A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.44A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.44A, wherein X is O, each $L^1$ is the same or different halo, and Ar is:

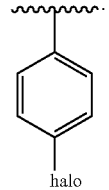

halo

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.44A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is:

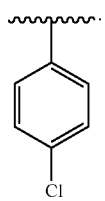 [SMILES: *c1ccc(Cl)cc1]

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is phenyl substituted with at least one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is phenyl substituted with one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is:

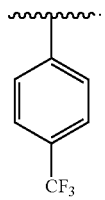

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is phenyl substituted with at least one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is phenyl substituted with one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.44A, wherein X is O, each $L^1$ is the same or different halo, and Ar is:

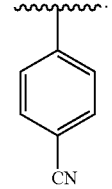

In the substituent "$(R^3)_{0-1}$", the "0-1" means that there is no $R^3$ substituent present (i.e., there would be a H instead of the $R^3$ substituent), or that there is one $R^3$ substituent present at the indicated position. Each $R^3$ is independently selected. In one example $R^3$ in the $=N-(R^3)_{0-1}$ moiety is a $C_1$-$C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45, and X is O.

In another embodiment of this invention the compound of formula 1.0 is a compound of formula 1.45 and $L^1$ is halo.

In another embodiment of this invention the compound of formula 1.0 is a compound of formula 1.45, said compound having the formula:

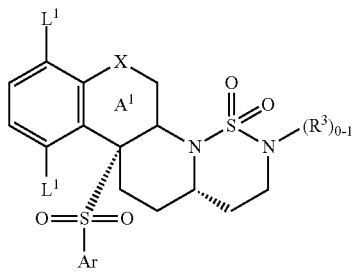

(1.45A)

wherein each $L^1$ is the same or different halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45A, wherein each $L^1$ is the same halo. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45, n is 2 and $L^1$ is F.

In another embodiment of this invention the compound of formula 1.0 is a compound of formula 1.45A, wherein each $L^1$ is F. All other substituents are as defined for formula 1.0. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45 and Ar is phenyl.

In another embodiment of this invention the compound of formula 1.0 is a compound of formula 1.45, Ar is phenyl substituted with halo.

In another embodiment of this invention the compound of formula 1.0 is a compound of formula 1.45 and Ar is phenyl substituted with one halo.

In another embodiment of this invention the compound of formula 1.0 is a compound of formula 1.45 and Ar is:

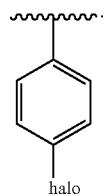

In another embodiment of this invention the compound of formula 1.0 is a compound of formula 1.45 and Ar is phenyl substituted with at least one Cl.

In another embodiment of this invention the compound of formula 1.0 is a compound of formula 1.45 and Ar is phenyl substituted with a Cl.

In another embodiment of this invention the compound of formula 1.0 is a compound of formula 1.45 and Ar is:

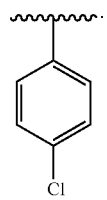 [SMILES: *c1ccc(Cl)cc1]

In another embodiment of this invention the compound of formula 1.0 is a compound of formula 1.45 and Ar is phenyl substituted with at least one —$CF_3$.

In another embodiment of this invention the compound of formula 1.0 is a compound of formula 1.45 and Ar is phenyl substituted with a —$CF_3$.

In another embodiment of this invention the compound of formula 1.0 is a compound of formula 1.45 and Ar is:

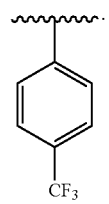

In another embodiment of this invention the compound of formula 1.0 is a compound of formula 1.45 and Ar is phenyl substituted with at least one —CN.

In another embodiment of this invention the compound of formula 1.0 is a compound of formula 1.45 and Ar is phenyl substituted with a —CN.

In another embodiment of this invention the compound of formula 1.0 is a compound of formula 1.45 and Ar is:

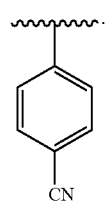

In another embodiment of this invention the compound of formula 1.0 is a compound of formula 1.45, X is O, each $L^1$ is halo, and Ar is phenyl substituted with at least one halo.

In another embodiment of this invention the compound of formula 1.0 is a compound of formula 1.45, X is O, n is 2, each $L^1$ is the same or different halo, and Ar is phenyl substituted with one halo.

In another embodiment of this invention the compound of formula 1.0 is a compound of formula 1.45, X is O, n is 2, $L^1$ is F, and Ar is phenyl substituted with one Cl.

In another embodiment of this invention the compound of formula 1.0 is a compound of formula 1.45, X is O, n is 2, each $L^1$ is the same or different halo, and Ar is:

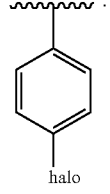

In another embodiment of this invention the compound of formula 1.0 is a compound of formula 1.45, X is O, n is 2, each $L^1$ is the same or different halo, and Ar is:

In another embodiment of this invention the compound of formula 1.0 is a compound of formula 1.45, X is O, each $L^1$ is halo, and Ar is phenyl substituted with at least one —$CF_3$.

In another embodiment of this invention the compound of formula 1.0 is a compound of formula 1.45, X is O, n is 2, each $L^1$ is the same or different halo, and Ar is phenyl substituted with one —$CF_3$.

In another embodiment of this invention the compound of formula 1.0 is a compound of formula 1.45, X is O, n is 2, $L^1$ is F, and Ar is phenyl substituted with one —$CF_3$.

In another embodiment of this invention the compound of formula 1.0 is a compound of formula 1.45, X is O, n is 2, each $L^1$ is the same or different halo, and Ar is:

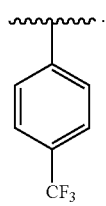

In another embodiment of this invention the compound of formula 1.0 is a compound of formula 1.45, X is O, each $L^1$ is halo, and Ar is phenyl substituted with at least one —CN.

In another embodiment of this invention the compound of formula 1.0 is a compound of formula 1.45, X is O, n is 2, each $L^1$ is the same or different halo, and Ar is phenyl substituted with one —CN.

In another embodiment of this invention the compound of formula 1.0 is a compound of formula 1.45, X is O, n is 2, $L^1$ is F, and Ar is phenyl substituted with one —CN.

In another embodiment of this invention the compound of formula 1.0 is a compound of formula 1.45, X is O, n is 2, each $L^1$ is the same or different halo, and Ar is:

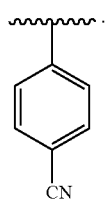

In another embodiment of this invention the compound of formula 1.0 is a compound of formula 1.45, said compound having the formula (1.45A):

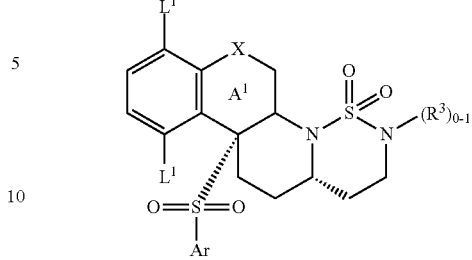

(1.45A)

wherein X is O, each $L^1$ is the same or different halo, and Ar is phenyl substituted with at least one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45A, wherein X is O, each $L^1$ is the same or different halo, and Ar is phenyl substituted with one halo. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45A, wherein X is O, each $L^1$ is the same or different halo, and Ar is:

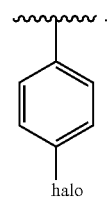

In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$(R^3)_{0-1}$ moiety is =N—H (i.e., this N is not substituted).

In another embodiment of this invention the compound of formula 1.0 is a compound of formula 1.45A, wherein X is O, each $L^1$ is the same or different halo, and Ar is phenyl substituted with one Cl. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the =N—$(R^3)_{0-1}$ moiety is a $C_1$-$C_6$ alkyl group. Preferably, the =N—$R^3)_{0-1}$ moiety is =N—H (i.e., this N is not substituted).

In another embodiment of this invention the compound of formula 1.0 is a compound of formula 1.45, wherein X is O, each $L^1$ is the same or different halo, and Ar is:

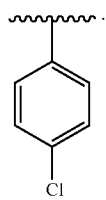

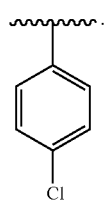

In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45A, wherein X is O, each $L^1$ is the same or different halo, and Ar is phenyl substituted with at least one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45A, wherein X is O, each $L^1$ is the same or different halo, and Ar is phenyl substituted with one $-CF_3$. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45, wherein X is O, each $L^1$ is the same or different halo, and Ar is:

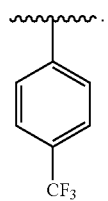

In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45A, wherein X is O, each $L^1$ is the same or different halo, and Ar is phenyl substituted with at least one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45A, wherein X is O, each $L^1$ is the same or different halo, and Ar is phenyl substituted with one $-CN$. In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R^3)_{0-1}$ moiety is a $C_1-C_6$ alkyl group. Preferably, the $=N-(R^3)_{0-1}$ moiety is $=N-H$ (i.e., this N is not substituted).

In another embodiment of this invention the compound of formula 1.0 is a compound of formula 1.45, wherein X is O, each $L^1$ is the same or different halo, and Ar is:

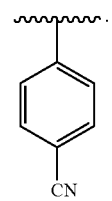

In the substituent "$(R^3)_{0-1}$", the "0-1" means that there is no $R^3$ substituent present (i.e., there would be a H instead of the $R^3$ substituent), or that there is one $R^3$ substituent present at the indicated position. In one example $R^3$ in the $=N-(R)_{0-1}$ moiety is a $C_1-C_6$ alkyl group. Preferably, the $=N-(R^3)_{0-1}$ moiety is $=N-H$ (i.e., this N is not substituted).

Another embodiment of this invention is directed to any one of the embodiments for formula 1.34 wherein a compound of formula 1.35C is used instead of the compound of formula 1.34.

Another embodiment of this invention is directed to any one of the embodiments for formula 1.34A wherein a compound of formula 1.35C is used in stead of the compound of formula 1.34, wherein in the compound of formula 1.35C each $L^1$ is para to each other (i.e., the compound has the formula:

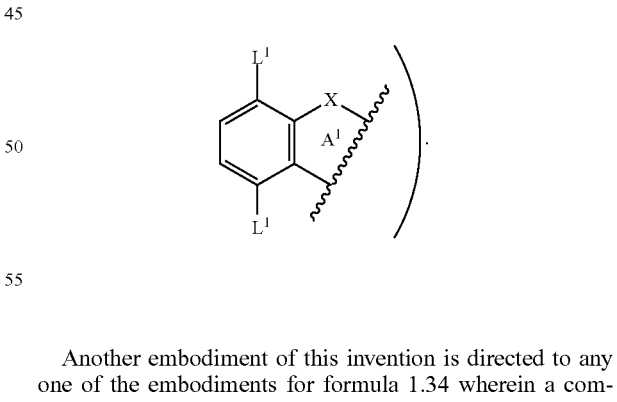

Another embodiment of this invention is directed to any one of the embodiments for formula 1.34 wherein a compound of formula 1.36C is used instead of the compound of formula 1.34.

Another embodiment of this invention is directed to any one of the embodiments for formula 1.34A wherein a compound of formula 1.36C is used in stead of the compound of formula 1.34, wherein in the compound of formula 1.36C each $L^1$ is para to each other (i.e., the compound has the formula:

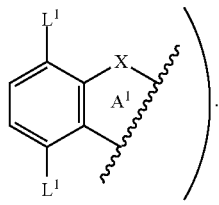

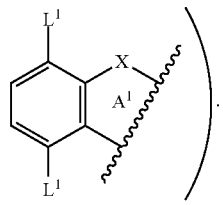

Another embodiment of this invention is directed to any one of the embodiments for formula 1.34 wherein a compound of formula 1.37C is used instead of the compound of formula 1.34.

Another embodiment of this invention is directed to any one of the embodiments for formula 1.34A wherein a compound of formula 1.37C is used in stead of the compound of formula 1.34, wherein in the compound of formula 1.37C each $L^1$ is para to each other (i.e., the compound has the formula:

Another embodiment of this invention is directed to any one of the embodiments for formula 1.34 wherein a compound of formula 1.35D is used instead of the compound of formula 1.34.

Another embodiment of this invention is directed to any one of the embodiments for formula 1.34A wherein a compound of formula 1.35D is used in stead of the compound of formula 1.34, wherein in the compound of formula 1.35D each $L^1$ is para to each other (i.e., the compound has the formula:

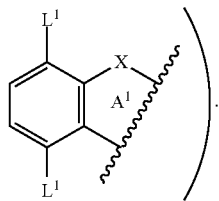

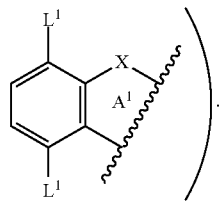

Another embodiment of this invention is directed to any one of the embodiments for formula 1.34 wherein a compound of formula 1.38C is used instead of the compound of formula 1.34.

Another embodiment of this invention is directed to any one of the embodiments for formula 1.34A wherein a compound of formula 1.38C is used in stead of the compound of formula 1.34, wherein in the compound of formula 1.38C each $L^1$ is para to each other (i.e., the compound has the formula:

Another embodiment of this invention is directed to any one of the embodiments for formula 1.34 wherein a compound of formula 1.36D is used instead of the compound of formula 1.34.

Another embodiment of this invention is directed to any one of the embodiments for formula 1.34A wherein a compound of formula 1.36D is used in stead of the compound of formula 1.34, wherein in the compound of formula 1.36D each $L^1$ is para to each other (i.e., the compound has the formula:

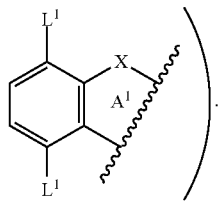

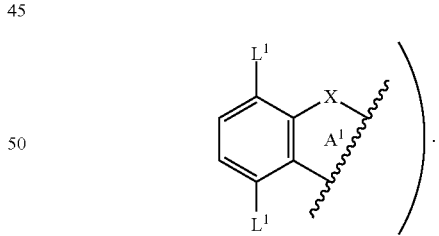

Another embodiment of this invention is directed to any one of the embodiments for formula 1.34 wherein a compound of formula 1.39C is used instead of the compound of formula 1.34.

Another embodiment of this invention is directed to any one of the embodiments for formula 1.34A wherein a compound of formula 1.39C is used in stead of the compound of formula 1.34, wherein in the compound of formula 1.39C each $L^1$ is para to each other (i.e., the compound has the formula:

Another embodiment of this invention is directed to any one of the embodiments for formula 1.34 wherein a compound of formula 1.37D is used instead of the compound of formula 1.34.

Another embodiment of this invention is directed to any one of the embodiments for formula 1.34A wherein a compound of formula 1.37D is used in stead of the compound of formula 1.34, wherein in the compound of formula 1.37D each $L^1$ is para to each other (i.e., the compound has the formula:

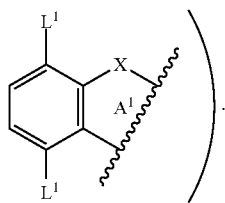

Another embodiment of this invention is directed to any one of the embodiments for formula 1.34 wherein a compound of formula 1.38D is used instead of the compound of formula 1.34.

Another embodiment of this invention is directed to any one of the embodiments for formula 1.34A wherein a compound of formula 1.38D is used in stead of the compound of formula 1.34, wherein in the compound of formula 1.38D each $L^1$ is para to each other (i.e., the compound has the formula:

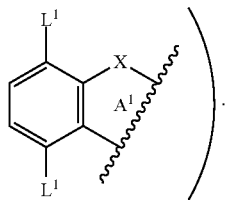

Another embodiment of this invention is directed to any one of the embodiments for formula 1.34 wherein a compound of formula 1.39D is used instead of the compound of formula 1.34.

Another embodiment of this invention is directed to any one of the embodiments for formula 1.34A wherein a compound of formula 1.39D is used in stead of the compound of formula 1.34, wherein in the compound of formula 1.39D each $L^1$ is para to each other (i.e., the compound has the formula:

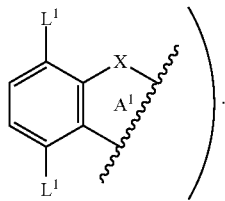

Another embodiment of this invention is directed to any one of the embodiments for formula 1.34 wherein a compound of formula 1.35E is used instead of the compound of formula 1.34.

Another embodiment of this invention is directed to any one of the embodiments for formula 1.34A wherein a compound of formula 1.35E is used in stead of the compound of formula 1.34, wherein in the compound of formula 1.35E each $L^1$ is para to each other (i.e., the compound has the formula:

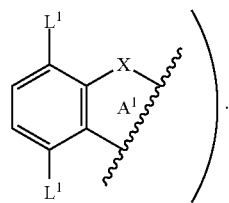

Another embodiment of this invention is directed to any one of the embodiments for formula 1.34 wherein a compound of formula 1.36E is used instead of the compound of formula 1.34.

Another embodiment of this invention is directed to any one of the embodiments for formula 1.34A wherein a compound of formula 1.36E is used in stead of the compound of formula 1.34, wherein in the compound of formula 1.36E each $L^1$ is para to each other (i.e., the compound has the formula:

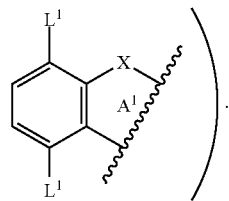

Another embodiment of this invention is directed to any one of the embodiments for formula 1.34 wherein a compound of formula 1.37E is used instead of the compound of formula 1.34.

Another embodiment of this invention is directed to any one of the embodiments for formula 1.34A wherein a compound of formula 1.37E is used in stead of the compound of formula 1.34, wherein in the compound of formula 1.37E each $L^1$ is para to each other (i.e., the compound has the formula:

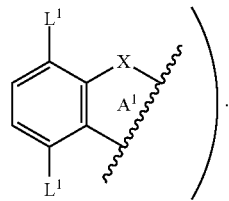

Another embodiment of this invention is directed to any one of the embodiments for formula 1.34 wherein a compound of formula 1.38E is used instead of the compound of formula 1.34.

Another embodiment of this invention is directed to any one of the embodiments for formula 1.34A wherein a compound of formula 1.38E is used in stead of the compound of formula 1.34, wherein in the compound of formula 1.38E each $L^1$ is para to each other (i.e., the compound has the formula:

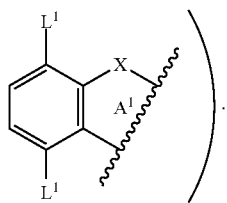

Another embodiment of this invention is directed to any one of the embodiments for formula 1.34 wherein a compound of formula 1.39E is used instead of the compound of formula 1.34.

Another embodiment of this invention is directed to any one of the embodiments for formula 1.34A wherein a compound of formula 1.39E is used in stead of the compound of formula 1.34, wherein in the compound of formula 1.39E each $L^1$ is para to each other (i.e., the compound has the formula:

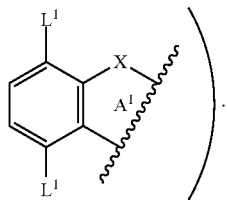

Another embodiment of this invention is directed to any one of the embodiments for formula 1.40 wherein a compound of formula 1.40C is used instead of the compound of formula 1.40.

Another embodiment of this invention is directed to any one of the embodiments for formula 1.40A wherein a compound of formula 1.40C is used in stead of the compound of formula 1.40, wherein in the compound of formula 1.40C each $L^1$ is para to each other (i.e., the compound has the formula:

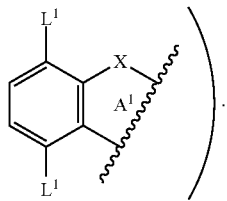

Another embodiment of this invention is directed to any one of the embodiments for formula 1.41 wherein a compound of formula 1.41C is used instead of the compound of formula 1.41.

Another embodiment of this invention is directed to any one of the embodiments for formula 1.41A wherein a compound of formula 1.41C is used in stead of the compound of formula 1.41A, wherein in the compound of formula 1.40C each $L^1$ is para to each other (i.e., the compound has the formula:

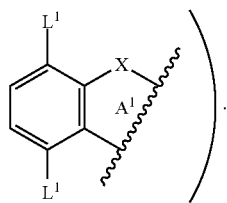

Another embodiment of this invention is directed to any one of the embodiments for formula 1.42 wherein a compound of formula 1.42C is used instead of the compound of formula 1.42.

Another embodiment of this invention is directed to any one of the embodiments for formula 1.42A wherein a compound of formula 1.42C is used in stead of the compound of formula 1.42A, wherein in the compound of formula 1.42C each $L^1$ is para to each other (i.e., the compound has the formula:

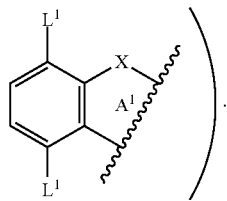

Another embodiment of this invention is directed to any one of the embodiments for formula 1.43 wherein a compound of formula 1.43C is used instead of the compound of formula 1.43.

Another embodiment of this invention is directed to any one of the embodiments for formula 1.43A wherein a compound of formula 1.43C is used in stead of the compound of formula 1.43A, wherein in the compound of formula 1.43C each $L^1$ is para to each other (i.e., the compound has the formula:

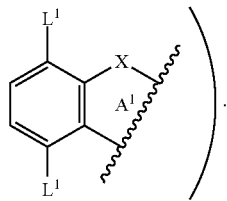

Another embodiment of this invention is directed to any one of the embodiments for formula 1.44 wherein a compound of formula 1.44C is used instead of the compound of formula 1.44.

Another embodiment of this invention is directed to any one of the embodiments for formula 1.44A wherein a compound of formula 1.44C is used in stead of the compound of formula 1.44A, wherein in the compound of formula 1.44C each $L^1$ is para to each other (i.e., the compound has the formula:

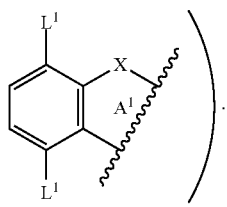

Another embodiment of this invention is directed to any one of the embodiments for formula 1.45 wherein a compound of formula 1.45C is used instead of the compound of formula 1.45.

Another embodiment of this invention is directed to any one of the embodiments for formula 1.45A wherein a compound of formula 1.45C is used in stead of the compound of formula 1.45A, wherein in the compound of formula 1.45C each $L^1$ is para to each other (i.e., the compound has the formula:

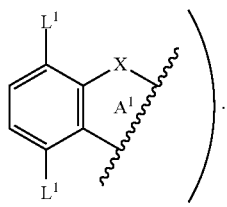

Another embodiment of this invention is directed to any one of the embodiments directed to the compounds of formulas: 1.18B, 1.19B, 1.19C, 1.20B, 1.22B, 1.24B, 1.24C, 1.25B, 1.25C, 1.28A, 1.29A, 1.32A, 1.33A, 1.35A, 1.36A, 1.38A, 1.39A, 1.41A, 1.42A, 1.44A, and 1.45A wherein the H bound to the carbon at the ring juncture of rings $A^1$ and Q is cis to the —$SO_2Ar$ moiety, that is the —$SO_2Ar$ moiety has the stereochemistry

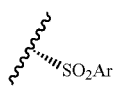

and the H at the $A^1$ and Q ring juncture has the stereochemistry

Another embodiment of this invention is directed to any one of the embodiments directed to the compounds of formulas: 1.18B, 1.19B, 1.19C, 1.20B, 1.22B, 1.24B, 1.24C, 1.25B, 1.25C, 1.28A, 1.29A, 1.32A, 1.33A, 1.35A, 1.36A, 1.38A, and 1.39A wherein the H bound to the carbon at the ring juncture of rings $A^1$ and Q is cis to the —$SO_2Ar$ moiety, that is the —$SO_2Ar$ moiety has the stereochemistry

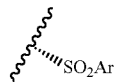

and the H at the $A^1$ and Q ring juncture has the stereochemistry

and the $R^3$ groups have the stereochemistry

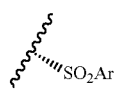

Another embodiment of this invention is directed to any one of the embodiments directed to the compounds of formulas: 1.35C, 1.36C, 1.38C, 1.39C, 1.35D, 1.36D, 1.38D, 1.39D, 1.35E, 1.36E, 1.38E, 1.39E, 1.41C, 1.42C, 1.44C, and 1.45C wherein the H bound to the carbon at the ring juncture of rings $A^1$ and Q is cis to the —$SO_2Ar$ moiety, that is the —$SO_2Ar$ moiety has the stereochemistry

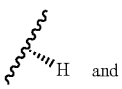

and the H at the $A^1$ and Q ring juncture has the stereochemistry

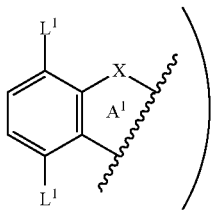 and each $L^1$ is para to each other (i.e., the compound has the formula:

Another embodiment of this invention is directed to any one of the embodiments directed to the compounds of formulas: 1.35C, 1.36C, 1.38C, 1.39C, 1.35D, 1.36D, 1.38D, 1.39D, 1.35E, 1.36E, 1.38E, 1.39E, 1.41C, and 1.42C wherein the H bound to the carbon at the ring juncture of rings $A^1$ and Q is cis to the —$SO_2Ar$ moiety, that is the —$SO_2Ar$ moiety has the stereochemistry

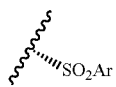

and the H at the A¹ and Q ring juncture has the stereochemistry

and the R³ groups have the stereochemistry

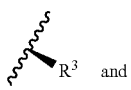

each L¹ is para to each other (i.e., the compound has the formula:

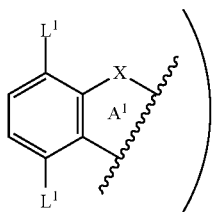

In another embodiment, the present invention is directed to compounds of Formula (1.0), or pharmaceutically acceptable salts, solvates or esters thereof, as described herein above.

Another embodiment of this invention is directed to compounds of formula (1.0).

Another embodiment of this invention is directed to pharmaceutically acceptable salts of the compounds of formula (1.0).

Another embodiment of this invention is directed to solvates of the compounds of formula (1.0).

Another embodiment of this invention is directed to pharmaceutically acceptable esters of the compounds of formula (1.0).

Another embodiment of this invention is directed to compounds of formula (1.0) wherein Ar is unsubstituted aryl (e.g., unsubstituted phenyl).

Another embodiment of this invention is directed to compounds of formula (1.0) wherein Ar is substituted aryl (e.g., substituted phenyl).

Another embodiment of this invention is directed to compounds of formula (1.0) wherein Ar is unsubstituted heteroaryl (e.g., unsubstituted pyridyl).

Another embodiment of this invention is directed to compounds of formula (1.0) wherein Ar is substituted heteroaryl (e.g., substituted pyridyl).

Another embodiment of this invention is directed to a compound of formula (1.0) wherein said compound is selected from the group consisting of: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, $1.9^{41}$, $1.9^{42}$, 1.10, $1.10^{41}$, $1.10^{42}$, 2.10, $2.10^{41}$, $2.10^{42}$, 3.10, 1.10A, 2.10A, 3.10A, $3.10^{41}$, $3.10^{42}$, 1.11, $1.11^{41}$, $1.11^{42}$, 2.11, $2.11^{41}$, $2.11^{42}$, 3.11, $3.11^{41}$, $3.11^{42}$, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a compound of formula (1.0) wherein said compound is selected from the group consisting of: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a compound of the formula (1.0) wherein said compound is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, $1.9^{42}$, 1.10A, $1.10^{42}$, 2.10A, $2.10^{42}$, 3.10A, $3.10^{42}$, 1.11A, $1.11^{42}$, 2.11A, $2.11^{42}$, 3.11A, $3.11^{42}$, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the L¹ groups are para to each other.

Another embodiment of this invention is directed to a compound of the formula (1.0) wherein said compound is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.10A, 2.10A, 3.10A, 1.11A, 2.11A, 3.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is unsubstituted aryl (e.g., unsubstituted phenyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, $1.9^{42}$, 1.10A, $1.10^{42}$, 2.10A, $2.10^{42}$, 3.10A, $3.10^{42}$, 1.11A, $1.11^{42}$, 2.11A, $2.11^{42}$, 3.11A, $3.11^{42}$, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is unsubstituted aryl (e.g., unsubstituted phenyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.10A, 2.10A, 3.10A, 1.11A, 2.11A, 3.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is substituted aryl (e.g., substituted phenyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, $1.9^{42}$, 1.10A, $1.10^{42}$, 2.10A, $2.10^{42}$, 3.10A, $3.10^{42}$, 1.11A, $1.11^{42}$, 2.11A, $2.11^{42}$, 3.11A, $3.11^{42}$, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is substituted aryl (e.g., substituted phenyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.10A, 2.10A, 3.10A, 1.11A, 2.11A, 3.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is unsubstituted heteroaryl (e.g., unsubstituted pyridyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, $1.9^{42}$, 1.10A, $1.10^{42}$, 2.10A, $2.10^{42}$, 3.10A, $3.10^{42}$, 1.11A, $1.11^{42}$, 2.11A, $2.11^{42}$, 3.11A, $3.11^{42}$, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is unsubstituted heteroaryl (e.g., unsubstituted pyridyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.10A, 2.10A, 3.10A, 1.11A, 2.11A, 3.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to compounds of formula (1.0) wherein Ar is substituted heteroaryl (e.g., substituted pyridyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.9$^{42}$, 1.10A, 1.10$^{42}$, 2.10A, 2.10$^{42}$, 3.10A, 3.10$^{42}$, 1.11A, 1.11$^{42}$, 2.11A, 2.11$^{42}$, 3.11A, 3.11$^{42}$, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the L$^1$ groups are para to each other.

Another embodiment of this invention is directed to compounds of formula (1.0) wherein Ar is substituted heteroaryl (e.g., substituted pyridyl), and said compound of formula (1.0) is selected from the group consisting of: 1.1A, 2.1A, 1.2A, 1.3A, 2.3A, 1.4A, 1.5A, 2.5A, 1.6A, 1.7A, 2.7A, 1.8A, 2.8A, 1.9A, 1.10A, 2.10A, 3.10A, 1.11A, 2.11A, 3.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the L$^1$ groups are para to each other.

Another embodiment of this invention is directed to a compound of formula (1.0) wherein said compound is selected from the group consisting of: 1.1, 1.1A, 2.1A, 1.2, 1.2A, 1.3, 1.3A, 2.3A, 1.4, 1.4A, 1.5, 1.5A, and 2.5A, and wherein all substituents are as defined for formula (1.0).

Another embodiment of this invention is directed to a pharmaceutically acceptable salt of a compound of formula (1.0) selected from the group consisting of: 1.1, 1.1A, 2.1A, 1.2, 1.2A, 1.3, 1.3A, 2.3A, 1.4, 1.4A, 1.5, 1.5A, and 2.5A, and wherein all substituents are as defined for formula (1.0).

Another embodiment of this invention is directed to a pharmaceutically acceptable ester of a compound of formula (1.0) selected from the group consisting of: 1.1, 1.1A, 2.1A, 1.2, 1.2A, 1.3, 1.3A, 2.3A, 1.4, 1.4A, 1.5, 1.5A, and 2.5A, and wherein all substituents are as defined for formula (1.0).

Another embodiment of this invention is directed to a solvate of a compound of formula (1.0) selected from the group consisting of: 1.1, 1.1A, 2.1A, 1.2, 1.2A, 1.3, 1.3A, 2.3A, 1.4, 1.4A, 1.5, 1.5A, and 2.5A, and wherein all substituents are as defined for formula (1.0).

Another embodiment of this invention is directed to a compound of the formula (1.0) wherein said compound is selected from the group consisting of: 1.1A, 1.2A, 1.3A, 1.4A, and 1.5A, and all substituents are as defined for formula (1.0).

Another embodiment of this invention is directed to compounds of formula (1.0) wherein Ar is unsubstituted aryl (e.g., unsubstituted phenyl), and said compound of formula (1.0) is selected from the group consisting of: 1.1A, 2.1A, 1.2A, 1.3A, 2.3A, 1.4A, 1.5A, and 2.5A, and all substituents are as defined for formula (1.0).

Another embodiment of this invention is directed to compounds of formula (1.0) wherein Ar is substituted aryl (e.g., substituted phenyl), and said compound of formula (1.0) is selected from the group consisting of: 1.1A, 2.1A, 1.2A, 1.3A, 2.3A, 1.4A, 1.5A, and 2.5A, and all substituents are as defined for formula (1.0).

Another embodiment of this invention is directed to compounds of formula (1.0) wherein Ar is unsubstituted heteroaryl (e.g., unsubstituted pyridyl), and said compound of formula (1.0) is selected from the group consisting of: 1.1A, 2.1A, 1.2A, 1.3A, 2.3A, 1.4A, 1.5A, and 2.5A, and all substituents are as defined for formula (1.0).

Another embodiment of this invention is directed to compounds of formula (1.0) wherein Ar is substituted heteroaryl (e.g., substituted pyridyl), and said compound of formula (1.0) is selected from the group consisting of: 1.1A, 2.1A, 1.2A, 1.3A, 2.3A, 1.4A, 1.5A, and 2.5A, and all substituents are as defined for formula (1.0).

Another embodiment of this invention is directed to compounds of Formula (1.0), or pharmaceutically acceptable salts, solvates and/or esters thereof, wherein:

R$^1$ is selected from the group consisting of H and (C$_1$-C$_6$) alkyl;

Ar is unsubstituted aryl or aryl substituted with one or more L$^1$ groups; and each L$^1$ is independently selected from the group consisting of halogen, (C$_1$-C$_6$)alkyl, —CN, and —CF$_3$.

Each R$^1$, for compounds of formula (1.0), is independently selected from the group consisting of H and alkyl. Examples of alkyl groups include but are not limited to: —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —C(CH$_3$)CH$_2$CH$_3$, —CH$_2$CH(CH$_3$)$_2$, etc.

Ar includes any chemically stable, optionally substituted aryl group. Non-limiting examples of such aryl groups include phenyl, naphthyl, biphenyl, anthacenyl, etc.

Each L$^1$ is independently selected from the group consisting of halogen (halo), alkyl, —CN, and —CF$_3$. When an L$^1$ is halo, each halo is independently F, Cl, Cr, or I. When an L$^1$ is alkyl, non-limiting example of said alkyl include: —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —C(CH$_3$)CH$_2$CH$_3$, —CH$_2$CH(CH$_3$)$_2$, etc.

Another embodiment of this invention is directed to Compound 4a.

Another embodiment of this invention is directed to Compound 4b.

Another embodiment of this invention is directed to Compound 5a.

Another embodiment of this invention is directed to Compound 5a1.

Another embodiment of this invention is directed to Compound 5b.

Another embodiment of this invention is directed to Compound 5b2.

Another embodiment of this invention is directed to Compound 5b3.

Another embodiment of this invention is directed to Compound 5b4.

Another embodiment of this invention is directed to Compound 5b5.

Another embodiment of this invention is directed to Compound 5c.

Another embodiment of this invention is directed to Compound 5d.

Another embodiment of this invention is directed to Compound 5e.

Another embodiment of this invention is directed to Compound 6a.

Another embodiment of this invention is directed to Compound 6b.

Another embodiment of this invention is directed to Compound 7a.

Another embodiment of this invention is directed to Compound 7b.

Another embodiment of this invention is directed to Compound 7d.

Another embodiment of this invention is directed to Compound 7e.

Another embodiment of this invention is directed to Compound 7f.

Another embodiment of this invention is directed to Compound 7g.

Another embodiment of this invention is directed to Compound 8a.

Another embodiment of this invention is directed to Compound 8a1.

Another embodiment of this invention is directed to Compound 8b1.

Another embodiment of this invention is directed to Compound 8b.

Another embodiment of this invention is directed to Compound 8c1.

Another embodiment of this invention is directed to Compound 8c.

Another embodiment of this invention is directed to Compound 8d.

Another embodiment of this invention is directed to Compound 8d1.

Another embodiment of this invention is directed to Compound 8d2.

Another embodiment of this invention is directed to Compound 8e.

Another embodiment of this invention is directed to Compound 8e1.

Another embodiment of this invention is directed to Compound 8f.

Another embodiment of this invention is directed to Compound 8g.

Another embodiment of this invention is directed to Compound 8h.

Another embodiment of this invention is directed to Compound 10b.

Another embodiment of this invention is directed to Compound 11b1.

Another embodiment of this invention is directed to Compound 11b2.

Another embodiment of this invention is directed to Compound 11b3.

Another embodiment of this invention is directed to Compound 12b1.

Another embodiment of this invention is directed to Compound 12b2.

Another embodiment of this invention is directed to Compound 12b3.

Another embodiment of this invention is directed to Compound 13b1.

Another embodiment of this invention is directed to Compound 13b2.

Another embodiment of this invention is directed to Compound 13b3.

Another embodiment of this invention is directed to Compound 14b1.

Another embodiment of this invention is directed to Compound 14b2.

Another embodiment of this invention is directed to Compound 14b3.

Another embodiment of this invention is directed to Compound 16b.

Another embodiment of this invention is directed to Compound 17b.

Another embodiment of this invention is directed to Compound 20b.

Another embodiment of this invention is directed to Compound 28.

Another embodiment of this invention is directed to Compound 29.

Another embodiment of this invention is directed to Compound 30.

Another embodiment of this invention is directed to Compound 31.

Another embodiment of this invention is directed to Compound 33.

Another embodiment of this invention is directed to Compound 36.

Another embodiment of this invention is directed to Compound 36a.

Another embodiment of this invention is directed to Compound 36b.

Another embodiment of this invention is directed to Compound 36c.

Another embodiment of this invention is directed to Compound 36d.

Another embodiment of this invention is directed to Compound 36e.

Another embodiment of this invention is directed to Compound 36f.

Another embodiment of this invention is directed to Compound 37.

Another embodiment of this invention is directed to Compound 38.

Another embodiment of this invention is directed to Compound 40.

Another embodiment of this invention is directed to Compound 41.

Another embodiment of this invention is directed to Compound 42.

Another embodiment of this invention is directed to Compound 42a.

Another embodiment of this invention is directed to Compound 42b.

Another embodiment of this invention is directed to Compound 43.

Another embodiment of this invention is directed to Compound 44.

Another embodiment of this invention is directed to Compound 45.

Another embodiment of this invention is directed to Compound 46.

Another embodiment of this invention is directed to Compound 47.

Another embodiment of this invention is directed to Compound 48.

Another embodiment of this invention is directed to Compound 49.

Another embodiment of this invention is directed to Compound 50.

Another embodiment of this invention is directed to Compound 51.

Another embodiment of this invention is directed to a solvate of Compound 4a.

Another embodiment of this invention is directed to a solvate of Compound 4b.

Another embodiment of this invention is directed to a solvate of Compound 5a.

Another embodiment of this invention is directed to a solvate of Compound 5a1.

Another embodiment of this invention is directed to a solvate of Compound 5b.

Another embodiment of this invention is directed to a solvate of Compound 5b2.

Another embodiment of this invention is directed to a solvate of Compound 5b3.

Another embodiment of this invention is directed to a solvate of Compound 5b4.

Another embodiment of this invention is directed to a solvate of Compound 5b5.

Another embodiment of this invention is directed to a solvate of Compound 5c.

Another embodiment of this invention is directed to a solvate of Compound 5d.

Another embodiment of this invention is directed to a solvate of Compound 5e.

Another embodiment of this invention is directed to a solvate of Compound 6a.

Another embodiment of this invention is directed to a solvate of Compound 6b.

Another embodiment of this invention is directed to a solvate of Compound 7a.

Another embodiment of this invention is directed to a solvate of Compound 7b.

Another embodiment of this invention is directed to a solvate of Compound 7d.

Another embodiment of this invention is directed to a solvate of Compound 7e.

Another embodiment of this invention is directed to a solvate of Compound 7f.

Another embodiment of this invention is directed to a solvate of Compound 7g.

Another embodiment of this invention is directed to a solvate of Compound 8a.

Another embodiment of this invention is directed to a solvate of Compound 8a1

Another embodiment of this invention is directed to a solvate of Compound 8b1

Another embodiment of this invention is directed to a solvate of Compound 8b.

Another embodiment of this invention is directed to a solvate of Compound 8c1.

Another embodiment of this invention is directed to a solvate of Compound 8c.

Another embodiment of this invention is directed to a solvate of Compound 8d.

Another embodiment of this invention is directed to a solvate of Compound 8d1.

Another embodiment of this invention is directed to a solvate of Compound 8d2.

Another embodiment of this invention is directed to a solvate of Compound 8e.

Another embodiment of this invention is directed to a solvate of Compound 8e1.

Another embodiment of this invention is directed to a solvate of Compound 8f.

Another embodiment of this invention is directed to a solvate of Compound 8g.

Another embodiment of this invention is directed to a solvate of Compound 8h.

Another embodiment of this invention is directed to a solvate of Compound 10b.

Another embodiment of this invention is directed to a solvate of Compound 11b1.

Another embodiment of this invention is directed to a solvate of Compound 11b2.

Another embodiment of this invention is directed to a solvate of Compound 11b3.

Another embodiment of this invention is directed to a solvate of Compound 12b1.

Another embodiment of this invention is directed to a solvate of Compound 12b2.

Another embodiment of this invention is directed to a solvate of Compound 12b3.

Another embodiment of this invention is directed to a solvate of Compound 5a.

Another embodiment of this invention is directed to a solvate of Compound 13b1.

Another embodiment of this invention is directed to a solvate of Compound 13b2.

Another embodiment of this invention is directed to a solvate of Compound 13b3.

Another embodiment of this invention is directed to a solvate of Compound 14b1.

Another embodiment of this invention is directed to a solvate of Compound 14b2.

Another embodiment of this invention is directed to a solvate of Compound 14b3.

Another embodiment of this invention is directed to a solvate of Compound 16b.

Another embodiment of this invention is directed to a solvate of Compound 17b.

Another embodiment of this invention is directed to a solvate of Compound 20b.

Another embodiment of this invention is directed to a solvate of Compound 28.

Another embodiment of this invention is directed to a solvate of Compound 29.

Another embodiment of this invention is directed to a solvate of Compound 30.

Another embodiment of this invention is directed to a solvate of Compound 31.

Another embodiment of this invention is directed to a solvate of Compound 33.

Another embodiment of this invention is directed to a solvate of Compound 36.

Another embodiment of this invention is directed to a solvate of Compound 36a.

Another embodiment of this invention is directed to a solvate of Compound 36b.

Another embodiment of this invention is directed to a solvate of Compound 36c.

Another embodiment of this invention is directed to a solvate of Compound 36d.

Another embodiment of this invention is directed to a solvate of Compound 36e.

Another embodiment of this invention is directed to a solvate of Compound 36f.

Another embodiment of this invention is directed to a solvate of Compound 37.

Another embodiment of this invention is directed to a solvate of Compound 38.
Another embodiment of this invention is directed to a solvate of Compound 40.
Another embodiment of this invention is directed to a solvate of Compound 41.
Another embodiment of this invention is directed to a solvate of Compound 42.
Another embodiment of this invention is directed to a solvate of Compound 42a.
Another embodiment of this invention is directed to a solvate of Compound 42b.
Another embodiment of this invention is directed to a solvate of Compound 43.
Another embodiment of this invention is directed to a solvate of Compound 44.
Another embodiment of this invention is directed to a solvate of Compound 45.
Another embodiment of this invention is directed to a solvate of Compound 46.
Another embodiment of this invention is directed to a solvate of Compound 47.
Another embodiment of this invention is directed to a solvate of Compound 48.
Another embodiment of this invention is directed to a solvate of Compound 49.
Another embodiment of this invention is directed to a solvate of Compound 50.
Another embodiment of this invention is directed to a solvate of Compound 51.

Another embodiment of this invention is directed to a compound of formula (1.0) selected from the group consisting of the compounds of formulas: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to a compound of formula (1.0) selected from the group consisting of the compounds of formulas: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a compound of formula (1.0) selected from the group consisting of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a compound of formula (1.0) selected from the group consisting of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutically acceptable salt of the compound of formula (1.0) selected from the group consisting of the pharmaceutically acceptable salts of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to a pharmaceutically acceptable salt of the compound of formula (1.0) selected from the group consisting of the pharmaceutically acceptable salts of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a pharmaceutically acceptable salt of the compound of formula (1.0) selected from the group consisting of the pharmaceutically acceptable salts of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{A2}$, $1.10^{A2}$, $2.10^{A2}$, $3.10^{A2}$, $1.11^{A2}$, $2.11^{A2}$, and $3.11^{A2}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a solvate of the compound of formula (1.0) selected from the group consisting of the solvates of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to a solvate of the compound of formula (1.0) selected from the group consisting of the solvates of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a solvate of the compound of formula (1.0) selected from the group consisting of the solvates of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{A2}$, $1.10^{A2}$, $2.10^{A2}$, $3.10^{A2}$, $1.11^{A2}$, $2.11^{A2}$, and $3.11^{A2}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutically acceptable ester of the compound of formula (1.0) selected from the group consisting of the pharmaceutically acceptable esters of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to a pharmaceutically acceptable ester of the compound of formula (1.0) selected from the group consisting of the pharmaceutically acceptable esters of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.42A, 1.42C, 1.43, 1.43A, 1.43C, 1.44, 1.44A, 1.44C, 1.45, 1.45A, and 1.45C, and wherein all substituents are as defined for formula (1.0).

Another embodiment of this invention is directed to a pharmaceutically acceptable ester of the compound of formula (1.0) selected from the group consisting of the pharmaceutically acceptable esters of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising at least one compound selected from the group consisting of: 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51, and a pharmaceutically acceptable carrier.

Another embodiment of this invention is directed to a pharmaceutical composition comprising a compound selected from the group consisting of: 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51, and a pharmaceutically acceptable carrier.

Another embodiment of this invention is directed to a pharmaceutical composition comprising at least one solvate selected from the group consisting of: the solvates of compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51, and a pharmaceutically acceptable carrier.

Another embodiment of this invention is directed to a pharmaceutical composition comprising a solvate selected from the group consisting of: the solvates of compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51, and a pharmaceutically acceptable carrier.

Another embodiment of this invention is directed to a pharmaceutical composition comprising at least one compound selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and a pharmaceutically acceptable carrier.

Another embodiment of this invention is directed to a pharmaceutical composition comprising at least one compound selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and a pharmaceutically acceptable carrier.

Another embodiment of this invention is directed to a pharmaceutical composition comprising a compound selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and a pharmaceutically acceptable carrier.

Another embodiment of this invention is directed to a pharmaceutical composition comprising a compound selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and a pharmaceutically acceptable carrier.

Another embodiment of this invention is directed to a pharmaceutical composition comprising at least one solvate of a compound wherein said solvate is selected from the group consisting of: the solvates of compounds 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.9^{41}$, $2.10^{41}$, $3.10^{41}$, $1.11^{41}$, $2.11^{41}$, and $3.11^{41}$, and a pharmaceutically acceptable carrier.

Another embodiment of this invention is directed to a pharmaceutical composition comprising at least one solvate of a compound wherein said solvate is selected from the group consisting of: the solvates of compounds 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and a pharmaceutically acceptable carrier.

Another embodiment of this invention is directed to a pharmaceutical composition comprising a solvate of a compound wherein said solvate is selected from the group consisting of: the solvates of compounds 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and a pharmaceutically acceptable carrier.

Another embodiment of this invention is directed to a pharmaceutical composition comprising a solvate of a compound wherein said solvate is selected from the group consisting of: the solvates of compounds 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, and 1.45C, and a pharmaceutically acceptable carrier.

Another embodiment of this invention is directed to a pharmaceutical composition comprising a pharmaceutically acceptable carrier and at least one compound selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier and at least one compound selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier and a compound selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier and a compound selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, and 3.17, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier, an effective amount of one or more (e.g., one) compounds of formula (1.0), and an effective amount of one or more (e.g., one) other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a pharmaceutical composition comprising a pharmaceutically acceptable carrier, an effective amount of one or more (e.g., one) compounds of formula (1.0), and an effective amount of one or more (e.g., one) BACE inhibitors.

Another embodiment of this invention is directed to a pharmaceutical composition comprising a pharmaceutically acceptable carrier, an effective amount of one or more (e.g., one) compounds of formula (1.0), and an effective amount of one or more (e.g., one) other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe), wherein the compound of formula (1.0) is selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$.

Another embodiment of this invention is directed to a pharmaceutical composition comprising a pharmaceutically acceptable carrier, an effective amount of one or more (e.g., one) compounds of formula (1.0), and an effective amount of one or more (e.g., one) other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe), wherein the compound of formula (1.0) is selected from the group consisting of: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

Another embodiment of this invention is directed to a pharmaceutical composition comprising a pharmaceutically acceptable carrier, an effective amount of one or more (e.g., one) compounds of formula (1.0), and an effective amount of one or more (e.g., one) BACE inhibitors, wherein the compound of formula (1.0) is selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$.

Another embodiment of this invention is directed to a pharmaceutical composition comprising a pharmaceutically acceptable carrier, an effective amount of a compound of formula (1.0), and an effective amount of a BACE inhibitor, wherein the compound of formula (1.0) is selected from the group consisting of: 1.1 to 1.18, 2.1, 2.3, 2.5, 2.7, 2.8, 2.10, 3.10, 2.11, 3.11, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26A, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$.

Another embodiment of this invention is directed to a pharmaceutical composition comprising a pharmaceutically acceptable carrier, an effective amount of one or more (e.g., one) compounds of formula (1.0), and an effective amount of one or more (e.g., one) BACE inhibitors, wherein the compound of formula (1.0) is selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier, an effective amount of a compound of formula (1.0), and an effective amount of a BACE inhibitor, wherein the compound of formula (1.0) is selected from the group consisting of: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to a pharmaceutical composition comprising a pharmaceutically acceptable carrier, an effective amount of one or more (e.g., one) compounds of formula (1.0), and an effective amount of one or more (e.g., one) BACE inhibitors, wherein the compound of formula (1.0) is selected from the group consisting of: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

Another embodiment of this invention is directed to a pharmaceutical composition comprising a pharmaceutically acceptable carrier, an effective amount of a compound of formula (1.0), and an effective amount of a BACE inhibitor, wherein the compound of formula (1.0) is selected from the group consisting of: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

Another embodiment of this invention is directed to combination therapies for (1) inhibiting gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (1.0) and the administration of one or more (e.g., one) other pharmaceutical active ingredients (e.g., drugs). The compounds of formula (1.0) and the other drugs can be administered separately (i.e., each is in its own separate dosage form), or the compounds of formula (1.0) can be combined with the other drugs in the same dosage form.

Thus, another embodiment of this invention is directed to any one of the (1) methods of inhibiting gamma-secretase, or (2) methods of treating one or more neurodegenerative diseases, or (3) methods of inhibiting the deposition of amyloid protein (e.g., amyloid beta protein) in, on or around neurological tissue (e.g., the brain), or (4) methods of treating Alzheimer's disease, that are described herein, wherein one or more compounds of formula (1.0) are used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to any one of the (1) methods of inhibiting gamma-secretase, or (2) methods of treating one or more neurodegenerative diseases, or (3) methods of inhibiting the deposition of amyloid protein (e.g., amyloid beta protein) in, on or around neurological tissue (e.g., the brain), or (4) methods of treating Alzheimer's disease, that are described herein, wherein a compound of formula (1.0) is used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Thus, another embodiment of this invention is directed to a method of treating Alzheimer's disease in a patient in need of such treatment, said method comprising administering to said patient an effective amount (i.e., a therapeutically effective amount) of one or more (e.g., 1, 2 or 3, or 1 or 2, or 1) compounds of formula (1.0), in combination with an effective amount (i.e., a therapeutically effective amount) of one or more cholinesterase inhibitors. Examples of cholinesterase inhibitors include, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept brand of donepezil hydrochloride).

Another embodiment of this invention is directed to a method of treating Alzheimer's disease in a patient in need of such treatment, said method comprising administering to said patient an effective amount (i.e., a therapeutically effective amount) of a compound of formula (1.0), in combination with an effective amount (i.e., a therapeutically effective amount) of one or more cholinesterase inhibitors. Examples of cholinesterase inhibitors include, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride).

Another embodiment of this invention is directed to a method of treating Alzheimer's disease in a patient in need of such treatment comprising administering an effective amount of one or more compounds of formula (1.0).

Another embodiment of this invention is directed to a method of inhibiting the deposition of amyloid protein in, on or around neurological tissue in a patient in need of such treatment comprising administering an effective amount of one or more compounds of formula (1.0).

Another embodiment of this invention is directed to a method of treating one or more neurodegenerative diseases in a patient in need of such treatment comprising administering an effective amount of one or more compounds of formula (1.0).

Another embodiment of this invention is directed to a method of inhibiting gamma secretase in a patient in need of such treatment comprising administering an effective amount of one or more compounds of formula (1.0).

Another embodiment of this invention is directed to a method of inhibiting gamma secretase in a patient in need of such treatment comprising administering an effective amount of one or more compounds of formula (1.0) and an effective amount of one or more BACE inhibitors.

Another embodiment of this invention is directed to a method of treating one or more neurodegenerative diseases in a patient in need of such treatment comprising administering an effective amount of one or more compounds of formula (1.0) and an effective amount of one or more BACE inhibitors.

Another embodiment of this invention is directed to a method of inhibiting the deposition of amyloid protein in, on or around neurological tissue in a patient in need of such treatment comprising administering an effective amount of one or more compounds of formula (1.0) and an effective amount of one or more BACE inhibitors.

Another embodiment of this invention is directed to a method of treating Alzheimer's disease in a patient in need of such treatment comprising administering an effective amount of one or more compounds of formula (1.0) and an effective amount of one or more BACE inhibitors.

Another embodiment of this invention is directed to a method of inhibiting gamma secretase in a patient in need of such treatment comprising administering an effective amount of a compound of formula (1.0) and an effective amount of a BACE inhibitor.

Another embodiment of this invention is directed to any one of the methods described herein wherein the compound of formula (1.0) is selected from the group consisting of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to any one of the methods described herein wherein the compound of formula (1.0) is selected from the group consisting of the pharmaceutically acceptable salts of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to any one of the methods described herein wherein the compound of formula (1.0) is selected from the group consisting of the pharmaceutically acceptable esters of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to any one of the methods described herein wherein the compound of formula (1.0) is selected from the group consisting of the solvates of the compounds of formulas: 1.1, 2.1, 1.1A, 2.1A, 1.2, 1.2A, 1.3, 2.3, 1.3A, 2.3A, 1.4, 1.4A, 1.5, 2.5, 1.5A, 2.5A, 1.6, 1.6A, 1.7, 2.7, 1.7A, 2.7A, 1.8, 2.8, 1.8A, 2.8A, 1.9, 1.9A, 1.10, 2.10, 3.10, 1.10A, 2.10A, 3.10A, 1.11, 2.11, 3.11, 1.11A, 2.11A, 3.11A, 1.12 to 1.18, 2.13, 3.13, 2.14, 3.14, 2.16, 3.16, 2.17, 3.17, 1.18A, 1.18B, 1.18C, 1.19, 1.19A, 1.19B, 1.19C, 1.20, 1.20A, 1.20B, 1.20C, 1.21, 1.21A, 1.21B, 1.21C, 1.22, 1.22A, 1.22B, 1.22C, 1.23, 1.23A, 1.23B, 1.23C, 1.24, 1.24A, 1.24B, 1.24C, 1.25, 1.25A, 1.25B, 1.25C, 1.26, 1.26a, 1.27, 1.27A, 1.28, 1.28A, 1.29, 1.29A, 1.30, 1.30A, 1.31, 1.31A, 1.32, 1.32A, 1.33, 1.33A, 1.34, 1.34A, 1.35, 1.35A, 1.35C, 1.35D, 1.35E, 1.36, 1.36A, 1.36C, 1.36D, 1.36E, 1.37, 1.37A, 1.37C, 1.37D, 1.37E, 1.38, 1.38A, 1.38C, 1.38D, 1.38E, 1.39, 1.39A, 1.39C, 1.39D, 1.39E, 1.40, 1.40A, 1.40C, 1.41, 1.41A, 1.41C, 1.42, 1.42A, 1.42C, 1.43, 1.43A, 1.43C, 1.44, 1.44A, 1.44C, 1.45, 1.45A, 1.45C, $1.9^{41}$, $1.10^{41}$, $2.10^{41}$, $3.10^{41}$, $1.11^{41}$, $2.11^{41}$, and $3.11^{41}$, and wherein all substituents are as defined for formula (1.0).

Another embodiment of this invention is directed to any one of the methods described herein wherein the compound of formula (1.0) is selected from the group consisting of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to any one of the methods described herein wherein the compound of formula (1.0) is selected from the group consisting of the pharmaceutically acceptable salts of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to any one of the methods described herein wherein the compound of formula (1.0) is selected from the group consisting of the pharmaceutically acceptable esters of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to any one of the methods described herein wherein the compound of formula (1.0) is selected from the group consisting of the solvates of the compounds of formulas: 1.1A, 1.2A, 1.3A, 1.4A, 1.5A, 1.6A, 1.7A, 1.8A, 1.9A, 1.10A, 1.11A, 1.12 to 1.17, 1.18B, 1.18C, 1.19B, 1.19C, 1.20B, 1.20C, 1.21B, 1.21C, 1.22B, 1.22C, 1.23B, 1.23C, 1.24B, 1.24C, 1.25B, 1.25C, 1.26A, 1.27A, 1.28A, 1.29A, 1.30A, 1.31A, 1.32A, 1.33A, 1.34A, 1.35A, 1.35C, 1.35D, 1.35E, 1.36A, 1.36C, 1.36D, 1.36E, 1.37A, 1.37C, 1.37D, 1.37E, 1.38A, 1.38C, 1.38D, 1.38E, 1.39A, 1.39C, 1.39D, 1.39E, 1.40A, 1.40C, 1.41A, 1.41C, 1.42A, 1.42C, 1.43A, 1.43C, 1.44A, 1.44C, 1.45A, 1.45C, 2.1A, 2.3A, 2.5A, 2.7A, 2.8A, 2.10A, 3.10A, 2.1A, 3.11A, 2.13, 3.13, 2.14, 3.14, 2.16, 3.16, 2.17, 3.17, $1.9^{42}$, $1.10^{42}$, $2.10^{42}$, $3.10^{42}$, $1.11^{42}$, $2.11^{42}$, and $3.11^{42}$, and all substituents are as defined for formula (1.0), and wherein in said compounds 1.12 to 1.17, 1.35C, 1.35D, 1.35E, 1.36C, 1.36D, 1.36E, 1.37C, 1.37D, 1.37E, 1.38C, 1.38D, 1.38E, 1.39C, 1.39D, 1.39E, 1.40C, 1.42C, 1.43C, 1.44C, 1.45C, 2.13, 3.13, 2.14, 3.14, 2.16, 3.16, 2.17, and 3.17 n is 2 and the $L^1$ groups are para to each other.

Another embodiment of this invention is directed to any one of the methods described herein wherein the compound of formula (1.0) is selected from the group consisting of the compounds of formulas: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

Another embodiment of this invention is directed to any one of the methods described herein wherein the compound of formula (1.0) is selected from the group consisting of the solvates of the compounds of formulas: Compounds 4a, 4b, 5a, 5a1, 5b, 5b2, 5b3, 5b4, 5b5, 5c, 5d, 5e, 6a, 6b, 7a, 7b, 7d, 7e, 7f, 7g, 8a, 8a1, 8b, 8b1, 8c, 8c1, 8d, 8d1, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36a, 36b, 36c, 36d, 36e, 36f, 37, 38, 40, 41, 42, 42a, 42b, 43, 44, 45, 46, 47, 48, 49, 50, and 51.

Examples of cholinesterase inhibitors are tacrine, donepezil, rivastigmine, galantamine, pyridostigmine and neostigmine, with tacrine, donepezil, rivastigmine and galantamine being preferred.

Examples of m₁ antagonists are known in the art. Examples of m₂ antagonists are also known in the art; in particular, m₂ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 2, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 2000 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

As used above, and throughout this disclosure, the following terms, unless otherwise indicated, shall be understood to have the following meanings:

"Patient" includes both human and animals.

"Mammal" means humans and other mammalian animals.

"At least one" means that there is at least one, for example, 1, 2 or 3, or 1 or 2, or 1.

"One or more" means at least one, for example, 1, 2 or 3, or 1 or 2, or 1.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl (unless expressly defined otherwise). Non-limiting examples of suitable alkyl groups include methyl, ethyl, n-propyl, isopropyl and t-butyl.

"Alkylene" means a divalent aliphatic hydrocarbon radical derived from an alkyl group, as defined above. Both "open" valences may be on the same carbon atom, or on different carbon atoms. Examples of alkylene groups include $C_1$-$C_6$ alkylene groups, for example, $C_1$ to $C_4$ alkylene groups, and in another example, $C_1$-$C_3$ alkylene groups, and in another example $C_1$ to $C_2$ alkylene groups. Non-limiting examples of alkylene groups include —CH₂—, —CH₂—CH₂—, —CH(CH₃)—, etc.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable saturated monocyclic cycloalkyls include cyclopropyl, cyclopentyl, cyclohexyl, cycloheptyl and the like, and non-limiting examples of non-aromatic, unsaturated monocyclic cycloalkyls include cyclopentenyl, cyclohexenyl, etc. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Fluorine, chlorine and bromine are preferred.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl (substituted or unsubstituted, heteroaryl (substituted or unsubstituted, alkylene-aryl, heteroarylalkenyl, heteroarylalkynyl, hydroxy, hydroxyalkyl, alkoxy, aryloxy, aryl substituted alkoxy, acyl, aroyl, halo, nitro, cyano, carboxy, alkoxycarbonyl, aryloxycarbonyl, arylalkoxycarbonyl, alkylsulfonyl, arylsulfonyl, heteroarylsulfonyl, alkylthio, arylthio, heteroarylthio, arylalkylthio, heteroarylalkylthio, cycloalkyl, heterocycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and -alkylene-aryl (unless expressly defined otherwise). The term "ring system substituent" may also mean a single moiety in which two available hydrogens on two adjacent carbon atoms are simultaneously replaced (e.g., one H on each carbon) on a ring system. Examples of such moiety are methylenedioxy, ethylenedioxy, —C(CH$_3$)$_2$— and the like which form moieties such as, for example:

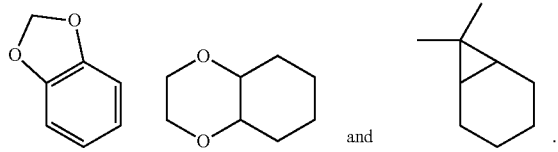

"Heterocycloalkyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist in protected form, for example, as an —N(Boc), —N(CBz), —N(Tos) group and the like; such protected forms are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of non-aromatic, unsaturated monocyclic heterocycloalkyl rings include thiazolinyl, 2,3-dihydrofuranyl, 2,3-dihydrothiophenyl, etc.

It should be noted that in the hetero-atom containing ring systems of this invention, there are no hydroxyl groups on carbon atoms adjacent to a N, O or S, as well as there are no N or S groups on carbon atoms adjacent to another heteroatom. Thus, for example, in the ring:

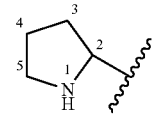

there is no —OH attached directly to carbons marked 2 and 5.

It should also be noted that tautomeric forms such as, for example, the moieties:

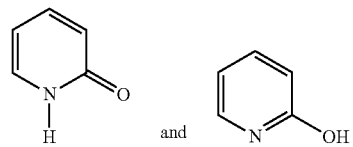 [SMILES: O=c1cccc[nH]1 ; Oc1ccccn1]

are considered equivalent in this invention.

"Hydroxyalkyl" means an alkyl group substituted with a hydroxyl (—OH) group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an —O-alky; group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an —O-aryl group in which the aryl group is as previously described. Non-limiting examples of suitable aryloxy groups include phenoxy and naphthoxy. The bond to the parent moiety is through the ether oxygen.

"Alkylthio" means an —S-alkyl group in which the alkyl group is as previously described. Non-limiting examples of suitable alkylthio groups include methylthio and ethylthio. The bond to the parent moiety is through the sulfur.

"Arylthio" means an —S-aryl group in which the aryl group is as previously described. Non-limiting examples of suitable arylthio groups include phenylthio and naphthylthio. The bond to the parent moiety is through the sulfur.

"Arylalkylthio" means an —S-alkylene-aryl group in which the alkylene and aryl groups are as previously described. A non-limiting example of a suitable arylalkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an —C(O)—O-alkylene-aryl group. A non-limiting example of a suitable arylalkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is a lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When a group is substituted with "one or more" substituents, the indicated group may be substituted with one substituent, two substituents, etc., provided that the resulting substituted group forms a stable structure, as described above.

The term "optionally substituted" means optional substitution with the specified groups, radicals or moieties. For example, an aryl optionally substituted with an indicated group of substituents includes unsubstituted aryl as well as aryl substituted with any of the indicated substituents.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York, herein incorporated by reference in its entirety.

When any variable (e.g., aryl, heterocycloalkyl, $R^2$, etc.) occurs more than one time in any constituent or in Formula (I), its definition on each occurrence is independent of its definition at every other occurrence (unless otherwise expressly indicated).

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

"Effective amount" or "therapeutically effective amount" is meant to describe an amount of compound or a composition of the present invention effective in preventing the formation and/or deposition of amyloid protein, and thus producing the desired therapeutic, ameliorative, inhibitory or preventative effect.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The compounds according to the invention have pharmacological properties; in particular, the compounds of Formula (I) can inhibit gamma-secretase, and are therefore useful in the treatment or prevention of neurodegenerative diseases, e.g., Alzheimer's Disease.

Representative compounds of the invention include but are not limited to the compounds and Examples described herein.

Pharmaceutical compositions can comprise one or more of the compounds of Formula (I). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given.

The following solvents, reagents, and conditions may be referred to by their abbreviations in parenthesis:

Acetyl (Ac), i.e., CH$_3$C(O)—
Butyl (Bu)
Cyclopropyl (Pr-c)
Dichloroethane (DCE)
Dichloromethane (DCM)
Diethyl ether (Et$_2$O)
Diisobutylaluminum hydride (DIBAL-H)
Dimethyl formamide (DMF)
Ethanol (EtOH)
Ethyl (Et)
Ethyl acetate (EtOAc)
High resolution mass spectrometry (HRMS)
Lithium diisopropyl amide (LDA)
Liquid chromatography/mass spectrometry (LCMS)
m-Chloroperoxybenzoic acid (mCPBA)
Mesyl (Ms), i.e., —S(O)$_2$CH$_3$
Methanol (MeOH)
Methyl (Me)
Nuclear magnetic resonance spectroscopy (NMR)
Preparative thin-layer chromatography (PTLC)
Pyridine (Pyr)
Room temperature (RT)
Tert-butyldimethylsilyl (TBS)
Tetrabutyl ammonium fluoride (TBAF)
Tetrahydrofuran (THF)
Trifluoroacetic acid (TFA)
Trimethylsilyl (TMS)
Trimethylsilyl chloride (TMSCl)
Triethylamine (NEt$_3$ or Et$_3$N)

Compounds of Formula (1.0) can be prepared by various methods well known to those skilled in the art, and by the methods described below. The following methods are typical.

Scheme 1

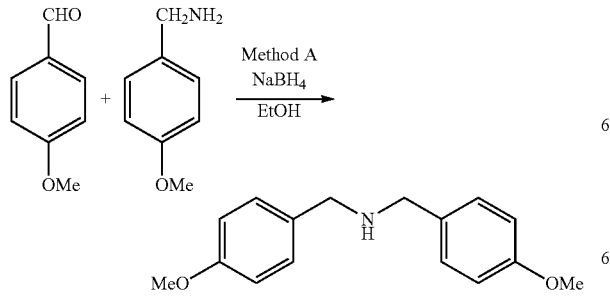

Scheme 2

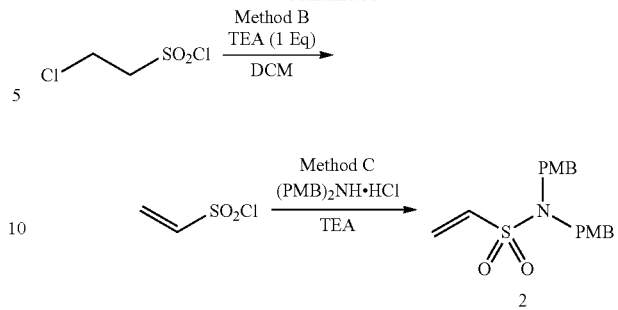

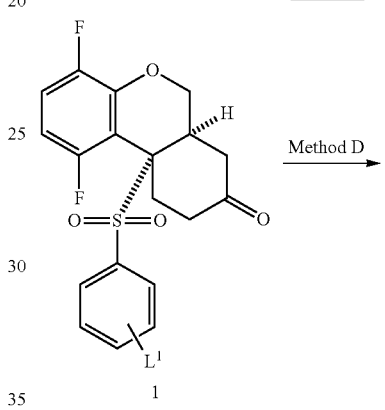

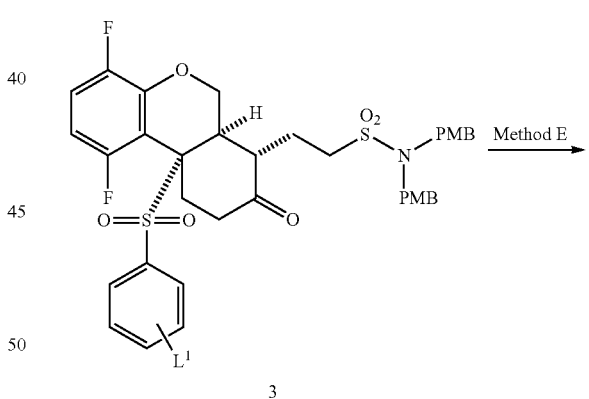

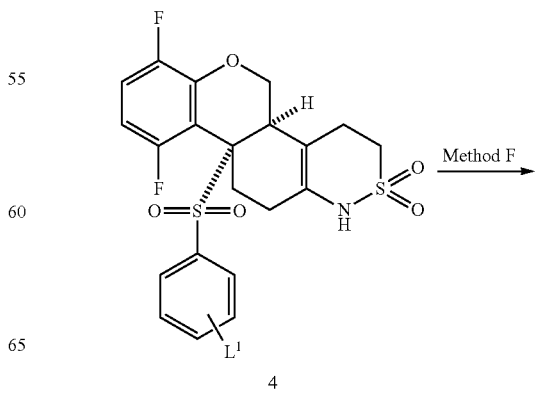

351
-continued
352
Scheme 2A
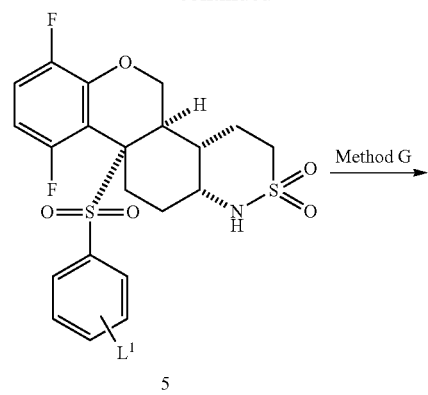
5
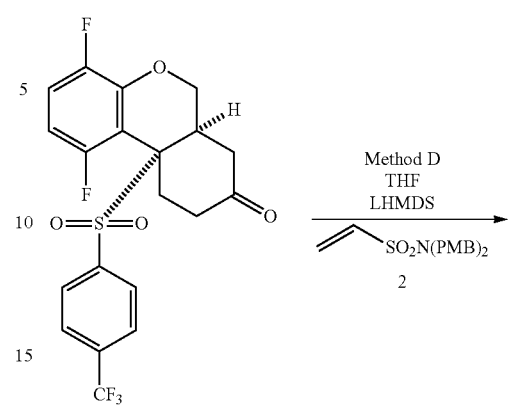
1a
Method G →
Method D
THF
LHMDS
─────→
$CH_2=CH-SO_2N(PMB)_2$
2
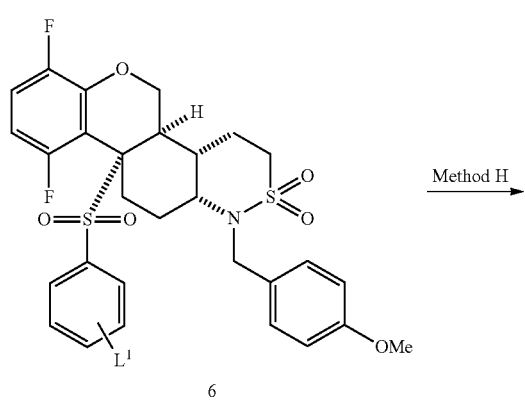
6
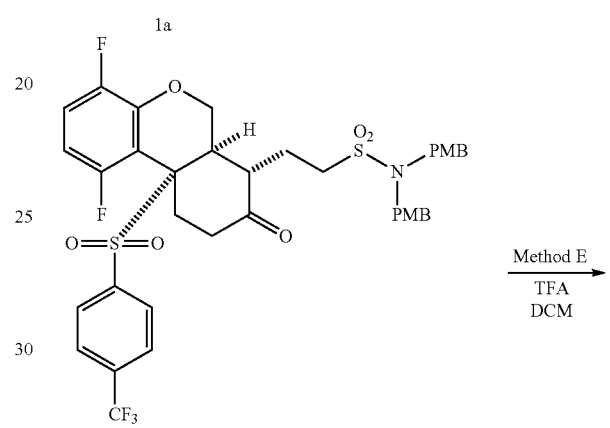
3a
Method H →
Method E
TFA
DCM
─────→
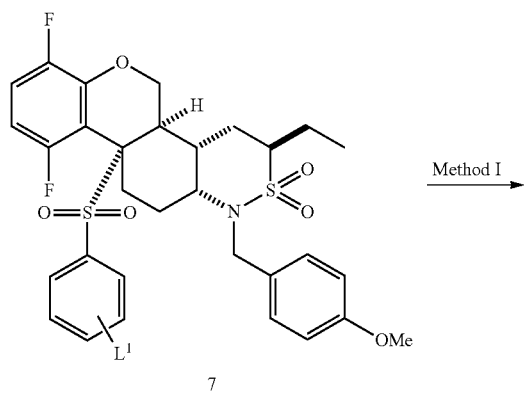
7
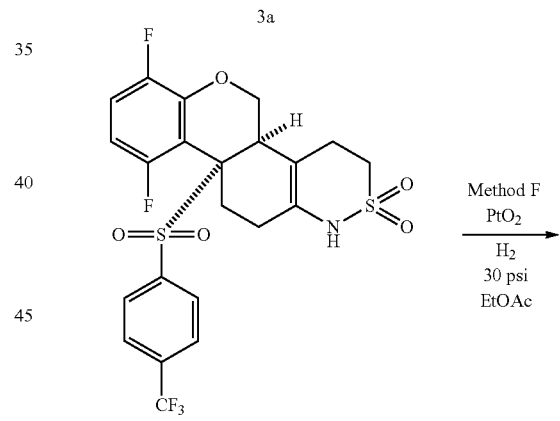
4a
Method I →
Method F
$PtO_2$
$H_2$
30 psi
EtOAc
─────→
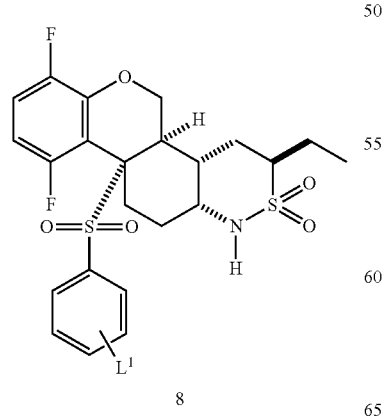
8
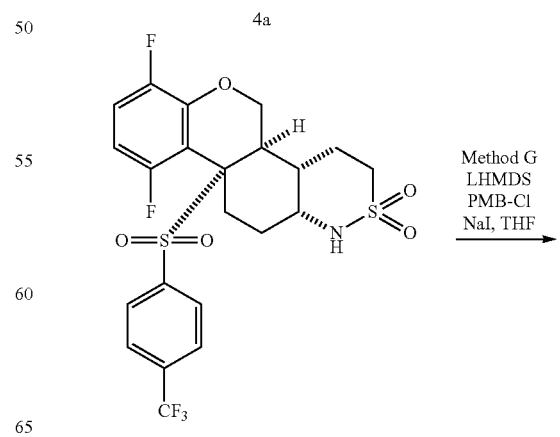
5a
Method G
LHMDS
PMB-Cl
NaI, THF
─────→

353
-continued
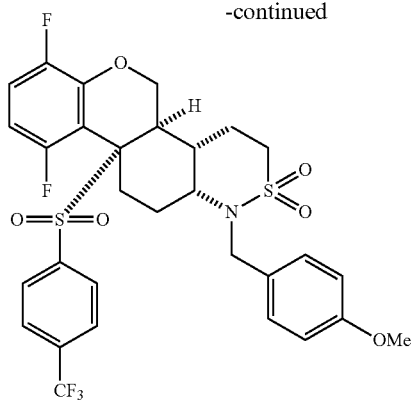
6a
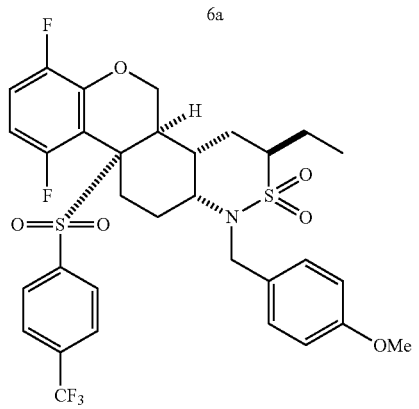
7a
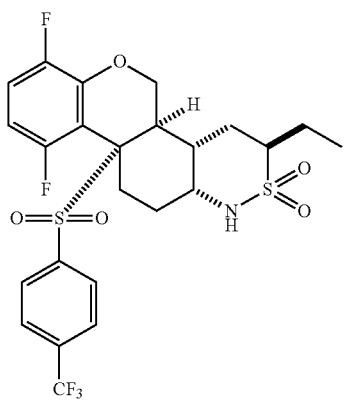
8a
Scheme 2B
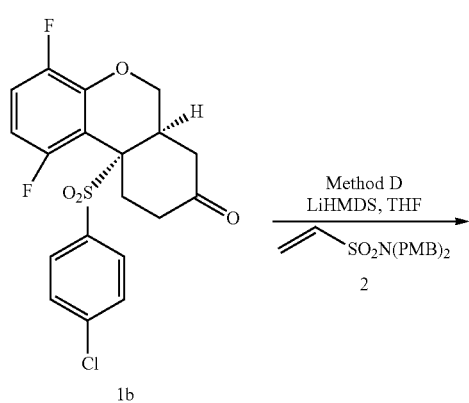
1b
354
-continued
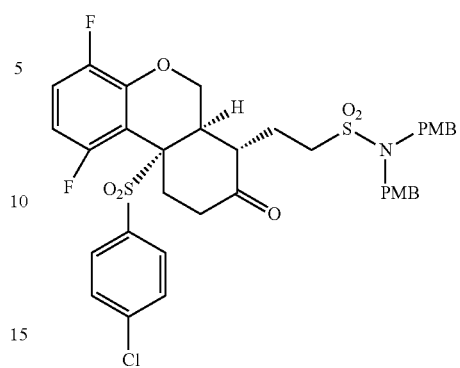
3b
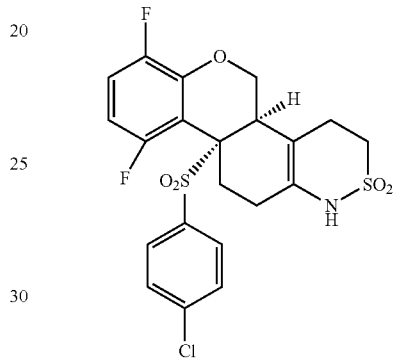
4b
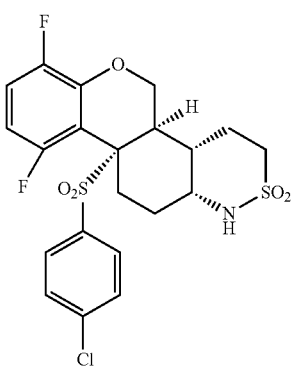
5b
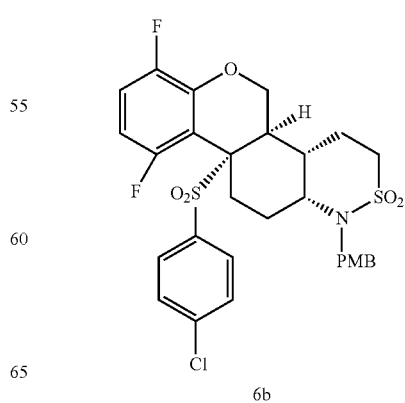
6b

355
-continued
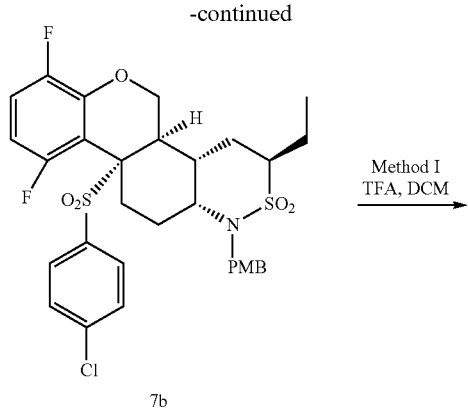
7b
Method I
TFA, DCM
→
356
-continued
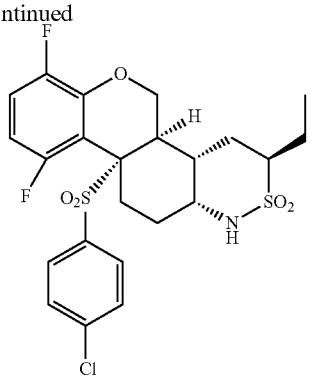
8b
Scheme 3
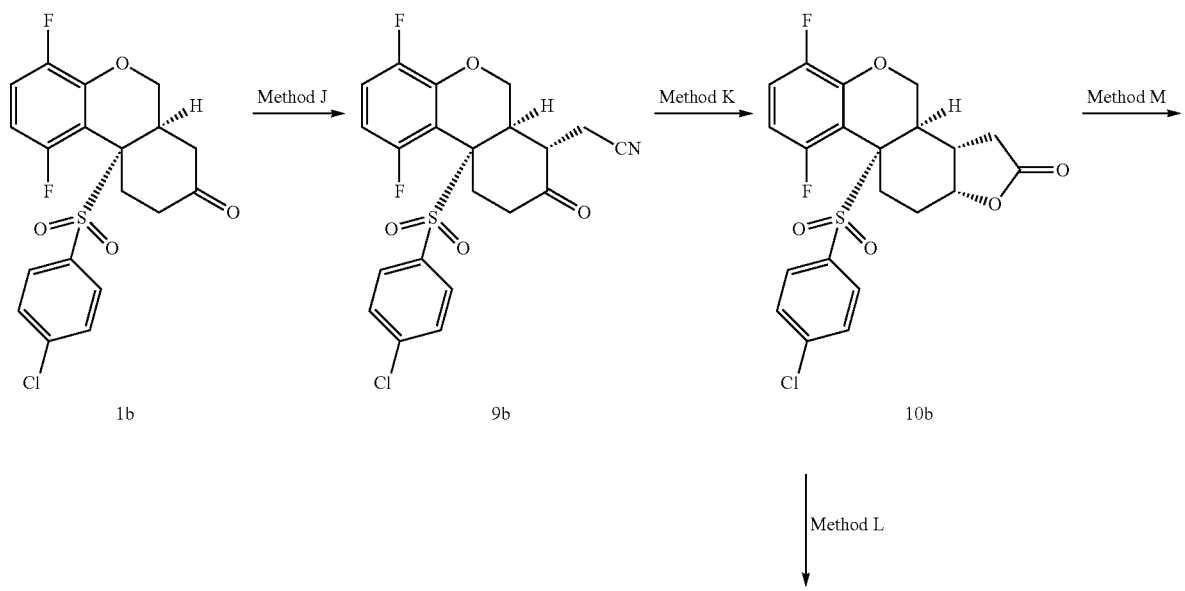
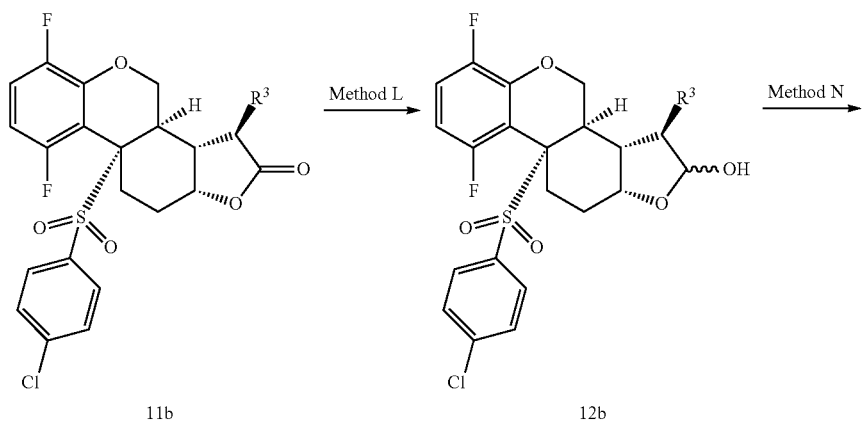

-continued
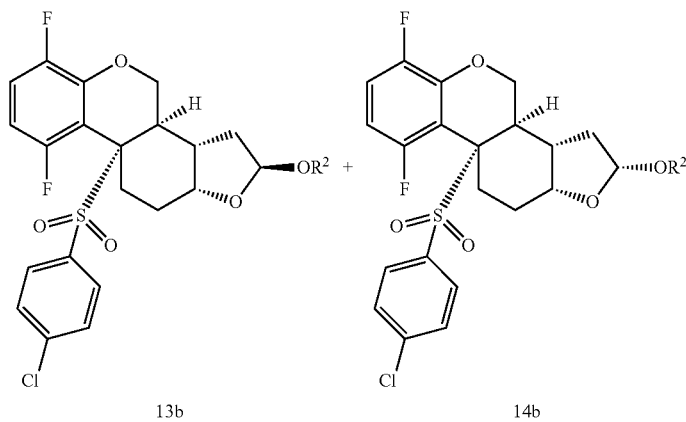
Scheme 3A
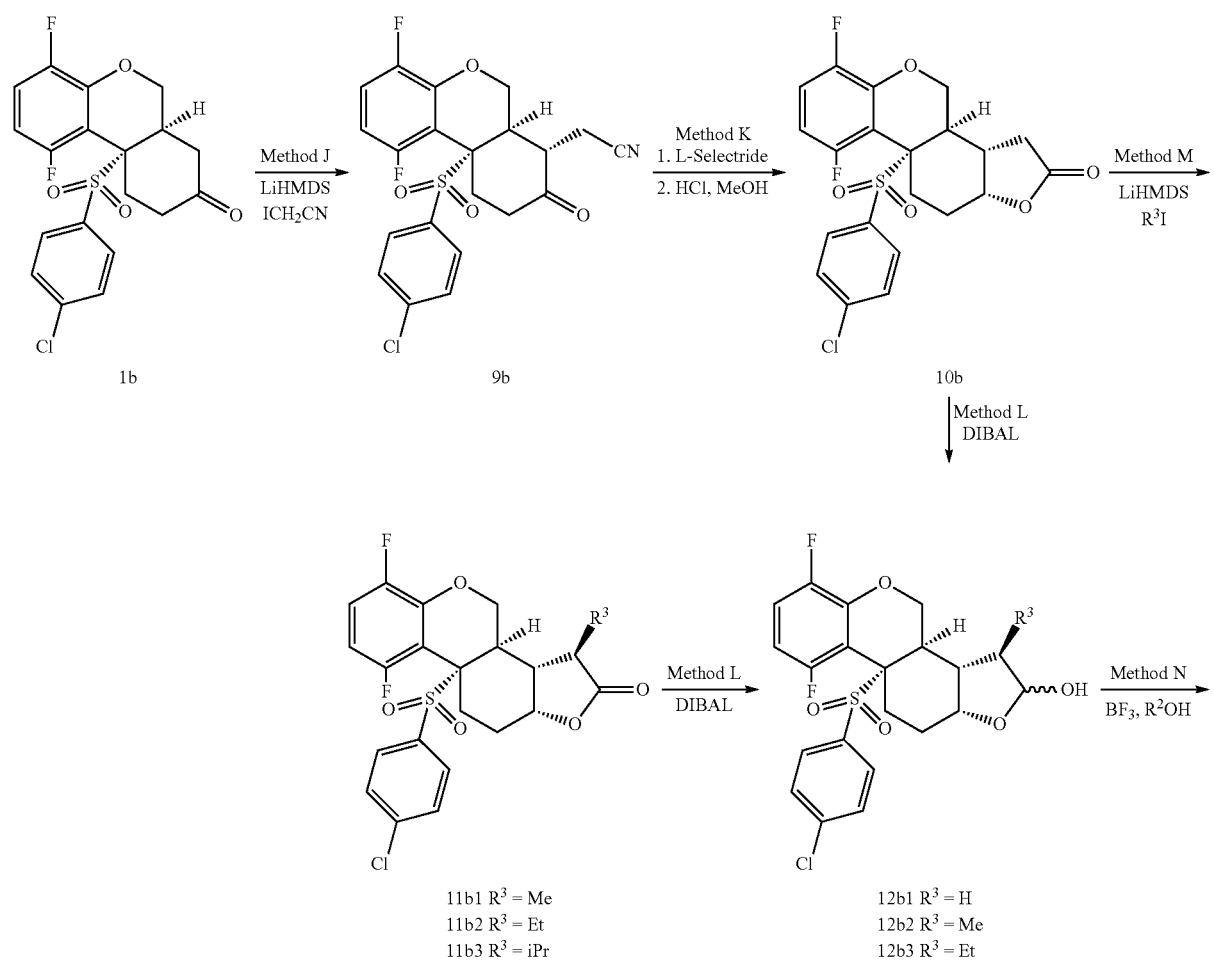
11b1 R³ = Me
11b2 R³ = Et
11b3 R³ = iPr
12b1 R³ = H
12b2 R³ = Me
12b3 R³ = Et

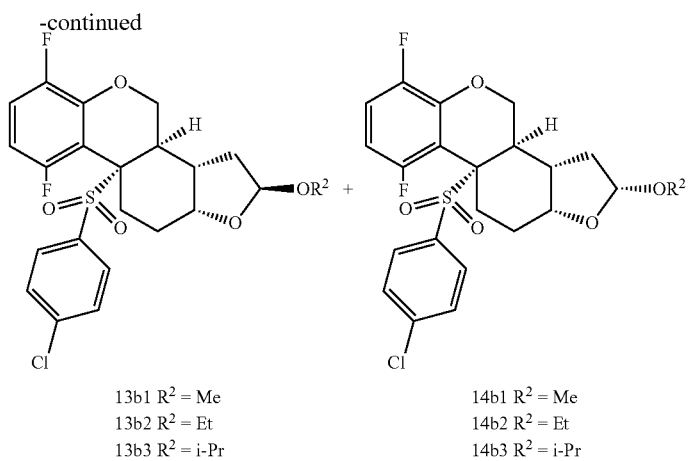
13b1 R² = Me
13b2 R² = Et
13b3 R² = i-Pr
14b1 R² = Me
14b2 R² = Et
14b3 R² = i-Pr
Scheme 4
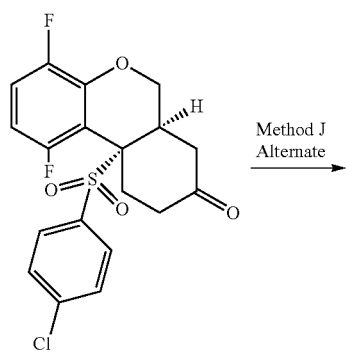
1b
Method J
Alternate
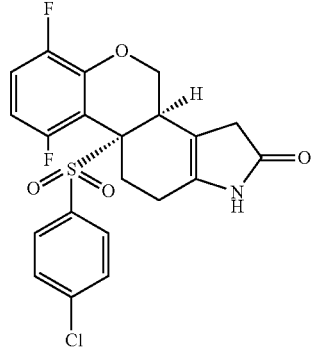
17b
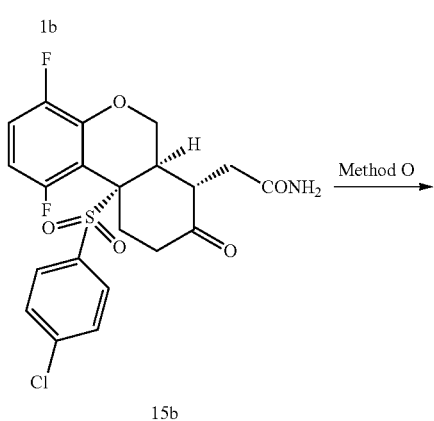
15b
Method O
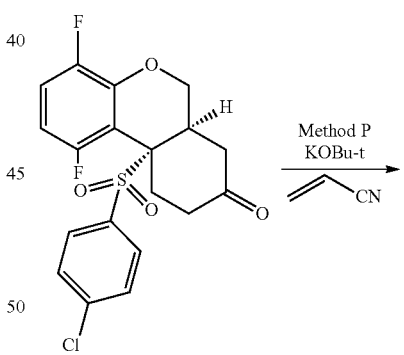
Method P
KOBu-t
Scheme 5
16b
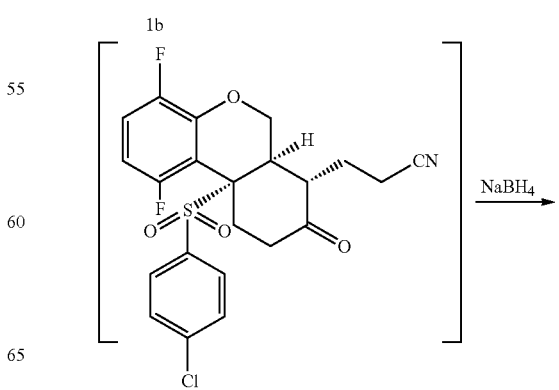
1b
NaBH₄

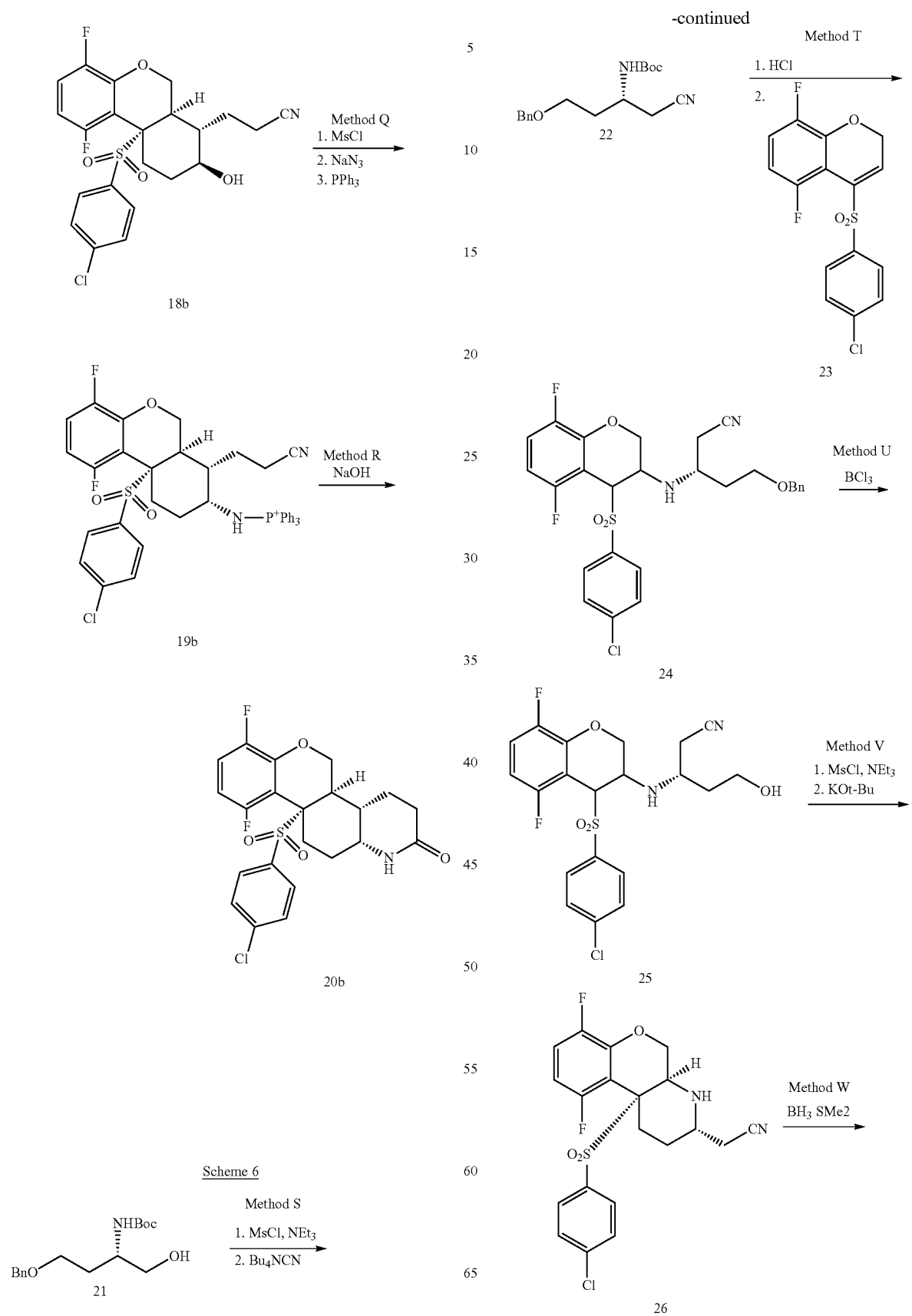

363
-continued
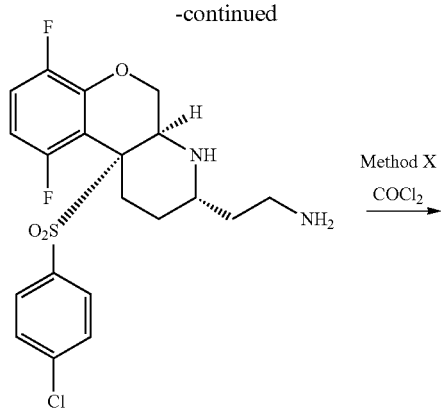
27
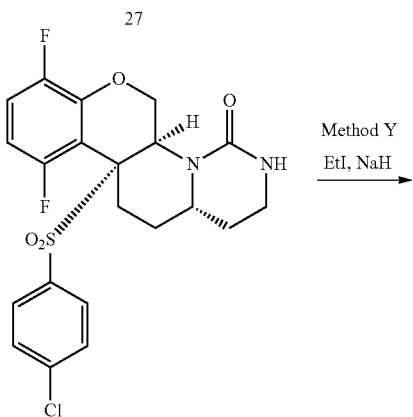
28
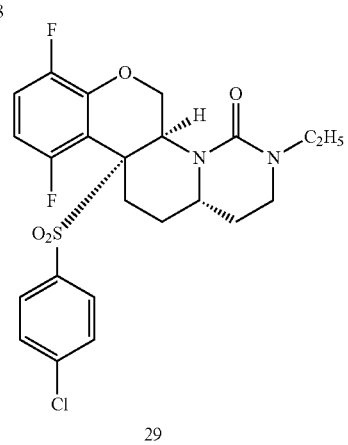
29
Scheme 7
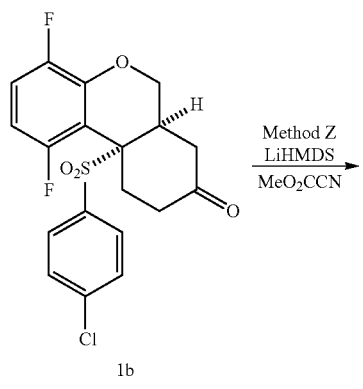
1b
→ Method X
COCl₂
→ Method Y
EtI, NaH
Method Z
LiHMDS
MeO₂CCN
364
-continued
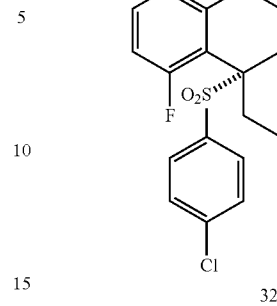
32
→ Method AA
MeNHNH₂
NH₄OAc
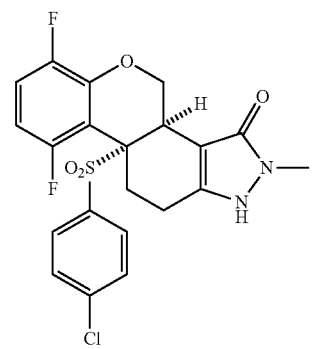
33
Scheme 8
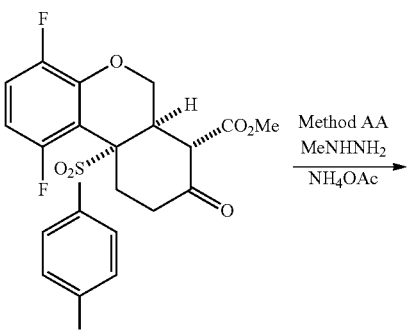
1a
→ Method D
LiHMDS, THF
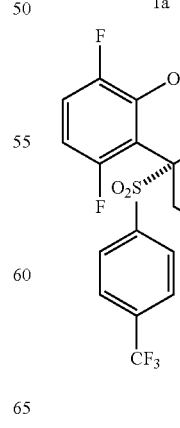
3a
→ Method AB
1. NaBH₄, THF
2. MsCl, Et₃N, CH₂Cl₂

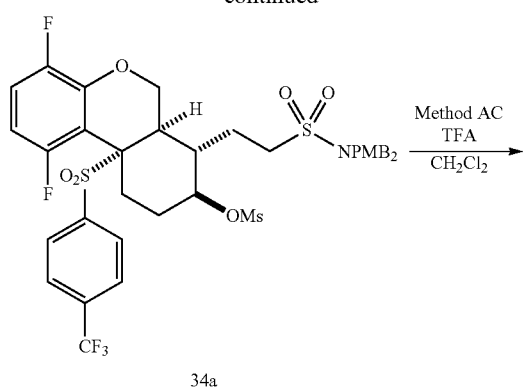
34a
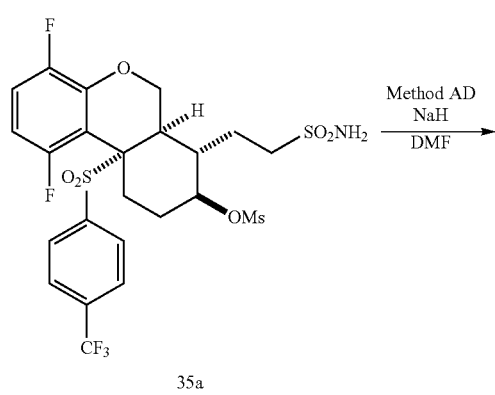
35a
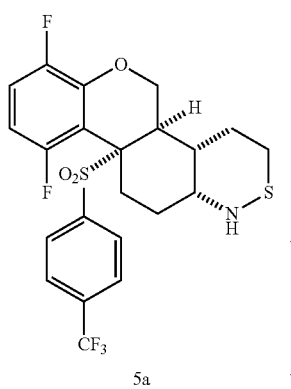
5a
Scheme 9
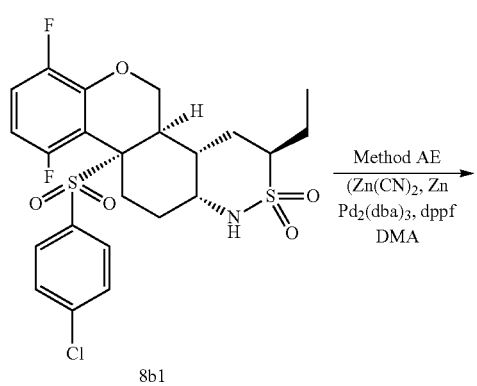
8b1
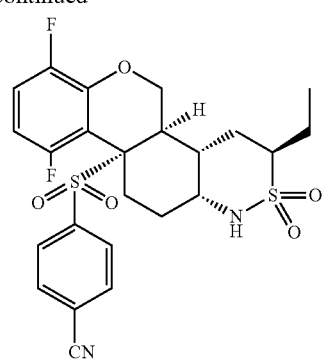
8c1
Scheme 10
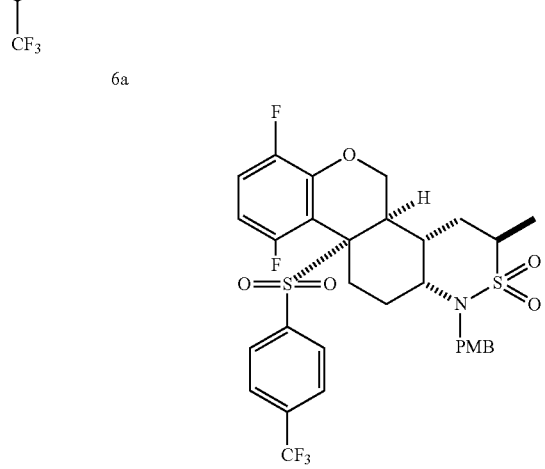
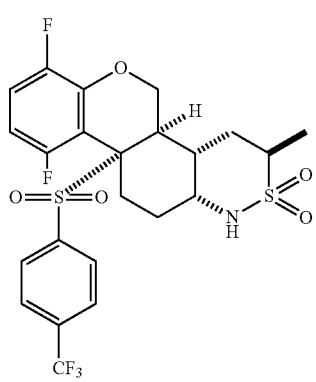
8d Scheme 11
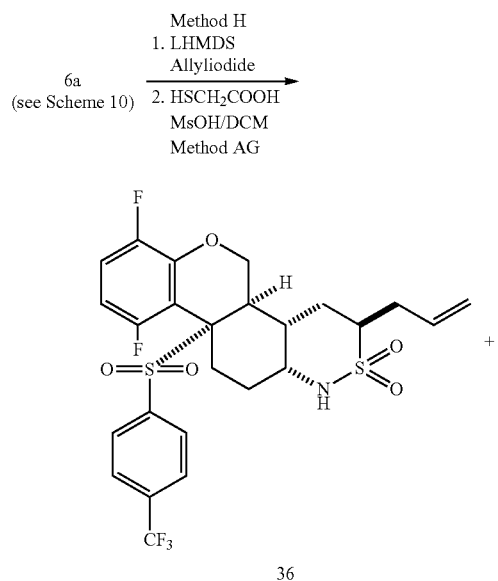
36
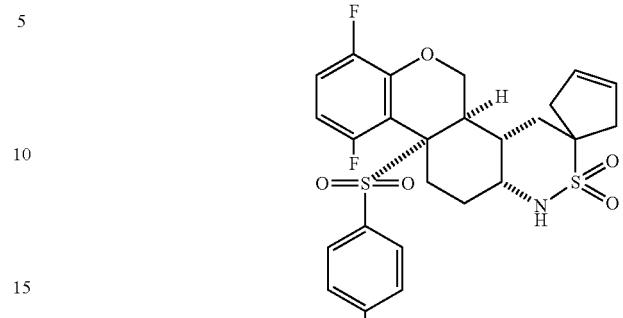
38
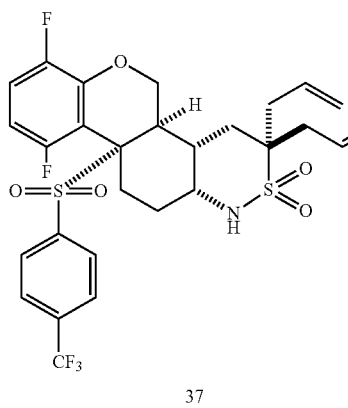
37
Scheme 13
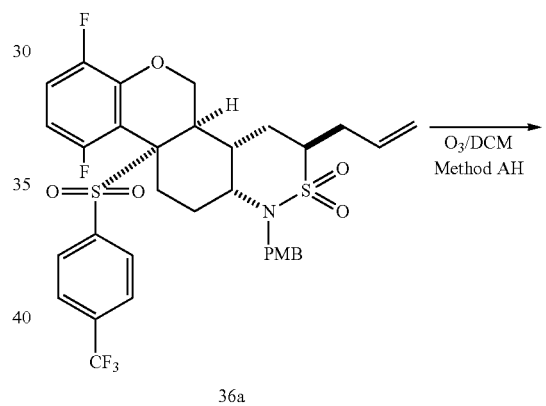
36a
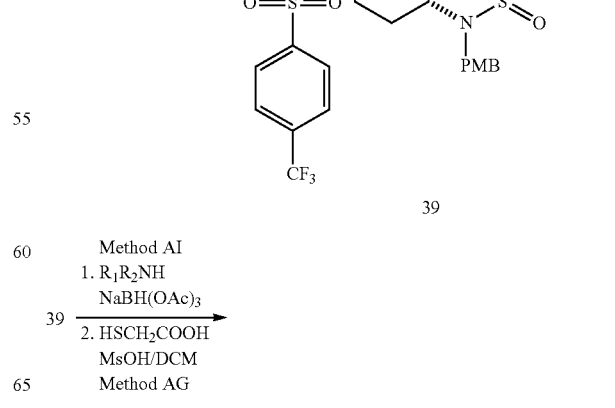
39
Scheme 12
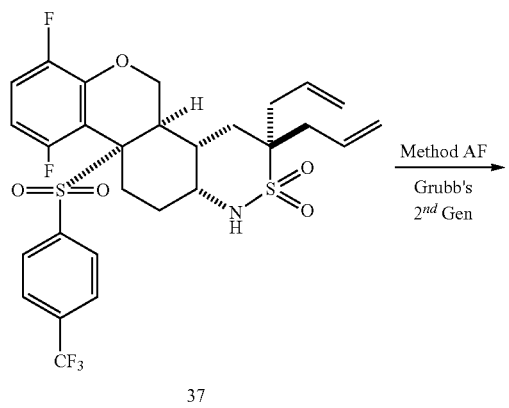
37
Method AI
1. R₁R₂NH
   NaBH(OAc)₃
39 →
2. HSCH₂COOH
   MsOH/DCM
   Method AG

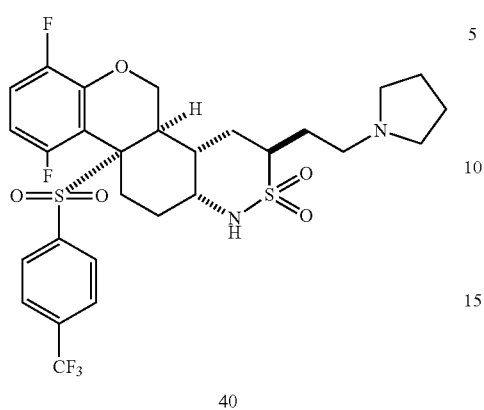
40
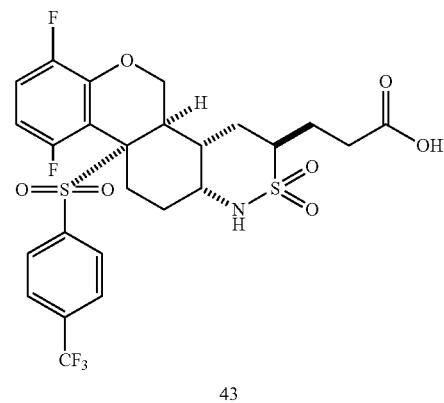
43
Scheme 14
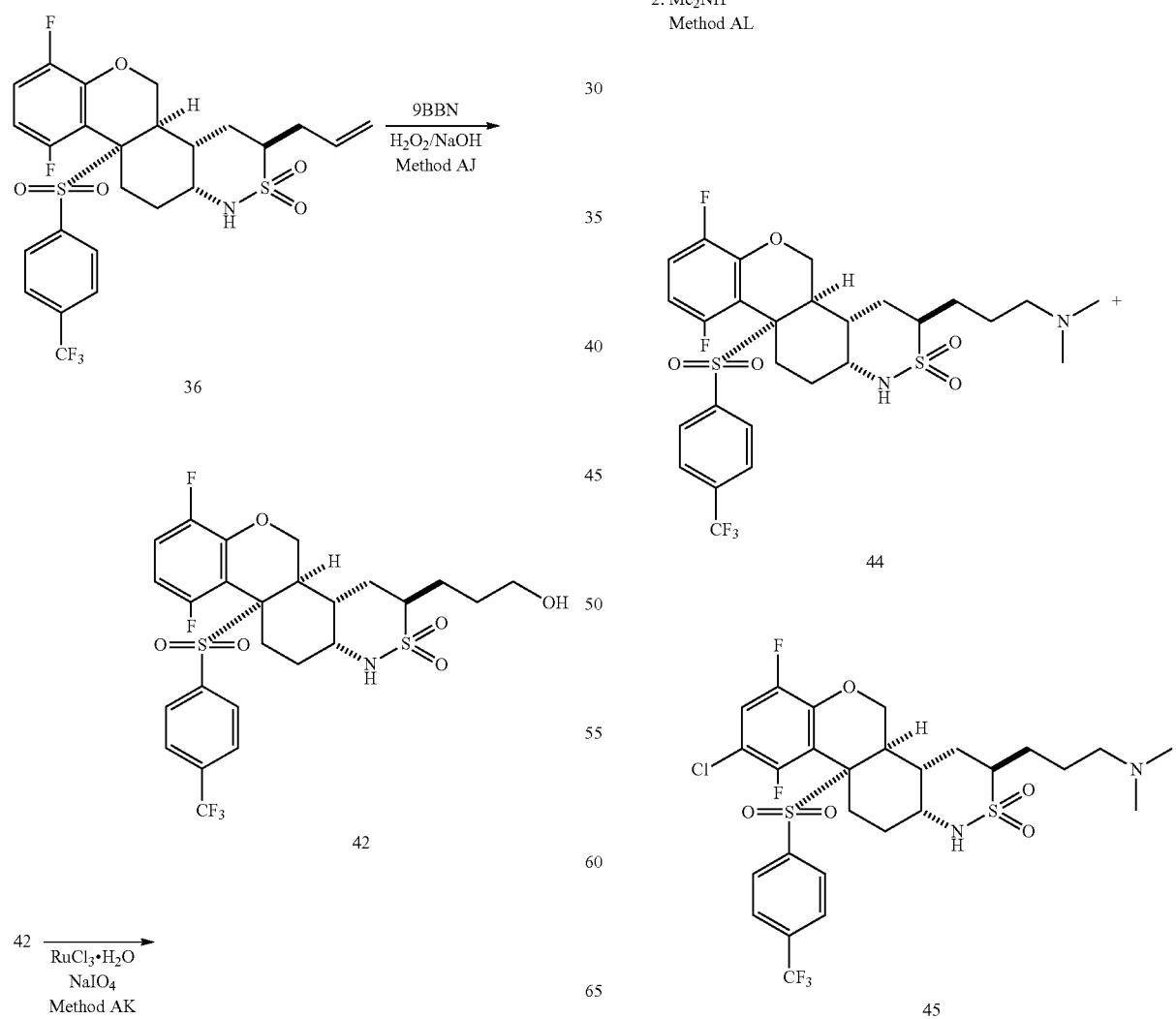

Scheme 15

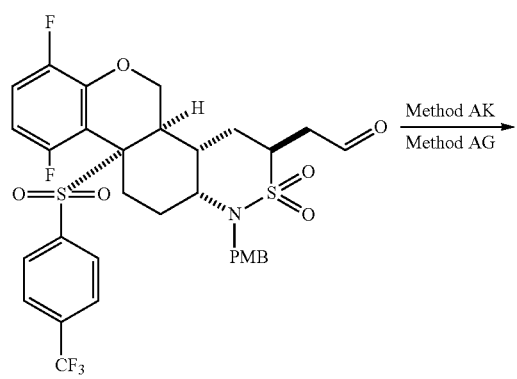

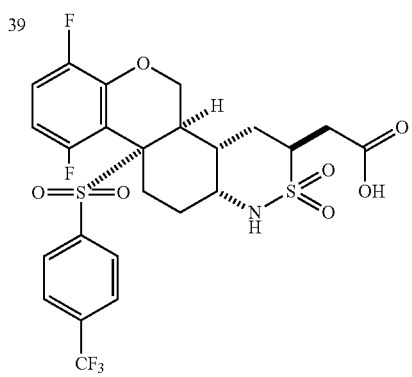

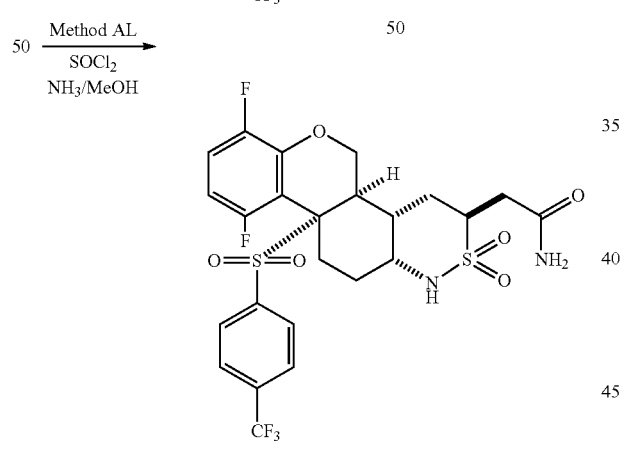

Scheme 16

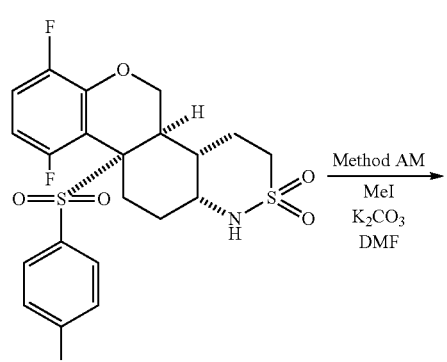

Synthesis Ketone 1b 10a-(4-Chloro-benzenesulfonyl)-1,4-difluoro-6a,9,10,10a-tetrahydro-6H,7H-benzo[c]chromen-8-one

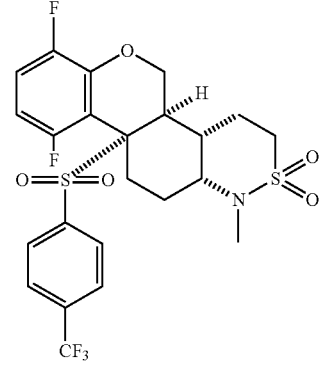

A mixture of 10.8 g (31.5 mmol) of the vinylsulphone product of step 3 of Example 17 and 24 g (165 mmol) of the 3-trimethylsiloxy-1,3-butadiene in 100 mL of trifluorotoluene in a sealed tube was heated at 150° C. for 15 h. It was concentrated, the residue was dissolved in 50 mL of THF. To this solution was added 3 mL of 1N HCl, the mixture was stirred at room temperature for 30 min. It was diluted with 300 mL of methylene chloride, washed with 50 mL of brine, and concentrated. The residue was recrystallized from ethyl acetate to give 6.8 g of the ketone. Chromatography of the mother liquid over SiO₂ gave additional 3.4 g of the ketone.

Ketone 1a is made by a similar procedure.

Scheme 1
Method A

Bis-4-methoxydibenzylamine.HCl is prepared according to reported procedure[1]: A mixture of 4-methoxybenzylamine (10 g, 0.073 mol) and 4-methoxybenzaldehyde (10 g, 0.0734 mol) was heated under reflux in ethanol (100 mL) for 2 hours. The reaction mixture was cooled to room temperature and the solvent was removed in vacuo. The crude imine formed was redissolved in anhydrous methanol (50 mL) and cooled to 0° C. Sodium borohydride (2.8 g, 0.0736 mol) was added and the mixture stirred for 1 h. The reaction mixture was warmed to 40° C. and maintained at that temperature for 1 h. It was cooled to room temperature and stirred overnight. The solvent was removed in vacuo and treated with 10% aq. HCl (100 mL). The precipitated amine salt was washed several times with ethyl acetate and dried in vacuo to give 20 g of bis-4-methoxydibenzylamine.HCl.

([1]Anastasi, C.; Hantz, O.; Clercq, E. D.; Pannecouque, C.; Clayette, P.; Dereudre-Bosquet, N.; Dormont, D.; Gondois-Rey, F.; Hirsch, I.; Kraus, J-L. *J. Med. Chem.*, 2004, 47, 1183)

$^1$H-NMR (DMSO 400 MHz) δ 7.46 (d, 4H), 6.93 (d, 4H), 3.98 (s, 4H), 3.74 (s, 6H).

Scheme 1
Methods B and C

Choroethylsulfonyl chloride (3.4 g, 0.02 mol) was dissolved in dichloromethane (100 mL) and cooled to −78° C. under nitrogen. Triethylamine (2.12 g, 1 eq) was added and the reaction was stirred at −78° C. for 10 minutes. The reaction mixture was warmed to room temperature and stirred for 2 hours. Bis-4-methoxydibenzyl-amine.HCl (6 g, 0.02 mol) was added, followed by triethylamine (4.24 g, 2 eq) and the mixture was stirred at room temperature for 2 hours. The reaction mixture was diluted with dichloromethane (100 mL) and washed with 10% HCl and brine. The solvent was removed in vacuo and the product was isolated by silica gel chromatography using a gradient of 0-50% ethyl acetate/hexane mixture as eluent to afford 1.37 g of compound 2.
$^1$H-NMR (CDCl$_3$ 400 MHz) δ 7.25 (d, 4H), 6.87 (d, 4H), 6.26 (m, 2H), 5.86 (d, 1H), 4.19 (s, 4H), 3.81 (s, 6H).

Scheme 2A
Method D

To a solution of ketone 1a (2.5 g, 0.0056 mol) in THF (25 mL) at −78° C. was added LHMDS (1M solution in THF, 5.6 mL) and stirred for 1 hour. A solution of vinyl sulfonamide (2, see Scheme 1, 1.3 g, 0.00374 mol) in THF (10 mL) was cooled to −78° C. and transferred to the enolate solution via a cannula and the mixture was stirred at −78° C. for 1 hour. The reaction mixture was slowly warmed to room temperature and stirred overnight. The reaction was quenched by the addition of saturated NH$_4$Cl solution and extracted with ethyl acetate. The solvent was removed in vacuo and the product was isolated by silica gel chromatography using a gradient of 0-50% ethyl acetate/hexane mixture as eluent to afford 1.4 g of compound 3a. $^1$H-NMR (CDCl$_3$ 400 MHz) δ 7.84 (d, 2H), 7.8 (d, 2H), 7.20 (d, 4H), 7.11 (m, 1H), 6.86 (d, 4H), 6.51 (m, 1H), 5.20 (d, 1H), 4.38 (d, 1H), 4.26 (s, 4H), 3.80 (s, 6H), 3.05 (m, 1H), 2.93 (m, 1H), 2.86 (d, 1H), 2.76 (m, 1H), 2.44 (m, 3H), 2.15 (m, 3H).

Scheme 2A
Method E

Compound 3a (1.1 g, 0.00138 mol) was dissolved in dichloromethane (5 mL) and treated with trifluoroacetic acid (5 mL) at room temperature. The reaction mixture was stirred at room temperature for 2 hours. The solvent was removed in vacuo and the product was recrystallized from dichloromethane to give 0.5 g of compound 4a. $^1$H-NMR (CDCl$_3$ 400 MHz) δ 7.90 (d, 2H), 7.81 (d, 2H), 7.05 (m, 1H), 6.40 (m, 1H), 5.36 (s, 1H), 5.14 (d, 1H), 4.56 (d, 1H), 3.50 (s, 1H), 3.32 (m, 1H), 2.98 (m, 2H), 2.67 (m, 2H), 2.32 (m, 1H), 1.9 (m, 1H), 1.80 (m, 1H).

Scheme 2A
Method F

Compound 4a (0.45 g, 0.84 mmol) was dissolved in ethyl acetate (25 mL) and treated with PtO$_2$ (300 mg). The mixture was hydrogenated at 30 psi for 6 hours. The reaction mixture was passed through a short pad of celite and washed with ethyl acetate. The solvent was removed in vacuo and the product was isolated by silica gel chromatography using a gradient of 0-50% ethyl acetate/hexane mixture as eluent to afford 0.2 g of compound 5a. $^1$H-NMR (CDCl$_3$ 400 MHz) δ 7.85 (d, 2H), 7.82 (d, 2H), 7.12 (m, 1H), 6.48 (m, 1H), 5.25 (d, 1H), 4.63 (d, 1H), 4.54 (d, 1H), 3.77 (bs, 1H), 3.14 (m, 2H), 2.52 (m, 2H), 2.36 (m, 3H), 1.75 (m, 2H), 1.59 (m, 1H).

Compound 5a1 (see Table 6) is an enantiomer of Compound 5a.

Compound 48 (see Table 6) was prepared following procedures similar to Scheme 2A Method F.

Scheme 2A
Method G

Compound 5a (0.022 g, 0.041 mmol) was dissolved in THF and cooled to 0° C. and a solution of LHMDS (1M in THF, 0.05 mL, 1.2 eq) was added and stirred for 10 minutes. NaI (10 mg) was added followed by a solution of 4-methoxybenzylchloride (7 mg, 1.2 eq) at 0° C. and stirred for 4 hours. The reaction mixture was warmed to room temperature and stirred overnight. The solvent was removed in vacuo and the mixture was subjected to preparative TLC over silica gel (eluted with hexanes/ethyl acetate 70:30) to yield 18 mg of compound 6a. MS calculated for C$_{30}$H$_{29}$F$_5$NO$_6$S$_2$ m/z=657.7, observed m/z=675.4 (M$^+$+H$_2$O), Retention time=4.83 min.

Scheme 2A
Method H

To a mixture of compound 6a (0.018 g, 0.027 mmol) and ethyl iodide (6 mg, 0.038 mmol) in THF at 0° C. was added NaHMDS and the reaction mixture was stirred at 0° C. for 2 hours, warmed to room temperature and stirred overnight. The reaction was quenched by the addition of saturated NH$_4$Cl solution and the mixture was extracted with ethyl acetate. The solvent was removed in vacuo and the residue was subjected to preparative TLC over silica gel (eluted with hexanes/ethyl acetate 80:20) to yield 11 mg of compound 7a. MS calculated for C$_{32}$H$_{32}$F$_5$NO$_6$S$_2$ m/z=685.7, observed m/z=703.4 (M$^+$+H$_2$O), Retention time=4.96 min.

Scheme 2A
Method I

Compound 7a (11 mg) was dissolved in dichloromethane (1 mL) and treated with TFA (50 mg) at 0° C. and the mixture was slowly warmed to room temperature and stirred for 2 hours. The solvent was removed in vacuo and the mixture was subjected to preparative TLC over silica gel (eluted with hexanes/ethyl acetate 80:20) to yield 5 mg of compound 8a. $^1$H-NMR (CDCl$_3$ 400 MHz) δ 7.85 (d, 2H), 7.82 (d, 2H), 7.12 (m, 1H), 6.48 (m, 1H), 5.25 (d, 1H), 4.49 (d, 1H), 4.44 (d, 1H), 3.72 (bs, 1H), 3.13 (d, 1H), 2.46 (d, 1H), 2.29 (m, 1H), 2.12 (m, 1H), 1.97 (m, 1H), 1.78 (m, 1H), 1.53 (m, 5H), 1.16 (t, 3H).

This compound (8a) was resolved by chromatography on a Chiracel OD column eluting with 20% i-propyl alcohol in hexanes to give the following two enantiomers:

8a1, enantiomer A: Retention time=32.2 min on an Chiracel OD analytical column eluting with a gradient from 0-100% i-propyl alcohol in hexanes over 100 min.

8a2, enantiomer B: Retention time=37.9 min on an Chiracel OD analytical column eluting with a gradient from 0-100% i-propyl alcohol in hexanes over 100 min.

Compound 8c (see Table 6) is an enantiomer of Compound 8a.

Scheme 2B is an alternate to Scheme 2A.
Scheme 2B
Method D

To a solution of ketone 1b (6.0 g, 14.4 mmol) in THF (65 mL) at −78° C. was added LiHMDS (14.5 mL, 1M in THF) and the reaction was stirred for 1 hour. A solution of vinyl sulfonamide 2 (see Scheme 1, 3.3 g, 9.6 mmol) in THF (35 mL) was cooled to −78° C. and transferred to the enolate solution with a cannula and stirred at −78° C. for 1 hour. The reaction mixture was slowly warmed to room temperature and stirred for 16 hours. The reaction mixture was quenched with saturated aqueous $NH_4Cl$ solution and extracted with ethyl acetate. The solvent was removed in vacuo and the product was isolated by silica gel chromatography using 0-50% ethyl acetate in hexanes as eluent to afford 2.7 g of compound 3b. $^1$H-NMR ($CDCl_3$ 400 MHz) δ7.64 (d, J=8.0 Hz, 2H), 7.52 (d, J=7.6 Hz, 2H), 7.22 (d, J=8.4 Hz, 4H), 7.14 (m, 1H), 6.87 (d, J=8.4 Hz, 4H), 6.52 (m, 1H), 5.19 (d, J=13.2 Hz, 1H), 4.35 (d, J=12.8 Hz, 1H), 3.81 (s, 4H), 3.78 (s, 6H), 3.01 (m, 2H), 2.95 (m, 2H), 2.79 (m, 3H), 2.16 (3, 3H).

Scheme 2B
Method E

To a solution of compound 3b (2.7 g, 3.6 mmol) in dichloromethane (30 mL) at 0° C. was slowly added TFA (30 mL). After stirring at 0° C. for 30 minutes, the reaction mixture was warmed to room temperature and maintained at that temperature for 3 hours. The solvent was removed in vacuo and the product was isolated by silica gel chromatography using 0-50% ethyl acetate in hexanes as eluent to afford 1.5 g of compound 4b. $^1$H-NMR ($CDCl_3$ 400 MHz) δ8.81 (s, 1H), 7.80 (d, J=8.4 Hz, 2H), 7.73 (d, J=8.8 Hz, 2H), 7.34 (m, 1H), 6.70 (m, 1H), 4.85 (d, J=12.0 Hz, 1H), 4.57 (d, J=12.4 Hz, 1H), 3.39 (s, br, 1H), 3.33 (d, J=3.2 Hz, 1H), 3.29 (d, J=3.6 Hz, 1H), 3.80 (m, 1H), 2.69 (m, 2H), 2.10 (m, 2H), 1.64 (m, 1H).

Scheme 2B
Method F

A solution of compound 4b (1.7 g, 3.4 mmol) in ethyl acetate (100 mL) was treated with $PtO_2$ (700 mg) and the mixture was hydrogenated at atmospheric pressure for 24 hours. The reaction mixture was passed through a short pad of celite and washed with ethyl acetate. The solvent was removed in vacuo and the product was isolated by silica gel chromatography using 0-50% ethyl acetate in hexanes as eluent to afford 1.0 g of compound 5b. $^1$H-NMR ($CDCl_3$ 400 MHz) δ7.57 (d, J=8.4 Hz, 2H), 7.48 (d, J=8.8 Hz, 2H), 7.07 (m, 1H), 6.44 (m, 1H), 5.18 (d, J=14.8 Hz, 1H), 4.47 (d, J=12.8 Hz, 1H), 3.69 (d, J=2.8 Hz, 1H), 3.10-2.99 (m, 3H), 2.51-2.26 (m, 5H), 1.76-1.64 (m, 2H), 1.51 (m, 1H).

Compounds 5d and 8f (see Table 6) were also prepared in this method.

Compound 5e (see Table 6) is an enantiomer of Compound 5b.

Scheme 2B
Method G

Compound 5b (504 mg, 1.0 mmol) was dissolved in THF (16 mL) and cooled to −78° C. A solution of LiHMDS (1.1 mL, 1M in THF) was slowly added and the mixture was stirred at −78° C. for 1 hour. The reaction mixture was treated with a solution of NaI (75 mg, 0.50 mmol) in dimethylacteamide (0.4 mL) followed by 4-methoxybenzyl chloride (323 mg, 2.1 mmol). The reaction mixture was warmed to room temperature and stirred for 16 hours. The reaction mixture was quenched with saturated $NH_4Cl$ solution and extracted with ethyl acetate. The solvent was removed in vacuo and the product was isolated by silica gel chromatography using 0-50% ethyl acetate in hexanes as eluent to afford 410 mg of compound 6b. $^1$H NMR ($CDCl_3$ 400 MHz) δ 7.38 (dd, J=8.4, 4.8 Hz, 4H), 7.22 (d, J=8.8 Hz, 2H), 7.05 (td, J=9.5, 4.9 Hz, 1H), 7.00 (d, J=8.8 Hz, 2H), 6.47-6.38 (m, 1H), 5.10 (dd, J=12.8, 1.8 Hz, 1H), 4.92 (d, J=16.1 Hz, 1H), 4.44 (d, J=12.5 Hz, 1H), 3.92 (s, 3H), 3.60 (d, J=16.1 Hz, 1H), 3.55 (d, J=2.9 Hz, 1H), 3.33 (td, J=13.6, 3.7 Hz, 1H), 3.25-3.12 (m, 2H), 2.52-2.32 (m, 2H), 2.11-2.02 (m, 2H), 1.83-1.75 (m, 1H), 1.55-1.47 (m, 1H), 1.44-1.34 (m, 1H).

Scheme 2B
Method H

To a mixture of compound 6b (410 mg, 0.66 mmol) and ethyl iodide (135 mg, 1.25 mmol) in THF (20 mL) at 0° C. was added LiHMDS (1.25 mL, 1M in THF) and the mixture was stirred at that temperature for 1 hour. The reaction was quenched by addition of saturated $NH_4Cl$ solution and extracted with ethyl acetate. The solvent was removed in vacuo and the product was isolated by silica gel chromatography using 0-50% ethyl acetate in hexanes as eluent to afford 225 mg of compound 7b. $^1$H NMR ($CDCl_3$ 400 MHz) δ 7.39 (dd, J=8.1, 4.4 Hz, 4H), 7.21 (d, J=8.1 Hz, 2H), 7.19-6.98 (m, 3H), 6.47-6.39 (m, 1H), 5.12 (dd, J=13.1, 1.5 Hz, 1H), 4.92 (d, J=16.1 Hz, 1H), 4.43 (d, J=12.4 Hz, 1H), 3.93 (s, 3H), 3.60 (d, J=16.1 Hz, 1H), 3.56-3.52 (m, 1H), 3.32-3.11 (m, 2H), 2.49-2.40 (m, 1H), 2.33-2.22 (m, 1H), 2.08-1.98 (m, 1H), 1.81-1.76 (m, 1H), 1.69-1.56 (m, 1H), 1.55-1.43 (m, 2H), 1.40-1.30 (m, 1H), 1.24-1.21 (m, 1H), 1.16 (t, J=7.3 Hz, 3H).

Scheme 2B
Method I

To a solution of compound 7b (225 mg, 0.35 mmol) in dichloromethane (2.0 mL) at 0° C. was slowly added TFA (1.0 mL) and the mixture was stirred at that temperature for 30 minutes. The solvent was removed in vacuo and the mixture was subjected to preparative TLC over silica gel eluting with 70% hexanes in ethyl acetate to give 58 mg of compound 8b. $^1$H-NMR ($CDCl_3$ 400 MHz) δ 7.62 (d, J=8.0 Hz, 2H), 7.53 (d, J=8.0 Hz, 2H), 7.11 (m, 1H), 6.47 (m, 1H), 5.26 (d, J=16.0 Hz, 1H), 4.52 (m, 2H), 3.71 (m, 1H), 3.11 (m, 2H), 2.50-2.20 (m, 3H), 2.14 (m, 1H), 1.97 (m, 1H), 1.76 (m, 2H), 1.53 (m, 2H), 1.14 (t, J=8.0 Hz, 3H).

This compound (8b) was resolved by chromatography on a Chiracel OD column eluting with i-propyl alcohol to give the following two enantiomers:

8b1, enantiomer A: Retention time=66.3 min, rotation=−49.724 @ 10.65 mg/mL in dichloromethane.

8b2, enantiomer B: Retention time=72.4 min, rotation=+51.156 @ 10.65 mg/mL in dichloromethane.

Compound 8e (see table 6) is an enantiomer of 8b.
Scheme 3A
Method J

To a stirred solution of 1.23 g (3.0 mmol) of the ketone 1b in 30 mL of THF was added 4.2 mL (4.2 mmol) of LiHMDS at −78° C. After 45 min., a solution of 0.83 g (5.0 mmol) of iodoacetonitrile was added. The mixture was warmed to room temperature overnight. It was quenched with 60 mL of water and extracted with three 50 mL portions of ethyl acetate. The combined ethyl acetate layers were concentrated in vacuo and the residue was purified by $SiO_2$ chromatography eluting with a gradient from 10% to 40 ethyl acetate in hexanes to give 0.74 g of the nitrile 9b. LCMS: retention time=4.18 min, calcd. for $C_{21}H_{17}ClF_2NO_4S$ ($MH^+$), m/z=452.1; observed: m/z=452.2.

Scheme 3A
Method K

To a cooled (−78° C.) solution of 0.7 g (1.55 mmol) of compound 9b in 8 mL of THF was added 3 mL (3 mmol) of L-Selectride in THF. After 2 h, the reaction was quenched with 20 mL of methanol, and concentrated. The residue was dissolved in 20 mL of methanol and 1 mL of concentrated hydrochloric acid. It was stirred at reflux for 2 h. It was diluted with 40 mL of water, extracted with three 60 mL portions of methylene chloride. The combined organic extracts were concentrated, the residue was purified by chromatography eluting with a gradient from 20% to 40% ethyl acetate in hexanes to give 0.475 g of compound 10b. LCMS: retention time=4.34 min, calcd. for $C_{21}H_{19}ClF_2O_6S$ $(M+H_2O)^+$, m/z=472.1; observed: m/z=472.3.

Scheme 3A
Method L

To a stirred suspension of 0.15 g (0.33 mmol) of compound 10b in 10 mL of diethyl ether was added 2 mL (2.0 mmol) of DIBAL in THF. After 2 h, it was quenched with 2 mL of methanol and 30 mL of 5% HCl solution. The mixture was extracted with two 40 mL portions of methylene chloride. The combined organic extracts were concentrated, the residue was purified by chromatography eluting with a gradient of 20% to 40% ethyl acetate in hexanes to give 0.125 g of compound 12b1. LCMS: retention time=3.89 min, calcd. for $C_{21}H_{21}ClF_2O_6S$ $(M+H_2O)^+$, m/z=474.1; observed: m/z=474.3.

Compounds 12b2 and 12b3 in Scheme 3A were prepared by procedures similar to those used to prepare Compound 12b1. Compounds 12b1 to 12b3 are listed in Table 1.

TABLE 1

| Compound | Mol. Wt. | Retention Time (min) | Observed m/z |
|---|---|---|---|
| 12b1 | 456.1 | 3.89 | 474.3 $(M + H_2O)^+$ |
| 12b2 | 470.1 | 4.24 | 474.3 $(M + H_2O)^+$ |
| 12b3 | 484.1 | 4.31 | 502.3 $(M + H_2O)^+$ |

Scheme 3A
Method M

To a stirred solution of 0.12 g (0.26 mmol) of compound 10b in 5 mL of THF was added 0.38 mL (0.38 mmol) of LiHMDS at −78° C. After 40 min., a solution of 0.37 g (2.6 mmol) of iodomethane was added. The mixture was warmed to room temperature overnight. It was quenched with 30 mL of water and extracted with two 50 mL portions of ethyl acetate. The combined organic extracts were concentrated, the residue was purified by chromatography eluting with 20% to 50% ethyl acetate in hexanes to give compound 11b1. LCMS: retention time=4.32 min, calcd. for $C_{22}H_{21}ClF_2O_6S$ $(M+H_2O)^+$, m/z=486.1; observed: m/z=486.3.

Compounds 11b2 and 11b3 in Scheme 3A were prepared by procedures similar to those used to prepare Compound 11b1. Compounds 11b1 to 11b3 are listed in Table 2.

TABLE 2

| Compound | Mol. Wt. | Retention Time (min) | Observed m/z |
|---|---|---|---|
| 11b1 | 468.1 | 4.32 | 486.3 $(M + H_2O)^+$ |

TABLE 2-continued

| Compound | Mol. Wt. | Retention Time (min) | Observed m/z |
|---|---|---|---|
| 11b2 | 482.1 | 4.63 | 500.3 (M + H₂O)⁺ |
| 11b3 | 496.1 | 4.77 | 514.3 (M + H₂O)⁺ |

Scheme 3A

Method N

Method N: To a solution of 0.03 g (0.066 mmol) of compound 12b1 in 4 mL of methanol and 2 mL of methylene chloride was added $BF_3$—$OEt_2$ at −20° C. It was warmed to room temperature with stirring. After the addition of 0.5 mL of triethylamine, the mixture was concentrated. The residue was purified by preparative TLC eluting with 30% ethyl acetate in hexanes to give 0.008 g of compound 13b1 and 0.007 g of compound 14b1. LCMS: retention time=4.66 min, calcd. for 13b1 $C_{22}H_{23}ClF_2O_6S$ (M+H₂O)⁺, m/z=488.1; observed: m/z=488.3; LCMS: retention time=4.56 min, calcd. for 14b1 $C_{22}H_{23}ClF_2O_6S$ (M+H₂O)⁺, m/z=488.1; observed: m/z=488.3

Compounds 13b2, 13b3, 14b2 and 14b3 in Scheme 3A were prepared by procedures similar to those used to prepare Compounds 13b1 and 14b1. Compounds 13b2, 13b3, 14b2 and 14b3 are listed in Table 3.

TABLE 3

| Compound | Mol. Wt. | Retention Time (min) | Observed m/z |
|---|---|---|---|
| 13b1 | 470.1 | 4.66 | 488.3 (M + H₂O)⁺ |
| 13b2 | 470.1 | 4.56 | 488.3 (M + H₂O)⁺ |
| 14b1 | 484.1 | 5.10 | 502.3 (M + H₂O)⁺ |
| 14b2 | 484.1 | 5.05 | 502.3 (M + H₂O)⁺ |

TABLE 3-continued

| Compound | Mol. Wt. | Retention Time (min) | Observed m/z |
|---|---|---|---|
| 13b3 (structure) | 498.1 | 5.32 | 516.3 (M + H$_2$O)$^+$ |
| 14b3 (structure) | 498.1 | 5.29 | 516.3 (M + H$_2$O)$^+$ |

Scheme 7
Method J (Alternate)

To a stirred solution of 3.0 g (7.27 mmol) of the ketone 1b in 40 mL of THF was added 10 mL (10 mmol) of LiHMDS at −78° C. After 45 min., a solution of 1.83 g (11 mmol) of iodoacetonitrile was added. The mixture was stirred at −78° C. for 2 h, then warmed to room temperature over 5 h. It was quenched with 15 mL of water, and the mixture was stirred at room temperature overnight. It was diluted with 100 mL of water, the precipitate was collected by filtration to give 1.31 g of the amide compound 15b. LCMS: retention time=3.32 min, calcd. for C$_{21}$H$_{19}$ClF$_2$NO$_5$S, m/z=470.1 (M+H)$^+$; observed: m/z=470.3.

Scheme 4
Method O

A mixture of 0.2 g (0.43 mmol) of compound 15b, 0.66 g (3 mmol) of sodium triacetoxyborohydride and 0.3 g (5 mmol) of acetic acid in 30 mL of 1,2-dichloroethane was stirred at room temperature for 50 h. The mixture was diluted with 100 mL of water and extracted with three 80 mL portions of methylene chloride. The combined organic extracts were concentrated, the residue was purified by chromatography eluting with a gradient from 40% to 80% ethyl acetate in hexanes to give 0.042 g of compound 16b and 0.074 g of compound 17b.

Compound 16b: LCMS: retention time=3.73 min, calcd. for C$_{21}$H$_{19}$ClF$_2$NO$_4$S (M+H)$^+$, m/z=454.1; observed: m/z=454.3.

Compound 17b: LCMS: retention time=3.80 min, calcd. for C$_{21}$H$_{17}$ClF$_2$NO$_4$S (MH)$^+$, m/z=452.1; observed: m/z=452.3.

Scheme 5
Method P

To a suspension of the 0.3 g (0.73 mmol) of the ketone 1b in 35 mL of t-BuOH were added 0.06 g (1.1 mmol) of acrylonitrile and 0.25 mL (0.25 mmol) of potassium tert-butoxide in THF. The mixture was stirred at room temperature for 16 h. Without purification, 0.1 g (2.5 mmol) of sodium borohydride and 15 mL of methanol were added. After stirring for 30 min., it was diluted with 40 m of water and extracted with two 80 mL portions of ethyl acetate. The combined organic extracts were concentrated, the residue was purified by chromatography eluting with a gradient from 30% to 55% ethyl acetate in hexanes to give 0.18 g of compound 18b as a mixture of diastereomers (cis:trans ca. 1:2.5). LCMS: retention time=3.96 min, calcd. for C$_{22}$H$_{21}$ClF$_2$NO$_4$S (MH)$^+$, m/z=468.1; observed: m/z=468.3.

Scheme 5
Method Q

A mixture of 0.18 g (0.43 mmol) of compound 18b, 0.15 g (1.5 mmol) of triethylamine and 0.11 g (1 mmol) of methanesulfonyl chloride in 4 mL of methylene chloride was stirred at room temperature for 1.5 h. The mixture was diluted with 60 mL of methylene chloride, washed with 25 mL of water, and concentrated. The residue was treated with 0.01 g of 18-crown-6 and 0.046 g (0.7 mmol) of sodium azide in 6 mL of DMF, and stirred at 70° C. for 18 h. It was diluted with 40 mL of water, and extracted with two 50 mL portions of ethyl acetate. The combined organic extracts were concentrated and the residue was dissolved in 10 mL of THF and 0.1 mL of water. Triphenylphosphine (0.32 g, 2 mmol) of was added. The mixture was stirred at reflux for 3 h, then concentrated. The residue was dissolved in 15 mL of methanol and 2 mL of concentrated HCl and stirred at reflux for 18 h. It was concentrated, diluted with 30 mL of saturated NaHCO$_3$, extracted with three 60 mL portions of methylene chloride. The combined organic extracts were concentrated; the residue was purified by chromatography eluting with a gradient from 2% to 6% methanol in methylene chloride plus 1% ammonium hydroxide to give 0.085 g of compound 19b. LCMS: retention time=3.66 min, calcd. for C$_{40}$H$_{35}$ClF$_2$N$_2$O$_3$PS (M$^+$), m/z=727.2; observed m/z=727.4.

Scheme 5
Method R

A mixture of 0.082 g (0.011 mmol) of compound 19b, 5 mL of 1N aqueous NaOH and 8 mL of THF was stirred at room temperature for 16 h and then at reflux for 7 h. It was diluted with 25 mL of water, extracted with three 40 mL portions of methylene chloride. The combined organic extracts were concentrated, the residue was purified by preparative TLC eluting with 6% methanol in methylene chloride to give 0.009 g of compound 20b. LCMS: retention time=3.84 min, calcd. for C$_{22}$H$_{21}$ClF$_2$NO$_4$S (M+H)$^+$, m/z=468.1; observed m/z=468.3.

Scheme 6
Method S (3-Benzyloxy-1-hydroxymethyl-propyl)-carbamic acid tert-butyl ester 21 (7.4 g, 25 mmol) was dissolved in 100 ml dichloromethane. Mesyl chloride (4.3 g, 37.5 mmol) and triethylamine (5.0 g, 50 mmol) were added. The reaction was stirred at room temperature for 20 minutes. 100 ml dichloromethane and 100 ml water were added. The organic layer was washed with brine (100 ml), dried over sodium sulfate and concentrated. The residue was dissolved in 200 ml toluene. Tetrabutylammonium cyanide (10 g, 37.5 mmol) was added and the reaction was stirred at room temperature overnight. The organic layer was washed with two 100 mL portions of water, brine (100 ml), dried over sodium sulfate and concentrated. The residue was purified by column eluting with a gradient of ethyl acetate in hexanes from 100% to 30% to give 6.4 g of the desired nitrile 22. $^1$H NMR (CDCl$_3$ 400 MHz) δ 7.29-7.38 (m, 5H), 5.20 (d, J=5.9 Hz, 1H), 4.50 (m, 2H), 3.91 (m, 1H), 3.54-3.66 (m, 2H), 2.60-2.77 (m, 2H), 1.89-1.99 (m, 2H), 1.44 (s, 9H).

Scheme 6
Method T

[3-Benzyloxy-1(R)-cyanomethyl-propyl]-carbamic acid tert-butyl ester 22 (6.4 g, 21 mmol) was dissolved in 20 ml dichloromethane. 4N HCl in dioxane (20 ml) was added and the reaction was stirred at room temperature for 1 hour. The solvent was removed and the residue was dissolved in 200 ml THF and 4-(4-Chlorobenzene-sulfonyl)-5,8-difluoro-2H-chromene 23 was added. Diisopropylethylamine (10 ml) was added and the reaction was stirred at room temperature overnight, then heated under reflux for 5 hours. The reaction was cooled to room temperature and 100 ml ethyl acetate was added. The organic layer was washed with brine (100 ml), dried over sodium sulfate and concentrated. The residue was purified by SiO$_2$ column chromatography eluting with a gradient of ethyl acetate in hexanes from 100% to 30% to give 6.0 g of the desired sulfone 24 as a mixture of two diastereomers. This compound was used directly in subsequent reactions.

Scheme 6
Method U

5-Benzyloxy-3(R)-[4-(4-chloro-benzenesulfonyl)-5,8-difluoro-chroman-3-yl-amino]-pentanenitrile 24 (0.9 g, 1.64 mmol) was dissolved in 20 ml dichloromethane and the reaction was cooled to −78° C. Boron trichloride (1M in Hexane, 8.2 ml) was then added and the reaction was stirred 30 minutes. The reaction was quenched by adding 50 ml saturated sodium bicarbonate solution and 100 ml dichloromethane was added. The organic layer was washed with brine (100 ml), dried over sodium sulfate and concentrated. The residue was purified by SiO$_2$ column chromatography eluting with a gradient of ethyl acetate in hexanes from 0% to 75% to give 0.64 g of the desired alcohol 25 as a mixture of diastereomers. This compound was used directly in subsequent reactions.

Scheme 6
Method V

3-[4-(4-Chloro-benzenesulfonyl)-5,8-difluoro-chroman-3-yl-(R)-amino]-5-hydroxy-pentanenitrile 25 (1.7 g, 3.7 mmol) was dissolved in 50 ml dichloromethane. Mesyl chloride (1 ml) and triethylamine (2 ml) were added. The reaction was stirred at room temperature for 5 minutes. 500 ml dichloromethane and 50 ml water were added. The organic layer was washed with 1N HCl solution (2×100 ml), brine (100 ml), dried over sodium sulfate and concentrated. The residue was dissolved in 100 ml dry THF and KOt-Bu (1M in t-BuOH, 4.5 ml) was added. The reaction was stirred at room temperature for 10 minutes. 100 ml of ethyl acetate was added. The organic layer was washed with brine (2×100 ml), dried over sodium sulfate and concentrated. The residue was purified by SiO$_2$ chromatography eluting with a gradient of ethyl acetate in hexanes 100% to 40% to give 0.72 g of the desired cis tricycle 26. $^1$H NMR (CDCl$_3$ 400 MHz δ 7.59 (d, J=8.8 Hz, 2H), 7.50 (d, J=8.8 Hz, 2H), 7.06-7.13 (m, 1H), 6.40-6.47 (m, 1H), 5.18 (dd, J=11.7 and 2.9 Hz, 1H), 4.29 (dd, J=11.7 and 1.5 Hz, 1H), 3.82 (d, J=7.3 Hz, 1H), 3.36 (bs, 1H), 2.62-2.82 (m, 2H), 2.32-2.52 (m, 2H), 2.70-2.86 (m, 2H), 1.52 (m, 1H)

0.51 g of the corresponding trans compound was also isolated from the reaction.

Scheme 6
Method W (4aR)-10bR-[(4-Chlorophenylsulfonyl)-7,10-difluoro-1,3,4,4a,5,10b-hexahydro-2H-[1]benzopyrano[3,4-b]pyridine-3(S)-acetonitrile 26 (0.47 g, 1.1 mmol) was dissolved in 100 ml THF and borane-dimethylsulfide complex (2M in THF, 5.4 ml) was added. The reaction was heated to 60° C. for three hours. The reaction was cooled to room temperature and 100 ml water was added dropwise to quench the reaction. 100 ml 2N NaOH solution and 200 ml ethyl acetate were added. The organic layer was washed with brine (100 ml), dried over sodium sulfate and concentrated. The residue was dissolved in 100 ml methanol. 10 ml 1N HCl in ether was added and the reaction was stirred at room temperature for one hour. The solvent was removed and the residue was partitioned between 100 ml 1N NaOH solution and 100 ml ethyl acetate. The organic layer was washed with brine (100 ml), dried over sodium sulfate and concentrated. The product was purified by SiO2 chromatography eluting with a gradient of dichloromethane (containing 0.7N NH$_3$) in MeOH from 0 to 50% to give 0.40 g of the desired amine 27. $^1$H NMR (CDCl$_3$ 400 MHz δ 7.59 (d, J=8.8 Hz, 2H), 7.47 (d, J=8.8 Hz, 2H), 7.02-7.10 (m, 1H), 6.37-6.45 (m, 1H), 5.15 (dd, J=11.7 and 2.2 Hz, 1H), 4.25 (dd, J=11.7 and 1.5 Hz, 1H), 3.86 (s, 1H), 2.95-3.03 (m, 1H), 2.82 (t, J=5.8 Hz, 2H), 2.38-2.45 (m, 2H), 1.94-2.05 (m, 1H), 1.45-2.55 (m, 2H), 1.32-1.44 (m, 1H).

Scheme 6
Method X (4aR)-10bR-[(4-Chlorophenyl)sulfonyl]-7,10-difluoro-1,3,4,4a,5,10b-hexahydro-2H-[1]benzopyran[3,4-b]pyridine-3(S)-ethylamine 27 (0.13 g, 0.29 mmol) was dissolved in 30 ml dichloromethane. Phosgene (20% in toluene, 0.2 ml) and triethylamine (0.2 ml) were added. The reaction was stirred at room temperature for three hours. 70 ml dichloromethane was added. The organic layer was washed with brine (100 ml), dried over sodium sulfate and concentrated. The product was purified by SiO$_2$ chromatography eluting with a gradient of ethyl acetate in hexanes from 50% to 100% to give 75 mg of tetracycle 28. $^1$H NMR (CDCl$_3$ 400 MHz δ 7.64 (d, J=8.8 Hz, 2H), 7.43 (d, J=8.8 Hz, 2H), 7.02-7.09 (m, 1H), 6.55-6.62 (m, 1H), 5.15 (dd, J=11.7 and 2.2 Hz, 1H), 4.25 (dd, J=11.7 and 1.5 Hz, 1H), 3.86 (s, 1H), 2.95-3.03 (m, 1H), 2.82 (t, J=5.8 Hz, 2H), 2.38-2.45 (m, 2H), 1.94-2.05 (m, 1H), 1.45-2.55 (m, 2H), 1.32-1.44 (m, 1H)

Using methods similar to those in Scheme 6 above and substituting SO$_2$(NH$_2$)$_2$ for phosgene, Compound 30 was prepared. Compounds 28 and 30 are listed in Table 4.

TABLE 4

| Compound | Mol. Wt. | Retention Time (min) | Observed m/z |
|---|---|---|---|
| 28 | 468.9 | 3.67 | 469.3 |

TABLE 4-continued

| Compound | Mol. Wt. | Retention Time (min) | Observed m/z |
|---|---|---|---|
| (structure 30) | 505.0 | 4.15 | 505.3 |

Scheme 6
Method Y (5aR,13aS)-11bR-[(4-Chlorophenyl)sulfonyl]-8,11-difluoro-2,3,5a,6,11b,12,13,13a-octahydro[1]benzopyrano[4',3':5,6]pyrido[1,2-c]pyrimidin-4(1H)-one 28 (40 mg, 0.085 mmol) was dissolved in 5 ml DMF. Iodoethane (40 µl) and sodium hydride (60% in oil, 20 mg) were added. The reaction was stirred at room temperature for ten minutes. 25 ml ethyl acetate and 25 ml hexane were added. The organic layer was washed with water (50 ml), brine (50 ml), dried over sodium sulfate and concentrated. The product was purified by $SiO_2$ chromatography eluting with a gradient of ethyl acetate in hexanes from 0% to 60% to give 36 mg of the desired compound 29. $^1$H NMR (CDCl$_3$ 400 MHz δ 7.61 (d, J=8.8 Hz, 2H), 7.40 (d, J=8.8 Hz, 2H), 6.99-7.06 (m, 1H), 6.54-6.61 (m, 1H), 5.39-5.43 (m, 1H), 4.41 (dd, J=11.0 and 4.4 Hz, 1H), 4.09-4.05 (m, 1H), 3.37 (q, J=7.4 Hz, 2H), 3.21-3.33 (m, 2H), 3.10-3.17 (m, 1H), 2.60-2.68 (m, 2H), 2.82 (t, J=5.8 Hz, 2H), 1.96-2.05 (m, 1H), 1.81-1.90 (m, 1H), 1.64-1.72 (m, 1H), 1.47-1.59 (m, 1H), 1.10 (t, J=7.3 Hz, 3H).

Using methods similar to those in Scheme 6 and substituting sulfamide 30 for pyrimidinone 28, Compound 31 was prepared. Table 5 lists compounds 29 and 31.

TABLE 5

| Compound | Mol. Wt. | Retention Time (min) | Observed m/z |
|---|---|---|---|
| (structure 29) | 497.0 | 4.18 | 497.3 |
| (structure 31) | 533.0 | 4.62 | 533.3 |

Scheme 7
Method Z

Ketone 1b (300 mg, 0.73 mmol) was dissolved in 10 mL THF and cooled −78° C. under nitrogen. Lithium hexamethyldisilazide (0.76 mL, 1 N in THF, 1.05 eq) was added slowly to the above solution at the same temperature. Twenty minutes later, a solution of methyl cyanoformate (85 mg, 1.1 eq)/1 mL THF was added. The reaction was kept at −78° C. for 30 min and warmed up to 0° C. in 2 h. The reaction was quenched by saturated NH$_4$Cl. Ethyl acetate was added and the organic layer was washed with water, brine and dried over Na$_2$SO$_4$. After evaporation of the solvent, flash chromatography (hexane/ethyl acetate, 75:25) afforded the desired product 32 (60 mg). $^1$H NMR (CDCl$_3$ 400 MHz) δ 2.00 (m, 1H) 2.50 (m, 2H) 2.60 (m, 1H) 3.75 (br s, 1H) 4.50 (dd, J=4.5, 11.7 Hz, 1H) 4.50 (dd, J=2.0, 11.7 Hz, 1H) 6.43 (m, 1H) 7.00 (m, 1H) 7.47 (d, J=9.0 Hz, 2H) 7.68 (d, J=9.0 Hz, 2H).

Scheme 7
Method AA

The keto ester 32 (24 mg, 0.05 mmol)/1 mL ethanol/NH$_4$OAc (8 mg, 2 eq)/methyl hydrazine (3 mg, 1.2 eq) were mixed and heated to 40° C. under nitrogen for 14 h. The solvent was removed, ethyl acetate was added, and the organic layer was washed with water, brine and dried over Na$_2$SO$_4$. After evaporation of the solvent, prep TLC eluting with hexane/ethyl acetate, 5:1) afforded the desired product 33 (5 mg). LCMS: Retention time=3.75 min, calcd for $C_{21}H_{17}ClF_2N_2O_4S$ m/z=466.1, observed m/z=467.3 (M+1)$^+$.

Scheme 8
Method AB

To a solution of compound 3a (5.23 g, 6.59 mmol) in tetrahydrofuran (65 mL) cooled in a 0° C., ice water bath was added NaBH$_4$ (1.25 g, 33 mmol). After stirring at 0° C. for 40 minutes, the reaction mixture was concentrated. The resulting foam was partitioned between water (50 mL) and dichloromethane (50 mL). This mixture was then extracted with dichloromethane (1×100 mL, 2×25 mL). The combined, milky white organic layers were dried over Na$_2$SO$_4$, filtered, and concentrated to provide a pale yellow solid. This solid was suspended in dichloromethane (65 mL), and then triethylamine (2.75 mL, 19.7 mmol) and methanesulfonyl chloride (0.77 mL, 9.04 mmol) were added. After stirring for 16 h at room temperature, the reaction solution was absorbed onto silica gel (25 g) and purified by silica gel chromatography eluting with a gradient of ethyl acetate/hexanes (10/90 to 90/10 over 50 min) to afford compound 34a (4.28 g) as a pale yellow solid. LCMS retention time=5.34 min, calcd for $C_{39}H_{41}F_5NO_{10}S_3^+$ m/z=874.2, observed m/z=874.5 (M+1)$^+$.

Scheme 8
Method AC

To a room temperature solution of compound 34a (4.28 g, 4.9 mmol) in tetrahydrofuran (25 mL) was added trifluoroacetic acid (25 mL). After stirring for 16 h at room temperature, the reaction mixture was concentrated. This residue was partitioned between dichloromethane (150 mL) and ethyl acetate (275 mL). The organics were then washed with saturated aqueous NaHCO$_3$ (2×), washed with brine (1×) dried over Na$_2$SO$_4$, filtered, and absorbed onto silica gel (20 g). This absorbed crude material was purified by silica gel chromatography with a gradient of ethyl acetate/hexanes (30/70 to 0/100 over 25 min, holding gradient at 0/100 for an additional 10 min) to afford compound 35a (2.17 g) as a yellow solid. LCMS retention time=4.32 min, calcd for $C_{23}H_{25}F_5NO_8S_3{}^+$ m/z=634.1, observed m/z=634.3, (M+1)$^+$

Scheme 8
Method AD

To a room temperature solution of compound 35a (2.17 g, 3.42 mmol) in dimethylformamide (34 mL) was added NaH (60% oil dispersion, 0.68 g, 17 mmol). After stirring for 5 h at room temperature, this reaction mixture was carefully quenched with water. The mixture was diluted with ethyl acetate (300 mL). The resulting mixture was then washed with aqueous 1M HCl (1×100 mL), washed with water (4×50 mL), washed with brine (1×50 mL), dried over Na$_2$SO$_4$, filtered, and concentrated to provide 2.01 g of a yellow solid. This crude solid was stirred with 0.5% methanol in diethyl ether (100 mL) for 15 minutes, and then filtered. The isolated solid was washed with diethyl ether (50 mL) and dried under vacuum overnight to afford compound 5a (1.33 g) as a white solid. LCMS: retention time=4.40 min, calcd for $C_{22}H_{21}F_5NO_5S_2{}^+$ m/z=538.1, observed m/z=538.3 (M+1)$^+$,

Scheme 9
Method AE

A mixture of 0.35 g (0.66 mmol) of the chloro compound 8b1, 0.025 g (0.026 mmol) of Pd$_2$(dba)$_3$, 0.055 g (0.095 mmol) of dppf, 0.06 g (0.51 mmol) of zinc cyanide and 0.03 g (0.46 mmol) of zinc power in 14 mL of DMA in a sealed tube was heated at 150° C. for 1 h in microwave (Biotage). It was diluted with 50 mL of water, and extracted with three 50 mL portions of methylene chloride. The combined organic extracts were dried over Na$_2$SO$_4$, filtered and concentrated. The residue was purified by chromatography eluting with a gradient from 15% to 75% ethyl acetate in hexanes to give 0.30 g of the cyano compound 8c1. MS: Calcd. for $C_{24}H_{25}F_2N_2O_5S_2$ (MH+), 523.1. found 523.3. Retention time: 4.11 min.

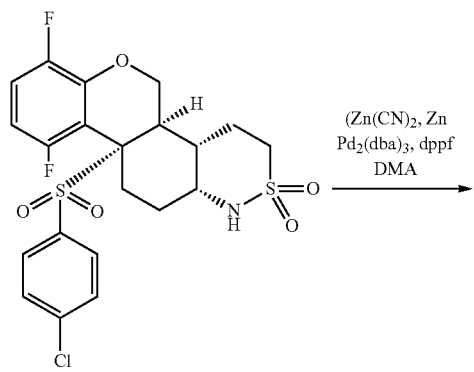

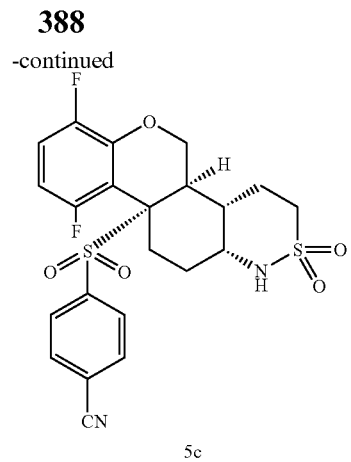

Similar application of this method on tetracycle 5b yields cyanophenyl analog 5C: MS Calcd. for $C_{22}H_{21}F_2N_2O_5S_2$ (M+H)$^+$, 495.1. found 495.3, Retention time=3.79 min.

Scheme 10
Method H

Compound 8d: Compound 6a (2.0 g, 0.003 mol) was suspended in 50 mL THF and treated with 0.85 g (2 eq) MeI followed by LHMDS (6.0 mL, 1M in THF) at 0° C. Stirred at 0° C. for 2 hours and warmed to room temperature and stirred overnight. The reaction was worked up as in Method H to get compound 7d and used as such for next step.

Scheme 10
Method AG

Compound 7d (1.7 g, 0.0025 mol) was dissolved in DCM (50 mL) and treated with mercaptoacetic acid (1.0 g, 4 eq) followed by methanesulfonic acid (0.8 g, 3 eq) at 0° C. Stirred at 0° C. for 30 minutes and warmed to room temperature and stirred for 4 hours. Quenched with 25 mL 1M NaOH solution and extracted with ethyl acetate. The solvent was removed in vacuo and triturated with ether to get 1.2 g compound 8d as white solid. $^1$H-NMR (CDCl$_3$ 400 MHz) δ 7.85 (d, 2H), 7.82 (d, 2H), 7.11 (m, 1H), 6.47 (m, 1H), 5.24 (d, 1H), 4.68 (d, 1H), 4.54 (d, 1H), 3.74 (s, 1H), 3.27 (m, 1H), 3.15 (d, 1H), 2.37 (m, 3H), 2.07 (m, 2H), 1.80 (m, 2H), 1.53 (m, 1H), 1.42 (d, 3H).

This compound (8d) was resolved by chromatography on a Chiralcel OD column eluting with 50% i-propyl alcohol in hexanes to give the following two enantiomers:

8d1, enantiomer A: Retention time 31 min on an Chiralcel OD preparative column eluting with 50% i-propyl alcohol in hexanes.

8d2, enantiomer B: Retention time 54 min on an Chiralcel OD preparative column eluting with 50% i-propyl alcohol in hexanes.

8d1, enantiomer A: $^1$H-NMR (CDCl$_3$ 400 MHz) δ 7.82 (m, 4H), 7.11 (m, 1H), 6.47 (m, 1H), 5.24 (d, 1H), 4.58 (d, 1H), 4.53 (d, 1H), 3.74 (s, 1H), 3.27 (m, 1H), 3.13 (d, 1H), 2.37 (m, 3H), 2.07 (m, 2H), 1.80 (m, 2H), 1.53 (m, 1H), 1.42 (d, 3H). Optical rotation: $[\alpha]_D^{22}=-50.73°$ (c 1.0, MeOH)

8d2, enantiomer B: $^1$H-NMR (CDCl$_3$ 400 MHz) δ 7.82 (m, 4H), 7.11 (m, 1H), 6.47 (m, 1H), 5.24 (d, 1H), 4.58 (d, 1H), 4.53 (d, 1H), 3.74 (s, 1H), 3.27 (m, 1H), 3.13 (d, 1H), 2.37 (m, 3H), 2.07 (m, 2H), 1.80 (m, 2H), 1.53 (m, 1H), 1.42 (d, 3H). Optical rotation: $[\alpha]_D^{22}=+50.26°$ (c 1.0, MeOH)

Using methods similar to those in Scheme 10, compounds 7e, 7f, 7g, 8e1, 8g (8h is an enantiomer of 8g), 36d, 46, 47, 48 and 49 (see Table 6) were prepared.

Scheme 11
Method H and Method AG

Compound 36 and 37: Compound 6a (1.0 g, 0.0015 mol) was dissolved in THF (50 mL) and treated with allyl iodide (0.77 g, 3 eq) followed by LHMDS (4.5 mL, 3 eq) at 0° C. The reaction mixture was warmed to room temperature and stirred for 2 hours. Quenched by the addition of water and extracted with ethyl acetate. The solvent was removed in vacuo and the product 36a (identified in Scheme 13) was subjected to deprotection according to method AG. The final products were isolated by silica gel chromatography using 0-50% ethyl acetate hexane mixture as eluent to afford 0.2 g of compound 37 and 0.4 g of monoallyl compound 36.

Compound 36. $^1$H-NMR (CDCl$_3$ 400 MHz) δ 7.75 (m, 4H), 7.04 (m, 1H), 6.39 (m, 1H), 5.69 (m, 1H), 5.11 (m, 3H), 4.37 (d, 1H), 3.57 (m, 4H), 2.99 (d, 1H), 2.78 (m, 1H), 2.39 (d, 1H), 2.26 (m, 2H), 1.82 (m, 1H), 1.38 (m, 2H), 1.16 (m, 1H).

Compound 36a. $^1$H-NMR (CDCl$_3$ 400 MHz) δ 7.40 (m, 4H), 7.26 (m, 4H), 7.20 (d, 2H), 7.18 (m, 1H), 6.45 (m, 1H), 5.81 (m, 1H), 5.24 (d, 1H), 5.08 (m, 2H), 4.38 (d, 1H), 4.11 (s, 3H), 3.92 (m, 2H), 3.29 (m, 1H), 3.17 (d, 1H), 3.04 (m, 1H), 2.47 (m, 1H), 2.69 (m, 1H), 2.24 (m, 2H), 1.79 (m, 1H), 1.38 (m, 1H), 1.26 (m, 1H).

Using methods similar to those in Scheme 11, compounds 36b, 36e, 46 and 47 (see Table 6) were prepared.

Scheme 12
Method AF

Compound 38: Compound 37 (0.01 g, 0.016 mmol) was dissolved in DCM (2 mL) and treated with Grubb's second generation metathesis catalyst (3 mg, 20 mol %) and stirred at room temperature for 2 hours. The reaction mixture was diluted with ethyl acetate and passed through a small pad of celite. The solvent was removed in vacuo and the product was purified by preparative TLC using 30% ethylacetate/hexane as eluent to get 4 mg compound 38. $^1$H-NMR (CDCl$_3$ 400 MHz) δ 7.82 (m, 4H), 7.11 (m, 1H), 6.48 (m, 1H), 5.75 (m, 2H), 5.28 (d, 2H), 4.60 (d, 1H), 4.13 (m, 2H), 3.64 (s, 1H), 3.27 (m, 3H), 2.56 (m, 1H), 2.40 (m, 2H), 2.04 (m, 2H), 1.25 (m, 2H).

Scheme 13
Method AH

Compound 39: Compound 36a (0.3 g, 0.00043 mol) was dissolved in DCM (50 mL) and cooled to −78° C. A stream of ozone was passed through the solution for 10 minutes. Nitrogen gas was bubbled though the above solution and treated with 150 mg (1.3 eq) triphenyl phosphine and stirred at room temperature for 1 hour. The solvent was removed in vacuo and the product was purified by silica gel column chromatography to afford 0.235 g of compound 39. $^1$H-NMR (CDCl$_3$ 400 MHz) δ 9.86 (s, 1H), 7.66 (d, 2H), 7.44 (m, 4H), 7.08 (m, 3H), 6.43 (m, 1H), 5.13 (d, 1H), 5.00 (d, 1H), 4.85 (d, 1H), 4.11 (m, 1H), 3.92 (s, 3H), 3.41 (m, 4H), 2.85 (m, 1H), 2.53 (m, 1H), 2.04 (m, 2H), 1.79 (m, 4H).

Scheme 13
Method AI

Compound 40: Compound 39 (0.045 g, 0.0643 mmol) was dissolved in DCM (2 mL) and treated with 10 μL pyrrolidine and 28 mg (2 eq) sodium tricaetoxy borohydride and stirred at room temperature overnight. The reaction mixture was directly applied to preparative TLC and eluted with 5% MeOH/DCM as eluent. This material was deprotected according to Method AG to afford 2 mg of Compound 40. $^1$H-NMR (CDCl$_3$ 400 MHz) δ 7.85 (m, 4H), 6.99 (m, 1H), 6.33 (m, 1H), 5.00 (d, 1H), 4.44 (d, 1H), 4.00 (m, 3H), 3.60 (m, 3H), 2.88 (m, 2H), 2.80 (m, 4H), 2.16 (m, 2H), 1.88 (m, 4H), 1.62 (m, 2H), 1.09 (m, 4H).

Using methods similar to those in Scheme 13, compound 41 in Table 6 was prepared.

Scheme 14
Method AJ

Compound 42: Compound 41 (0.1 g, 0.00017 mol) was dissolved in THF (10 mL) and cooled to 0° C. A solution of 9BBN (2.5 mL, 7 eq) was added at 0° C. and slowly warmed to room temperature and stirred overnight. The reaction mixture was cooled to and treated with 5 mL 1M NaOH and 5 mL 30% H$_2$O$_2$ and stirred for 2 hours. Water was added and extracted with ethyl acetate. The solvent was removed in vacuo and the product was isolated by reverse phase HPLC to get 50 mg compound 42. $^1$H-NMR (CDCl$_3$ 400 MHz) δ 7.71 (m, 4H), 7.01 (m, 1H), 6.36 (m, 1H), 5.07 (d, 1H), 4.46 (d, 1H), 3.54 (m, 3H), 3.23 (s, 1H), 2.96 (m, 1H), 2.93 (d, 1H), 2.36 (d, 1H), 2.23 (m, 3H), 1.94 (m, 1H), 1.83 (m, 1H), 1.67 (m, 5H), 1.48 (m, 1H).

Compounds 42a and 42b (see Table 6) were prepared following procedures similar to Scheme 14 Method AJ.

Scheme 14
Method AK

Compound 43: Compound 42 (0.011 g, 0.0184 mmol) was dissolved in a mixture of solvents (EtOAc/CH$_3$CN/H$_2$O; 1/1/2) and treated with RuCl$_3$.H$_2$O (3 mg, 0.5 eq) and NaIO$_4$ (12 mg, 3 eq). The reaction mixture was stirred at room temperature for 2 hours. Diluted with ethyl acetate and passed through a short pad of celite. The solvent was removed in vacuo and the product was purified by reverse phase HPLC to afford 7 mg of compound 43. $^1$H-NMR (CDCl$_3$ 400 MHz) δ 7.71 (m, 4H), 7.02 (m, 1H), 6.37 (m, 1H), 5.06 (d, 1H), 4.48 (d, 1H), 3.35 (s, 1H), 2.92 (m, 2H), 2.53 (m, 2H), 2.35 (d, 1H), 2.19 (m, 3H), 1.86 (m, 2H), 1.61 (m, 5H).

Scheme 14
Method AL

Compound 44 and compound 45: Compound 42 (0.02 g, 0.0335 mmol) was dissolved in SOCl$_2$ (2 mL) and stirred at 60° C. overnight. The excess SOCl$_2$ was removed in vacuo and treated with 1 mL dimethylamine (40% solution in water) and stirred at 60° C. overnight. The solvent was removed in vacuo and the products were isolated by reverse phase HPLC to afford 4.5 mg of compound 44 and 7 mg of compound 45.

Compound 44: $^1$H-NMR (CDCl$_3$ 400 MHz) δ 7.82 (m, 4H), 7.26 (m, 1H), 6.46 (m, 1H), 5.23 (d, 1H), 4.63 (d, 1H), 3.79 (m, 4H), 3.33 (m, 1H), 3.17 (d, 1H), 3.01 (m, 2H), 2.73 (s, 6H), 2.43 (m, 3H), 2.01 (m, 3H), 1.80 (m, 2H), 1.49 (m, 1H).

Compound 45: $^1$H-NMR (CDCl$_3$ 400 MHz) δ 7.84 (m, 4H), 7.22 (s, 1H), 5.22 (d, 1H), 4.63 (d, 1H), 3.90 (m, 1H), 3.69 (s, 1H), 3.33 (m, 1H), 3.22 (d, 1H), 3.03 (m, 2H), 2.72 (s, 6H), 2.42 (m, 2H), 2.33 (m, 1H), 2.05 (m, 5H), 1.83 (d, 1H), 1.71 (m, 1H), 1.50 (m, 1H).

Using methods similar to those in Scheme 14, compounds 42b, 36f, 36c, 36d in Table 6 were prepared.

Scheme 15

Using methods similar to those in Scheme 14, compounds 50 and 51 were prepared.

Scheme 16
Method AM

Compound 5b5: Compound 5a (0.025 g, 0.0465 mmol) was dissolved in DMF (1 mL) and treated with K$_2$CO$_3$ (10 mg, 1.5 eq) and MeI (20 mg, 3 eq). The reaction mixture was stirred at room temperature for 48 hours. Diluted with ethyl acetate and passed through a short pad of celite. The solvent was removed in vacuo and the product was purified by reverse phase HPLC to afford 12 mg of compound 5b5. $^1$H-NMR (CDCl$_3$ 400 MHz) δ 7.81 (m, 4H), 7.12 (m, 1H), 6.48 (m, 1H), 5.24 (d, 1H), 4.49 (d, 1H), 3.40 (s, 1H), 3.24 (m, 3H), 2.70 (s, 3H), 2.24 (m, 4H), 1.86 (m, 2H), 1.34 (m, 1H).
Using methods similar to those in Scheme 16, compounds 5b2, 5b3 and 5b4 in Table 6 were prepared.
TABLE 6
| Compound | Mol. Wt. | Retention Time (min) | Observed m/z |
|---|---|---|---|
| 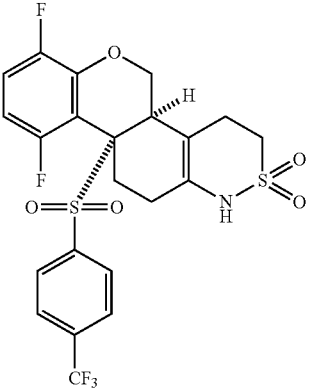<br>4a | 535.50 | 4.18 | 536.3 |
| 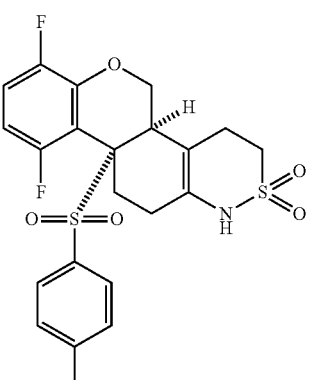<br>4b | 501.95 | 4.19 | 502.3 |
| 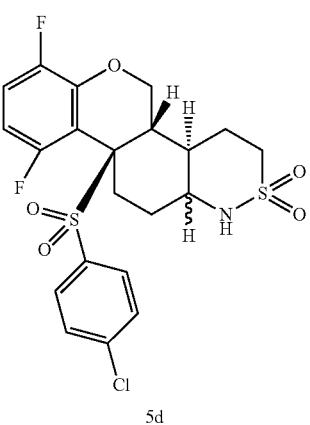<br>5d | 503.96 | 4.10 | 504.3 |

TABLE 6-continued
| Compound | Mol. Wt. | Retention Time (min) | Observed m/z |
|---|---|---|---|
| 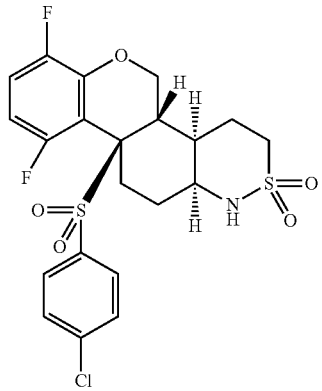 5e | 503.96 | 4.24 | 504.3 |
| 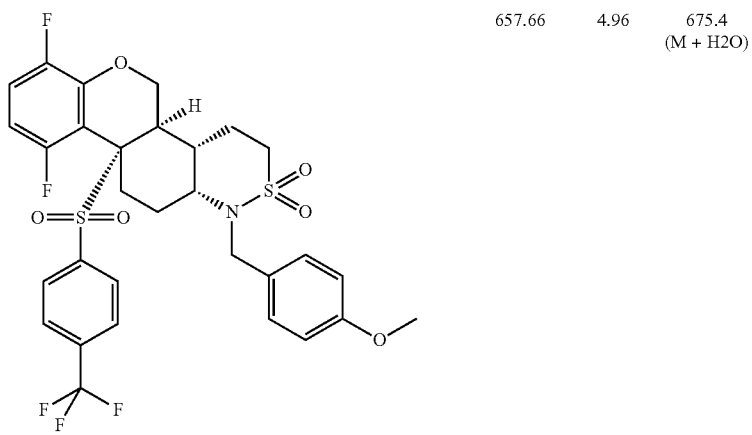 6a | 657.66 | 4.96 | 675.4 (M + H2O) |
| 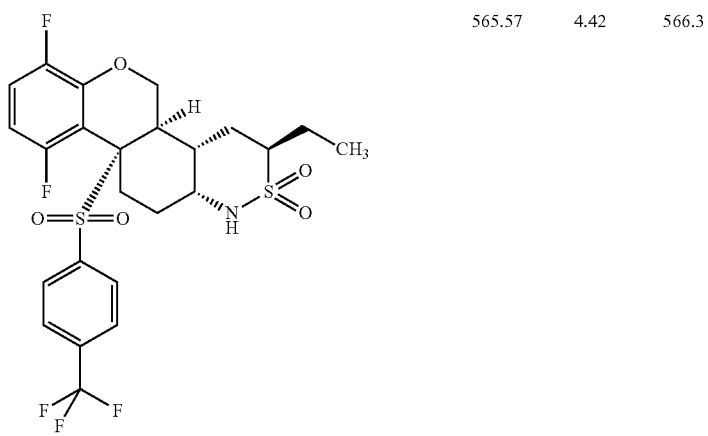 8a | 565.57 | 4.42 | 566.3 |

TABLE 6-continued
| Compound | Mol. Wt. | Retention Time (min) | Observed m/z |
|---|---|---|---|
| 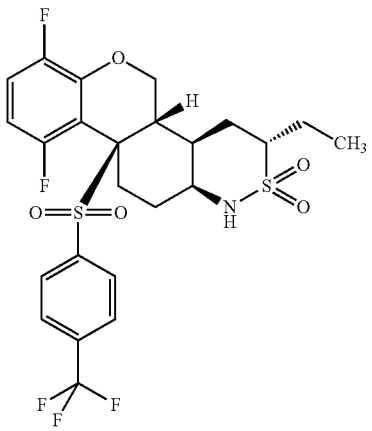 8c | 565.57 | 4.4 | 566.3 |
| 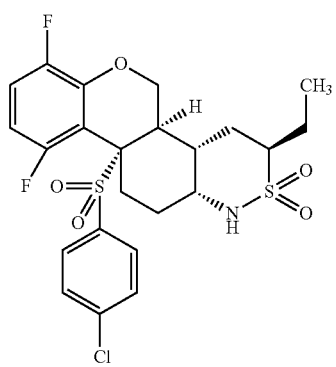 8b | 532.02 | 4.39 | 532.3 |
| 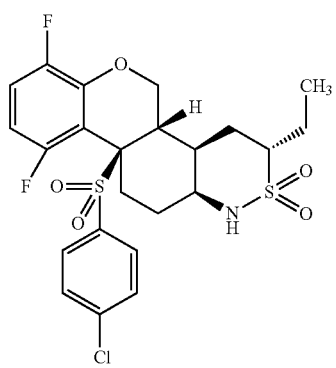 8e | 532.02 | 4.88 | 532.3 |

TABLE 6-continued
| Compound | Mol. Wt. | Retention Time (min) | Observed m/z |
|---|---|---|---|
| 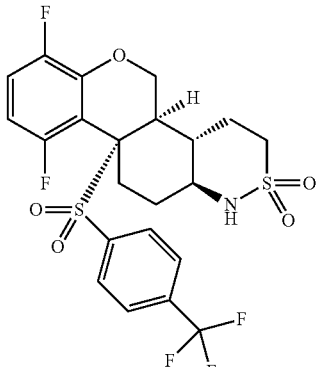<br>8f | 537.51 | 4.36 | 538.3 |
| 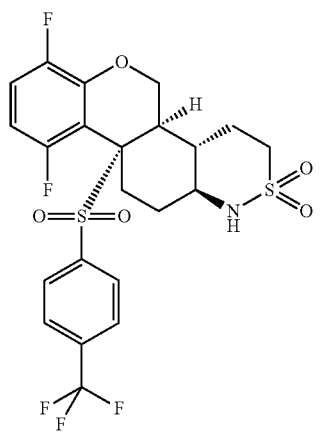<br>5a | 537.51 | 4.19 | 538.3 |
| 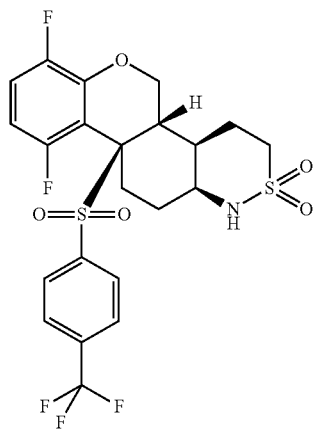<br>5a1 | 537.51 | 4.07 | 538.3 |

TABLE 6-continued
| Compound | Mol. Wt. | Retention Time (min) | Observed m/z |
|---|---|---|---|
| 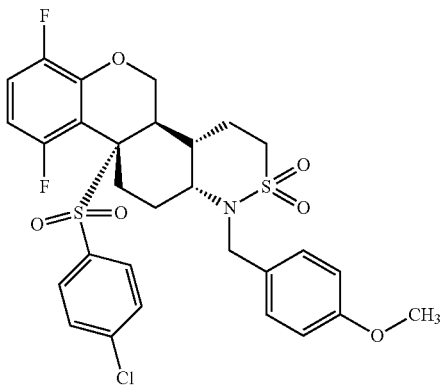 6b | 624.11 | 4.80 | 641.4 (M + H2O) |
| 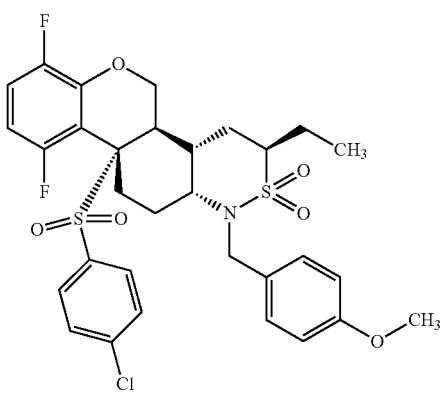 7b | 652.16 | 5.11 | 652.4 |
| 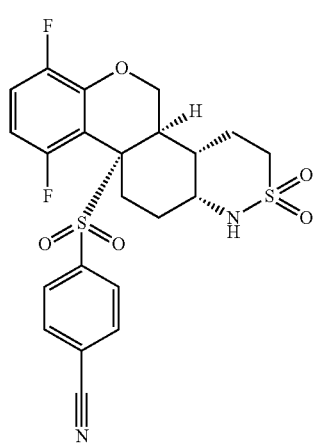 5c | 494.53 | 3.91 | 495.3 |

TABLE 6-continued
| Compound | Mol. Wt. | Retention Time (min) | Observed m/z |
|---|---|---|---|
| 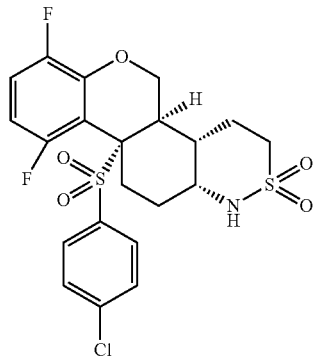 5b | 503.96 | 4.23 | 504.3 |
| 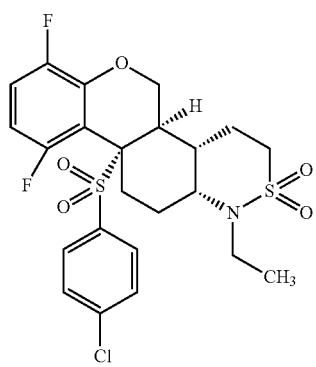 5b2 | 532.02 | 4.60 | 532.3 |
| 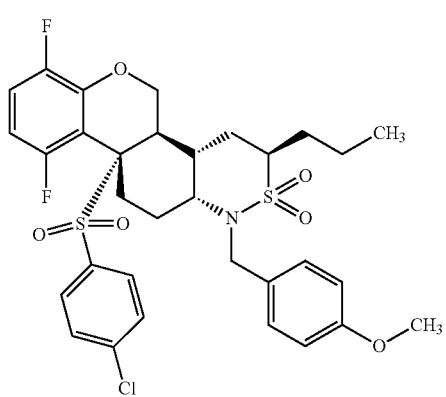 7e | 666.19 | 5.39 | 667.4 |

TABLE 6-continued
| Compound | Mol. Wt. | Retention Time (min) | Observed m/z |
|---|---|---|---|
| 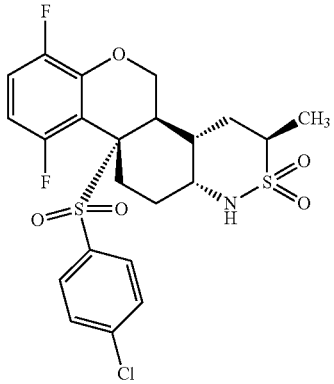 8e | 517.99 | 4.39 | 518.3 |
| 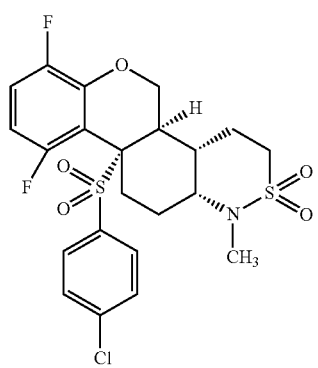 5b3 | 517.99 | 4.44 | 518.3 |
| 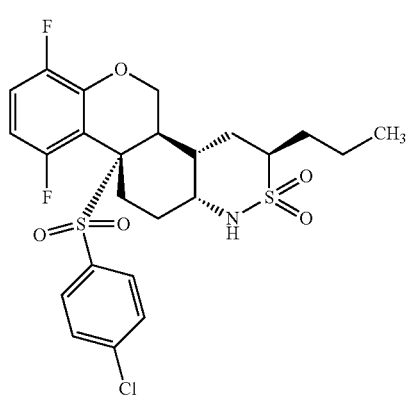 7f | 546.04 | 4.69 | 546.3 |

TABLE 6-continued
| Compound | Mol. Wt. | Retention Time (min) | Observed m/z |
|---|---|---|---|
| 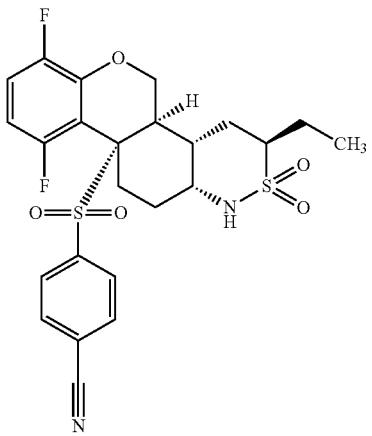 8c1 | 522.58 | 4.20 | 523.3 |
| 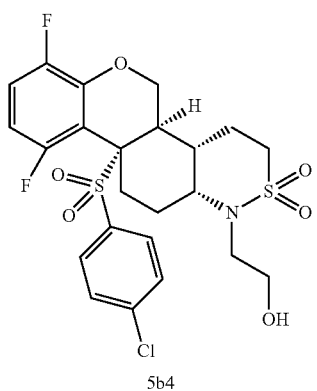 5b4 | 548.01 | 5.04 | 549.3 |
| 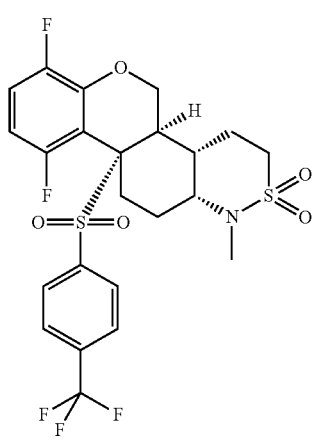 5b5 | 551.54 | 4.51 | 552.3 |

TABLE 6-continued
| Compound | Mol. Wt. | Retention Time (min) | Observed m/z |
|---|---|---|---|
| 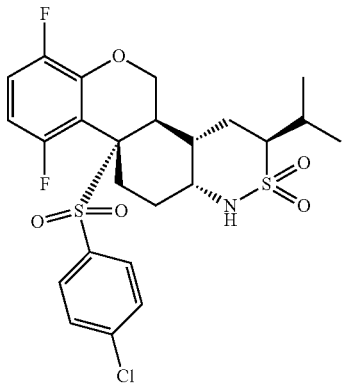 7g | 546.04 | 4.69 | 546.3 |
| 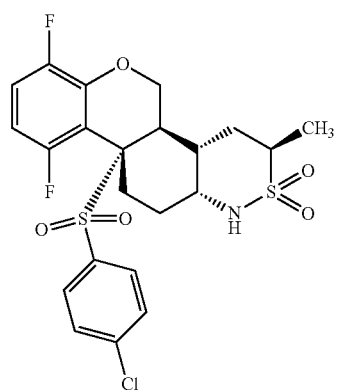 8g | 517.99 | 4.46 | 518.3 |
| 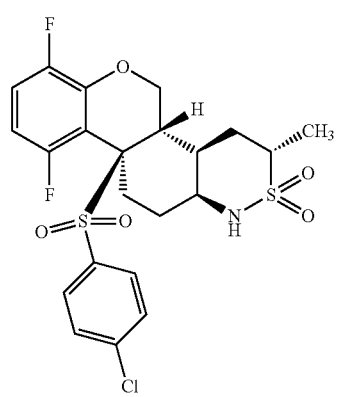 8h | 517.99 | 4.47 | 518.3 |

TABLE 6-continued
| Compound | Mol. Wt. | Retention Time (min) | Observed m/z |
|---|---|---|---|
| 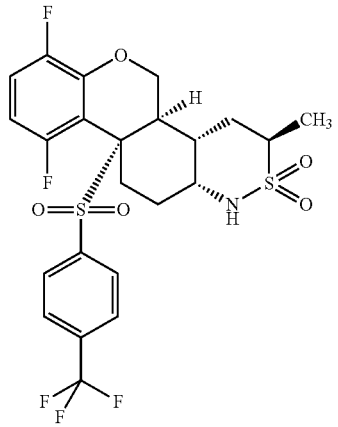<br>8d | 551.54 | 4.39 | 552.3 |
| 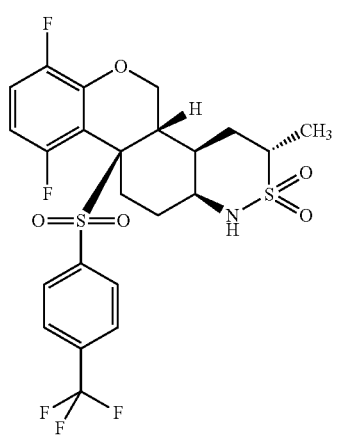<br>8d2 | 551.54 | 4.4 | 552.3 |
| 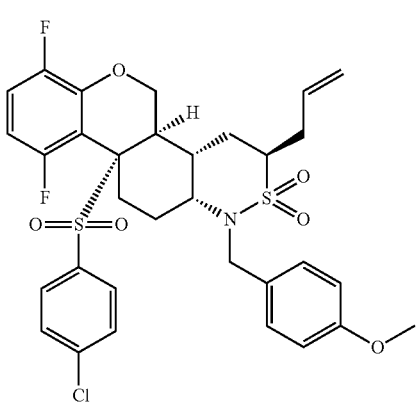<br>36b | 664.17 | 5.28 | 644.4 |

TABLE 6-continued
| Compound | Mol. Wt. | Retention Time (min) | Observed m/z |
|---|---|---|---|
| 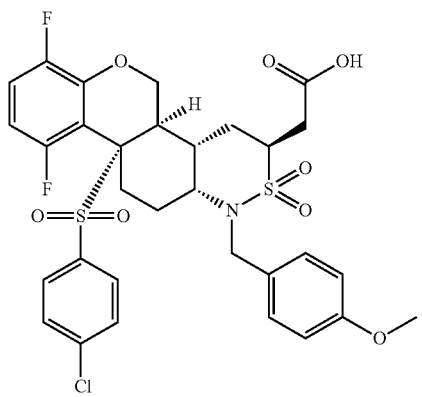 36c | 682.15 | 4.65 | 682.4 |
| 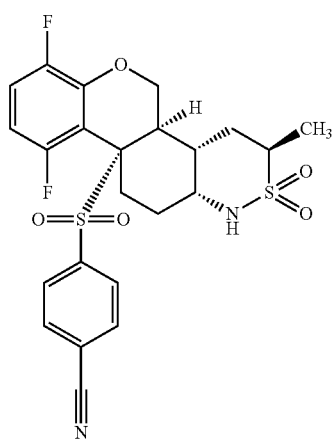 8e1 | 508.55 | 4.20 | 509.3 |
| 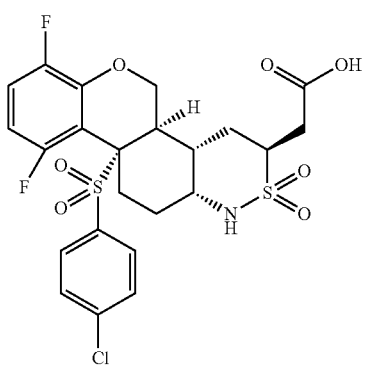 36d | 562.00 | 3.95 | 562.3 |

TABLE 6-continued
| Compound | Mol. Wt. | Retention Time (min) | Observed m/z |
|---|---|---|---|
| 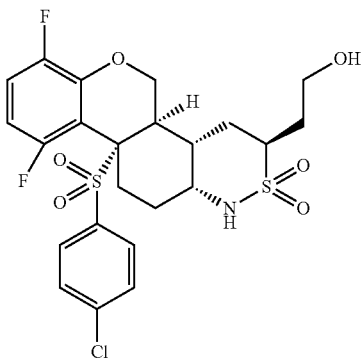 42a | 548.01 | 4.2 | 549.3 |
| 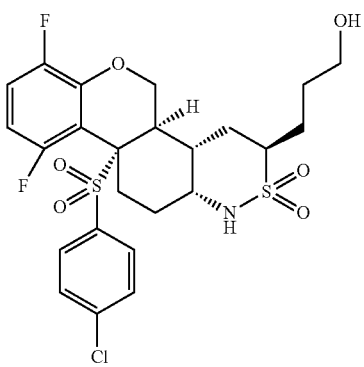 42b | 562.04 | 4.0 | 562.3 |
| 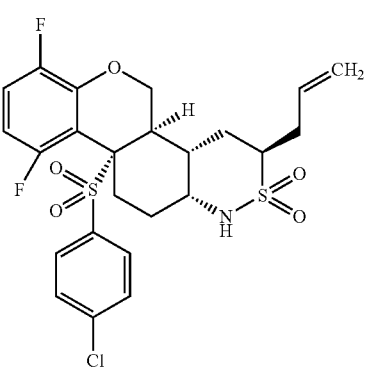 36e | 544.03 | 4.69 | 544.3 |

TABLE 6-continued
| Compound | Mol. Wt. | Retention Time (min) | Observed m/z |
|---|---|---|---|
| 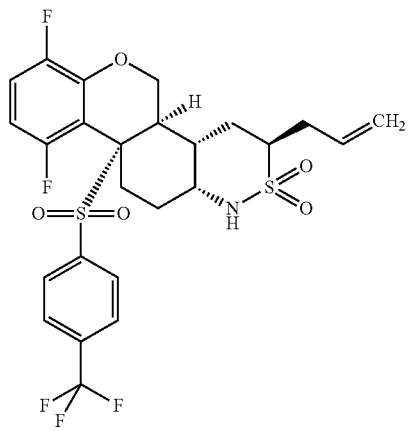 36 | 577.58 | 4.76 | 578.3 |
| 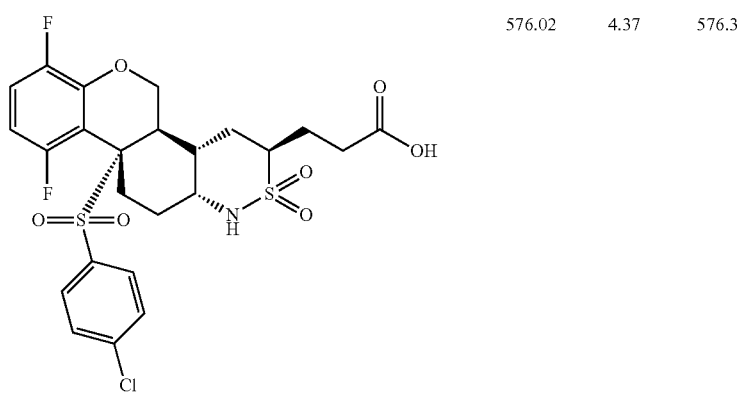 36f | 576.02 | 4.37 | 576.3 |
| 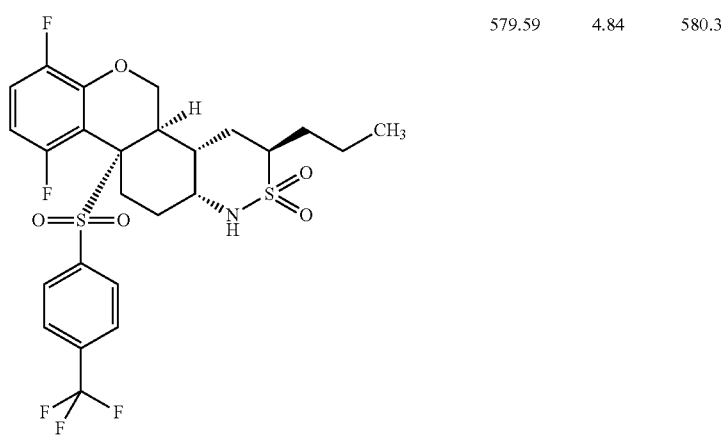 7g | 579.59 | 4.84 | 580.3 |

TABLE 6-continued
| Compound | Mol. Wt. | Retention Time (min) | Observed m/z |
|---|---|---|---|
| 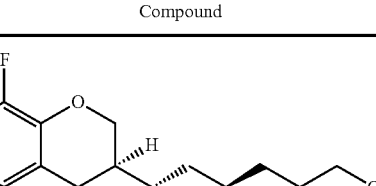 42 | 595.59 | 4.06 | 596.3 |
| 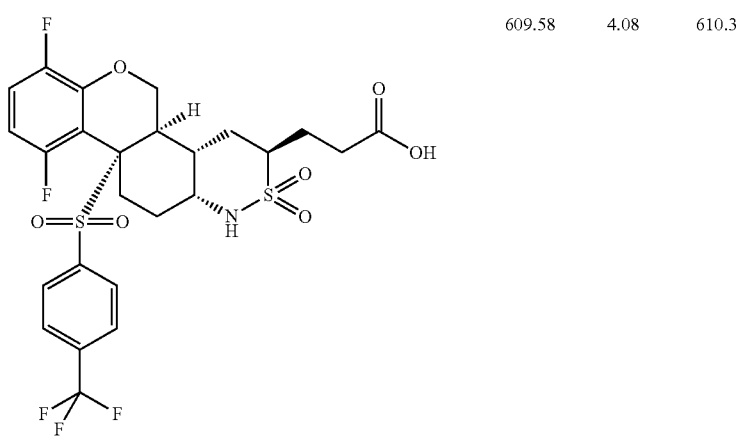 43 | 609.58 | 4.08 | 610.3 |
| 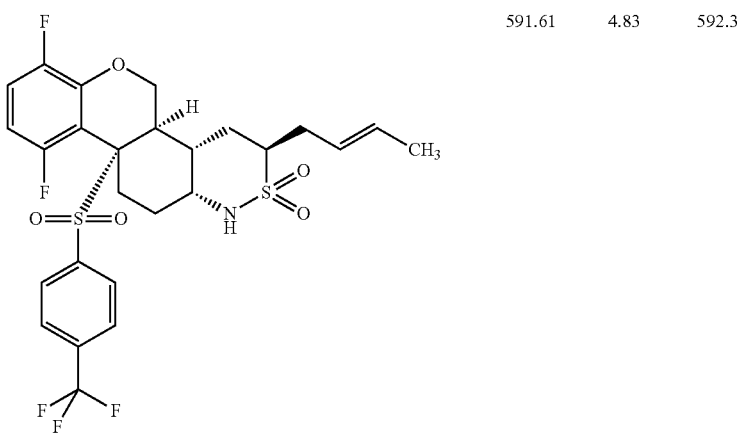 46 | 591.61 | 4.83 | 592.3 |

TABLE 6-continued
| Compound | Mol. Wt. | Retention Time (min) | Observed m/z |
|---|---|---|---|
| 44 | 622.66 | 3.08 | 623.3 |
| 45 | 657.11 | 3.25 | 657.4 |
| 47 | 653.67 | 5.18 | 654.4 |
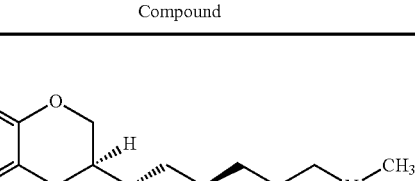

TABLE 6-continued
| Compound | Mol. Wt. | Retention Time (min) | Observed m/z |
|---|---|---|---|
| 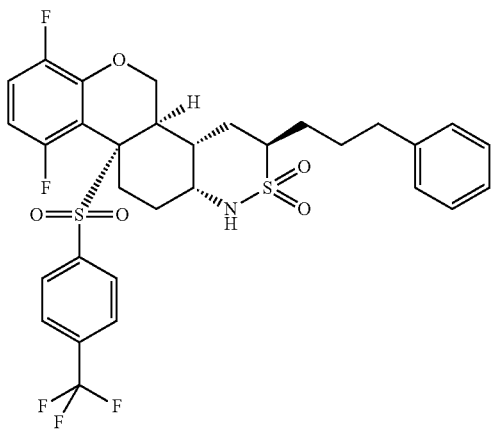
48 | 655.69 | 5.19 | 656.4 |
| 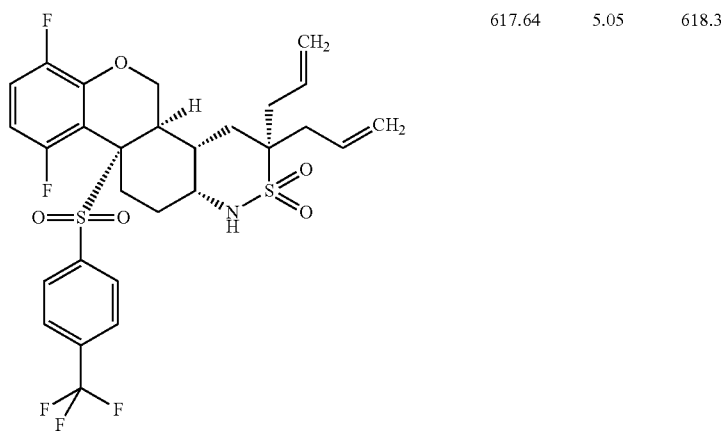
37 | 617.64 | 5.05 | 618.3 |
| 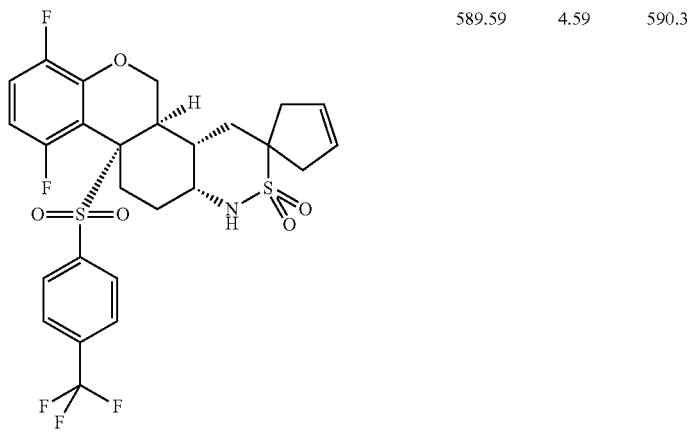
38 | 589.59 | 4.59 | 590.3 |

TABLE 6-continued
| Compound | Mol. Wt. | Retention Time (min) | Observed m/z |
|---|---|---|---|
| 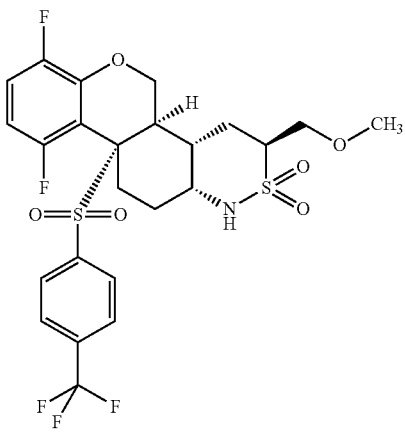<br>49 | 581.57 | 4.4 | 582.3 |
| 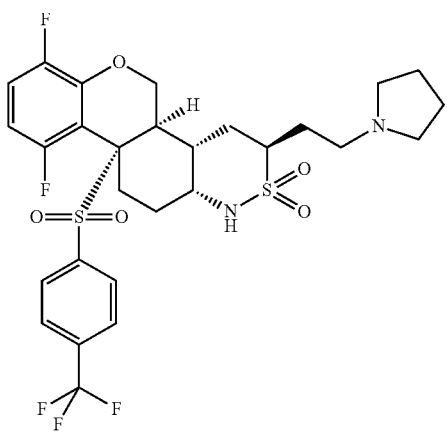<br>40 | 634.67 | 3.50 | 635.3 |
| 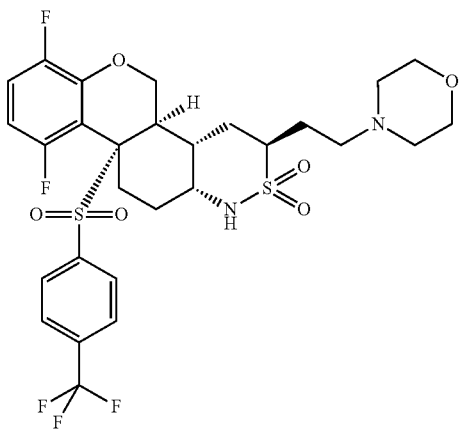<br>41 | 650.67 | 3.45 | 651.4 |

TABLE 6-continued

| Compound | Mol. Wt. | Retention Time (min) | Observed m/z |
|---|---|---|---|
| 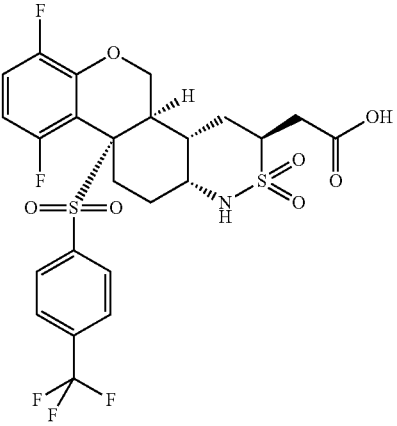<br>50 | 595.55 | 4.4 | 596.3 |
| 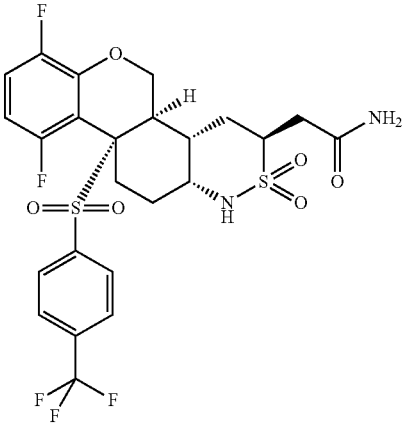<br>51 | 594.57 | 4.12 | 595.3 |

ASSAY

The pharmacological properties of the compounds of this invention may be evaluated by a number of pharmacological assays. The exemplified pharmacological assays, which are described later, have been carried out with the compounds according to the present invention, as well as with salts thereof.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents.

Antibodies WO2, G2-10, and G2-11 were obtained from Dr. Konrad Beyreuther (University of Heidelberg, Heidelberg, Germany). WO2 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction.

The construct SPC99-lon, which contains the first 18 residues and the C-terminal 99 amino acids of APP carrying the London mutation, has been described (Zhang, L., Song, L., and Parker, E. (1999) J. Biol. Chem. 274, 8966-8972). Upon insertion into the membrane, the 17 amino acid signal peptide is processed, leaving an additional leucine at the N-terminus of Aβ. SPC99-lon was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation.

C99 expression in cells was induced with 0.1 g/mL tetracycline for 20 h. The cells were pretreated with 1M phorbol 12-myristate 13-acetate (PMA) and 1M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis.

To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

Compounds 4a, 4b, 5a, 5a1, 8a, 5b, 5b2, 5b3, 5b5, 5c, 5d, 5e, 7b, 7e, 7f, 7g, 8a, 8a1, 8b, 8b1, 8c, 8c1, 8d, 8d2, 8e, 8e1, 8f, 8g, 8h, 10b, 11b1, 11b2, 11b3, 12b1, 12b2, 12b3, 13b1, 13b2, 13b3, 14b1, 14b2, 14b3, 16b, 17b, 20b, 28, 29, 30, 31, 33, 36, 36b, 36c, 36d, 36e, 36f, 37, 38, 40, 41, 42, 42a, 42b, 43, 44, 45, 46, 47, 48, 49, 50 and 51 had an IC$_{50}$ in the range of 1.3 nM to 8680 nM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

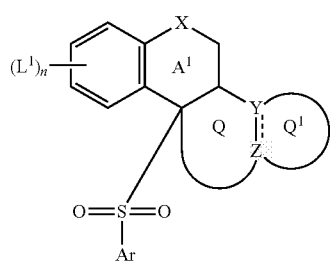

(1.0)

or a pharmaceutically acceptable salt thereof, wherein:
X is selected from the group consisting of —C(R$^1$)$_2$—, —O—, —S—, —S(O$_2$)—, —NR$^1$—, and —N(C(O)R$^1$)—;

The dotted line ( ---- ) represents an optional bond between Y and Z;

Y is selected from the group consisting of N, CH and C, and when Y is N the optional bond is absent, when Y is CH the optional bond is absent, and when Y is C the optional bond is present;

Z is selected from the group consisting of: CH, C, and N, provided that both Y and Z are not N, and when Z is N the optional bond is absent, when Z is CH the optional bond is absent, and when Z is C the optional bond is present;

Q represents a 5 to 8 membered ring fused to Rings A$^1$ and Q$^1$, wherein Y and Z are as defined above and the remaining Q ring members are —CH$_2$— groups;

Q$^1$ is a 5 to 7 membered ring (including Y and Z) fused to Ring Q, said Q$^1$ ring comprising at least one heteroatom selected from the group consisting of N, S, S(O), and S(O)$_2$, or Q$^1$ is a 5 membered ring comprising an oxygen atom; or Q$^1$ is a 5 to 7 membered ring (including Y and Z) fused to Ring Q, said Q$^1$ ring comprising at least one heteroatom selected from the group consisting of N, S, S(O), and S(O)$_2$, or Q$^1$ is a 5 membered ring comprising an oxygen atom; and said Q$^1$ ring being substituted with 1 to 3 substituents independently selected from the group consisting of: R$^3$ substituents;

Each R$^1$ is independently selected from the group consisting of H and alkyl;

R$^2$ is selected from the group consisting of: H, and alkyl;

Each R$^3$ substituent is independently selected from the group consisting of: (1) alkyl, (2) alkoxyalkyl-, (3) hydroxyalkyl, (4) —OR$^2$, (5) arylalkyl-, (6) =O, (7) substituted arylalkyl-, (8) alkenyl, (9) heterocycloalkylalkyl-, (10) -alkyl-C(O)OH, (11) -alkyl-NR$^5$R$^6$, wherein R$^5$ and R$^6$ are each independently selected from the group consisting of: H and alkyl, (12) -alkyl-C(O) NR$^5$R$^6$, wherein R$^5$ and R$^6$ are as defined in (11), (13) arylalkenyl-, (14) -alkyl-C(O)OR$^7$ wherein R$^7$ is a C$_1$ to C$_6$ alkyl group, and (15) substituted arylalkenyl-, wherein said substituted arylalkenyl- is substituted with 1 to 3 substituents independently selected from the group consisting of: —OR$^5$, —NR$^5$R$^6$, —CF$_3$, —CN, —C(O)$_2$R$^5$, and —C(O)NR$^5$R$^6$, and wherein R$^5$ and R$^6$ are as defined in (11); or two R$^3$ groups bound to the same carbon, taken together with the carbon to which they are bound, form a cycloalkyl ring or form a cycloalkenyl ring;

Ar is selected from the group consisting of: (a) unsubstituted aryl, (b) aryl substituted with one or more L$^1$ groups, (c) unsubstituted heteroaryl, and (d) substituted heteroaryl substituted with one or more L$^1$ groups;

each L$^1$ is independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$) alkyl, -alkylene-OH, halo(C$_1$-C$_6$)alkyl, hydroxyalkoxy-, and alkoxyalkoxy-; and n is 0, 1, 2 or 3.

2. The compound of claim 1 or a pharmaceutically acceptable salt thereof, wherein Y is CH, Z is CH, Q is a 6 membered ring, and Q$^1$ is a 6 membered ring comprising a nitrogen atom and a —S(O)$_2$— group, or wherein Y is —CH, Q is a 6 membered ring, Q$^1$ is a 6 membered ring comprising a nitrogen atom and a —S(O)$_2$— group, and said Q$^1$ ring is substituted with 1 to 3 substituents.

3. The compound of claim 1 or a pharmaceutically acceptable salt thereof, wherein Y is CH, Z is CH, Q is a 6 membered ring, or wherein Y is CH, Z is CH, Q is a 6 membered ring, Q$^1$ is a 5 membered ring comprising an oxygen atom and said $Q^1$ ring is substituted with 1 to 3 substituents.

4. The compound of claim 1 or a pharmaceutically acceptable salt thereof, wherein Y is CH, Z is CH, Q is a 6 membered ring, and $Q^1$ is a 5 membered ring comprising a nitrogen atom; or wherein Y is CH, Q is a 6 membered ring, $Q^1$ is a 5 membered ring comprising a nitrogen atom, and said $Q^1$ ring is substituted with 1 to 3 substituents.

5. The compound of claim 1 or a pharmaceutically acceptable salt thereof, wherein Y is C, Z is C, the optional bond between Y and Z is present, Q is a 6 membered ring, and $Q^1$ is a 5 membered ring comprising a nitrogen atom; or wherein Y is C, Z is C, the optional bond between Y and Z is present, Q is a 6 membered ring, $Q^1$ is a 5 membered ring comprising a nitrogen atom, and said $Q^1$ ring is substituted with 1 to 3 substituents.

6. The compound of claim 1 or a pharmaceutically acceptable salt thereof, wherein Y is CH, Z is CH, Q is a 6 membered ring, and $Q^1$ is a 6 membered ring comprising a nitrogen atom or wherein Y is CH, Z is CH, Q is a 6 membered ring, $Q^1$ is a 6 membered ring comprising a nitrogen atom, and said $Q^1$ ring is substituted with 1 to 3 substituents.

7. The compound of claim 1 or a pharmaceutically acceptable salt thereof, wherein Y is N, Z is CH, Q is a 6 membered ring, and $Q^1$ is a 6 membered ring comprising a nitrogen atom in addition to the nitrogen atom at Y, or wherein Y is N, Z is CH, Q is a 6 membered ring, Q1 $Q^1$ is a 6 membered ring comprising a nitrogen atom in addition to the nitrogen atom at Y, and said $Q^1$ ring is substituted with 1 to 3.

8. The compound of claim 1 or a pharmaceutically acceptable salt thereof, wherein X is O, n is 2 and $L^1$ is F.

9. The compound of claim 1 or a pharmaceutically acceptable salt thereof, wherein Ar is selected from the group consisting of: phenyl, phenyl substituted with at least one Cl, phenyl substituted with a —$CF_3$ group, and phenyl substituted with a cyano group.

10. The compound of claim 1 or a pharmaceutically acceptable salt thereof, wherein X is O, n is 2, $L^1$ is F, and Ar is selected from the group consisting of phenyl substituted with one —$CF_3$, phenyl substituted with one —CN, and phenyl substituted with one Cl.

11. The compound of claim 1 or a pharmaceutically acceptable salt thereof, wherein n is 3.

12. The compound of claim 1 wherein said compound is selected from the group consisting of the compounds of formulas:

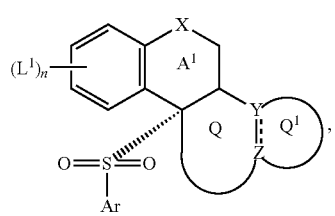

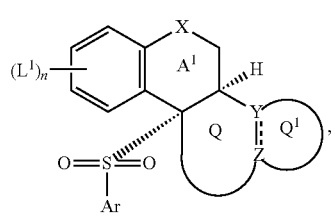

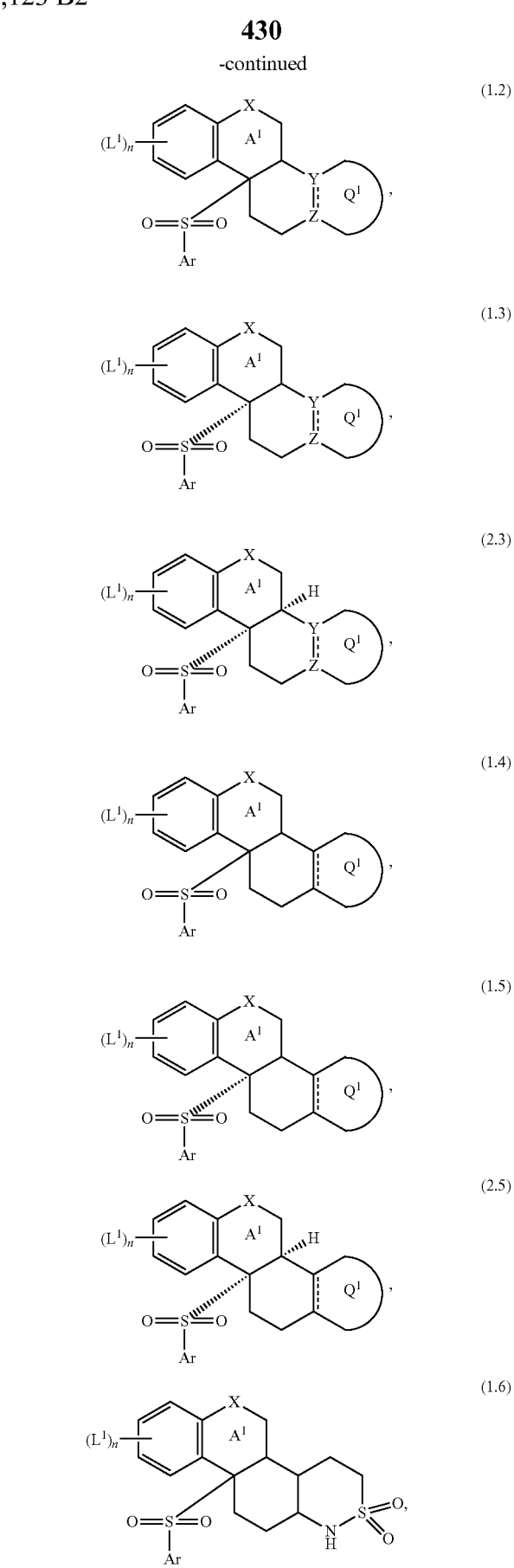

-continued
(1.7)
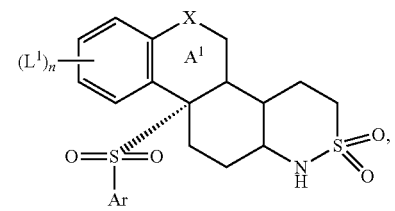
(2.7)
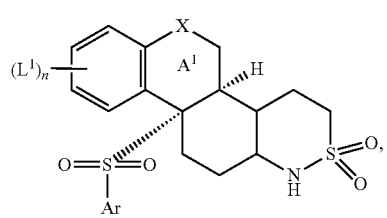
(1.8)
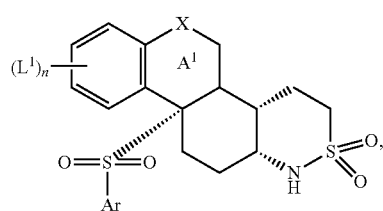
(2.8)
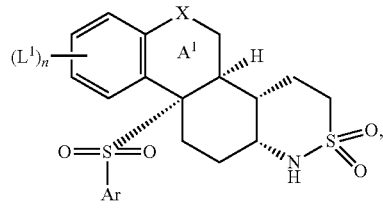
(1.9$^{A1}$)
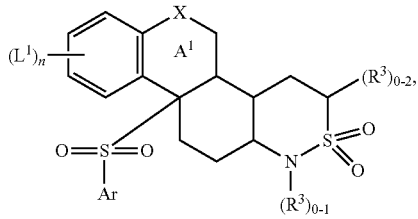
(1.9)
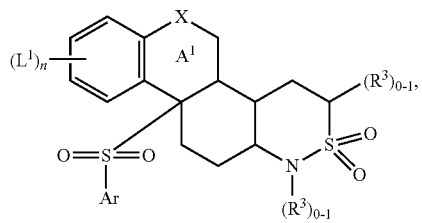
(1.10$^{A1}$)
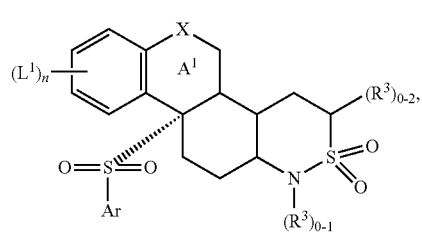
-continued
(1.10)
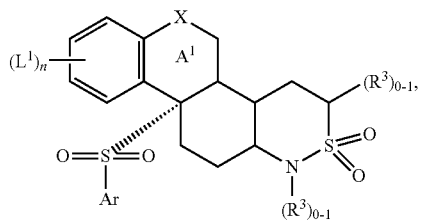
(2.10$^{A1}$)
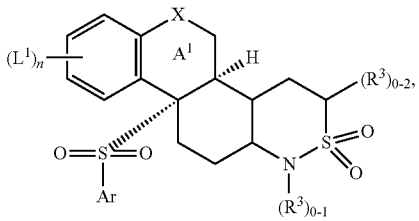
(2.10)
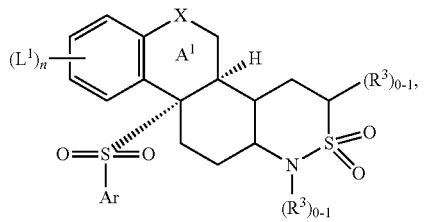
(3.10$^{A1}$)
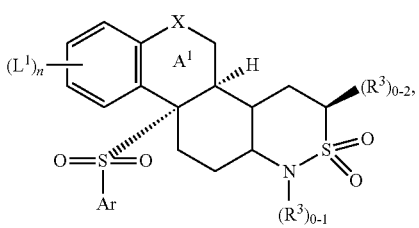
(3.10)
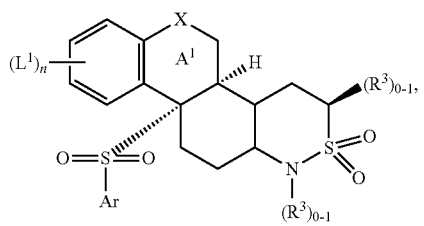
(1.11$^{A1}$)
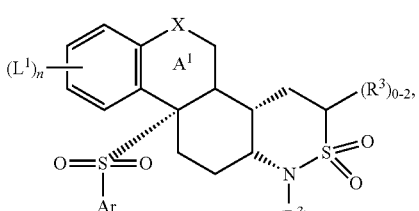
(1.11)
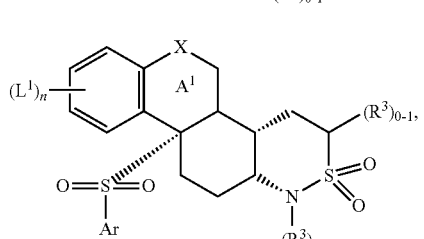

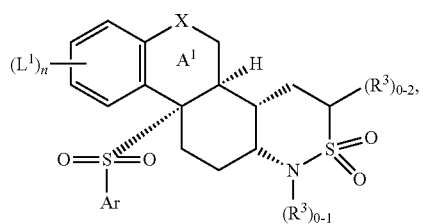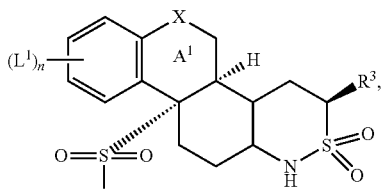

(3.16)
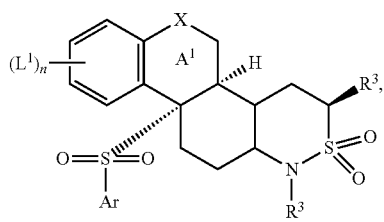
(1.17)
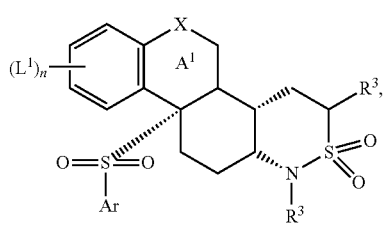
(2.17)
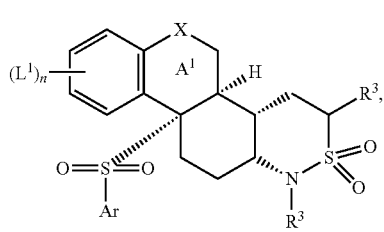
(3.17)
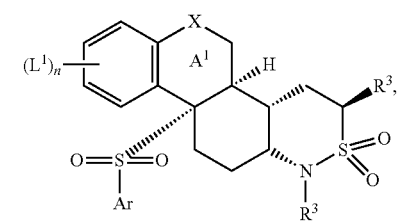
(1.18)
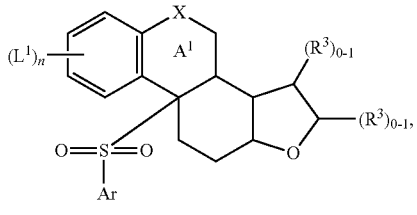
(1.19)
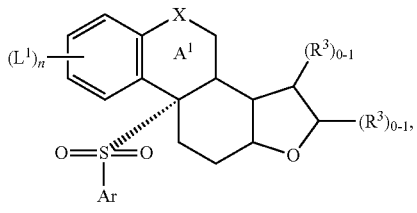
(1.20)
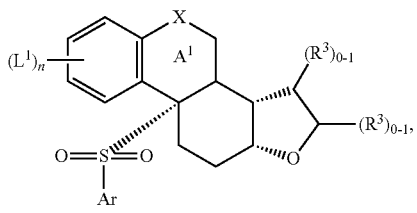
(1.18A)
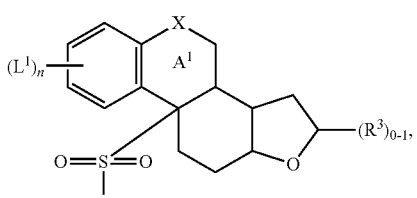
(1.19A)
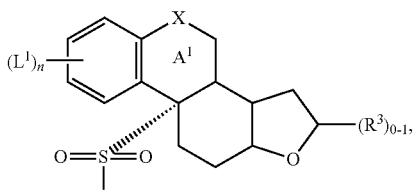
(1.20A)
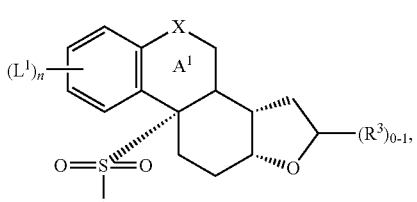
(1.21)
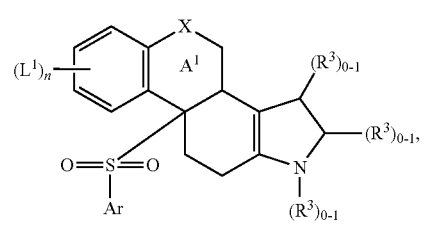
(1.22)
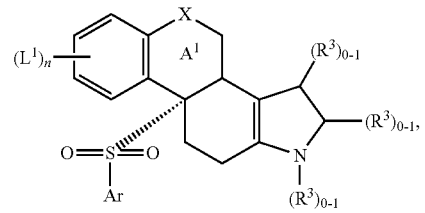
(1.21A)
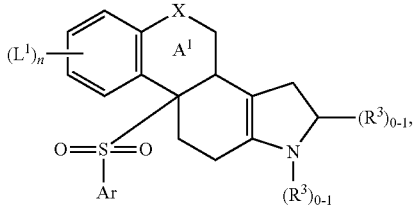
(1.22A)
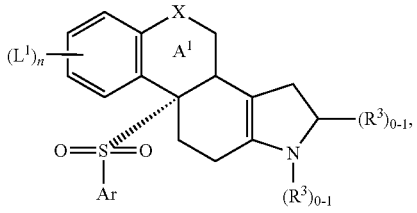

-continued

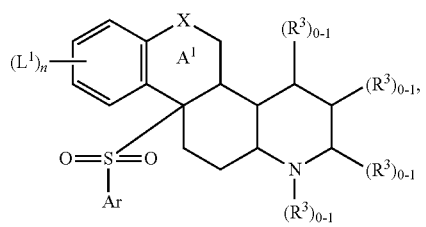
(1.34)
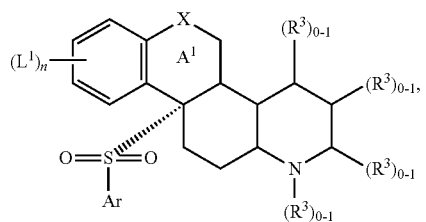
(1.35)
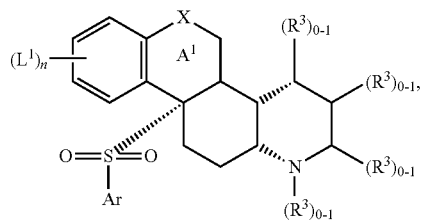
(1.36)
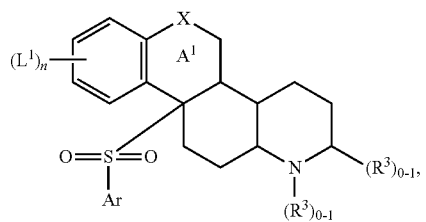
(1.37)
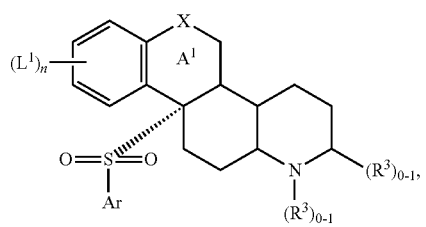
(1.38)
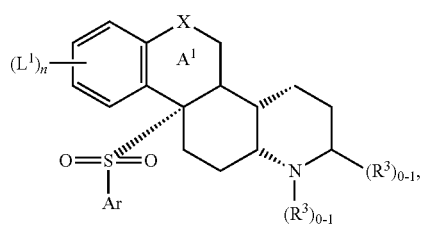
(1.39)
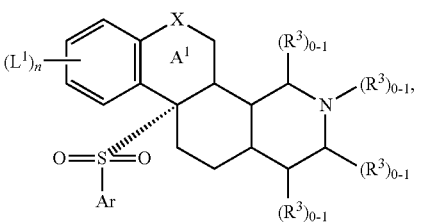
(1.35C)
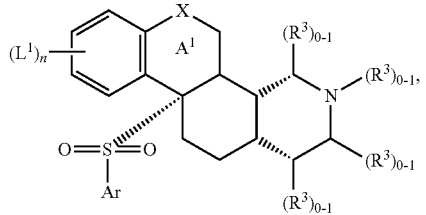
(1.36C)
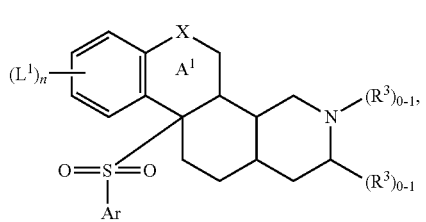
(1.37C)
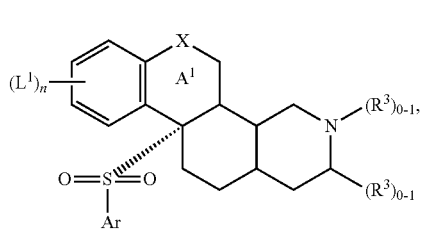
(1.38C)
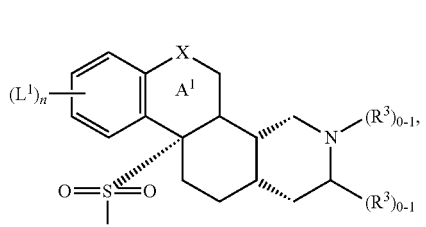
(1.39C)
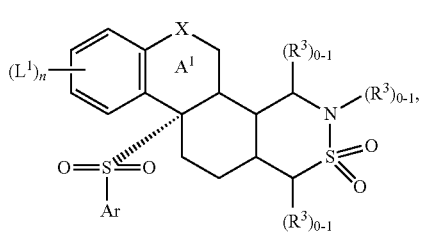
(1.35D)
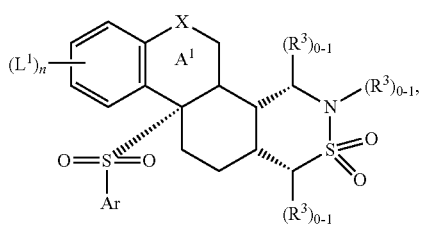
(1.36D)
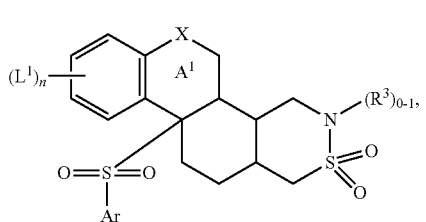
(1.37D)

-continued
(1.38D)
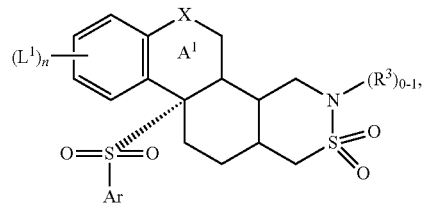
(1.39D)
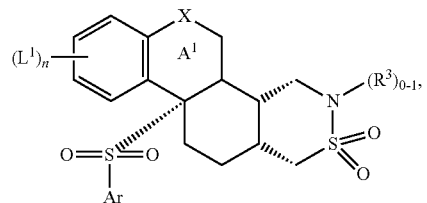
(1.35E)
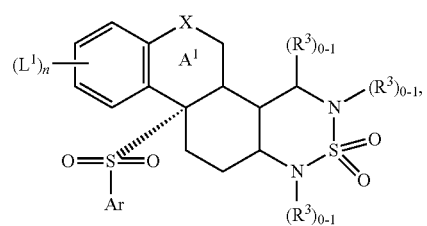
(1.36E)
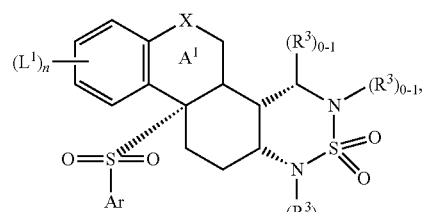
(1.37E)
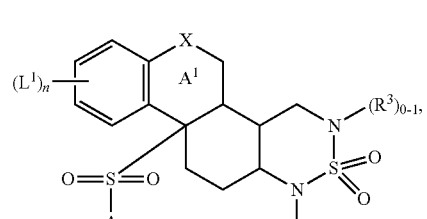
(1.38E)
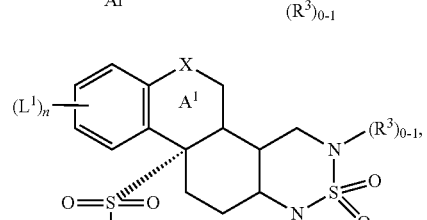
(1.39E)
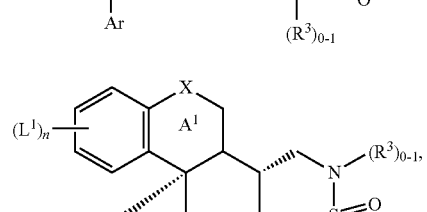
-continued
(1.40)
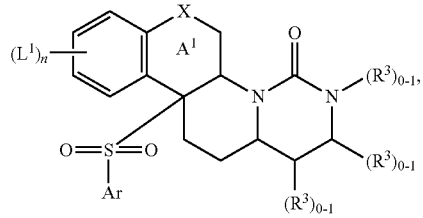
(1.41)
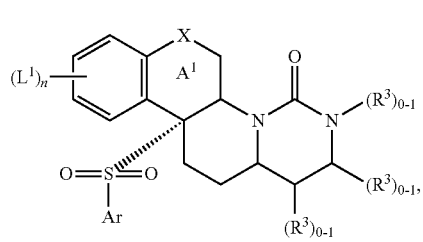
(1.42)
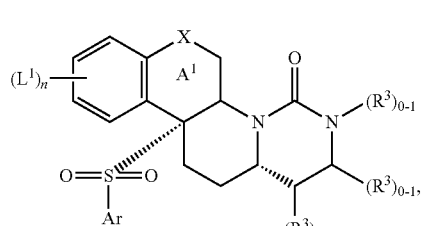
(1.40C)
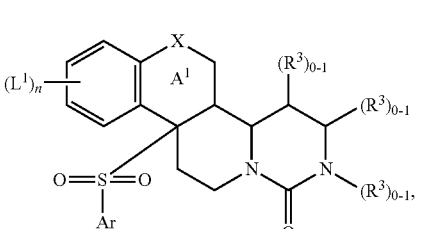
(1.41C)
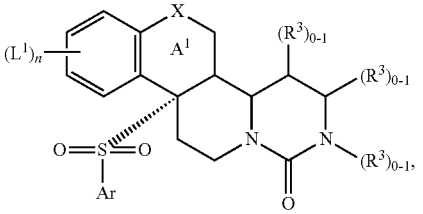
(1.43)
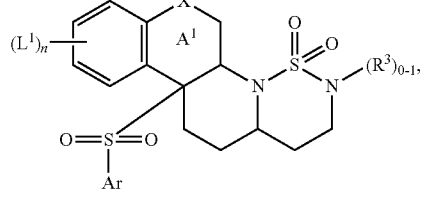
(1.42C)
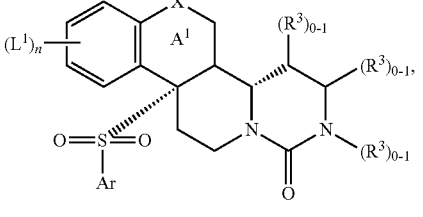

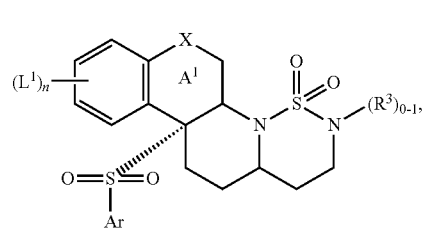 (1.44)
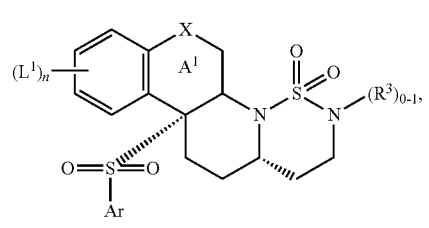 (1.45)
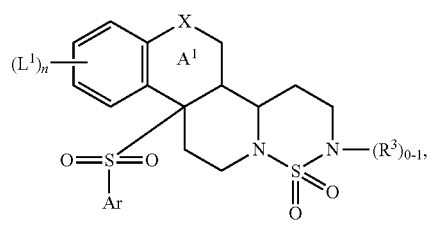 (1.43C)
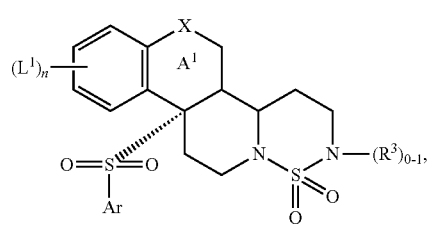 (1.44C)
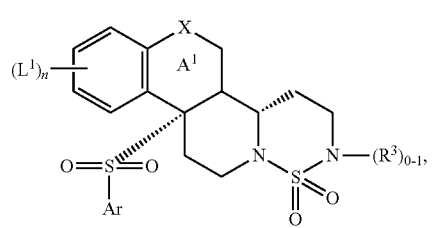 (1.45C)
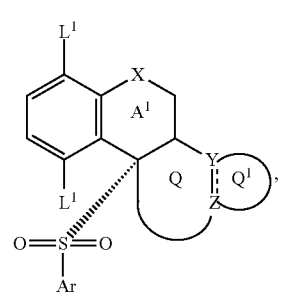 (1.1A)
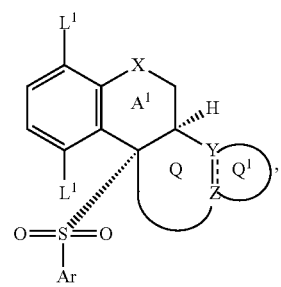 (2.1A)
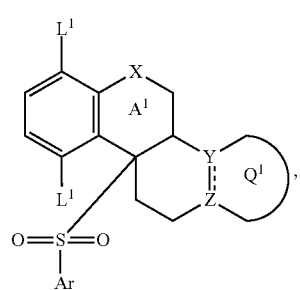 (1.2A)
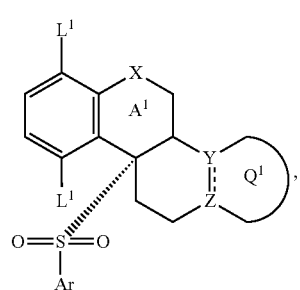 (1.3A)
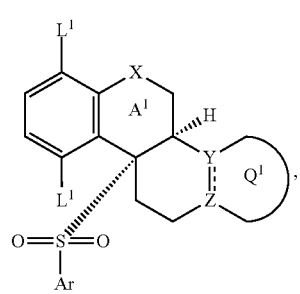 (2.3A)
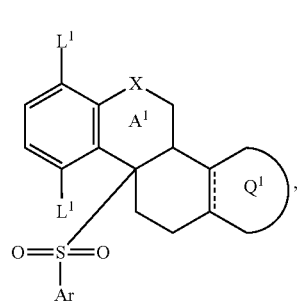 (1.4A)

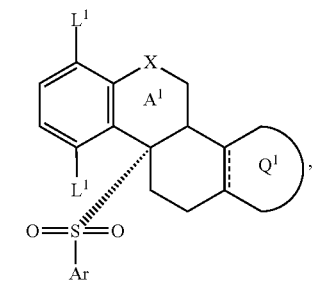
(1.5A)
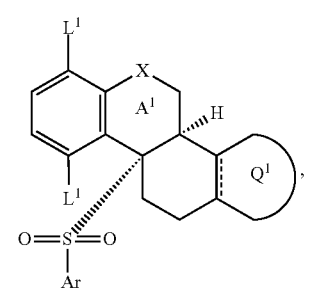
(2.5A)
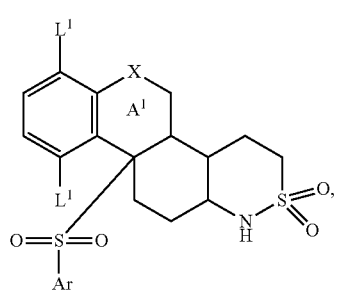
(1.6A)
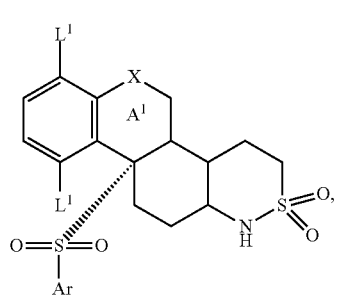
(1.7A)
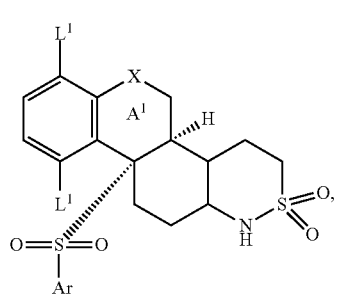
(2.7A)
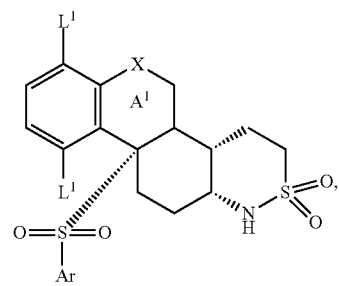
(1.8A)
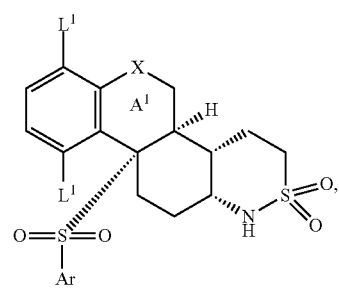
(2.8A)
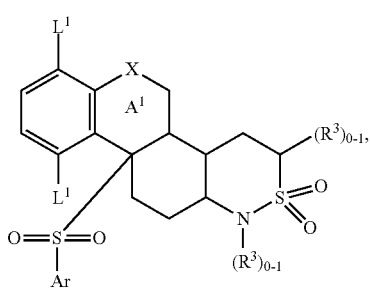
(1.9A)
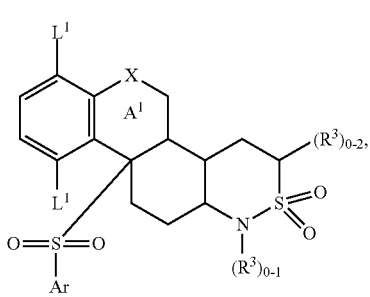
(1.9$^{A2}$)
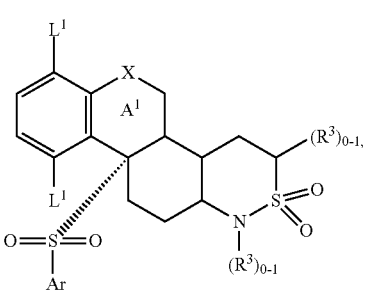
(1.10A)

-continued
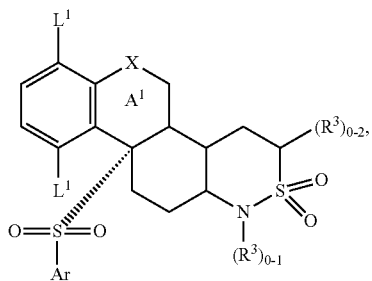
(1.10^42)
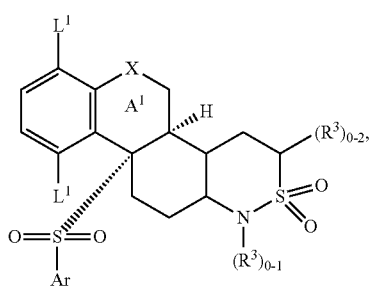
(2.10^42)
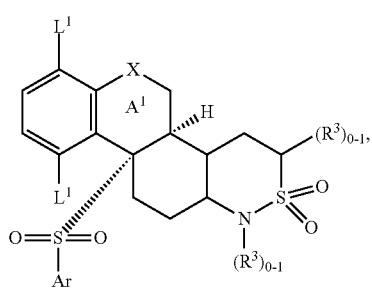
(2.10A)
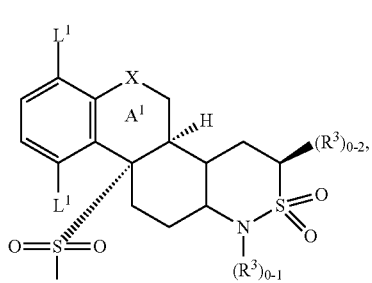
(3.10^42)
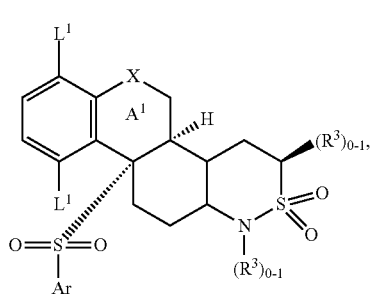
(3.10A)
-continued
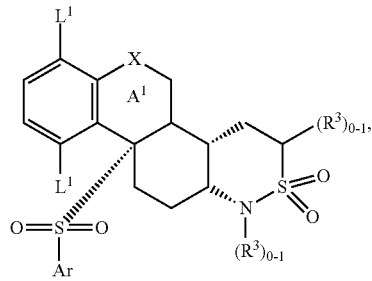
(1.11A)
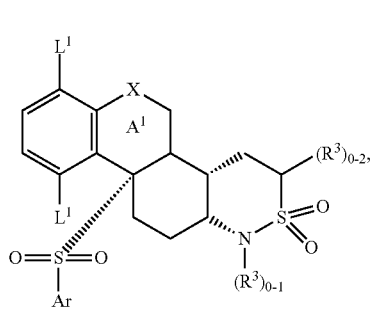
(1.11^42)
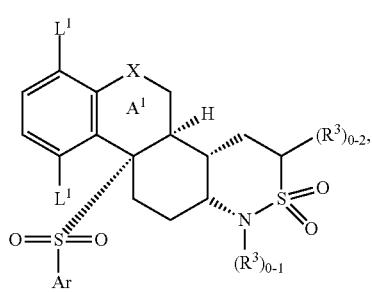
(2.11^42)
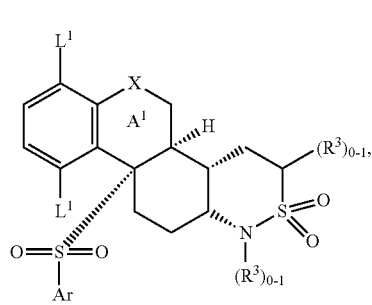
(2.11A)
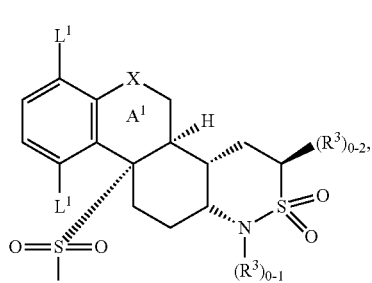
(3.11^42)

449
-continued
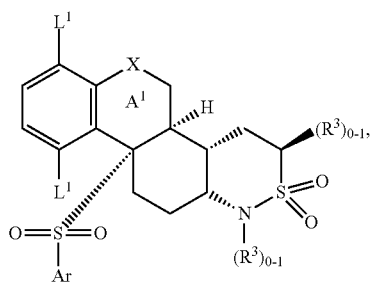
(3.11A)
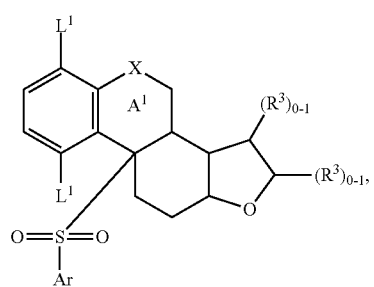
(1.18B)
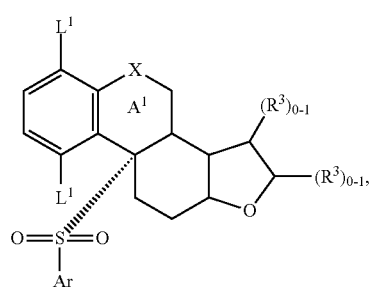
(1.19B)
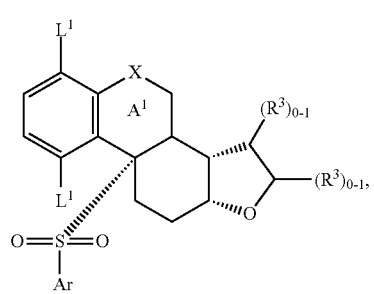
(1.20B)
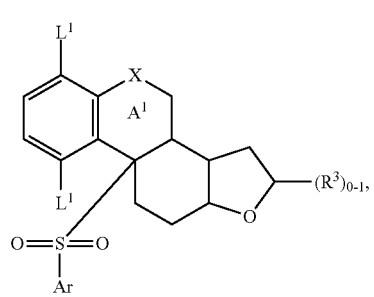
(1.18C)
450
-continued
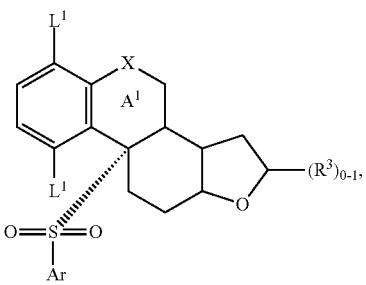
(1.19C)
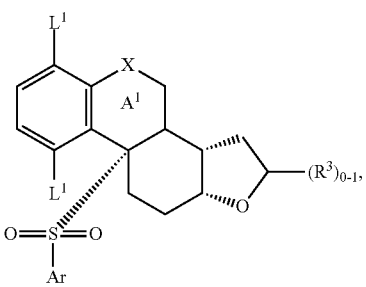
(1.20C)
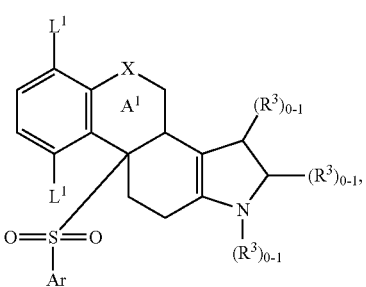
(1.21B)
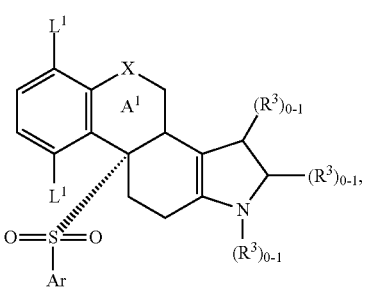
(1.22B)
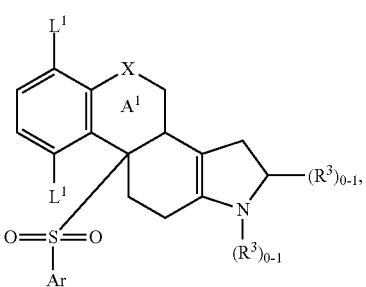
(1.21C)

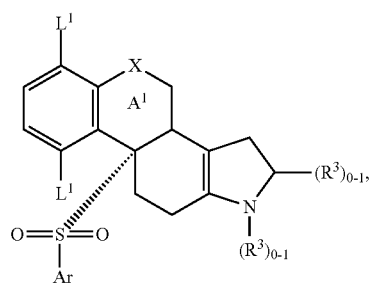
(1.22C)
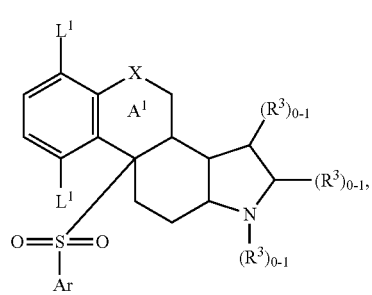
(1.23B)
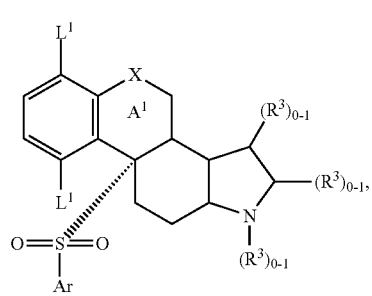
(1.24B)
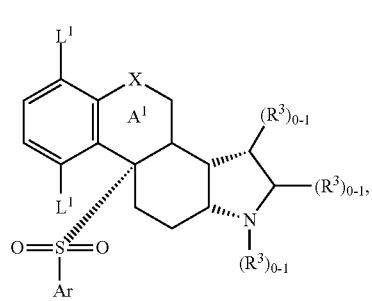
(1.25B)
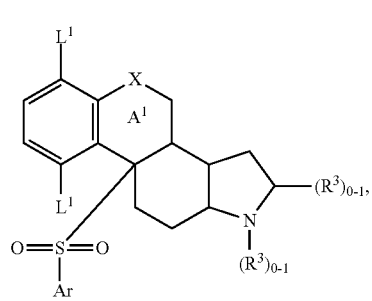
(1.23C)
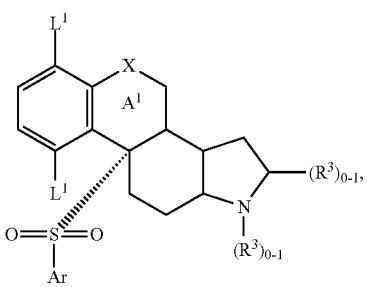
(1.24C)
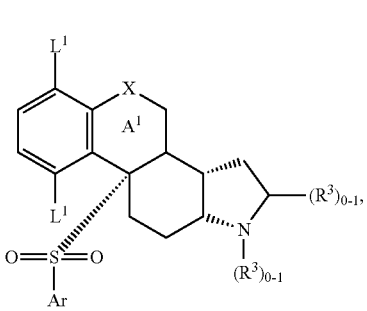
(1.25C)
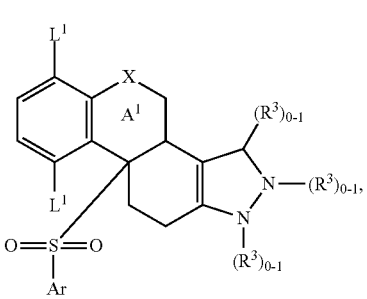
(1.26A)
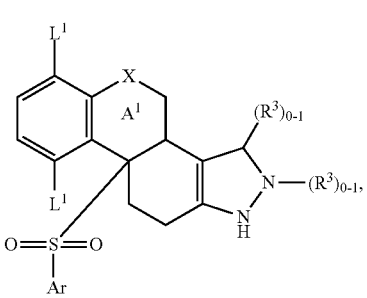
(1.27A)
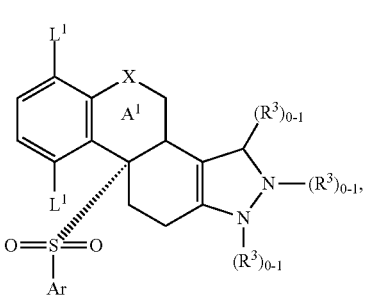
(1.28A)

(1.29A) 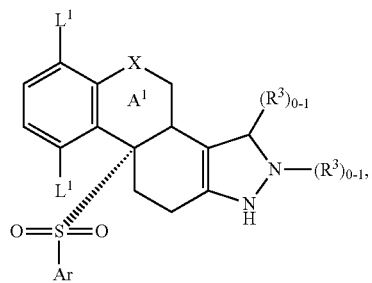
(1.30A) 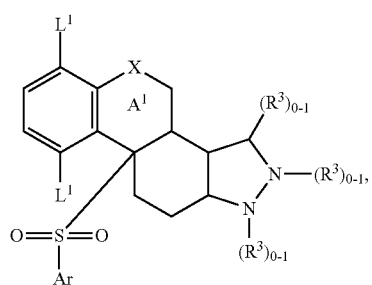
(1.31A) 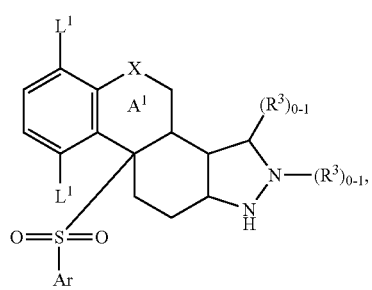
(1.32A) 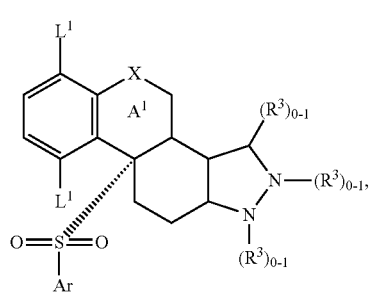
(1.33A) 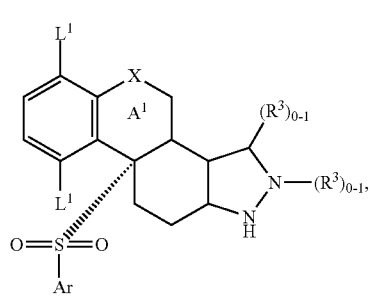
(1.34A) 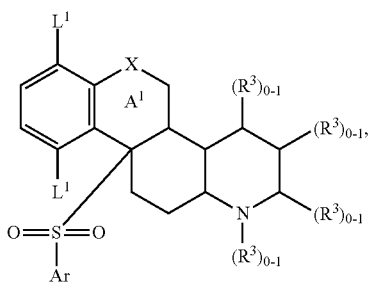
(1.35A) 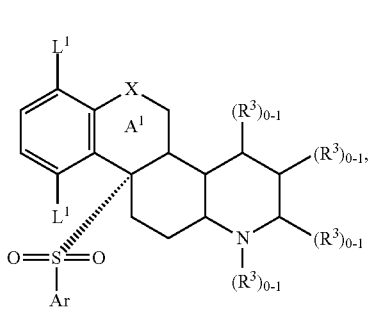
(1.36A) 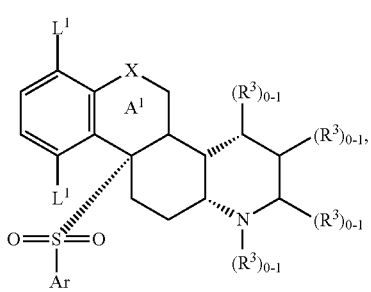
(1.37A) 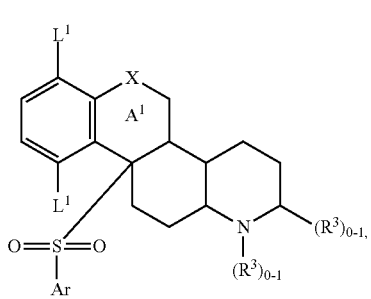
(1.38A) 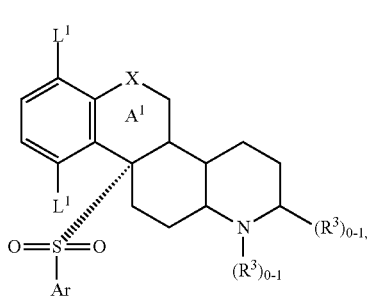

-continued
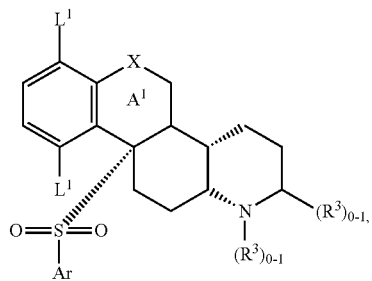 (1.39A)
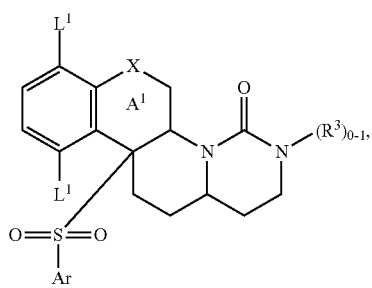 (1.40A)
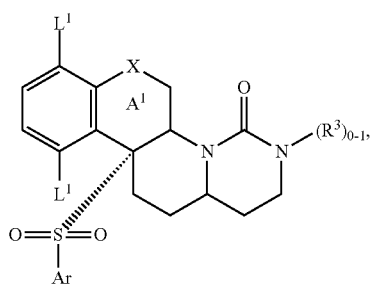 (1.41A)
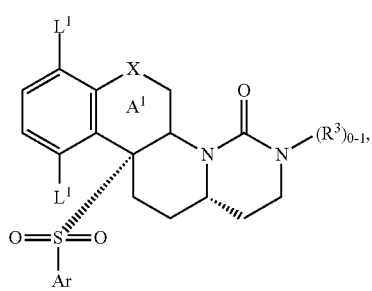 (1.42A)
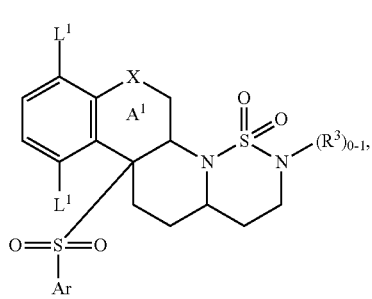 (1.43A)
-continued
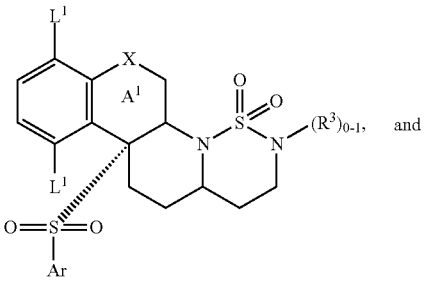 (1.44A) and
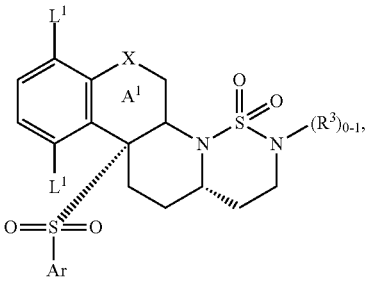 (1.45A)
or a pharmaceutically acceptable salt thereof.
13. A compound selected from the group consisting of:
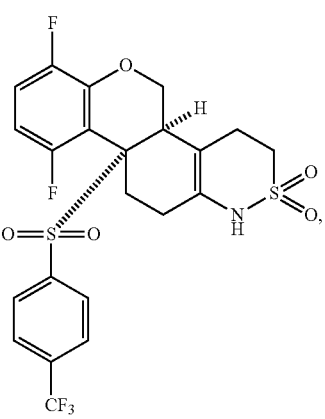 4a
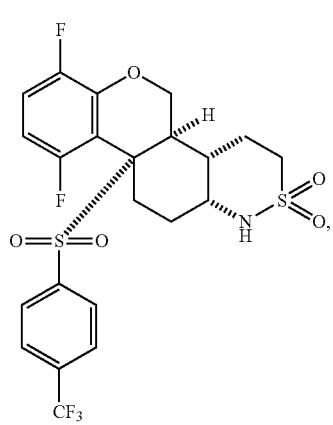 5a

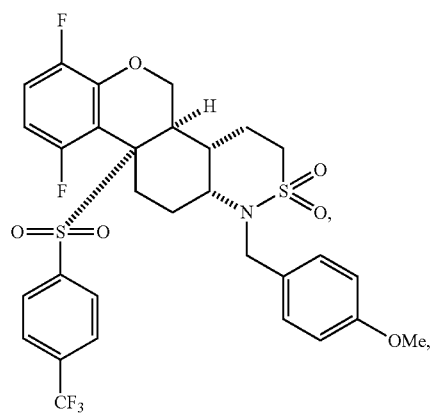
6a
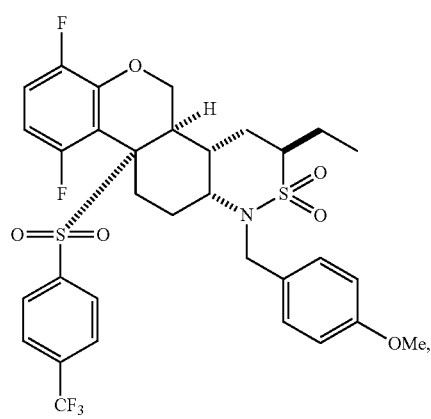
7a
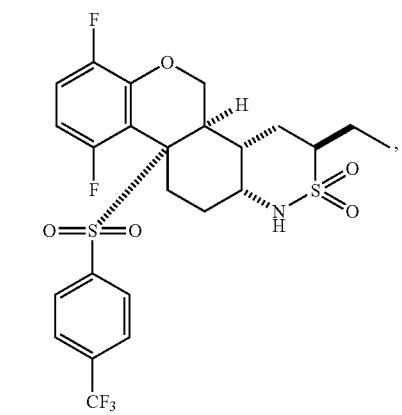
8a
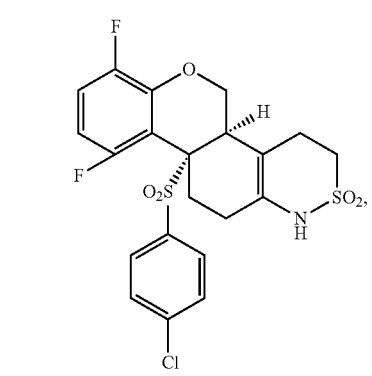
4b
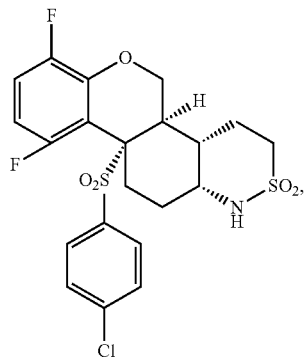
5b
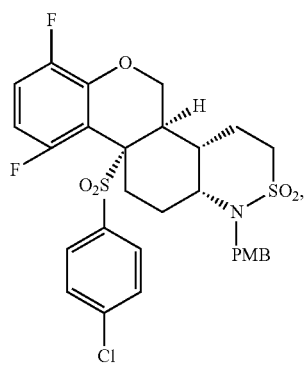
6b
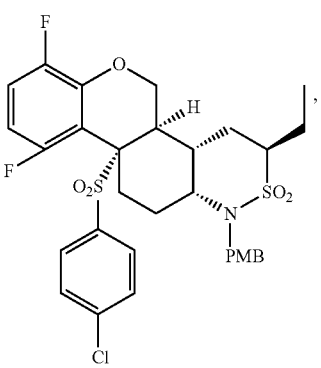
7b
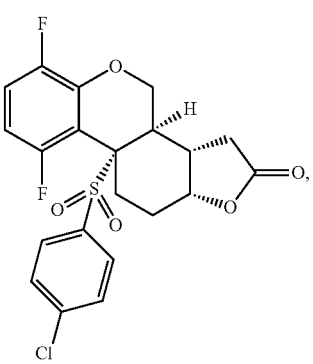
10b 11b1
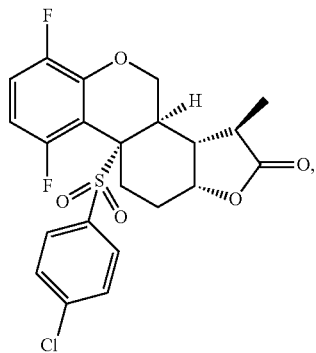
11b2
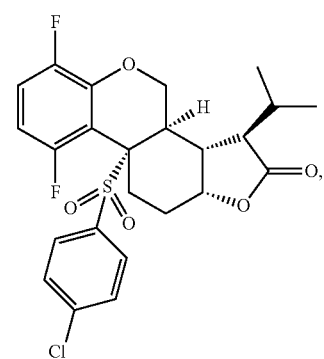
11b3
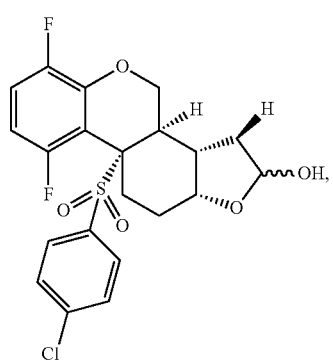
12b1
12b2
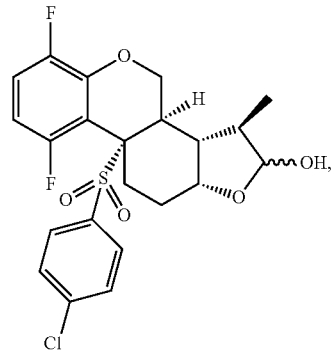
12b3
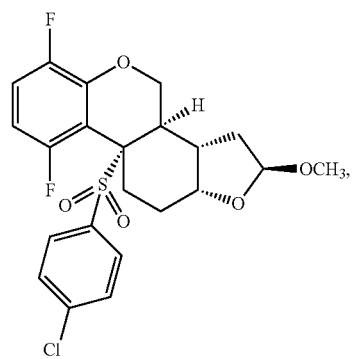
13b1
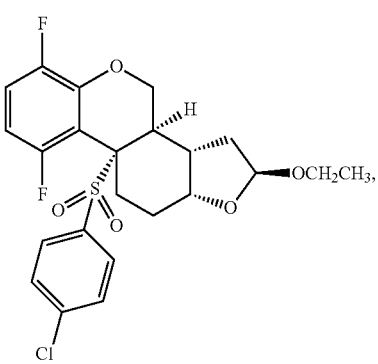
13b2

-continued
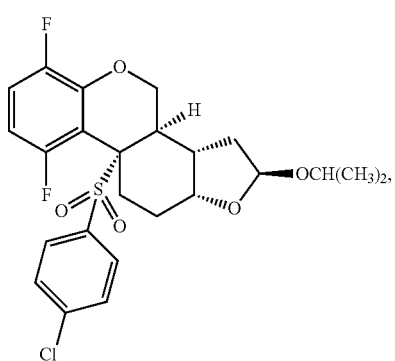 13b3
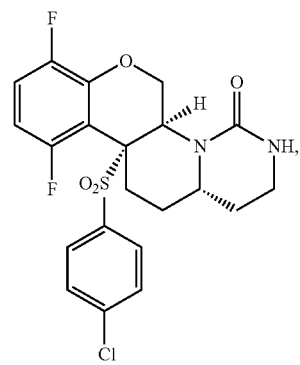 28
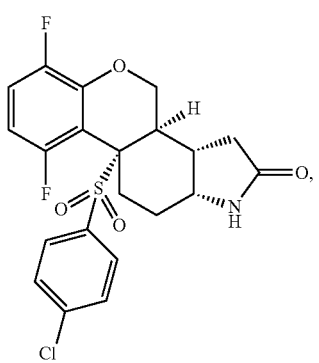 16b
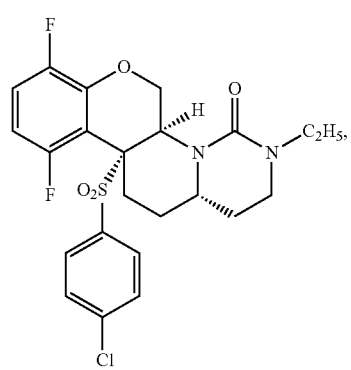 29
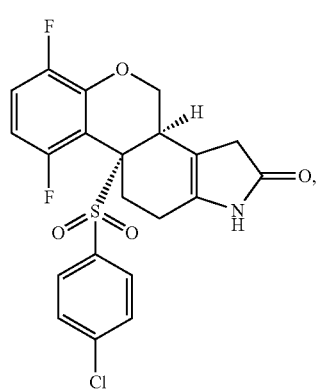 17b
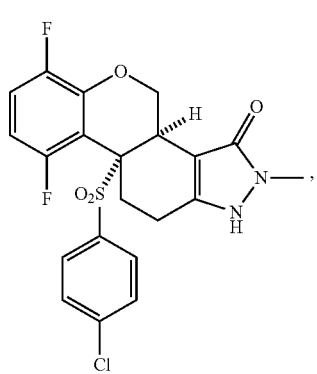 33
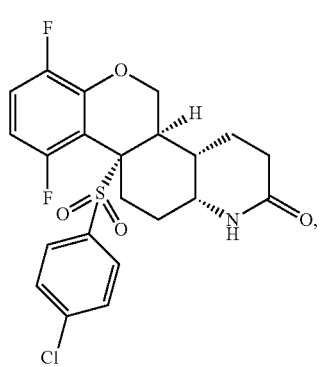 20b
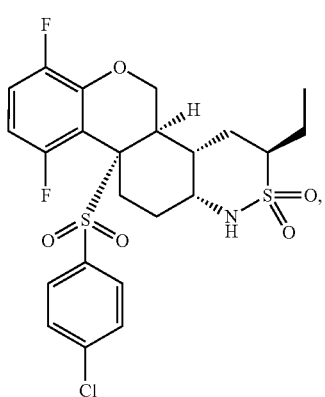 8b1

463
-continued
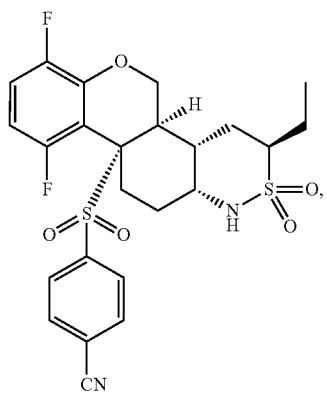
8c1
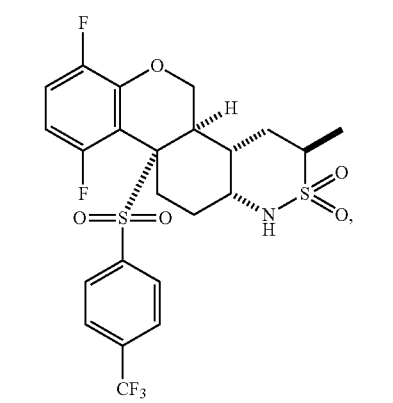
36
464
-continued
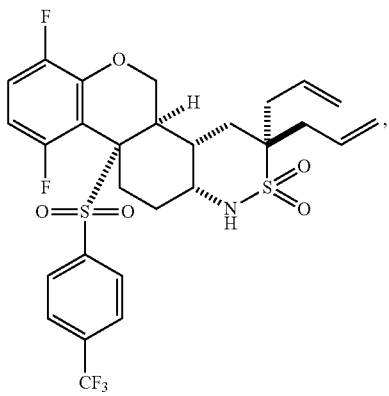
37
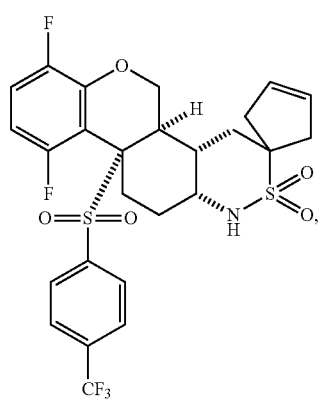
38
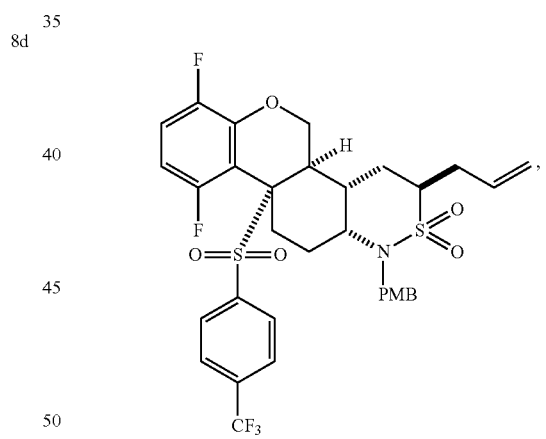
36a
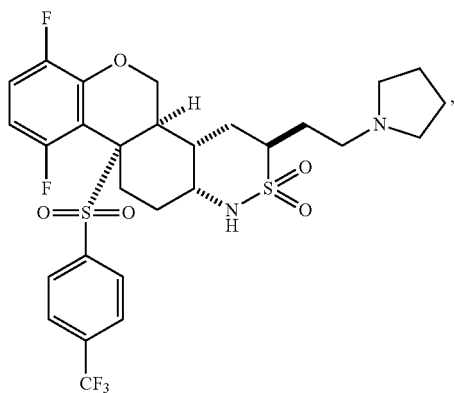
40

-continued
42
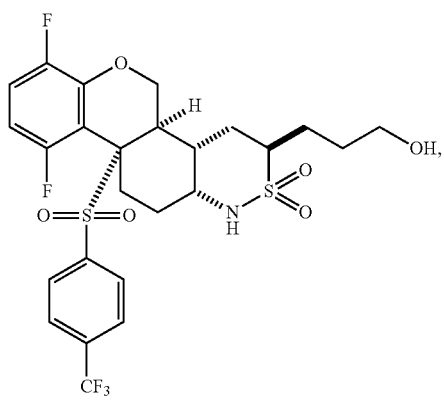
43
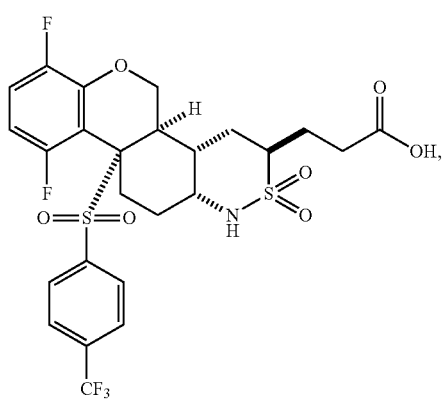
44
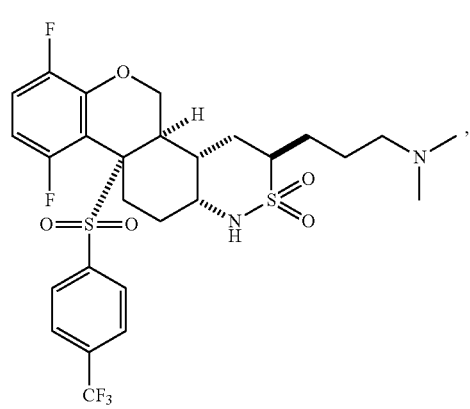
45
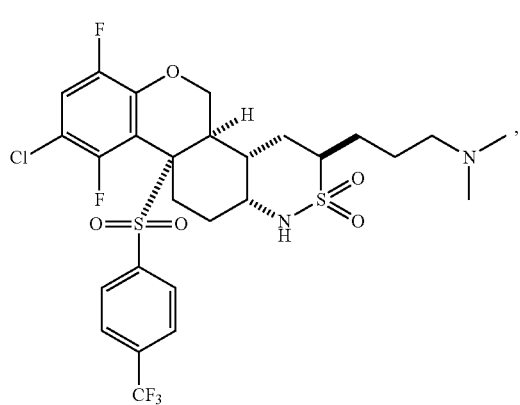
-continued
50
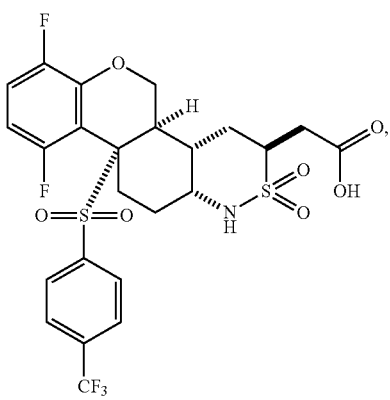
51
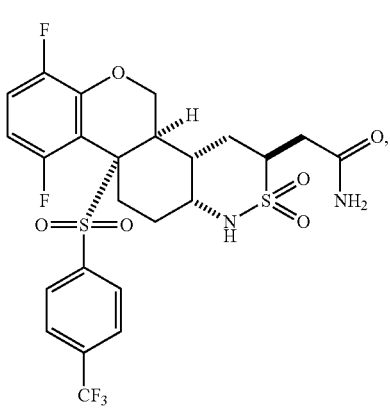
5b5
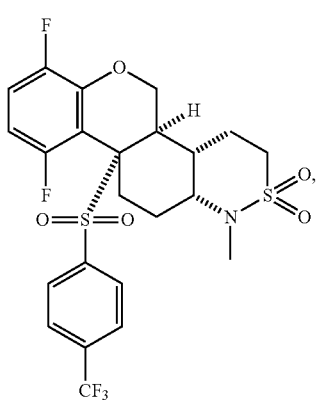
14b1
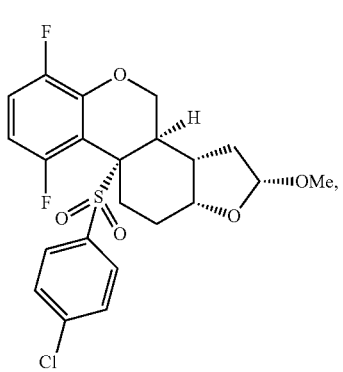

| | |
|---|---|
| 14b2 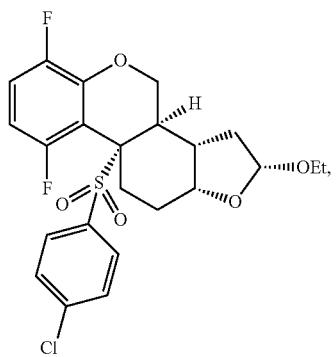 | 5c 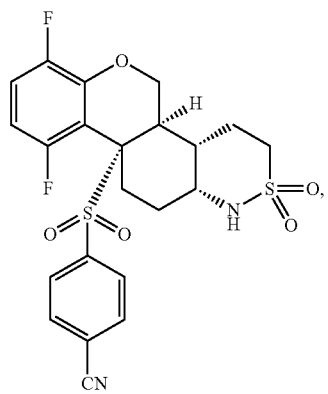 |
| 14b3 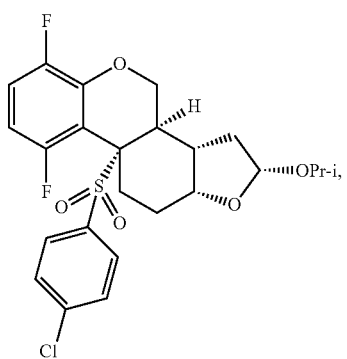 | 5d 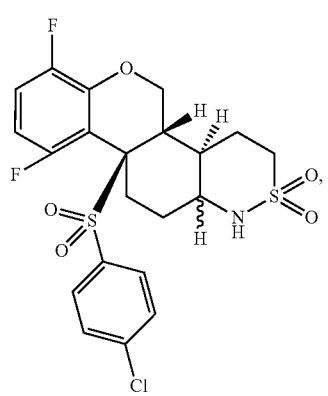 |
| 30 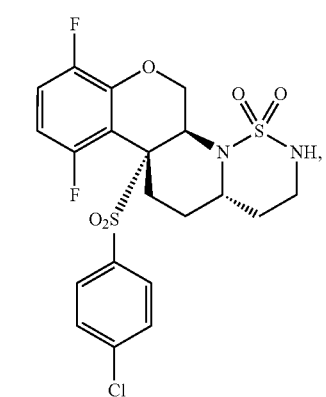 | 5e 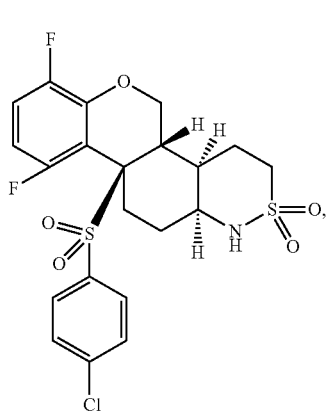 |
| 31 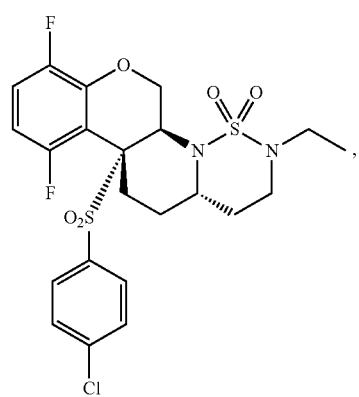 | 8c 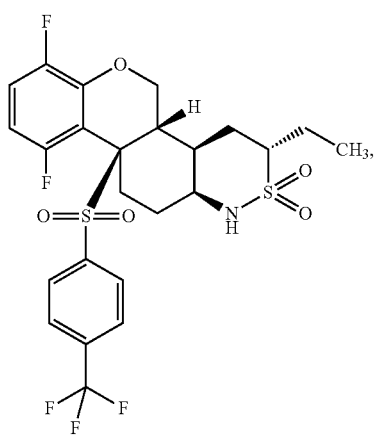 |

8b
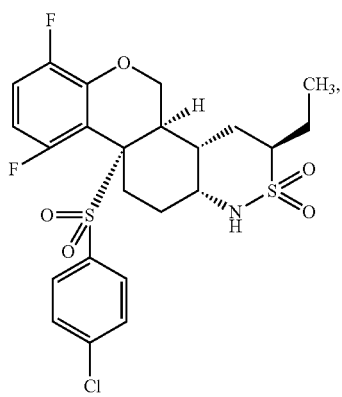
8e
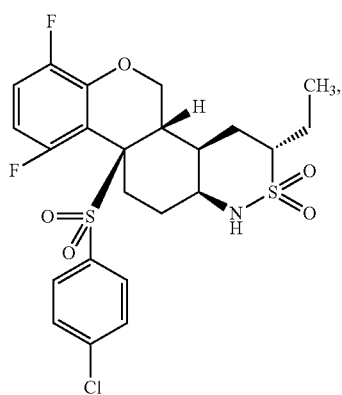
8f
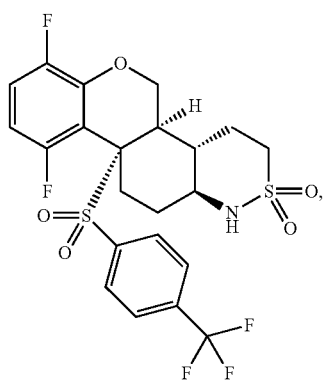
5a1
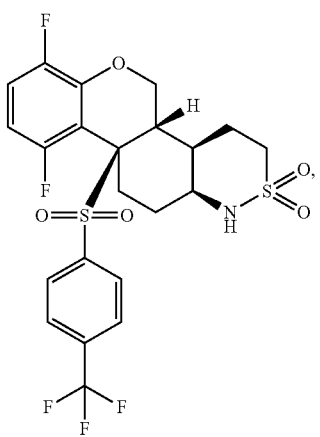
5b2
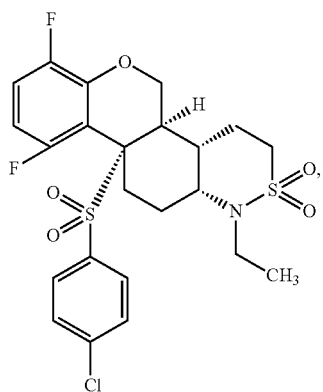
7e
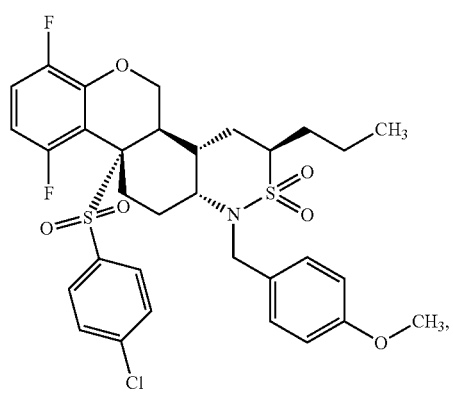
5b3
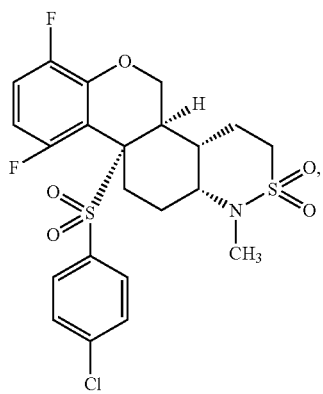
7f
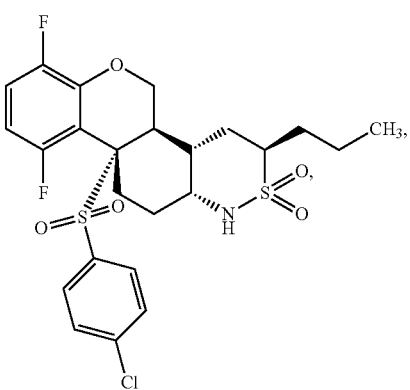

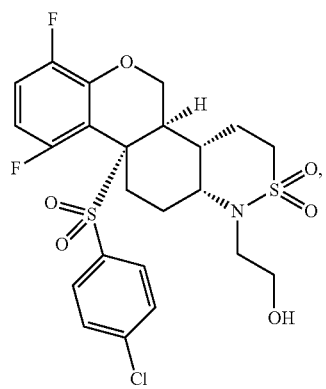
5b4
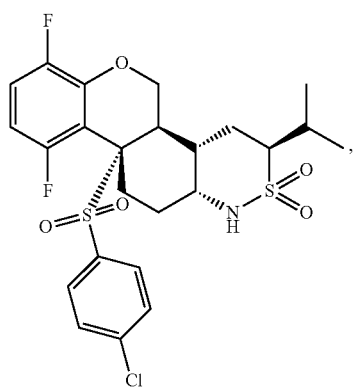
7g
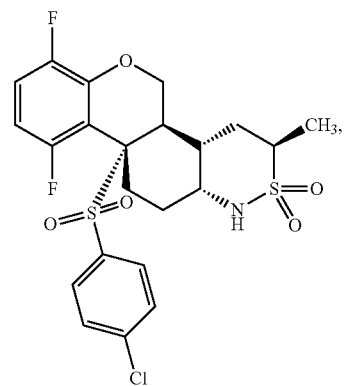
8g
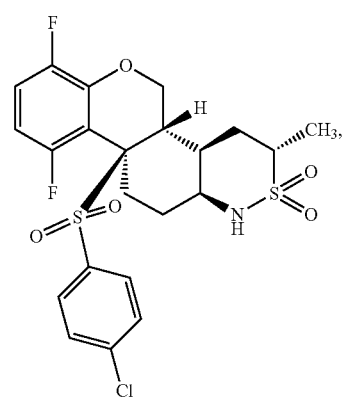
8h
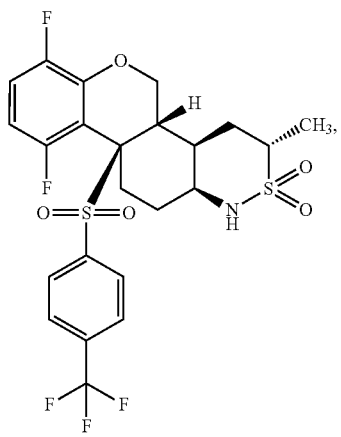
8d2
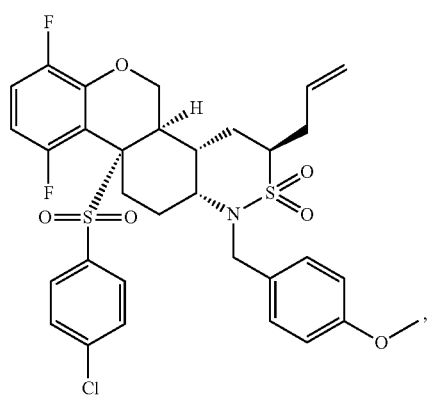
36b
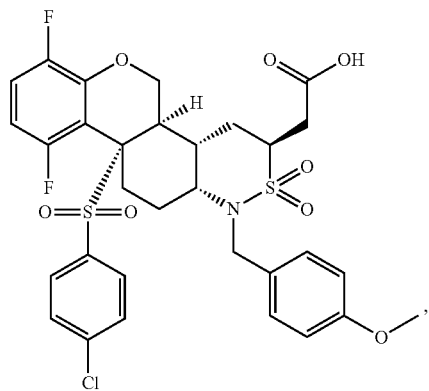
36c
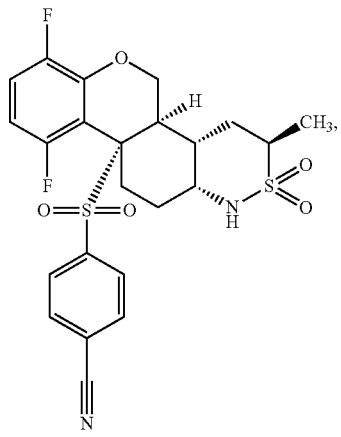
8e1

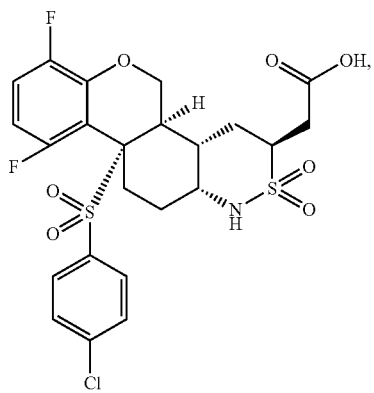
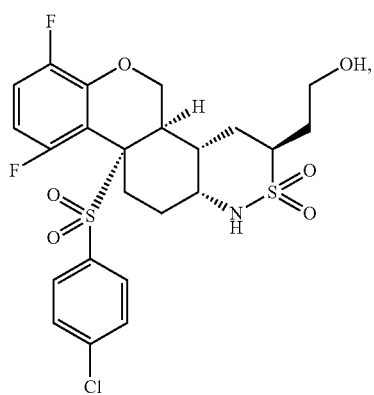
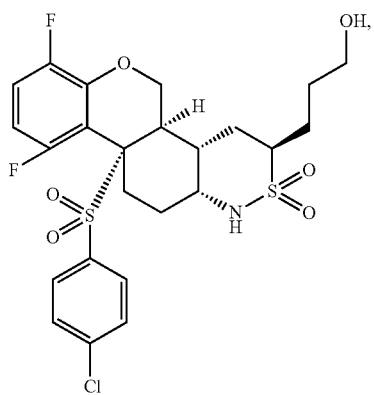
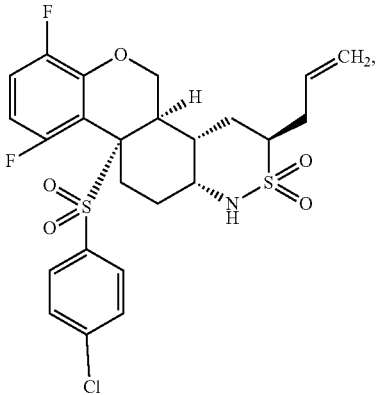
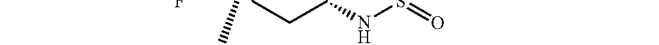

-continued

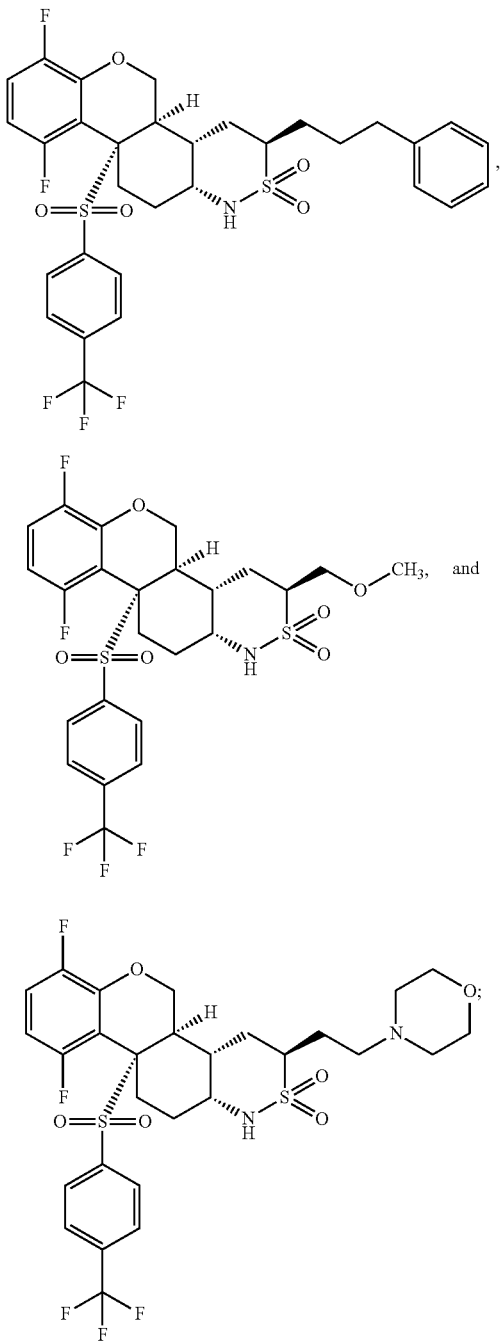

or a pharmaceutically acceptable salt thereof.

14. A pharmaceutical composition comprising a compound of claim 1 or a pharmaceutically acceptable salt thereof, and a pharmaceutically acceptable carrier.

15. A pharmaceutical composition comprising a pharmaceutically acceptable carrier, an effective amount of one or more compounds of claim 1 or a pharmaceutically acceptable salt thereof, and an effective amount of one or more other pharmaceutically active ingredients selected from the group consisting of: BACE inhibitors, muscarinic antagonists, cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors.

16. A pharmaceutical composition comprising a pharmaceutically acceptable carrier, an effective amount of one or more compounds of claim 1 or a pharmaceutically acceptable salt thereof, and an effective amount of one or more BACE inhibitors.

17. A pharmaceutical composition comprising a pharmaceutically acceptable carrier, an effective amount of one or more compounds of claim 13 or a pharmaceutically acceptable salt thereof, and an effective amount of one or more other pharmaceutically active ingredients selected from the group consisting of: BACE inhibitors, muscarinic antagonists, cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB 1 receptor inverse agonists or CB 1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors.

18. A pharmaceutical composition comprising a pharmaceutically acceptable carrier, an effective amount of one or more compounds of claim 13 or a pharmaceutically acceptable salt thereof, and an effective amount of one or more BACE inhibitors.

* * * * *